(12) United States Patent
Yanai et al.

(10) Patent No.: US 9,708,667 B2
(45) Date of Patent: Jul. 18, 2017

(54) MIRNA EXPRESSION SIGNATURE IN THE CLASSIFICATION OF THYROID TUMORS

(71) Applicant: ROSETTA GENOMICS, LTD., Rehovot (IL)

(72) Inventors: Gila Lithwick Yanai, Modiin (IL); Eti Meiri, Shoham (IL); Yael Spector, Tel Aviv (IL); Hila Benjamin, Rehovot (IL); Nir Dromi, Rehovot (IL)

(73) Assignee: ROSETTA GENOMICS, LTD., Rehovot (IL)

( * ) Notice: Subject to any disclaimer, the term of this patent is extended or adjusted under 35 U.S.C. 154(b) by 0 days.

(21) Appl. No.: 15/237,364

(22) Filed: Aug. 15, 2016

(65) Prior Publication Data

US 2017/0016076 A1 Jan. 19, 2017

Related U.S. Application Data

(63) Continuation-in-part of application No. PCT/US2015/030564, filed on May 13, 2015.

(60) Provisional application No. 62/321,498, filed on Apr. 12, 2016, provisional application No. 62/139,066, filed on Mar. 27, 2015, provisional application No. 62/069,353, filed on Oct. 28, 2014, provisional application No. 61/992,531, filed on May 13, 2014, provisional application No. 61/992,756, filed on May 13, 2014.

(51) Int. Cl.
*C12Q 1/68* (2006.01)
*C07H 21/02* (2006.01)
*C07H 21/04* (2006.01)
*G06F 19/18* (2011.01)
*G06F 19/20* (2011.01)

(52) U.S. Cl.
CPC ........... *C12Q 1/6886* (2013.01); *G06F 19/18* (2013.01); *G06F 19/20* (2013.01); *C12Q 2600/112* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS 8,945,829 B2 * 2/2015 Keutgen .............. C12Q 1/6886
435/6.14

OTHER PUBLICATIONS

Rossing, et al. (2012) Down-Regulation of microRNAs Controlling Tumourigenic Factors in Follicular Thyroid Carcinoma. Journal of Molecular Endocrinology, v.48(1):11-23.*

* cited by examiner

*Primary Examiner* — Jennifer McDonald
(74) *Attorney, Agent, or Firm* — Polsinelli PC; Ron Galant

(57) ABSTRACT

The present invention provides a method for classification of thyroid tumors through the analysis of the expression patterns of specific microRNAs in fine needle aspiration samples. Thyroid tumor classification according to a microRNA expression signature allows optimization of diagnosis and treatment, as well as determination of signature-specific therapy.

12 Claims, 34 Drawing Sheets

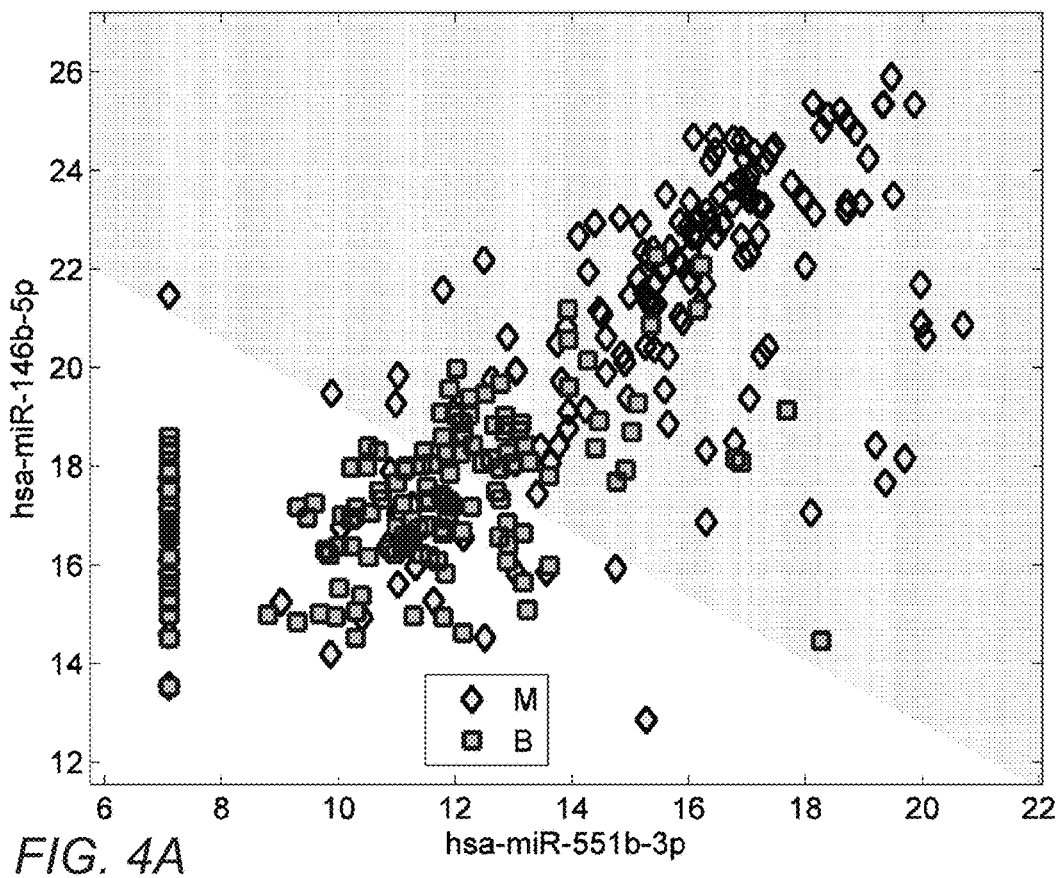
FIG. 4A
FIG. 4B
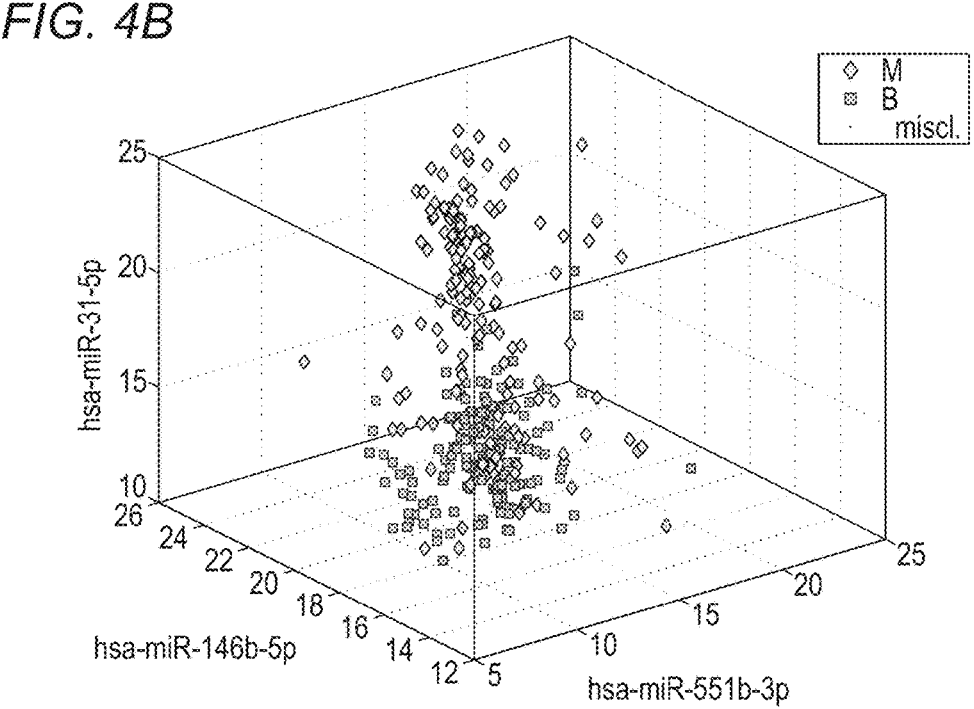

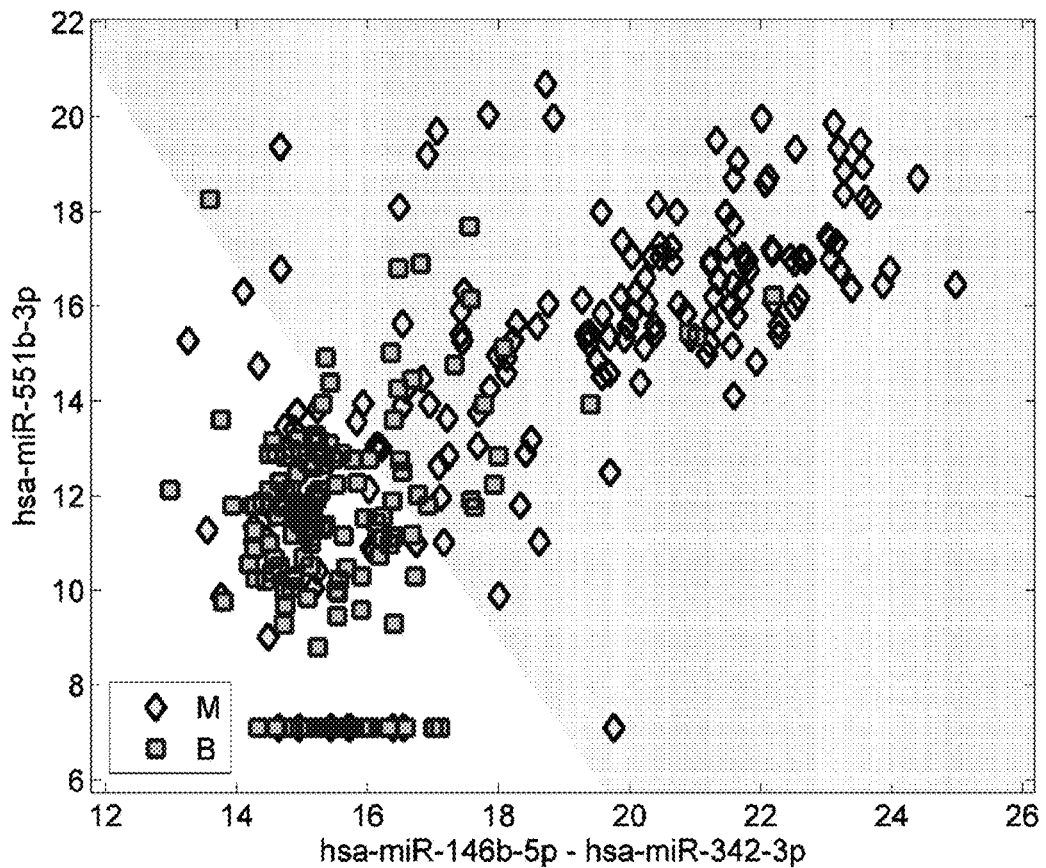
FIG. 6A
FIG. 6B
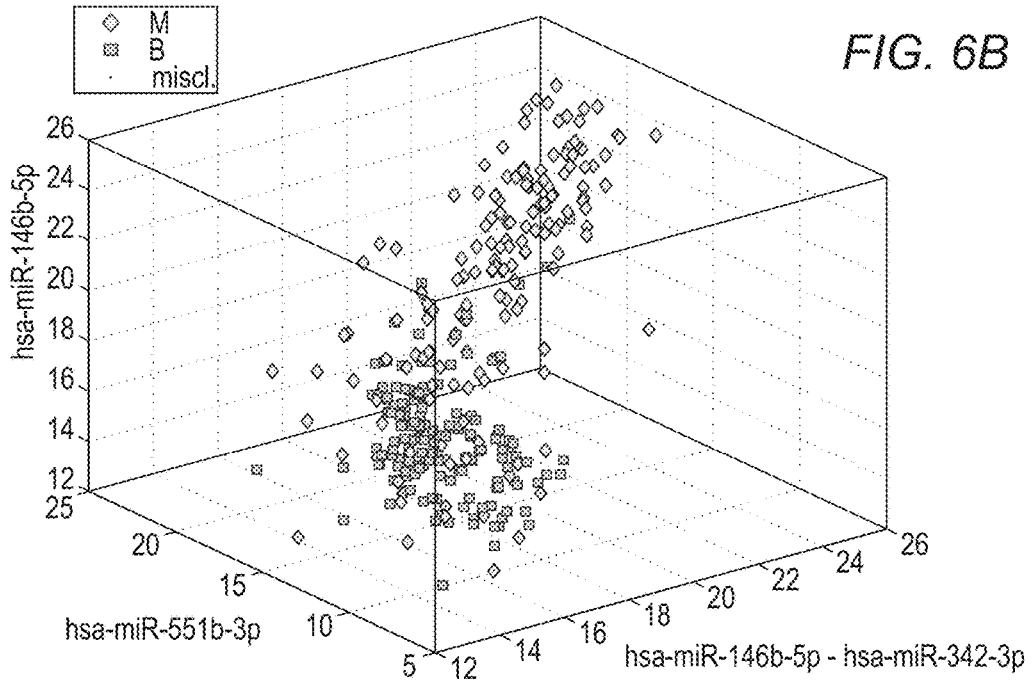

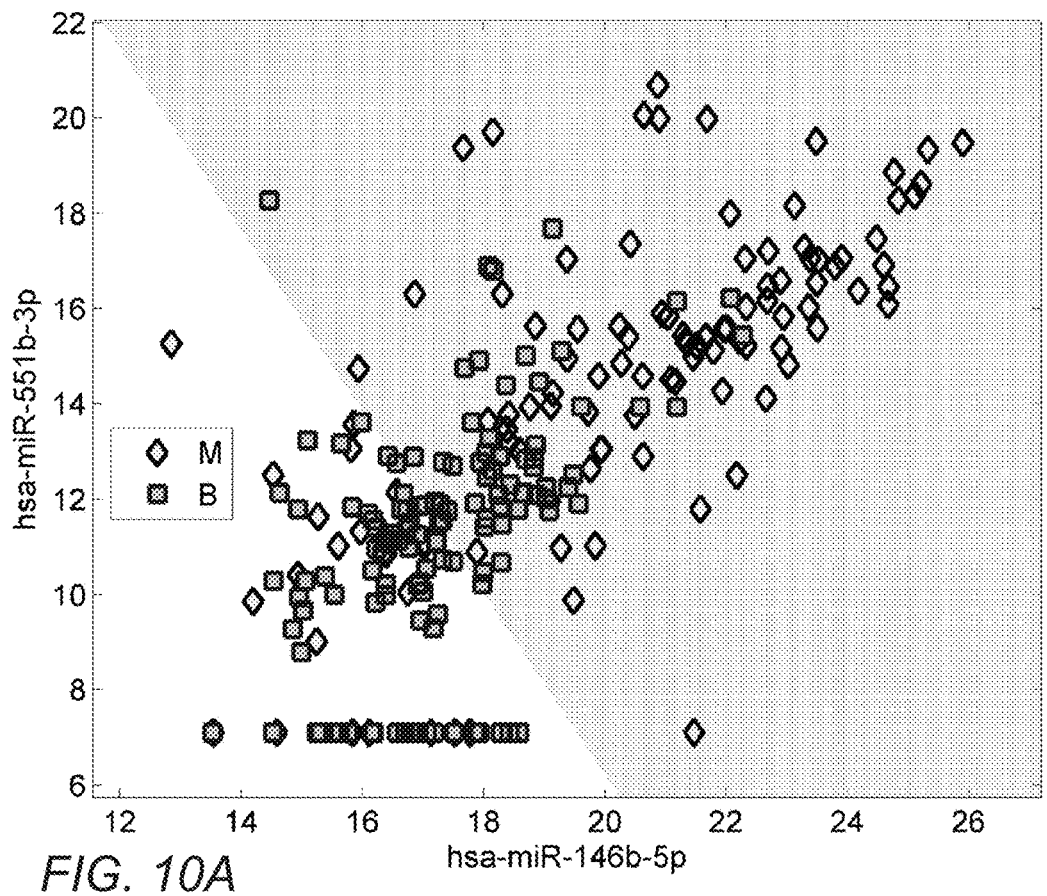
FIG. 10A
FIG. 10B
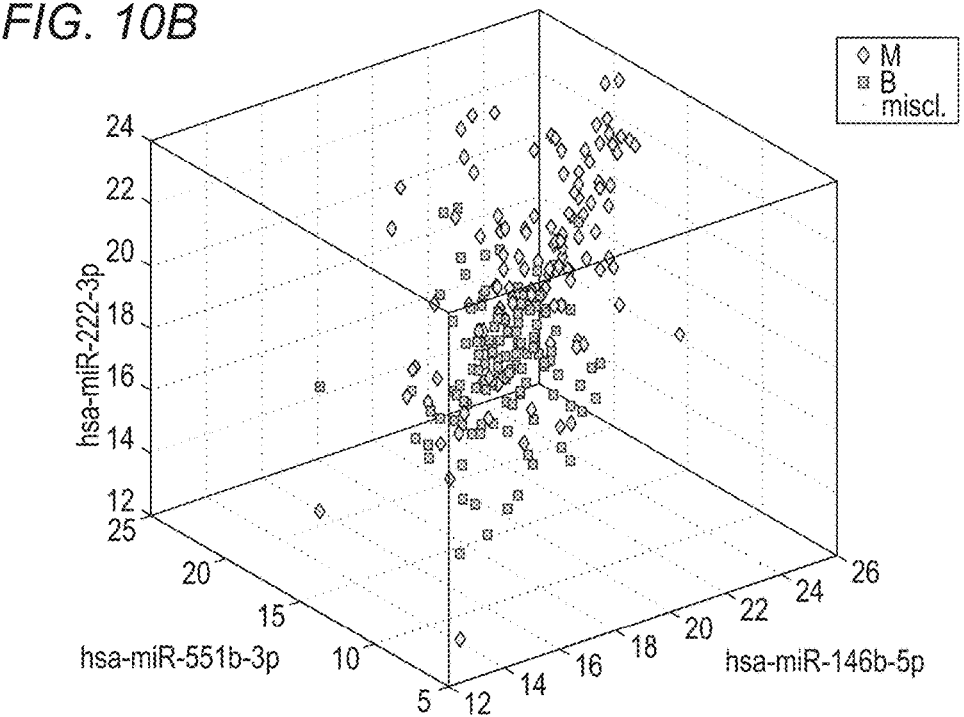

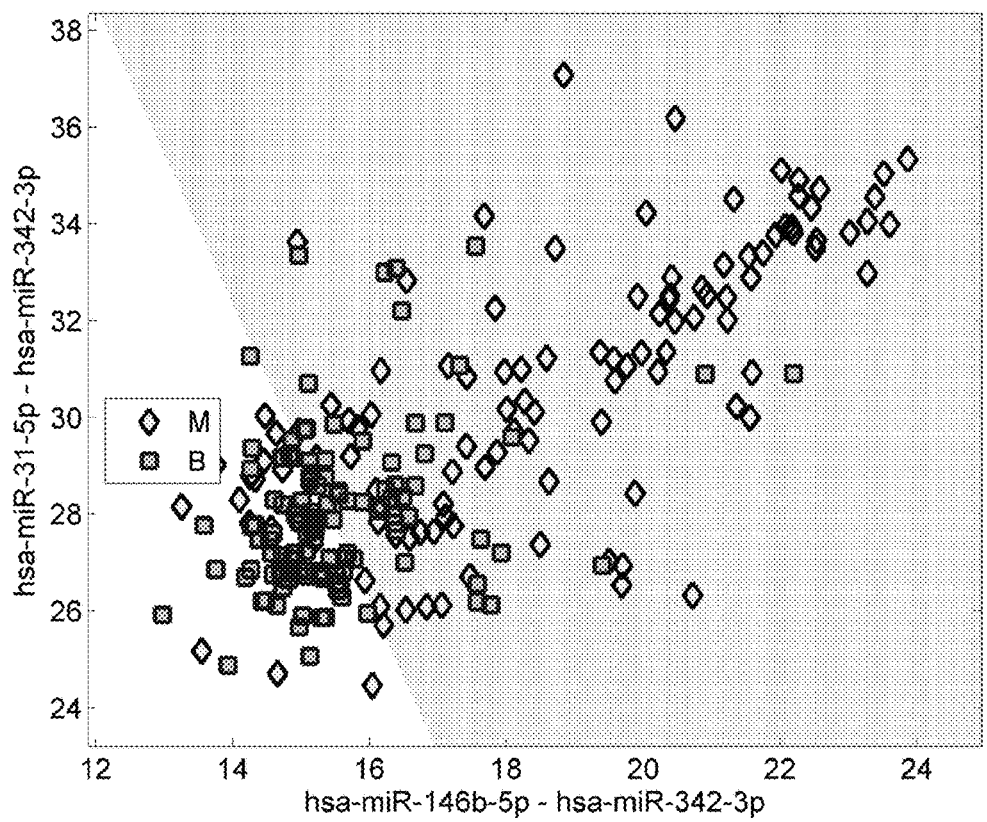
FIG. 20A
FIG. 20B
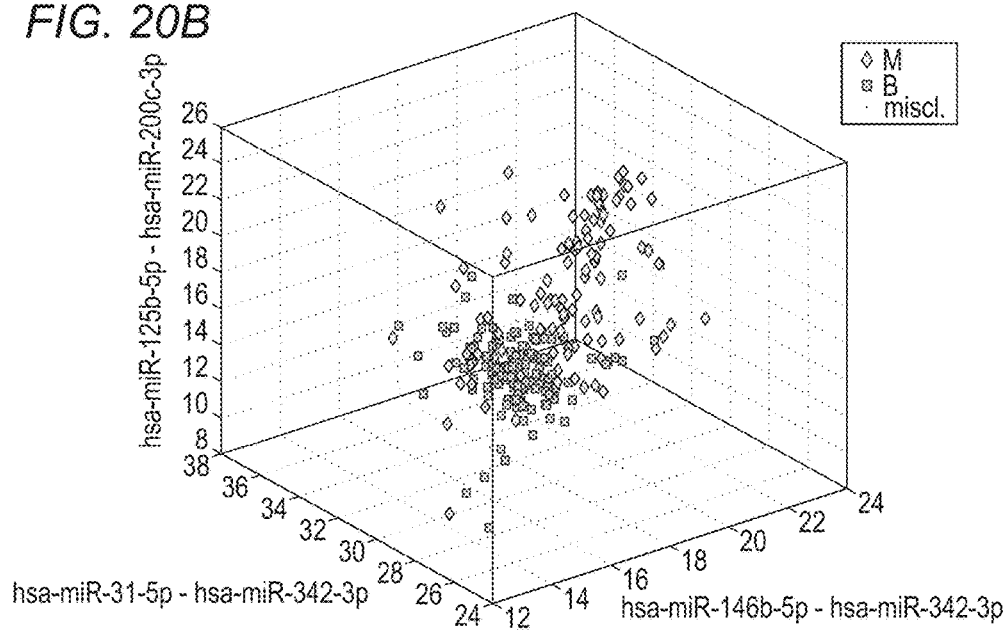

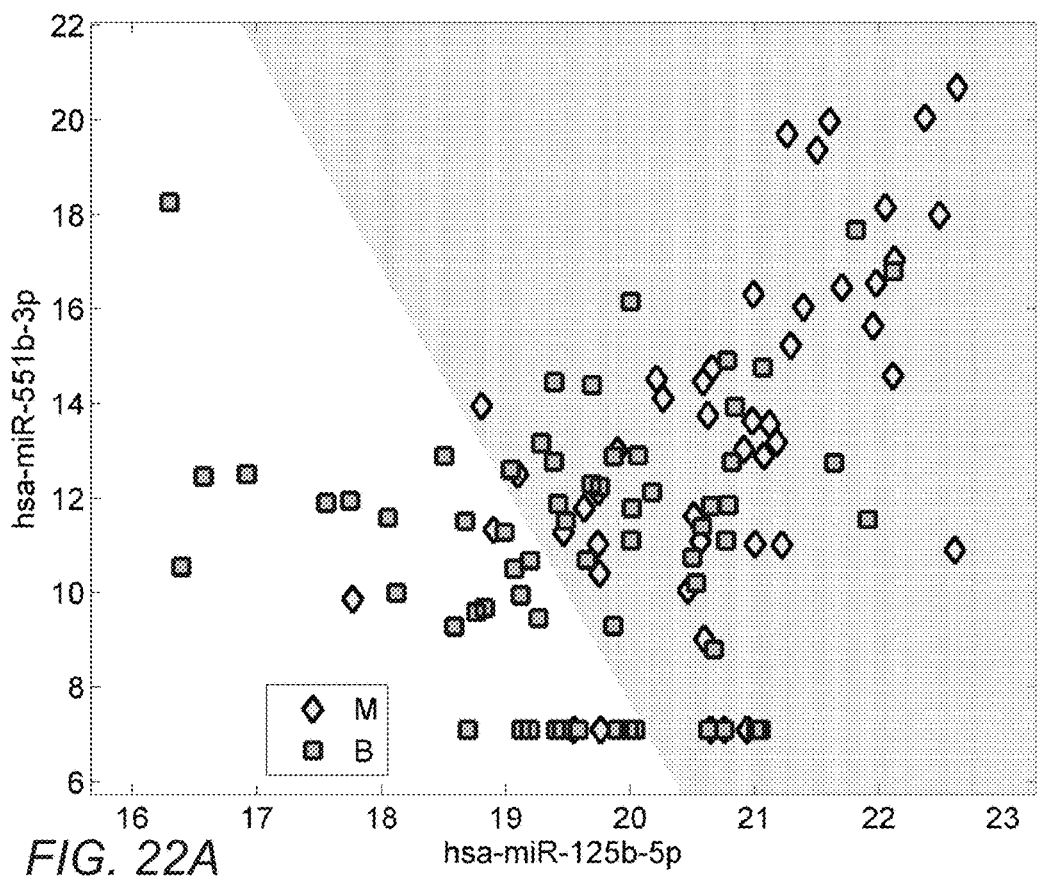
FIG. 22A
FIG. 22B
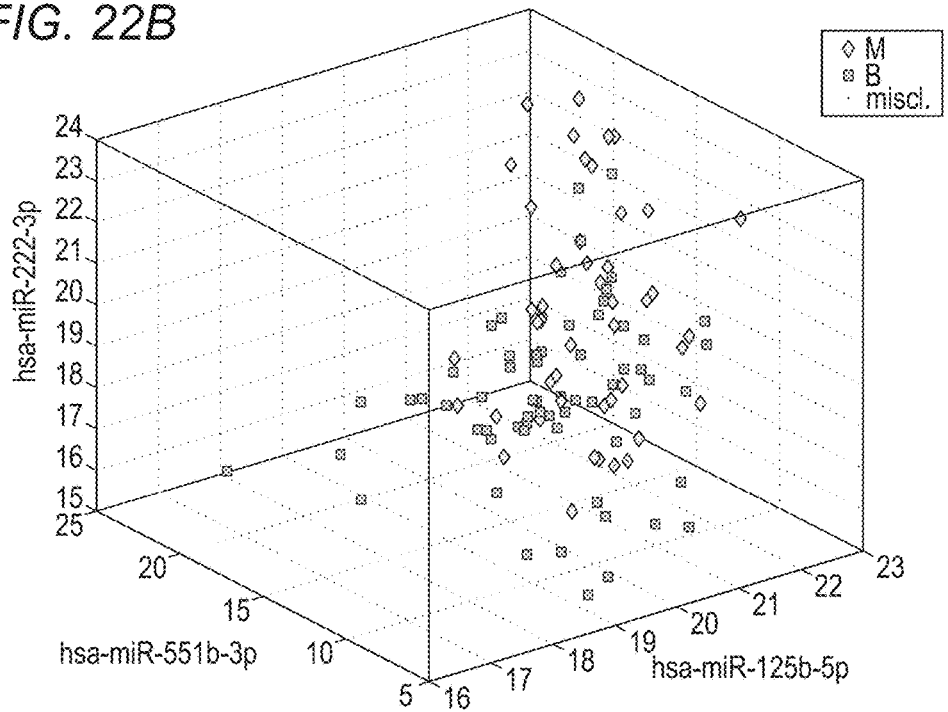

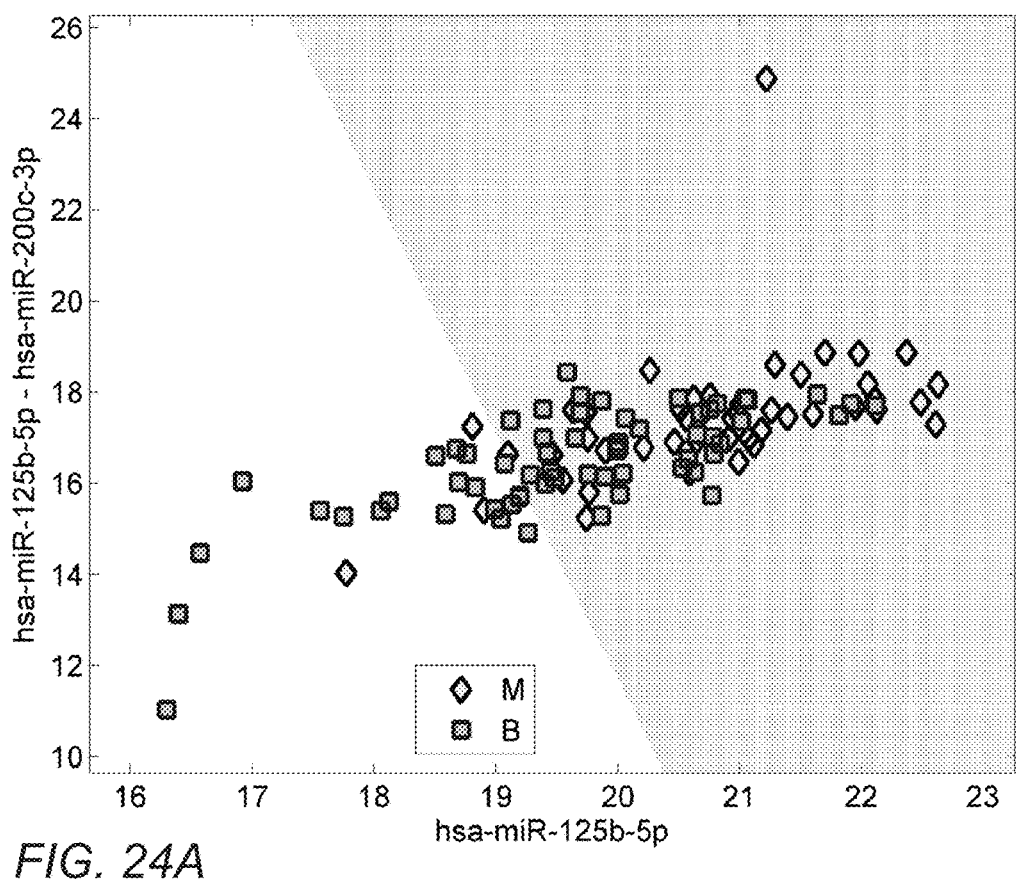
FIG. 24A
FIG. 24B
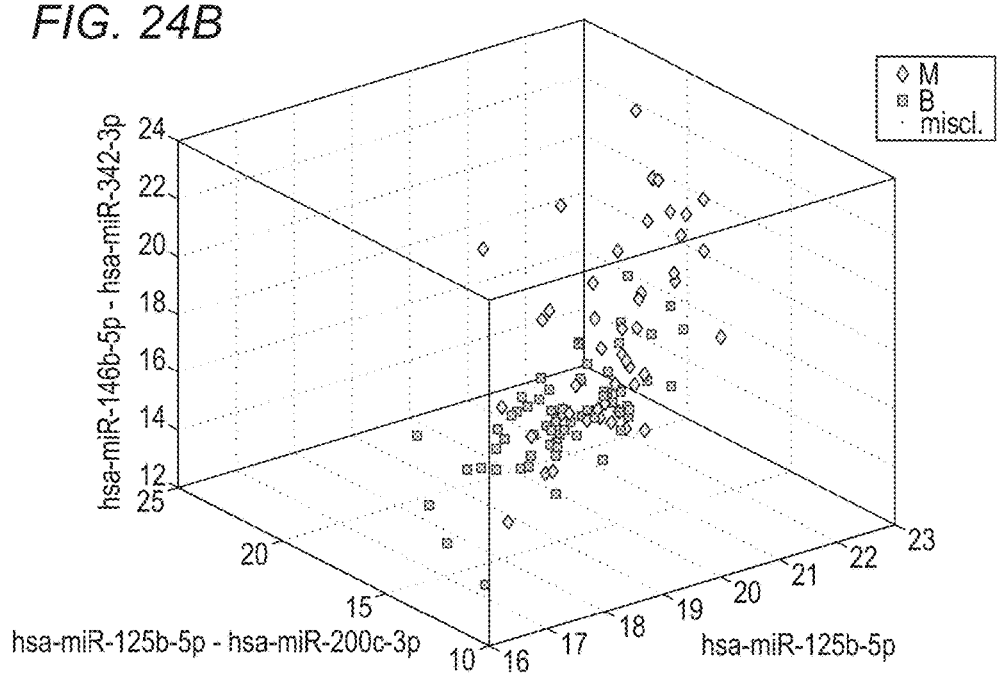

SEQUENCE LISTING

<160> NUMBER OF SEQ ID NOS: 347

<210> SEQ ID NO 1
<211> LENGTH: 21
<212> TYPE: DNA
<213> ORGANISM: Homo sapiens

<400> SEQUENCE: 1
agctacatct ggctactggg t                              21

<210> SEQ ID NO 2
<211> LENGTH: 24
<212> TYPE: DNA
<213> ORGANISM: Homo sapiens

```
<400> SEQUENCE: 2
agctacatct ggctactggg tctc                                          24

<210> SEQ ID NO 3
<211> LENGTH: 22
<212> TYPE: DNA
<213> ORGANISM: Homo sapiens

<400> SEQUENCE: 3
gacccatact tggtttcaga gg                                            22

<210> SEQ ID NO 4
<211> LENGTH: 21
<212> TYPE: DNA
<213> ORGANISM: Homo sapiens

<400> SEQUENCE: 4
gcgacccata cttggtttca g                                             21

<210> SEQ ID NO 5
<211> LENGTH: 21
<212> TYPE: DNA
<213> ORGANISM: Homo sapiens

<400> SEQUENCE: 5
aggcaagatg ctggcatagc t                                             21

<210> SEQ ID NO 6
<211> LENGTH: 23
<212> TYPE: DNA
<213> ORGANISM: Homo sapiens

<400> SEQUENCE: 6
aggcaagatg ctggcatagc tgt                                           23

<210> SEQ ID NO 7
<211> LENGTH: 21
<212> TYPE: DNA
<213> ORGANISM: Homo sapiens

<400> SEQUENCE: 7
ggcaagatgc tggcatagct g                                             21

<210> SEQ ID NO 8
<211> LENGTH: 22
<212> TYPE: DNA
<213> ORGANISM: Homo sapiens

<400> SEQUENCE: 8
tttgttcgtt cggctcgcgt ga                                            22

<210> SEQ ID NO 9
<211> LENGTH: 22
<212> TYPE: DNA
<213> ORGANISM: Homo sapiens

<400> SEQUENCE: 9
tccctgagac cctaacttgt ga                                            22

<210> SEQ ID NO 10
<211> LENGTH: 22
<212> TYPE: DNA
<213> ORGANISM: Homo sapiens
```

```
<400> SEQUENCE: 10
tgagaactga attccatagg ct                                          22

<210> SEQ ID NO 11
<211> LENGTH: 24
<212> TYPE: DNA
<213> ORGANISM: Homo sapiens

<400> SEQUENCE: 11
tgagaactga attccatagg ctgt                                        24

<210> SEQ ID NO 12
<211> LENGTH: 21
<212> TYPE: DNA
<213> ORGANISM: Homo sapiens

<400> SEQUENCE: 12
tcagtgcatg acagaacttg g                                           21

<210> SEQ ID NO 13
<211> LENGTH: 22
<212> TYPE: DNA
<213> ORGANISM: Homo sapiens

<400> SEQUENCE: 13
tcagtgcatg acagaacttg gg                                          22

<210> SEQ ID NO 14
<211> LENGTH: 23
<212> TYPE: DNA
<213> ORGANISM: Homo sapiens

<400> SEQUENCE: 14
tgtctgcccg catgcctgcc tct                                         23

<210> SEQ ID NO 15
<211> LENGTH: 22
<212> TYPE: DNA
<213> ORGANISM: Homo sapiens

<400> SEQUENCE: 15
aacattcaac ctgtcggtga gt                                          22

<210> SEQ ID NO 16
<211> LENGTH: 21
<212> TYPE: DNA
<213> ORGANISM: Homo sapiens

<400> SEQUENCE: 16
caaaacgtga ggcgctgcta t                                           21

<210> SEQ ID NO 17
<211> LENGTH: 23
<212> TYPE: DNA
<213> ORGANISM: Homo sapiens

<400> SEQUENCE: 17
tctcacacag aaatcgcacc cgt                                         23

<210> SEQ ID NO 18
<211> LENGTH: 24
<212> TYPE: DNA
```

```
<213> ORGANISM: Homo sapiens

<400> SEQUENCE: 18
tctcacacag aaatcgcacc cgtc                                          24

<210> SEQ ID NO 19
<211> LENGTH: 17
<212> TYPE: DNA
<213> ORGANISM: Homo sapiens

<400> SEQUENCE: 19
agctggtgtt gtgaatc                                                  17

<210> SEQ ID NO 20
<211> LENGTH: 23
<212> TYPE: DNA
<213> ORGANISM: Homo sapiens

<400> SEQUENCE: 20
agctggtgtt gtgaatcagg ccg                                           23

<210> SEQ ID NO 21
<211> LENGTH: 24
<212> TYPE: DNA
<213> ORGANISM: Homo sapiens

<400> SEQUENCE: 21
agctggtgtt gtgaatcagg ccgt                                          24

<210> SEQ ID NO 22
<211> LENGTH: 22
<212> TYPE: DNA
<213> ORGANISM: Homo sapiens

<400> SEQUENCE: 22
tcctgtactg agctgccccg ag                                            22

<210> SEQ ID NO 23
<211> LENGTH: 22
<212> TYPE: DNA
<213> ORGANISM: Homo sapiens

<400> SEQUENCE: 23
taatactgcc gggtaatgat gg                                            22

<210> SEQ ID NO 24
<211> LENGTH: 23
<212> TYPE: DNA
<213> ORGANISM: Homo sapiens

<400> SEQUENCE: 24
taatactgcc gggtaatgat gga                                           23

<210> SEQ ID NO 25
<211> LENGTH: 19
<212> TYPE: DNA
<213> ORGANISM: Homo sapiens

<400> SEQUENCE: 25
agtgaagcat tggactgta                                                19

<210> SEQ ID NO 26
<211> LENGTH: 21
```

```
<212> TYPE: DNA
<213> ORGANISM: Homo sapiens

<400> SEQUENCE: 26
atcacattgc cagggatttc c                                              21

<210> SEQ ID NO 27
<211> LENGTH: 21
<212> TYPE: DNA
<213> ORGANISM: Homo sapiens

<400> SEQUENCE: 27
taagccagtt tctgtctgat a                                              21

<210> SEQ ID NO 28
<211> LENGTH: 25
<212> TYPE: DNA
<213> ORGANISM: Homo sapiens

<400> SEQUENCE: 28
tttctaagcc agtttctgtc tgata                                          25

<210> SEQ ID NO 29
<211> LENGTH: 23
<212> TYPE: DNA
<213> ORGANISM: Homo sapiens

<400> SEQUENCE: 29
atgacagatt gacatggaca att                                            23

<210> SEQ ID NO 30
<211> LENGTH: 22
<212> TYPE: DNA
<213> ORGANISM: Homo sapiens

<400> SEQUENCE: 30
gctgactcct agtccagggc tc                                             22

<210> SEQ ID NO 31
<211> LENGTH: 21
<212> TYPE: DNA
<213> ORGANISM: Homo sapiens

<400> SEQUENCE: 31
tgctgactcc tagtccaggg c                                              21

<210> SEQ ID NO 32
<211> LENGTH: 21
<212> TYPE: DNA
<213> ORGANISM: Homo sapiens

<400> SEQUENCE: 32
gttcctgctg aactgagcca g                                              21

<210> SEQ ID NO 33
<211> LENGTH: 17
<212> TYPE: DNA
<213> ORGANISM: Homo sapiens

<400> SEQUENCE: 33
ctgtctgagc gccgctc                                                   17

<210> SEQ ID NO 34
```

```
<211> LENGTH: 18
<212> TYPE: DNA
<213> ORGANISM: Homo sapiens

<400> SEQUENCE: 34
atactctggt ttcttttc                                                  18

<210> SEQ ID NO 35
<211> LENGTH: 19
<212> TYPE: DNA
<213> ORGANISM: Homo sapiens

<400> SEQUENCE: 35
ttattgtcac gttctgatt                                                 19

<210> SEQ ID NO 36
<211> LENGTH: 21
<212> TYPE: DNA
<213> ORGANISM: Homo sapiens

<400> SEQUENCE: 36
cacgctcatg cacacaccca c                                              21

<210> SEQ ID NO 37
<211> LENGTH: 22
<212> TYPE: DNA
<213> ORGANISM: Homo sapiens

<400> SEQUENCE: 37
cacgctcatg cacacaccca ca                                             22

<210> SEQ ID NO 38
<211> LENGTH: 23
<212> TYPE: DNA
<213> ORGANISM: Homo sapiens

<400> SEQUENCE: 38
tggaagacta gtgattttgt tgt                                            23

<210> SEQ ID NO 39
<211> LENGTH: 23
<212> TYPE: DNA
<213> ORGANISM: Homo sapiens

<400> SEQUENCE: 39
taccctgtag atccgaattt gtg                                            23

<210> SEQ ID NO 40
<211> LENGTH: 23
<212> TYPE: DNA
<213> ORGANISM: Homo sapiens

<400> SEQUENCE: 40
taaggtgcat ctagtgcaga tag                                            23

<210> SEQ ID NO 41
<211> LENGTH: 21
<212> TYPE: DNA
<213> ORGANISM: Homo sapiens

<400> SEQUENCE: 41
caacaccagt cgatgggctg t                                              21
```

```
<210> SEQ ID NO 42
<211> LENGTH: 22
<212> TYPE: DNA
<213> ORGANISM: Homo sapiens

<400> SEQUENCE: 42
tagcttatca gactgatgtt ga                                              22

<210> SEQ ID NO 43
<211> LENGTH: 22
<212> TYPE: DNA
<213> ORGANISM: Homo sapiens

<400> SEQUENCE: 43
tgtaaacatc cttgactgga ag                                              22

<210> SEQ ID NO 44
<211> LENGTH: 22
<212> TYPE: DNA
<213> ORGANISM: Homo sapiens

<400> SEQUENCE: 44
tgctatgcca acatattgcc at                                              22

<210> SEQ ID NO 45
<211> LENGTH: 23
<212> TYPE: DNA
<213> ORGANISM: Homo sapiens

<400> SEQUENCE: 45
tggcagtgtc ttagctggtt gtt                                             23

<210> SEQ ID NO 46
<211> LENGTH: 22
<212> TYPE: DNA
<213> ORGANISM: Homo sapiens

<400> SEQUENCE: 46
agggacggga cgcggtgcag tg                                              22

<210> SEQ ID NO 47
<211> LENGTH: 23
<212> TYPE: DNA
<213> ORGANISM: Homo sapiens

<400> SEQUENCE: 47
tttggcacta gcacattttt gct                                             23

<210> SEQ ID NO 48
<211> LENGTH: 22
<212> TYPE: DNA
<213> ORGANISM: Homo sapiens

<400> SEQUENCE: 48
aacccgtaga tccgaacttg tg                                              22

<210> SEQ ID NO 49
<211> LENGTH: 22
<212> TYPE: DNA
<213> ORGANISM: Homo sapiens

<400> SEQUENCE: 49
tcgtaccgtg agtaataatg cg                                              22
```

-continued

```
<210> SEQ ID NO 50
<211> LENGTH: 22
<212> TYPE: DNA
<213> ORGANISM: Homo sapiens

<400> SEQUENCE: 50
gctacttcac aacaccaggg cc                                           22

<210> SEQ ID NO 51
<211> LENGTH: 21
<212> TYPE: DNA
<213> ORGANISM: Homo sapiens

<400> SEQUENCE: 51
taccacaggg tagaaccacg g                                            21

<210> SEQ ID NO 52
<211> LENGTH: 22
<212> TYPE: DNA
<213> ORGANISM: Homo sapiens

<400> SEQUENCE: 52
taacactgtc tggtaaagat gg                                           22

<210> SEQ ID NO 53
<211> LENGTH: 23
<212> TYPE: DNA
<213> ORGANISM: Homo sapiens

<400> SEQUENCE: 53
tgtagtgttt cctactttat gga                                          23

<210> SEQ ID NO 54
<211> LENGTH: 21
<212> TYPE: DNA
<213> ORGANISM: Homo sapiens

<400> SEQUENCE: 54
cataaagtag aaagcactac t                                            21

<210> SEQ ID NO 55
<211> LENGTH: 22
<212> TYPE: DNA
<213> ORGANISM: Homo sapiens

<400> SEQUENCE: 55
tgccctgtgg actcagttct gg                                           22

<210> SEQ ID NO 56
<211> LENGTH: 22
<212> TYPE: DNA
<213> ORGANISM: Homo sapiens

<400> SEQUENCE: 56
tgagaactga attccatggg tt                                           22

<210> SEQ ID NO 57
<211> LENGTH: 22
<212> TYPE: DNA
<213> ORGANISM: Homo sapiens

<400> SEQUENCE: 57
tcagtgcact acagaacttt gt                                           22
```

<210> SEQ ID NO 58
<211> LENGTH: 22
<212> TYPE: DNA
<213> ORGANISM: Homo sapiens

<400> SEQUENCE: 58
ctggtacagg cctgggggac ag                                              22

<210> SEQ ID NO 59
<211> LENGTH: 22
<212> TYPE: DNA
<213> ORGANISM: Homo sapiens

<400> SEQUENCE: 59
tctcccaacc cttgtaccag tg                                              22

<210> SEQ ID NO 60
<211> LENGTH: 23
<212> TYPE: DNA
<213> ORGANISM: Homo sapiens

<400> SEQUENCE: 60
ttaatgctaa tcgtgatagg ggt                                             23

<210> SEQ ID NO 61
<211> LENGTH: 23
<212> TYPE: DNA
<213> ORGANISM: Homo sapiens

<400> SEQUENCE: 61
aacattcaac gctgtcggtg agt                                             23

<210> SEQ ID NO 62
<211> LENGTH: 23
<212> TYPE: DNA
<213> ORGANISM: Homo sapiens

<400> SEQUENCE: 62
aacattcatt gctgtcggtg ggt                                             23

<210> SEQ ID NO 63
<211> LENGTH: 24
<212> TYPE: DNA
<213> ORGANISM: Homo sapiens

<400> SEQUENCE: 63
tttggcaatg gtagaactca cact                                            24

<210> SEQ ID NO 64
<211> LENGTH: 22
<212> TYPE: DNA
<213> ORGANISM: Homo sapiens

<400> SEQUENCE: 64
tcgtgtcttg tgttgcagcc gg                                              22

<210> SEQ ID NO 65
<211> LENGTH: 22
<212> TYPE: DNA
<213> ORGANISM: Homo sapiens

<400> SEQUENCE: 65

```
aactggccta caaagtccca gt                                              22

<210> SEQ ID NO 66
<211> LENGTH: 21
<212> TYPE: DNA
<213> ORGANISM: Homo sapiens

<400> SEQUENCE: 66
tagcagcaca gaaatattgg c                                               21

<210> SEQ ID NO 67
<211> LENGTH: 23
<212> TYPE: DNA
<213> ORGANISM: Homo sapiens

<400> SEQUENCE: 67
cgggtagaga gggcagtggg agg                                             23

<210> SEQ ID NO 68
<211> LENGTH: 22
<212> TYPE: DNA
<213> ORGANISM: Homo sapiens

<400> SEQUENCE: 68
acagtagtct gcacattggt ta                                              22

<210> SEQ ID NO 69
<211> LENGTH: 23
<212> TYPE: DNA
<213> ORGANISM: Homo sapiens

<400> SEQUENCE: 69
taacactgtc tggtaacgat gtt                                             23

<210> SEQ ID NO 70
<211> LENGTH: 22
<212> TYPE: DNA
<213> ORGANISM: Homo sapiens

<400> SEQUENCE: 70
taatactgcc tggtaatgat ga                                              22

<210> SEQ ID NO 71
<211> LENGTH: 23
<212> TYPE: DNA
<213> ORGANISM: Homo sapiens

<400> SEQUENCE: 71
cccagtgttc agactacctg ttc                                             23

<210> SEQ ID NO 72
<211> LENGTH: 23
<212> TYPE: DNA
<213> ORGANISM: Homo sapiens

<400> SEQUENCE: 72
cccagtgttt agactatctg ttc                                             23

<210> SEQ ID NO 73
<211> LENGTH: 22
<212> TYPE: DNA
<213> ORGANISM: Homo sapiens

<400> SEQUENCE: 73
```

```
tccttcattc caccggagtc tg                                          22

<210> SEQ ID NO 74
<211> LENGTH: 22
<212> TYPE: DNA
<213> ORGANISM: Homo sapiens

<400> SEQUENCE: 74
ctgtgcgtgt gacagcggct ga                                          22

<210> SEQ ID NO 75
<211> LENGTH: 22
<212> TYPE: DNA
<213> ORGANISM: Homo sapiens

<400> SEQUENCE: 75
acagcaggca cagacaggca gt                                          22

<210> SEQ ID NO 76
<211> LENGTH: 23
<212> TYPE: DNA
<213> ORGANISM: Homo sapiens

<400> SEQUENCE: 76
agctacattg tctgctgggt ttc                                         23

<210> SEQ ID NO 77
<211> LENGTH: 22
<212> TYPE: DNA
<213> ORGANISM: Homo sapiens

<400> SEQUENCE: 77
acctggcata caatgtagat tt                                          22

<210> SEQ ID NO 78
<211> LENGTH: 22
<212> TYPE: DNA
<213> ORGANISM: Homo sapiens

<400> SEQUENCE: 78
tgtcagtttg tcaaataccc ca                                          22

<210> SEQ ID NO 79
<211> LENGTH: 22
<212> TYPE: DNA
<213> ORGANISM: Homo sapiens

<400> SEQUENCE: 79
ctcagtagcc agtgtagatc ct                                          22

<210> SEQ ID NO 80
<211> LENGTH: 24
<212> TYPE: DNA
<213> ORGANISM: Homo sapiens

<400> SEQUENCE: 80
caagtcacta gtggttccgt ttag                                        24

<210> SEQ ID NO 81
<211> LENGTH: 21
<212> TYPE: DNA
<213> ORGANISM: Homo sapiens
```

```
<400> SEQUENCE: 81 agggtgcta tctgtgattg a                                          21

<210> SEQ ID NO 82
<211> LENGTH: 22
<212> TYPE: DNA
<213> ORGANISM: Homo sapiens

<400> SEQUENCE: 82
taatactgtc tggtaaaacc gt                                        22

<210> SEQ ID NO 83
<211> LENGTH: 21
<212> TYPE: DNA
<213> ORGANISM: Homo sapiens

<400> SEQUENCE: 83
gcagtccatg ggcatataca c                                         21

<210> SEQ ID NO 84
<211> LENGTH: 22
<212> TYPE: DNA
<213> ORGANISM: Homo sapiens

<400> SEQUENCE: 84
aagacgggag gaaagaaggg ag                                        22

<210> SEQ ID NO 85
<211> LENGTH: 22
<212> TYPE: DNA
<213> ORGANISM: Homo sapiens

<400> SEQUENCE: 85
aatcgtacag ggtcatccac tt                                        22

<210> SEQ ID NO 86
<211> LENGTH: 21
<212> TYPE: DNA
<213> ORGANISM: Homo sapiens

<400> SEQUENCE: 86
cagcagcaca ctgtggtttg t                                         21

<210> SEQ ID NO 87
<211> LENGTH: 22
<212> TYPE: DNA
<213> ORGANISM: Homo sapiens

<400> SEQUENCE: 87
ttcacaggga ggtgtcattt at                                        22

<210> SEQ ID NO 88
<211> LENGTH: 23
<212> TYPE: DNA
<213> ORGANISM: Homo sapiens

<400> SEQUENCE: 88
tcggggatca tcatgtcacg aga                                       23

<210> SEQ ID NO 89
<211> LENGTH: 21
<212> TYPE: DNA
<213> ORGANISM: Homo sapiens
```

```
<400> SEQUENCE: 89 aggggggaaag ttctatagtc c                                           21

<210> SEQ ID NO 90
<211> LENGTH: 21
<212> TYPE: DNA
<213> ORGANISM: Homo sapiens

<400> SEQUENCE: 90
aggaggcagc gctctcagga c                                            21

<210> SEQ ID NO 91
<211> LENGTH: 25
<212> TYPE: DNA
<213> ORGANISM: Homo sapiens

<400> SEQUENCE: 91
ggcggaggga agtaggtccg ttggt                                        25

<210> SEQ ID NO 92
<211> LENGTH: 24
<212> TYPE: DNA
<213> ORGANISM: Homo sapiens

<400> SEQUENCE: 92
tgggctaagg gagatgattg ggta                                         24

<210> SEQ ID NO 93
<211> LENGTH: 23
<212> TYPE: DNA
<213> ORGANISM: Homo sapiens

<400> SEQUENCE: 93
aaggagctta caatctagct ggg                                          23

<210> SEQ ID NO 94
<211> LENGTH: 21
<212> TYPE: DNA
<213> ORGANISM: Homo sapiens

<400> SEQUENCE: 94
tggaggagaa ggaaggtgat g                                            21

<210> SEQ ID NO 95
<211> LENGTH: 24
<212> TYPE: DNA
<213> ORGANISM: Homo sapiens

<400> SEQUENCE: 95
gtgggtaggg tttgggggag agcg                                         24

<210> SEQ ID NO 96
<211> LENGTH: 20
<212> TYPE: DNA
<213> ORGANISM: Homo sapiens

<400> SEQUENCE: 96
taggatgggg gtgagaggtg                                              20

<210> SEQ ID NO 97
<211> LENGTH: 19
<212> TYPE: DNA
```

<213> ORGANISM: Homo sapiens

<400> SEQUENCE: 97
gagggcgggt ggaggagga                                               19

<210> SEQ ID NO 98
<211> LENGTH: 23
<212> TYPE: DNA
<213> ORGANISM: Homo sapiens

<400> SEQUENCE: 98
ttagggagta gaagggtggg gag                                          23

<210> SEQ ID NO 99
<211> LENGTH: 23
<212> TYPE: DNA
<213> ORGANISM: Homo sapiens

<400> SEQUENCE: 99
tgaggatatg gcagggaagg gga                                          23

<210> SEQ ID NO 100
<211> LENGTH: 24
<212> TYPE: DNA
<213> ORGANISM: Homo sapiens

<400> SEQUENCE: 100
cccggacagg cgttcgtgcg acgt                                         24

<210> SEQ ID NO 101
<211> LENGTH: 20
<212> TYPE: DNA
<213> ORGANISM: Homo sapiens

<400> SEQUENCE: 101
gtgggttggg gcgggctctg                                              20

<210> SEQ ID NO 102
<211> LENGTH: 20
<212> TYPE: DNA
<213> ORGANISM: Homo sapiens

<400> SEQUENCE: 102
tcagggagtc aggggagggc                                              20

<210> SEQ ID NO 103
<211> LENGTH: 18
<212> TYPE: DNA
<213> ORGANISM: Homo sapiens

<400> SEQUENCE: 103
gggctcacat caccccat                                                18

<210> SEQ ID NO 104
<211> LENGTH: 17
<212> TYPE: DNA
<213> ORGANISM: Homo sapiens

<400> SEQUENCE: 104
ttggaggcgt gggtttt                                                 17

<210> SEQ ID NO 105
<211> LENGTH: 17

```
<212> TYPE: DNA
<213> ORGANISM: Homo sapiens

<400> SEQUENCE: 105
ggtgggggct gttgttt                                                  17

<210> SEQ ID NO 106
<211> LENGTH: 20
<212> TYPE: DNA
<213> ORGANISM: Homo sapiens

<400> SEQUENCE: 106
ggctccttgg tctagggta                                                20

<210> SEQ ID NO 107
<211> LENGTH: 20
<212> TYPE: DNA
<213> ORGANISM: Homo sapiens

<400> SEQUENCE: 107
ggatccgagt cacggcacca                                               20

<210> SEQ ID NO 108
<211> LENGTH: 17
<212> TYPE: DNA
<213> ORGANISM: Homo sapiens

<400> SEQUENCE: 108
ggatggagga ggggtct                                                  17

<210> SEQ ID NO 109
<211> LENGTH: 22
<212> TYPE: DNA
<213> ORGANISM: Homo sapiens

<400> SEQUENCE: 109
gagcttggat gagctgggct ga                                            22

<210> SEQ ID NO 110
<211> LENGTH: 22
<212> TYPE: DNA
<213> ORGANISM: Homo sapiens

<400> SEQUENCE: 110
gctgaactgg gctgagctgg gc                                            22

<210> SEQ ID NO 111
<211> LENGTH: 22
<212> TYPE: DNA
<213> ORGANISM: Homo sapiens

<400> SEQUENCE: 111
ttgaggagac atggtggggg cc                                            22

<210> SEQ ID NO 112
<211> LENGTH: 22
<212> TYPE: DNA
<213> ORGANISM: Homo sapiens

<400> SEQUENCE: 112
gagcaggcga ggctgggctg aa                                            22

<210> SEQ ID NO 113
```

```
<211> LENGTH: 25
<212> TYPE: DNA
<213> ORGANISM: Homo sapiens

<400> SEQUENCE: 113
aagggaggag gagcggaggg gccct                                              25

<210> SEQ ID NO 114
<211> LENGTH: 24
<212> TYPE: DNA
<213> ORGANISM: Homo sapiens

<400> SEQUENCE: 114
agggctggac tcagcggcgg agct                                               24

<210> SEQ ID NO 115
<211> LENGTH: 22
<212> TYPE: DNA
<213> ORGANISM: Homo sapiens

<400> SEQUENCE: 115
ttcagatccc agcggtgcct ct                                                 22

<210> SEQ ID NO 116
<211> LENGTH: 20
<212> TYPE: DNA
<213> ORGANISM: Homo sapiens

<400> SEQUENCE: 116
aactctagcc tgagcaacag                                                    20

<210> SEQ ID NO 117
<211> LENGTH: 22
<212> TYPE: DNA
<213> ORGANISM: Homo sapiens

<400> SEQUENCE: 117
tgggggagtg cagtgattgt gg                                                 22

<210> SEQ ID NO 118
<211> LENGTH: 20
<212> TYPE: DNA
<213> ORGANISM: Homo sapiens

<400> SEQUENCE: 118
gcggagagag aatggggagc                                                    20

<210> SEQ ID NO 119
<211> LENGTH: 21
<212> TYPE: DNA
<213> ORGANISM: Homo sapiens

<400> SEQUENCE: 119
agcatgacag aggagaggtg g                                                  21

<210> SEQ ID NO 120
<211> LENGTH: 20
<212> TYPE: DNA
<213> ORGANISM: Homo sapiens

<400> SEQUENCE: 120
ggaggttggg aagggcagag                                                    20
```

```
<210> SEQ ID NO 121
<211> LENGTH: 19
<212> TYPE: DNA
<213> ORGANISM: Homo sapiens

<400> SEQUENCE: 121
tgagggagtg ggtgggagg                                            19

<210> SEQ ID NO 122
<211> LENGTH: 22
<212> TYPE: DNA
<213> ORGANISM: Homo sapiens

<400> SEQUENCE: 122
aagtgattgg aggtgggtgg gg                                        22

<210> SEQ ID NO 123
<211> LENGTH: 17
<212> TYPE: DNA
<213> ORGANISM: Homo sapiens

<400> SEQUENCE: 123
cctgtctgag cgacgct                                              17

<210> SEQ ID NO 124
<211> LENGTH: 17
<212> TYPE: DNA
<213> ORGANISM: Homo sapiens

<400> SEQUENCE: 124
gagactctcc tgtgcag                                              17

<210> SEQ ID NO 125
<211> LENGTH: 22
<212> TYPE: DNA
<213> ORGANISM: Homo sapiens

<400> SEQUENCE: 125
tgcagattgt gggtgggagg ac                                        22

<210> SEQ ID NO 126
<211> LENGTH: 22
<212> TYPE: DNA
<213> ORGANISM: Homo sapiens

<400> SEQUENCE: 126
tgcagctggt ggagtctggg gg                                        22

<210> SEQ ID NO 127
<211> LENGTH: 22
<212> TYPE: DNA
<213> ORGANISM: Homo sapiens

<400> SEQUENCE: 127
tggagaagac tggagagggt at                                        22

<210> SEQ ID NO 128
<211> LENGTH: 25
<212> TYPE: DNA
<213> ORGANISM: Homo sapiens

<400> SEQUENCE: 128
actaccccag gatgccagca tagtt                                     25
```

```
<210> SEQ ID NO 129
<211> LENGTH: 22
<212> TYPE: DNA
<213> ORGANISM: Homo sapiens

<400> SEQUENCE: 129
agctggtttg atggggagcc at                                              22

<210> SEQ ID NO 130
<211> LENGTH: 22
<212> TYPE: DNA
<213> ORGANISM: Homo sapiens

<400> SEQUENCE: 130
cactgattat cgaggcgatt ct                                              22

<210> SEQ ID NO 131
<211> LENGTH: 22
<212> TYPE: DNA
<213> ORGANISM: Homo sapiens

<400> SEQUENCE: 131
cgcctgtgaa tagtcactgc ac                                              22

<210> SEQ ID NO 132
<211> LENGTH: 22
<212> TYPE: DNA
<213> ORGANISM: Homo sapiens

<400> SEQUENCE: 132
gacgtgaggg ggtgctacat ac                                              22

<210> SEQ ID NO 133
<211> LENGTH: 23
<212> TYPE: DNA
<213> ORGANISM: Homo sapiens

<400> SEQUENCE: 133
ggctggtccg aaggtagtga gtt                                             23

<210> SEQ ID NO 134
<211> LENGTH: 25
<212> TYPE: DNA
<213> ORGANISM: Homo sapiens

<400> SEQUENCE: 134
ggctggtccg agtgcagtgg tgttt                                           25

<210> SEQ ID NO 135
<211> LENGTH: 25
<212> TYPE: DNA
<213> ORGANISM: Homo sapiens

<400> SEQUENCE: 135
tgtccaaagt aaacgccctg acgca                                           25

<210> SEQ ID NO 136
<211> LENGTH: 18
<212> TYPE: DNA
<213> ORGANISM: Homo sapiens

<400> SEQUENCE: 136
ttcccggcca atgcatta                                                   18
```

```
<210> SEQ ID NO 137
<211> LENGTH: 22
<212> TYPE: DNA
<213> ORGANISM: Homo sapiens

<400> SEQUENCE: 137
tttggagggg ccgtgacaga tg                                              22

<210> SEQ ID NO 138
<211> LENGTH: 22
<212> TYPE: DNA
<213> ORGANISM: Homo sapiens

<400> SEQUENCE: 138
ctcccactgc ttcacttgac ta                                              22

<210> SEQ ID NO 139
<211> LENGTH: 19
<212> TYPE: RNA
<213> ORGANISM: Homo sapiens
<220> FEATURE:
<221> NAME/KEY: misc_feature
<222> LOCATION: (1)..(1)
<223> OTHER INFORMATION: n is a, c, g, or u

<400> SEQUENCE: 139
ngggccgagg gagcgagag                                                  19

<210> SEQ ID NO 140
<211> LENGTH: 19
<212> TYPE: RNA
<213> ORGANISM: Homo sapiens

<400> SEQUENCE: 140
agugcuuggc ugaggagcu                                                  19

<210> SEQ ID NO 141
<211> LENGTH: 22
<212> TYPE: DNA
<213> ORGANISM: Homo sapiens

<400> SEQUENCE: 141
tgaggtagta ggttgtatag tt                                              22

<210> SEQ ID NO 142
<211> LENGTH: 22
<212> TYPE: DNA
<213> ORGANISM: Homo sapiens

<400> SEQUENCE: 142
tgaggtagta ggttgtgtgg tt                                              22

<210> SEQ ID NO 143
<211> LENGTH: 22
<212> TYPE: DNA
<213> ORGANISM: Homo sapiens

<400> SEQUENCE: 143
tgaggtagta ggttgtatgg tt                                              22

<210> SEQ ID NO 144
<211> LENGTH: 22
<212> TYPE: DNA
```

```
<213> ORGANISM: Homo sapiens

<400> SEQUENCE: 144
agaggtagta ggttgcatag tt                                              22

<210> SEQ ID NO 145
<211> LENGTH: 22
<212> TYPE: DNA
<213> ORGANISM: Homo sapiens

<400> SEQUENCE: 145
tgaggtagta gattgtatag tt                                              22

<210> SEQ ID NO 146
<211> LENGTH: 22
<212> TYPE: DNA
<213> ORGANISM: Homo sapiens

<400> SEQUENCE: 146
tgaggtagta gtttgtacag tt                                              22

<210> SEQ ID NO 147
<211> LENGTH: 22
<212> TYPE: DNA
<213> ORGANISM: Homo sapiens

<400> SEQUENCE: 147
tgaggtagta gtttgtgctg tt                                              22

<210> SEQ ID NO 148
<211> LENGTH: 23
<212> TYPE: DNA
<213> ORGANISM: Homo sapiens

<400> SEQUENCE: 148
agcttcttta cagtgctgcc ttg                                             23

<210> SEQ ID NO 149
<211> LENGTH: 23
<212> TYPE: DNA
<213> ORGANISM: Homo sapiens

<400> SEQUENCE: 149
agcagcattg tacagggcta tga                                             23

<210> SEQ ID NO 150
<211> LENGTH: 24
<212> TYPE: DNA
<213> ORGANISM: Homo sapiens

<400> SEQUENCE: 150
aaaagtgctt acagtgcagg tagc                                            24

<210> SEQ ID NO 151
<211> LENGTH: 21
<212> TYPE: DNA
<213> ORGANISM: Homo sapiens

<400> SEQUENCE: 151
taaagtgctg acagtgcaga t                                               21

<210> SEQ ID NO 152
<211> LENGTH: 23
```

```
<212> TYPE: DNA
<213> ORGANISM: Homo sapiens

<400> SEQUENCE: 152
agcagcattg tacagggcta tca                                          23

<210> SEQ ID NO 153
<211> LENGTH: 24
<212> TYPE: DNA
<213> ORGANISM: Homo sapiens

<400> SEQUENCE: 153
tccctgagac cctttaacct gtga                                         24

<210> SEQ ID NO 154
<211> LENGTH: 20
<212> TYPE: DNA
<213> ORGANISM: Homo sapiens

<400> SEQUENCE: 154
tacagtatag atgatgtact                                              20

<210> SEQ ID NO 155
<211> LENGTH: 23
<212> TYPE: DNA
<213> ORGANISM: Homo sapiens

<400> SEQUENCE: 155
tctggctccg tgtcttcact ccc                                          23

<210> SEQ ID NO 156
<211> LENGTH: 22
<212> TYPE: DNA
<213> ORGANISM: Homo sapiens

<400> SEQUENCE: 156
tcgaggagct cacagtctag ta                                           22

<210> SEQ ID NO 157
<211> LENGTH: 22
<212> TYPE: DNA
<213> ORGANISM: Homo sapiens

<400> SEQUENCE: 157
tagcagcaca tcatggttta ca                                           22

<210> SEQ ID NO 158
<211> LENGTH: 22
<212> TYPE: DNA
<213> ORGANISM: Homo sapiens

<400> SEQUENCE: 158
ccagtattaa ctgtgctgct ga                                           22

<210> SEQ ID NO 159
<211> LENGTH: 22
<212> TYPE: DNA
<213> ORGANISM: Homo sapiens

<400> SEQUENCE: 159
tagcagcacg taaatattgg cg                                           22

<210> SEQ ID NO 160
```

```
<211> LENGTH: 22
<212> TYPE: DNA
<213> ORGANISM: Homo sapiens

<400> SEQUENCE: 160
actgcagtga aggcacttgt ag                                           22

<210> SEQ ID NO 161
<211> LENGTH: 24
<212> TYPE: DNA
<213> ORGANISM: Homo sapiens

<400> SEQUENCE: 161
caaagtgctt acagtgcagg tagt                                         24

<210> SEQ ID NO 162
<211> LENGTH: 22
<212> TYPE: DNA
<213> ORGANISM: Homo sapiens

<400> SEQUENCE: 162
tggagagaaa ggcagttcct ga                                           22

<210> SEQ ID NO 163
<211> LENGTH: 23
<212> TYPE: DNA
<213> ORGANISM: Homo sapiens

<400> SEQUENCE: 163
caacggaatc ccaaaagcag ctg                                          23

<210> SEQ ID NO 164
<211> LENGTH: 22
<212> TYPE: DNA
<213> ORGANISM: Homo sapiens

<400> SEQUENCE: 164
ctgccaattc cataggtcac ag                                           22

<210> SEQ ID NO 165
<211> LENGTH: 23
<212> TYPE: DNA
<213> ORGANISM: Homo sapiens

<400> SEQUENCE: 165
tgtgcaaatc catgcaaaac tga                                          23

<210> SEQ ID NO 166
<211> LENGTH: 23
<212> TYPE: DNA
<213> ORGANISM: Homo sapiens

<400> SEQUENCE: 166
taaagtgctt atagtgcagg tag                                          23

<210> SEQ ID NO 167
<211> LENGTH: 22
<212> TYPE: DNA
<213> ORGANISM: Homo sapiens

<400> SEQUENCE: 167
cattgcactt gtctcggtct ga                                           22
```

-continued

```
<210> SEQ ID NO 168
<211> LENGTH: 22
<212> TYPE: DNA
<213> ORGANISM: Homo sapiens

<400> SEQUENCE: 168
ttcaagtaat ccaggatagg ct                                              22

<210> SEQ ID NO 169
<211> LENGTH: 21
<212> TYPE: DNA
<213> ORGANISM: Homo sapiens

<400> SEQUENCE: 169
ttcaagtaat tcaggatagg t                                               21

<210> SEQ ID NO 170
<211> LENGTH: 22
<212> TYPE: DNA
<213> ORGANISM: Homo sapiens

<400> SEQUENCE: 170
tgtaaacatc ctacactcag ct                                              22

<210> SEQ ID NO 171
<211> LENGTH: 23
<212> TYPE: DNA
<213> ORGANISM: Homo sapiens

<400> SEQUENCE: 171
tgtaaacatc ctacactctc agc                                             23

<210> SEQ ID NO 172
<211> LENGTH: 22
<212> TYPE: DNA
<213> ORGANISM: Homo sapiens

<400> SEQUENCE: 172
tgtaaacatc cccgactgga ag                                              22

<210> SEQ ID NO 173
<211> LENGTH: 23
<212> TYPE: DNA
<213> ORGANISM: Homo sapiens

<400> SEQUENCE: 173
aaaagctggg ttgagagggc gaa                                             23

<210> SEQ ID NO 174
<211> LENGTH: 21
<212> TYPE: DNA
<213> ORGANISM: Homo sapiens

<400> SEQUENCE: 174
agccgcgggg atcgccgagg g                                               21

<210> SEQ ID NO 175
<211> LENGTH: 21
<212> TYPE: DNA
<213> ORGANISM: Homo sapiens

<400> SEQUENCE: 175
atcatagagg aaaatccacg t                                               21
```

```
<210> SEQ ID NO 176
<211> LENGTH: 23
<212> TYPE: DNA
<213> ORGANISM: Homo sapiens

<400> SEQUENCE: 176
aatgacacga tcactcccgt tga                                            23

<210> SEQ ID NO 177
<211> LENGTH: 17
<212> TYPE: DNA
<213> ORGANISM: Homo sapiens

<400> SEQUENCE: 177
tggagagaaa ggcagta                                                   17

<210> SEQ ID NO 178
<211> LENGTH: 20
<212> TYPE: DNA
<213> ORGANISM: Homo sapiens

<400> SEQUENCE: 178
ccctgagacc ctaaccttaa                                                20

<210> SEQ ID NO 179
<211> LENGTH: 22
<212> TYPE: DNA
<213> ORGANISM: Homo sapiens

<400> SEQUENCE: 179
tcaggctcag tcccctcccg at                                             22

<210> SEQ ID NO 180
<211> LENGTH: 22
<212> TYPE: DNA
<213> ORGANISM: Homo sapiens

<400> SEQUENCE: 180
tagtaccagt accttgtgtt ca                                             22

<210> SEQ ID NO 181
<211> LENGTH: 22
<212> TYPE: DNA
<213> ORGANISM: Homo sapiens

<400> SEQUENCE: 181
tattgcactt gtcccggcct gt                                             22

<210> SEQ ID NO 182
<211> LENGTH: 23
<212> TYPE: DNA
<213> ORGANISM: Homo sapiens

<400> SEQUENCE: 182
caaagtgctg ttcgtgcagg tag                                            23

<210> SEQ ID NO 183
<211> LENGTH: 98
<212> TYPE: DNA
<213> ORGANISM: Homo sapiens

<400> SEQUENCE: 183
gtggaccggc tggccccatc tggaagacta gtgattttgt tgttgtctta ctgcgctcaa    60
```

```
caacaaatcc cagtctacct aatggtgcca gccatcgc                              98
```

<210> SEQ ID NO 184
<211> LENGTH: 85
<212> TYPE: DNA
<213> ORGANISM: Homo sapiens

<400> SEQUENCE: 184

```
gtcttctgta tataccctgt agatccgaat ttgtgtaagg aattttgtgg tcacaaattc      60
gtatctaggg gaatatgtag ttgac                                           85
```

<210> SEQ ID NO 185
<211> LENGTH: 69
<212> TYPE: DNA
<213> ORGANISM: Homo sapiens

<400> SEQUENCE: 185

```
gttctaaggt gcatctagtg cagatagtga agtagattag catctactgc cctaagtgct      60
ccttctggc                                                             69
```

<210> SEQ ID NO 186
<211> LENGTH: 90
<212> TYPE: DNA
<213> ORGANISM: Homo sapiens

<400> SEQUENCE: 186

```
gtaccacctt gtcgggtagc ttatcagact gatgttgact gttgaatctc atggcaacac      60
cagtcgatgg gctgtctgac attttggtat                                      90
```

<210> SEQ ID NO 187
<211> LENGTH: 73
<212> TYPE: DNA
<213> ORGANISM: Homo sapiens

<400> SEQUENCE: 187

```
ggccggctgg ggttcctggg gatgggattt gcttcctgtc acaaatcaca ttgccaggga      60
tttccaaccg acc                                                        73
```

<210> SEQ ID NO 188
<211> LENGTH: 90
<212> TYPE: DNA
<213> ORGANISM: Homo sapiens

<400> SEQUENCE: 188

```
ggcagtcttt gctactgtaa acatccttga ctggaagctg taaggtgttc agaggagctt      60
tcagtcggat gtttacagcg gcaggctgcc                                      90
```

<210> SEQ ID NO 189
<211> LENGTH: 71
<212> TYPE: DNA
<213> ORGANISM: Homo sapiens

<400> SEQUENCE: 189

```
ggagaggagg caagatgctg gcatagctgt tgaactggga acctgctatg ccaacatatt      60
gccatctttc c                                                          71
```

<210> SEQ ID NO 190
<211> LENGTH: 90
<212> TYPE: DNA

<213> ORGANISM: Homo sapiens

<400> SEQUENCE: 190

```
gtgagtgttt ctttggcagt gtcttagctg gttgttgtga gcaatagtaa ggaagcaatc    60
agcaagtata ctgccctaga agtgctgcac                                     90
```

<210> SEQ ID NO 191
<211> LENGTH: 130
<212> TYPE: DNA
<213> ORGANISM: Homo sapiens

<400> SEQUENCE: 191

```
ggggagcggg atcccgggcc ccgggcgggc gggagggacg ggacgcggtg cagtgttgtt    60
ttttcccccg ccaatattgc actcgtcccg gcctccggcc ccccggcccc ccggcctcc   120
ccgctacccc                                                         130
```

<210> SEQ ID NO 192
<211> LENGTH: 90
<212> TYPE: DNA
<213> ORGANISM: Homo sapiens

<400> SEQUENCE: 192

```
tctgcttggc cgattttggc actagcacat ttttgcttgt gtctctccgc tctgagcaat    60
catgtgcagt gccaatatgg gaaaagcagg                                     90
```

<210> SEQ ID NO 193
<211> LENGTH: 82
<212> TYPE: DNA
<213> ORGANISM: Homo sapiens

<400> SEQUENCE: 193

```
gcctgttgcc acaaaccccgt agatccgaac ttgtggtatt agtccgcaca agcttgtatc    60
tataggtatg tgtctgttag gc                                             82
```

<210> SEQ ID NO 194
<211> LENGTH: 83
<212> TYPE: DNA
<213> ORGANISM: Homo sapiens

<400> SEQUENCE: 194

```
gctggcgacg ggacattatt acttttggta cgcgctgtga cacttcaaac tcgtaccgtg    60
agtaataatg cgccgtccac ggc                                            83
```

<210> SEQ ID NO 195
<211> LENGTH: 88
<212> TYPE: DNA
<213> ORGANISM: Homo sapiens

<400> SEQUENCE: 195

```
tgcgctcctc tcagtccctg agaccctaac ttgtgatgtt taccgtttaa atccacgggt    60
taggctcttg ggagctgcga gtcgtgct                                       88
```

<210> SEQ ID NO 196
<211> LENGTH: 89
<212> TYPE: DNA
<213> ORGANISM: Homo sapiens

<400> SEQUENCE: 196

```
accagacttt tcctagtccc tgagacccta acttgtgagg tattttagta acatcacaag    60
```

```
tcaggctctt gggacctagg cggagggga                                    89

<210> SEQ ID NO 197
<211> LENGTH: 87
<212> TYPE: DNA
<213> ORGANISM: Homo sapiens

<400> SEQUENCE: 197
tggtgtggtg gggcagctgg tgttgtgaat caggccgttg ccaatcagag aacggctact    60
tcacaacacc agggccacac cacacta                                       87

<210> SEQ ID NO 198
<211> LENGTH: 99
<212> TYPE: DNA
<213> ORGANISM: Homo sapiens

<400> SEQUENCE: 198
ccctggcatg gtgtggtggg gcagctggtg ttgtgaatca ggccgttgcc aatcagagaa    60
cggctacttc acaacaccag gccacacca cactacagg                           99

<210> SEQ ID NO 199
<211> LENGTH: 84
<212> TYPE: DNA
<213> ORGANISM: Homo sapiens

<400> SEQUENCE: 199
cgttgctgca gctggtgttg tgaatcaggc cgacgagcag cgcatcctct tacccggcta    60
tttcacgaca ccagggttgc atca                                          84

<210> SEQ ID NO 200
<211> LENGTH: 134
<212> TYPE: DNA
<213> ORGANISM: Homo sapiens

<400> SEQUENCE: 200
gaggaagccg gcggagttct ggtatcgttg ctgcagctgg tgttgtgaat caggccgacg    60
agcagcgcat cctcttaccc ggctatttca cgacaccagg gttgcatcat acccatcctc   120
tccaggcgag cctc                                                    134

<210> SEQ ID NO 201
<211> LENGTH: 118
<212> TYPE: DNA
<213> ORGANISM: Homo sapiens

<400> SEQUENCE: 201
gcgccctgtg tgtgtctctc tctgtgtcct gccagtggtt ttaccctatg gtaggttacg    60
tcatgctgtt ctaccacagg gtagaaccac ggacaggata ccggggcacc ctctgcgt     118

<210> SEQ ID NO 202
<211> LENGTH: 104
<212> TYPE: DNA
<213> ORGANISM: Homo sapiens

<400> SEQUENCE: 202
gtcggccggc cctgggtcca tcttccagta cagtgttgga tggtctaatt gtgaagctcc    60
taacactgtc tggtaaagat ggctcccggg tgggttctct cggc                   104

<210> SEQ ID NO 203
```

```
<211> LENGTH: 85
<212> TYPE: DNA
<213> ORGANISM: Homo sapiens

<400> SEQUENCE: 203
acagtgcagt cacccataaa gtagaaagca ctactaacag cactggaggg tgtagtgttt        60
cctactttat ggatgagtgt actgt                                              85

<210> SEQ ID NO 204
<211> LENGTH: 73
<212> TYPE: DNA
<213> ORGANISM: Homo sapiens

<400> SEQUENCE: 204
cctggcactg agaactgaat tccataggct gtgagctcta gcaatgccct gtggactcag        60
ttctggtgcc cgg                                                           73

<210> SEQ ID NO 205
<211> LENGTH: 80
<212> TYPE: DNA
<213> ORGANISM: Homo sapiens

<400> SEQUENCE: 205
gtatcctcag ctttgagaac tgaattccat gggttgtgtc agtgtcagac ctctgaaatt        60
cagttcttca gctgggatat                                                    80

<210> SEQ ID NO 206
<211> LENGTH: 84
<212> TYPE: DNA
<213> ORGANISM: Homo sapiens

<400> SEQUENCE: 206
ggtcttttga ggcaaagttc tgagacactc cgactctgag tatgatagaa gtcagtgcac        60
tacagaactt tgtctctaga ggct                                               84

<210> SEQ ID NO 207
<211> LENGTH: 82
<212> TYPE: DNA
<213> ORGANISM: Homo sapiens

<400> SEQUENCE: 207
tccccatggc cctgtctccc aaccctTGta ccagtgctgg gctcagaccc tggtacaggc        60
ctgggggaca gggacctggg ga                                                 82

<210> SEQ ID NO 208
<211> LENGTH: 85
<212> TYPE: DNA
<213> ORGANISM: Homo sapiens

<400> SEQUENCE: 208 gtccccccg gcccaggttc tgtgatacac tccgactcgg gctctggagc agtcagtgca        60
tgacagaact tgggcccgga aggac                                              85

<210> SEQ ID NO 209
<211> LENGTH: 87
<212> TYPE: DNA
<213> ORGANISM: Homo sapiens

<400> SEQUENCE: 209 tgtcccccc ggcccaggtt ctgtgataca ctccgactcg ggctctggag cagtcagtgc        60
```
atgacagaac ttgggcccgg aaggacc     87

<210> SEQ ID NO 210
<211> LENGTH: 89
<212> TYPE: DNA
<213> ORGANISM: Homo sapiens

<400> SEQUENCE: 210
taggctgtat gctgttaatg ctaatcgtga tagggttttt tgcctccaac tgactcctac     60
atattagcat taacagtgta tgatgcctg     89

<210> SEQ ID NO 211
<211> LENGTH: 87
<212> TYPE: DNA
<213> ORGANISM: Homo sapiens

<400> SEQUENCE: 211
ggttgcttca gtgaacattc aacgctgtcg gtgagtttgg aattaaaatc aaaaccatcg     60
accgttgatt gtaccctatg gctaacc     87

<210> SEQ ID NO 212
<211> LENGTH: 79
<212> TYPE: DNA
<213> ORGANISM: Homo sapiens

<400> SEQUENCE: 212
ggtcacaatc aacattcatt gctgtcggtg ggttgaactg tgtggacaag ctcactgaac     60
aatgaatgca actgtggcc     79

<210> SEQ ID NO 213
<211> LENGTH: 110
<212> TYPE: DNA
<213> ORGANISM: Homo sapiens

<400> SEQUENCE: 213
cggaaaattt gccaagggtt tgggggaaca ttcaacctgt cggtgagttt gggcagctca     60
ggcaaaccat cgaccgttga gtggaccctg aggcctggaa ttgccatcct     110

<210> SEQ ID NO 214
<211> LENGTH: 87
<212> TYPE: DNA
<213> ORGANISM: Homo sapiens

<400> SEQUENCE: 214 cctcccccg tttttggcaa tggtagaact cacactggtg aggtaacagg atccggtggt     60
tctagacttg ccaactatgg ggcgagg     87

<210> SEQ ID NO 215
<211> LENGTH: 66
<212> TYPE: DNA
<213> ORGANISM: Homo sapiens

<400> SEQUENCE: 215
cctcgggcta caacacagga cccgggcgct gctctgaccc ctcgtgtctt gtgttgcagc     60
cggagg     66

<210> SEQ ID NO 216
<211> LENGTH: 79
<212> TYPE: DNA

<213> ORGANISM: Homo sapiens

<400> SEQUENCE: 216
gggagctgag ggctgggtct ttgcgggcga gatgagggtg tcggatcaac tggcctacaa    60
agtcccagtt ctcggcccc                                                 79

<210> SEQ ID NO 217
<211> LENGTH: 71
<212> TYPE: DNA
<213> ORGANISM: Homo sapiens

<400> SEQUENCE: 217
cctggctcta gcagcacaga aatattggca cagggaagcg agtctgccaa tattggctgt    60
gctgctccag g                                                         71

<210> SEQ ID NO 218
<211> LENGTH: 92
<212> TYPE: DNA
<213> ORGANISM: Homo sapiens

<400> SEQUENCE: 218
tgtgctctgg gggctgtgcc gggtagagag ggcagtggga ggtaagagct cttcacccttt   60 caccaccttc tccacccagc atggccggca ca                                  92

<210> SEQ ID NO 219
<211> LENGTH: 83
<212> TYPE: DNA
<213> ORGANISM: Homo sapiens

<400> SEQUENCE: 219
ggccccgcca acccagtgtt cagactacct gttcaggagg ctctcaatgt gtacagtagt    60
ctgcacattg gttaggctgg gct                                            83

<210> SEQ ID NO 220
<211> LENGTH: 65
<212> TYPE: DNA
<213> ORGANISM: Homo sapiens

<400> SEQUENCE: 220
gagcatctta ccggacagtg ctggatttcc cagcttgact ctaacactgt ctggtaacga    60
tgttc                                                                65

<210> SEQ ID NO 221
<211> LENGTH: 89
<212> TYPE: DNA
<213> ORGANISM: Homo sapiens

<400> SEQUENCE: 221
gctcgggcag ccgtggccat cttactgggc agcattggat ggagtcaggt ctctaatact    60
gcctggtaat gatgacggcg gagccctgc                                      89

<210> SEQ ID NO 222
<211> LENGTH: 86
<212> TYPE: DNA
<213> ORGANISM: Homo sapiens

<400> SEQUENCE: 222 gggcggggc cctcgtctta cccagcagtg tttgggtgcg gttgggagtc tctaatactg    60
ccgggtaatg atggaggccc ctgtcc                                         86

<210> SEQ ID NO 223
<211> LENGTH: 68
<212> TYPE: DNA
<213> ORGANISM: Homo sapiens

<400> SEQUENCE: 223
ccctcgtctt acccagcagt gtttgggtgc ggttgggagt ctctaatact gccgggtaat    60
gatggagg                                                             68

<210> SEQ ID NO 224
<211> LENGTH: 83
<212> TYPE: DNA
<213> ORGANISM: Homo sapiens

<400> SEQUENCE: 224
ggccccgcca acccagtgtt cagactacct gttcaggagg ctctcaatgt gtacagtagt    60
ctgcacattg gttaggctgg gct                                            83

<210> SEQ ID NO 225
<211> LENGTH: 69
<212> TYPE: DNA
<213> ORGANISM: Homo sapiens

<400> SEQUENCE: 225
gtctacccag tgtttagact atctgttcag gactcccaaa ttgtacagta gtctgcacat    60
tggttaggc                                                            69

<210> SEQ ID NO 226
<211> LENGTH: 87
<212> TYPE: DNA
<213> ORGANISM: Homo sapiens

<400> SEQUENCE: 226
tccatgtgct tctcttgtcc ttcattccac cggagtctgt ctcataccca accagatttc    60
agtggagtga agttcaggag gcatgga                                        87

<210> SEQ ID NO 227
<211> LENGTH: 84
<212> TYPE: DNA
<213> ORGANISM: Homo sapiens

<400> SEQUENCE: 227
ccaggcgcag ggcagcccct gcccaccgca cactgcgctg ccccagaccc actgtgcgtg    60
tgacagcggc tgatctgtgc ctgg                                           84

<210> SEQ ID NO 228
<211> LENGTH: 104
<212> TYPE: DNA
<213> ORGANISM: Homo sapiens

<400> SEQUENCE: 228
ggctggacag agttgtcatg tgtctgcctg tctacacttg ctgtgcagaa catccgctca    60
cctgtacagc aggcacagac aggcagtcac atgacaaccc agcc                    104

<210> SEQ ID NO 229
<211> LENGTH: 107
<212> TYPE: DNA
<213> ORGANISM: Homo sapiens

<400> SEQUENCE: 229
gaacatccag gtctggggca tgaacctggc atacaatgta gatttctgtg ttcgttaggc    60
aacagctaca ttgtctgctg ggtttcaggc tacctggaaa catgttc                 107

<210> SEQ ID NO 230
<211> LENGTH: 116
<212> TYPE: DNA
<213> ORGANISM: Homo sapiens

<400> SEQUENCE: 230
cagctgctgg aaggtgtagg taccctcaat ggctcagtag ccagtgtaga tcctgtcttt    60
cgtaatcagc agctacatct ggctactggg tctctgatgg catcttctag cttctg       116

<210> SEQ ID NO 231
<211> LENGTH: 110
<212> TYPE: DNA
<213> ORGANISM: Homo sapiens

<400> SEQUENCE: 231
gctgctggaa ggtgtaggta ccctcaatgg ctcagtagcc agtgtagatc ctgtctttcg    60
taatcagcag ctacatctgg ctactgggtc tctgatggca tcttctagct              110

<210> SEQ ID NO 232
<211> LENGTH: 132
<212> TYPE: DNA
<213> ORGANISM: Homo sapiens

<400> SEQUENCE: 232
gctcttggcc tggcctcctg cagtgccacg ctccgtgtat ttgacaagct gagttggaca    60
ctccatgtgg tagagtgtca gtttgtcaaa taccccaagt gcggcacatg cttaccagct   120
ctaggccagg gc                                                       132

<210> SEQ ID NO 233
<211> LENGTH: 83
<212> TYPE: DNA
<213> ORGANISM: Homo sapiens

<400> SEQUENCE: 233
ggggctttca agtcactagt ggttccgttt agtagatgat tgtgcattgt ttcaaaatgg    60
tgccctagtg actacaaagc ccc                                           83

<210> SEQ ID NO 234
<211> LENGTH: 105
<212> TYPE: DNA
<213> ORGANISM: Homo sapiens

<400> SEQUENCE: 234
gtgaaactgg gctcaaggtg aggggtgcta tctgtgattg agggacatgg ttaatggaat    60
tgtctcacac agaaatcgca cccgtcacct tggcctactt atcac                   105

<210> SEQ ID NO 235
<211> LENGTH: 99
<212> TYPE: DNA
<213> ORGANISM: Homo sapiens

<400> SEQUENCE: 235
gaaactgggc tcaaggtgag gggtgctatc tgtgattgag gacatggtt aatggaattg    60 tctcacacag aaatcgcacc cgtcaccttg gcctactta                          99

```
<210> SEQ ID NO 236
<211> LENGTH: 98
<212> TYPE: DNA
<213> ORGANISM: Homo sapiens

<400> SEQUENCE: 236
acccaaaccc taggtctgct gactcctagt ccagggctcg tgatggctgg tgggccctga    60
acgaggggtc tggaggcctg ggtttgaata tcgacagc                            98

<210> SEQ ID NO 237
<211> LENGTH: 95
<212> TYPE: DNA
<213> ORGANISM: Homo sapiens

<400> SEQUENCE: 237
ggtctctgtg ttgggcgtct gtctgcccgc atgcctgcct ctctgttgct ctgaaggagg    60
caggggctgg gcctgcagct gcctgggcag agcgg                               95

<210> SEQ ID NO 238
<211> LENGTH: 79
<212> TYPE: DNA
<213> ORGANISM: Homo sapiens

<400> SEQUENCE: 238
cgctcccgcc ccgcgacgag cccctcgcac aaaccggacc tgagcgtttt gttcgttcgg    60
ctcgcgtgag cagggggcg                                                 79

<210> SEQ ID NO 239
<211> LENGTH: 64
<212> TYPE: DNA
<213> ORGANISM: Homo sapiens

<400> SEQUENCE: 239
ccccgcgacg agcccctcgc acaaaccgga cctgagcgtt ttgttcgttc ggctcgcgtg    60
aggc                                                                 64

<210> SEQ ID NO 240
<211> LENGTH: 98
<212> TYPE: DNA
<213> ORGANISM: Homo sapiens

<400> SEQUENCE: 240 cgagggata cagcagcaat tcatgttttg aagtgttcta aatggttcaa aacgtgaggc     60
gctgctatac ccctcgtgg ggaaggtaga aggtgggg                             98

<210> SEQ ID NO 241
<211> LENGTH: 69
<212> TYPE: DNA
<213> ORGANISM: Homo sapiens

<400> SEQUENCE: 241
gatgggcgtc ttaccagaca tggttagacc tggccctctg tctaatactg tctggtaaaa    60
ccgtccatc                                                            69

<210> SEQ ID NO 242
<211> LENGTH: 82
<212> TYPE: DNA
<213> ORGANISM: Homo sapiens
```

```
<400> SEQUENCE: 242
ggcgtgaggg tatgtgcctt tggactacat cgtggaagcc agcaccatgc agtccatggg     60
catatacact tgcctcaagg cc                                              82

<210> SEQ ID NO 243
<211> LENGTH: 200
<212> TYPE: DNA
<213> ORGANISM: Homo sapiens

<400> SEQUENCE: 243
accccaaggt ggagccccca gcgaccttcc ccttccagct gagcattgct gtgggggaga     60
gggggaagac gggaggaaag aagggagtgg ttccatcacg cctcctcact cctctcctcc    120
cgtcttctcc tctcctgccc ttgtctccct gtctcagcag ctccaggggt ggtgtgggcc    180
cctccagcct cctaggtggt                                                200

<210> SEQ ID NO 244
<211> LENGTH: 100
<212> TYPE: DNA
<213> ORGANISM: Homo sapiens

<400> SEQUENCE: 244
gtgctaacct ttggtacttg gagagtggtt atccctgtcc tgttcgtttt gctcatgtcg     60
aatcgtacag ggtcatccac ttttcagta tcaagagcgc                           100

<210> SEQ ID NO 245
<211> LENGTH: 116
<212> TYPE: DNA
<213> ORGANISM: Homo sapiens

<400> SEQUENCE: 245
ctgatctcca tcctccctgg ggcatcctgt actgagctgc ccgaggcccc ttcatgctgc     60
ccagctcggg gcagctcagt acaggatact cggggtggga gtcagcagga ggtgag        116

<210> SEQ ID NO 246
<211> LENGTH: 68
<212> TYPE: DNA
<213> ORGANISM: Homo sapiens

<400> SEQUENCE: 246
gcatcctgta ctgagctgcc ccgaggccct tcatgctgcc cagctcgggg cagctcagta     60
caggatac                                                              68

<210> SEQ ID NO 247
<211> LENGTH: 64
<212> TYPE: DNA
<213> ORGANISM: Homo sapiens

<400> SEQUENCE: 247
tcctgtactg agctgccccg agctgggcag catgaagggc ctcggggcag ctcagtacag     60
gatg                                                                  64

<210> SEQ ID NO 248
<211> LENGTH: 100
<212> TYPE: DNA
<213> ORGANISM: Homo sapiens

<400> SEQUENCE: 248
cggtcctgct cccgccccag cagcacactg tggtttgtac ggcactgtgg ccacgtccaa     60
```

```
accacactgt ggtgttagag cgagggtggg ggaggcaccg                          100
```

<210> SEQ ID NO 249
<211> LENGTH: 129
<212> TYPE: DNA
<213> ORGANISM: Homo sapiens

<400> SEQUENCE: 249

```
gggatgccac attcagccat tcagcgtaca gtgcctttca cagggaggtg tcatttatgt    60
gaactaaaat ataaatttca cctttctgag aagggtaatg tacagcatgc actgcatatg   120
tggtgtccc                                                          129
```

<210> SEQ ID NO 250
<211> LENGTH: 101
<212> TYPE: DNA
<213> ORGANISM: Homo sapiens

<400> SEQUENCE: 250

```
ggatgcacag atctcagaca tctcggggat catcatgtca cgagatacca gtgtgcactt    60
gtgacagatt gataactgaa aggtctggga gccactcatc t                       101
```

<210> SEQ ID NO 251
<211> LENGTH: 105
<212> TYPE: DNA
<213> ORGANISM: Homo sapiens

<400> SEQUENCE: 251

```
tgccagatgt gctctcctgg cccatgaaat caagcgtggg tgagacctgg tgcagaacgg    60
gaaggcgacc catacttggt ttcagaggct gtgagaataa ctgca                  105
```

<210> SEQ ID NO 252
<211> LENGTH: 96
<212> TYPE: DNA
<213> ORGANISM: Homo sapiens

<400> SEQUENCE: 252

```
agatgtgctc tcctggccca tgaaatcaag cgtgggtgag acctggtgca gaacgggaag    60
gcgacccata cttggtttca gaggctgtga gaataa                             96
```

<210> SEQ ID NO 253
<211> LENGTH: 96
<212> TYPE: DNA
<213> ORGANISM: Homo sapiens

<400> SEQUENCE: 253

```
gggacctgcg tgggtgcggg cgtgtgagtg tgtgtgtgtg agtgtgtgtc gctccgggtc    60
cacgctcatg cacacaccca cacgcccaca ctcagg                             96
```

<210> SEQ ID NO 254
<211> LENGTH: 96
<212> TYPE: DNA
<213> ORGANISM: Homo sapiens

<400> SEQUENCE: 254

```
tggtaagggt agagggatga gggggaaagt tctatagtcc tgtaattaga tctcaggact    60
atagaacttt cccctcatc cctctgccct ctacca                              96
```

<210> SEQ ID NO 255

```
<211> LENGTH: 59
<212> TYPE: DNA
<213> ORGANISM: Homo sapiens

<400> SEQUENCE: 255
tctcaggagg cagcgctctc aggacgtcac caccatggcc tgggctctgc tcctcctca      59

<210> SEQ ID NO 256
<211> LENGTH: 98
<212> TYPE: DNA
<213> ORGANISM: Homo sapiens

<400> SEQUENCE: 256
ctcggttgcc gtggttgcgg gccctgcccg cccgccagct cgctgacagc acgactcagg      60
gcggagggaa gtaggtccgt tggtcggtcg ggaacgag                              98

<210> SEQ ID NO 257
<211> LENGTH: 170
<212> TYPE: DNA
<213> ORGANISM: Homo sapiens

<400> SEQUENCE: 257
gttcagtcca gggcagcttc cctgttctgt taattaaact ttgggacatt aaaatgggct      60
aagggagatg attgggtaga aagtattatt ctattcattt gcctcccagc ctacaaaaat     120
gcctgcttgg ggtctaatac ttcaacggtt aaagatgcct ggaagagggc                170

<210> SEQ ID NO 258
<211> LENGTH: 93
<212> TYPE: DNA
<213> ORGANISM: Homo sapiens

<400> SEQUENCE: 258
ggtaactgcc ctcaaggagc ttacaatcta gctgggggta aatgacttgc acatgaacac      60
aactagactg tgagcttcta gagggcaggg acc                                   93

<210> SEQ ID NO 259
<211> LENGTH: 112
<212> TYPE: DNA
<213> ORGANISM: Homo sapiens

<400> SEQUENCE: 259
ttaggcgctg atgaaagtgg agttcagtag acagcccttt tcaagcccta cgagaaactg      60
gggtttctgg aggagaagga aggtgatgaa ggatctgttc tcgtgagcct ga             112

<210> SEQ ID NO 260
<211> LENGTH: 69
<212> TYPE: DNA
<213> ORGANISM: Homo sapiens

<400> SEQUENCE: 260
gtgggtaggg tttgggggag agcgtgggct ggggttcagg gacaccctct caccactgcc      60
ctcccacag                                                              69

<210> SEQ ID NO 261
<211> LENGTH: 82
<212> TYPE: DNA

<400> SEQUENCE: 261
tggtccctcc caatccagcc attcctcaga ccaggtggct cccgagccac cccaggctgt      60
```
aggatggggg tgagaggtgc ta          82

<210> SEQ ID NO 262
<211> LENGTH: 81
<212> TYPE: DNA
<213> ORGANISM: Homo sapiens

<400> SEQUENCE: 262
gctcgactcc tgttcctgct gaactgagcc agtgtgtaaa atgagaactg atatcagctc          60
agtaggcacc ggagggcggg t          81

<210> SEQ ID NO 263
<211> LENGTH: 57
<212> TYPE: DNA
<213> ORGANISM: Homo sapiens

<400> SEQUENCE: 263
cccggtgagg gcgggtggag gaggagggtc cccaccatca gccttcactg ggacggg          57

<210> SEQ ID NO 264
<211> LENGTH: 113
<212> TYPE: DNA
<213> ORGANISM: Homo sapiens

<400> SEQUENCE: 264
aagttaattt tgaagctgac ttttttaggg agtagaaggg tggggagcat gaacaatgtt          60
tctcactccc taccctcca ctccccaaaa aagtcagctt ctcttgttaa ctt          113

<210> SEQ ID NO 265
<211> LENGTH: 82
<212> TYPE: DNA
<213> ORGANISM: Homo sapiens

<400> SEQUENCE: 265
ggccccacgt ggtgaggata tggcagggaa ggggagtttc cctctattcc cttcccccca          60
gtaatcttca tcatgcggtg tc          82

<210> SEQ ID NO 266
<211> LENGTH: 59
<212> TYPE: DNA
<213> ORGANISM: Homo sapiens

<400> SEQUENCE: 266
gcgcgtgcgc ccgagcgcgg cccggtggtc cctcccggac aggcgttcgt gcgacgtgt          59

<210> SEQ ID NO 267
<211> LENGTH: 89
<212> TYPE: DNA
<213> ORGANISM: Homo sapiens

<400> SEQUENCE: 267
gaggaaaaga tcgaggtggg ttggggcggg ctctggggat ttggtctcac agcccggatc          60
ccagcccact taccttggtt actctccctt          89

<210> SEQ ID NO 268
<211> LENGTH: 65
<212> TYPE: DNA
<213> ORGANISM: Homo sapiens

<400> SEQUENCE: 268

```
caaatagctt cagggagtca ggggagggca gaaatagatg gccttcccct gctgggaaga    60
aagtg                                                               65

<210> SEQ ID NO 269
<211> LENGTH: 76
<212> TYPE: DNA
<213> ORGANISM: Homo sapiens

<400> SEQUENCE: 269
ttctgtgagg ggctcacatc accccatcaa agtggggact catggggaga ggggtagtt    60 aggagctttg atagag                                                   76

<210> SEQ ID NO 270
<211> LENGTH: 53
<212> TYPE: DNA
<213> ORGANISM: Homo sapiens

<400> SEQUENCE: 270
ggtgggggtt ggaggcgtgg gttttagaac ctatcccttt ctagccctga gca           53

<210> SEQ ID NO 271
<211> LENGTH: 91
<212> TYPE: DNA
<213> ORGANISM: Homo sapiens

<400> SEQUENCE: 271
gttctagagc atggtttctc atcatttgca ctactgatac ttggggtcag ataattgttt    60
gtggtggggg ctgttgtttg cattgtagga t                                  91

<210> SEQ ID NO 272
<211> LENGTH: 84
<212> TYPE: DNA
<213> ORGANISM: Homo sapiens

<400> SEQUENCE: 272
ggagtgacca aaagacaaga gtgcgagcct tctattatgc ccagacaggg ccaccagagg    60
gctccttggt ctaggggtaa tgcc                                          84

<210> SEQ ID NO 273
<211> LENGTH: 55
<212> TYPE: DNA
<213> ORGANISM: Homo sapiens

<400> SEQUENCE: 273
ccggatccga gtcacggcac caaatttcat gcgtgtccgt gtgaagagac cacca         55

<210> SEQ ID NO 274
<211> LENGTH: 58
<212> TYPE: DNA
<213> ORGANISM: Homo sapiens

<400> SEQUENCE: 274
gtgaatgacc cccttccaga gccaaaatca ccagggatgg aggagggtc ttgggtac      58

<210> SEQ ID NO 275
<211> LENGTH: 139
<212> TYPE: DNA
<213> ORGANISM: Homo sapiens

<400> SEQUENCE: 275
aactgggctg ggctgaactg ggctgggctg agctgagctt ggatgagctg ggctgaactg    60
```

```
ggctgggttg agctgggctg ggctgagttg agccaggctg atctgggctg agccgagctg    120
ggttaagccg agctgggtt                                                  139

<210> SEQ ID NO 276
<211> LENGTH: 194
<212> TYPE: DNA
<213> ORGANISM: Homo sapiens

<400> SEQUENCE: 276
ggctgggctg ggctgggctc tgctgtgctg tgctgaacag ggctgagctg aactgagctg    60
agctgggctg agctgggctc tgctgtgctg tgctgagcag ggctgagctg aactgggctg   120
agctgggctg agctgggctg agttgagcag agctgggttg agcagagctg ggctgggctg   180
ggctgagttg agcc                                                     194

<210> SEQ ID NO 277
<211> LENGTH: 72
<212> TYPE: DNA
<213> ORGANISM: Homo sapiens

<400> SEQUENCE: 277
cggtttctcc ttgaggagac atggtggggg ccggtcaggc agcccatgcc atgtgtcctc    60
atggagaggc cg                                                        72

<210> SEQ ID NO 278
<211> LENGTH: 80
<212> TYPE: DNA
<213> ORGANISM: Homo sapiens

<400> SEQUENCE: 278
ggcaggtgag caggcgaggc tgggctgaac ccgtgggtga ggagtgcagc ccagctgagg    60
cctctgctgt cttatctgtc                                                80

<210> SEQ ID NO 279
<211> LENGTH: 91
<212> TYPE: DNA
<213> ORGANISM: Homo sapiens

<400> SEQUENCE: 279
gtgggcaggg gaggaagaag ggaggaggag cggaggggcc cttgtcttcc cagagcctct    60
cccttcctcc cctcccccct cctctgctca t                                   91

<210> SEQ ID NO 280
<211> LENGTH: 86
<212> TYPE: DNA
<213> ORGANISM: Homo sapiens

<400> SEQUENCE: 280
gggcggctgc gcagagggct ggactcagcg gcggagctgg ctgctggcct cagttctgcc    60
tctgtccagg tccttgtgac ccgccc                                         86

<210> SEQ ID NO 281
<211> LENGTH: 68
<212> TYPE: DNA
<213> ORGANISM: Homo sapiens

<400> SEQUENCE: 281 ctggggggtag gagcgtggct tctggagcta gaccacatgg gttcagatcc cagcggtgcc   60
``` tctaactg 68

<210> SEQ ID NO 282
<211> LENGTH: 97
<212> TYPE: DNA
<213> ORGANISM: Homo sapiens

<400> SEQUENCE: 282
gagctatgat tgtgtagctg aactctagcc tgagcaacag agtgagatgg tcttgttttg    60
ttgcccaggc tggagtccag tgtcaagatc atggctc                             97

<210> SEQ ID NO 283
<211> LENGTH: 93
<212> TYPE: DNA
<213> ORGANISM: Homo sapiens

<400> SEQUENCE: 283
gagctccaaa tctgtgcacc tgggggagtg cagtgattgt ggaatgcaaa gtcccacaat    60
cactgtactc cccaggtgca cagattctct ctc                                 93

<210> SEQ ID NO 284
<211> LENGTH: 82
<212> TYPE: DNA
<213> ORGANISM: Homo sapiens

<400> SEQUENCE: 284
gattggactt tattgtcacg ttctgattgg ttagcctaag acttgttctg atccaatcag    60
aacatgaaaa taacgtccaa tc                                             82

<210> SEQ ID NO 285
<211> LENGTH: 82
<212> TYPE: DNA
<213> ORGANISM: Homo sapiens

<400> SEQUENCE: 285
gattggactt tattgtcacg ttctgattgg ttagcctaag acttgttctg atccaatcag    60
aacatgaaaa taacgtccaa tc                                             82

<210> SEQ ID NO 286
<211> LENGTH: 77
<212> TYPE: DNA
<213> ORGANISM: Homo sapiens

<400> SEQUENCE: 286
ttggctataa ctatcatttc caaggttgtg cttttaggaa atgttggctg tcctgcggag    60
agagaatggg gagccag                                                   77

<210> SEQ ID NO 287
<211> LENGTH: 113
<212> TYPE: DNA
<213> ORGANISM: Homo sapiens

<400> SEQUENCE: 287
agcatgacag aggagaggtg gaggtaggcg agagtaatat aatttctcca ggagaacatc    60 tgagaggga agttgctttc ctgccctggc cctttcaccc tcctgagttt ggg           113

<210> SEQ ID NO 288
<211> LENGTH: 55
<212> TYPE: DNA
<213> ORGANISM: Homo sapiens

<400> SEQUENCE: 288
aggaggttgg gaagggcaga gatgagcata aagtttttgc cttgtttttc ttttt     55

<210> SEQ ID NO 289
<211> LENGTH: 91
<212> TYPE: DNA
<213> ORGANISM: Homo sapiens

<400> SEQUENCE: 289
aagatgaggg agtgggtggg aggtgggaag gctgccccaa atggcctcta acatcccttc     60
cagtctcctc ctcctcctcc tccttcttct t     91

<210> SEQ ID NO 290
<211> LENGTH: 117
<212> TYPE: DNA
<213> ORGANISM: Homo sapiens

<400> SEQUENCE: 290
tatgtacccg gagccaaaag tgattggagg tgggtggggt taatgaatag acaagtgtta     60
aaactaaaag tcacgtctct ctctccttcc tcctcagttt tggcttgatt tttcatg     117

<210> SEQ ID NO 291
<211> LENGTH: 76
<212> TYPE: DNA
<213> ORGANISM: Homo sapiens

<400> SEQUENCE: 291
cttacctaga aattgttgcc tgtctgagcg acgcttcaaa ctcagcttca gcaggtctgc     60
agggacatca ggtagg     76

<210> SEQ ID NO 292
<211> LENGTH: 130
<212> TYPE: DNA
<213> ORGANISM: Homo sapiens

<400> SEQUENCE: 292
gtgtctctgt gtttgcaggt gtccagtgtg aggtgcagct ggtggagtct gggggaggct     60
tggtacagcc tggggatcc ctgagactct cctgtgcagc ctctggattc accttcagta     120
acagtgacat     130

<210> SEQ ID NO 293
<211> LENGTH: 63
<212> TYPE: DNA
<213> ORGANISM: Homo sapiens

<400> SEQUENCE: 293
gtcagcctgc aattagtgaa atggaggcac acatgctggt ttgcagattg tgggtgggag     60
gac     63

<210> SEQ ID NO 294
<211> LENGTH: 130
<212> TYPE: DNA
<213> ORGANISM: Homo sapiens

<400> SEQUENCE: 294
gtgtctctgt gtttgcaggt gtccagtgtg aggtgcagct ggtggagtct gggggaggct     60
tggtacagcc tggggatcc ctgagactct cctgtgcagc ctctggattc accttcagta     120
acagtgacat 130

<210> SEQ ID NO 295
<211> LENGTH: 88
<212> TYPE: DNA
<213> ORGANISM: Homo sapiens

<400> SEQUENCE: 295
ggccttggat ggagaagact ggagagggta tggaagtgct tggacgtagg acatctgcct    60
ctctggtctt tgtccatccc acagggcc    88

<210> SEQ ID NO 296
<211> LENGTH: 71
<212> TYPE: DNA
<213> ORGANISM: Homo sapiens

<400> SEQUENCE: 296
agctggttgg cattctggcc ctggttcatg ccaactcttg tgttgactac cccaggatgc    60
cagcatagtt g    71

<210> SEQ ID NO 297
<211> LENGTH: 103
<212> TYPE: DNA
<213> ORGANISM: Homo sapiens

<400> SEQUENCE: 297
ctgccaaaga gcagcaagat gagctggttt gatggggagc catcccttga tgaggagaac    60 ccttccccact ctcactcagc ctcacccagc tgccctgagg cag    103

<210> SEQ ID NO 298
<211> LENGTH: 82
<212> TYPE: DNA
<213> ORGANISM: Homo sapiens

<400> SEQUENCE: 298
gctcagaagt gatgaattga tcagatagac gaggccgggc ttgtccccgg ccactgatta    60
tcgaggcgat tctgatctgg gc    82

<210> SEQ ID NO 299
<211> LENGTH: 130
<212> TYPE: DNA
<213> ORGANISM: Homo sapiens

<400> SEQUENCE: 299
gctgggtgca gtagcttatg tctgtagtcc cagctacttg ggaggctgag gtgggaggat    60
cacctgaggt caggagtttg ggtctgccgt gagctgtgat tgcgcctgtg aatagtcact    120
gcactccagc    130

<210> SEQ ID NO 300
<211> LENGTH: 55
<212> TYPE: DNA
<213> ORGANISM: Homo sapiens

<400> SEQUENCE: 300
gacgtgaggg ggtgctacat acagcagctg tgtgtagtat gtgcctttct ctgtt    55

<210> SEQ ID NO 301
<211> LENGTH: 130
<212> TYPE: DNA
<213> ORGANISM: Homo sapiens

```
<400> SEQUENCE: 301
taggaattct ggaccaggct taaaagactg ggatgaggct ggtccgaagg tagtgagtta      60
tctccattga tagttcagtc tgtaacagat caaactcctt gttctactct tttttttttt    120
tttagacaga                                                            130

<210> SEQ ID NO 302
<211> LENGTH: 103
<212> TYPE: DNA
<213> ORGANISM: Homo sapiens

<400> SEQUENCE: 302
tgggctggtc cgagtgcagt ggtgtttaca agtatttgat tataactagt tacagatttc     60
tttgtttcct tctccactcc cactgcctca cttgactggc cta                      103

<210> SEQ ID NO 303
<211> LENGTH: 56
<212> TYPE: DNA
<213> ORGANISM: Homo sapiens

<400> SEQUENCE: 303
gctctgtcca aagtaaacgc cctgacgcac tgtgggaagg gtgagatggg caccgc         56

<210> SEQ ID NO 304
<211> LENGTH: 63
<212> TYPE: DNA
<213> ORGANISM: Homo sapiens

<400> SEQUENCE: 304
gtgagtggga gggggctgc agcccaaaga ggcaacaaag gcccttcccg gccaatgcat      60
tac                                                                   63

<210> SEQ ID NO 305
<211> LENGTH: 169
<212> TYPE: DNA
<213> ORGANISM: Homo sapiens

<400> SEQUENCE: 305
tgtcctcagg cctgctactg atcctgcagc cagaagttcc agaaagtgaa gggatttgga     60
ggggccgtga cagatgcagg tgccctcaac atccttgccc tgtcaccccc tgcccagaat    120
ttgctactta aatggtactt ctctgaagaa gatgaggagg aaggggaca                169

<210> SEQ ID NO 306
<211> LENGTH: 106
<212> TYPE: DNA
<213> ORGANISM: Homo sapiens

<400> SEQUENCE: 306
acagaattcc tcttctccct tctcctataa cctgttttat ttaattaatt aattttttag     60
gctagtcaag tgaagcagtg ggagtggaag gaacaaagaa atctgt                   106

<210> SEQ ID NO 307
<211> LENGTH: 45
<212> TYPE: RNA
<213> ORGANISM: Homo sapiens

<400> SEQUENCE: 307
ugagcucugc ggcgccaagg gaccgagggg ccgagggagc gagag                     45
```

<210> SEQ ID NO 308
<211> LENGTH: 75
<212> TYPE: RNA
<213> ORGANISM: Homo sapiens

<400> SEQUENCE: 308
agugcuuggc ugaggagcug gggccaaggg ggaacacaaa uaugguccug acccuacauu      60
cccagcccug ccucu      75

<210> SEQ ID NO 309
<211> LENGTH: 22
<212> TYPE: DNA
<213> ORGANISM: Artificial Sequence
<220> FEATURE:
<223> OTHER INFORMATION: General reverse primer

<400> SEQUENCE: 309
gcgagcacag aattaatacg ac      22

<210> SEQ ID NO 310
<211> LENGTH: 46
<212> TYPE: DNA
<213> ORGANISM: Artificial sequence
<220> FEATURE:
<223> OTHER INFORMATION: Primer for RT reaction
<220> FEATURE:
<221> NAME/KEY: misc_feature
<222> LOCATION: (45)..(45)
<223> OTHER INFORMATION: v is a,g, or c
<220> FEATURE:
<221> NAME/KEY: misc_feature
<222> LOCATION: (46)..(46)
<223> OTHER INFORMATION: n is a, g, c, or t

<400> SEQUENCE: 310
gcgagcacag aattaatacg actcactatc ggttttttt ttttvn      46

<210> SEQ ID NO 311
<211> LENGTH: 18
<212> TYPE: DNA
<213> ORGANISM: Artificial Sequence
<220> FEATURE:
<223> OTHER INFORMATION: General probe

<400> SEQUENCE: 311
aaaaccgata gtgagtcg      18

<210> SEQ ID NO 312
<211> LENGTH: 23
<212> TYPE: DNA
<213> ORGANISM: Artificial sequence
<220> FEATURE:
<223> OTHER INFORMATION: Specific forward primer

<400> SEQUENCE: 312
gcagctacat ctggctactg ggt      23

<210> SEQ ID NO 313
<211> LENGTH: 28
<212> TYPE: DNA
<213> ORGANISM: Artificial sequence
<220> FEATURE:
<223> OTHER INFORMATION: Specific forward primer

<400> SEQUENCE: 313
cagtcatttg gcgcgaccca tacttggt      28

<210> SEQ ID NO 314
<211> LENGTH: 21
<212> TYPE: DNA
<213> ORGANISM: Artificial sequence
<220> FEATURE:
<223> OTHER INFORMATION: Specific forward primer

<400> SEQUENCE: 314
aggcaagatg ctggcatagc t                                            21

<210> SEQ ID NO 315
<211> LENGTH: 28
<212> TYPE: DNA
<213> ORGANISM: Artificial sequence
<220> FEATURE:
<223> OTHER INFORMATION: Specific forward primer

<400> SEQUENCE: 315
cagtcatttg ggtttgttcg ttcggctc                                     28

<210> SEQ ID NO 316
<211> LENGTH: 28
<212> TYPE: DNA
<213> ORGANISM: Artificial sequence
<220> FEATURE:
<223> OTHER INFORMATION: Specific forward primer

<400> SEQUENCE: 316
cagtcatttg ggtccctgag accctaac                                     28

<210> SEQ ID NO 317
<211> LENGTH: 26
<212> TYPE: DNA
<213> ORGANISM: Artificial sequence
<220> FEATURE:
<223> OTHER INFORMATION: Specific forward primer

<400> SEQUENCE: 317
tggctgagaa ctgaattcca taggct                                       26

<210> SEQ ID NO 318
<211> LENGTH: 28
<212> TYPE: DNA
<213> ORGANISM: Artificial sequence
<220> FEATURE:
<223> OTHER INFORMATION: Specific forward primer

<400> SEQUENCE: 318
cagtcatttg gctcagtgca tgacagaa                                     28

<210> SEQ ID NO 319
<211> LENGTH: 23
<212> TYPE: DNA
<213> ORGANISM: Artificial sequence
<220> FEATURE:
<223> OTHER INFORMATION: Specific forward primer

<400> SEQUENCE: 319
tgtctgcccg catgcctgcc tct                                          23

<210> SEQ ID NO 320
<211> LENGTH: 28
<212> TYPE: DNA
<213> ORGANISM: Artificial sequence
<220> FEATURE:

```
<223> OTHER INFORMATION: Specific forward primer

<400> SEQUENCE: 320
cagtcatttg gcaacattca acctgtcg                                              28

<210> SEQ ID NO 321
<211> LENGTH: 21
<212> TYPE: DNA
<213> ORGANISM: Artificial sequence
<220> FEATURE:
<223> OTHER INFORMATION: Specific forward primer

<400> SEQUENCE: 321
caaaacgtga ggcgctgcta t                                                     21

<210> SEQ ID NO 322
<211> LENGTH: 28
<212> TYPE: DNA
<213> ORGANISM: Artificial sequence
<220> FEATURE:
<223> OTHER INFORMATION: Specific forward primer

<400> SEQUENCE: 322
cagtcatttg ggtctcacac agaaatcg                                              28

<210> SEQ ID NO 323
<211> LENGTH: 28
<212> TYPE: DNA
<213> ORGANISM: Artificial sequence
<220> FEATURE:
<223> OTHER INFORMATION: Specifc forward primer

<400> SEQUENCE: 323
cagtcatttg gcagctggtg ttgtgaat                                              28

<210> SEQ ID NO 324
<211> LENGTH: 28
<212> TYPE: DNA
<213> ORGANISM: Artificial sequence
<220> FEATURE:
<223> OTHER INFORMATION: Specific forward primer

<400> SEQUENCE: 324
cagtcatttg gctcctgtac tgagctgc                                              28

<210> SEQ ID NO 325
<211> LENGTH: 28
<212> TYPE: DNA
<213> ORGANISM: Artificial sequence
<220> FEATURE:
<223> OTHER INFORMATION: Specific forward primer

<400> SEQUENCE: 325
cagtcatttg ggtaatactg ccgggtaa                                              28

<210> SEQ ID NO 326
<211> LENGTH: 24
<212> TYPE: DNA
<213> ORGANISM: Artificial sequence
<220> FEATURE:
<223> OTHER INFORMATION: Specific forward primer

<400> SEQUENCE: 326
ttggcagtga agcattggac tgta                                                  24
```

```
<210> SEQ ID NO 327
<211> LENGTH: 28
<212> TYPE: DNA
<213> ORGANISM: Artificial sequence
<220> FEATURE:
<223> OTHER INFORMATION: Specific forward primer

<400> SEQUENCE: 327
cagtcatttg gcatcacatt gccaggga                                     28

<210> SEQ ID NO 328
<211> LENGTH: 29
<212> TYPE: DNA
<213> ORGANISM: Artificial sequence
<220> FEATURE:
<223> OTHER INFORMATION: Specific forward primer

<400> SEQUENCE: 328
catttggcta agccagtttc tgtctgata                                    29

<210> SEQ ID NO 329
<211> LENGTH: 27
<212> TYPE: DNA
<213> ORGANISM: Artificial sequence
<220> FEATURE:
<223> OTHER INFORMATION: Specific forward primer

<400> SEQUENCE: 329
tggcatgaca gattgacatg gacaatt                                      27

<210> SEQ ID NO 330
<211> LENGTH: 28
<212> TYPE: DNA
<213> ORGANISM: Artificial sequence
<220> FEATURE:
<223> OTHER INFORMATION: Specific forward primer

<400> SEQUENCE: 330
cagtcatttg gcgctgactc ctagtcca                                     28

<210> SEQ ID NO 331
<211> LENGTH: 22
<212> TYPE: DNA
<213> ORGANISM: Artificial sequence
<220> FEATURE:
<223> OTHER INFORMATION: Specific forward primer

<400> SEQUENCE: 331
cgttcctgct gaactgagcc ag                                           22

<210> SEQ ID NO 332
<211> LENGTH: 18
<212> TYPE: DNA
<213> ORGANISM: Artificial sequence
<220> FEATURE:
<223> OTHER INFORMATION: Specific forward primer

<400> SEQUENCE: 332
cctgtctgag cgccgctc                                                18

<210> SEQ ID NO 333
<211> LENGTH: 30
<212> TYPE: DNA
<213> ORGANISM: Artificial sequence
<220> FEATURE:
<223> OTHER INFORMATION: Specific forward primer
```

```
<400> SEQUENCE: 333
cagtcatttg gcatactctg gtttcttttc                                    30

<210> SEQ ID NO 334
<211> LENGTH: 30
<212> TYPE: DNA
<213> ORGANISM: Artificial sequence
<220> FEATURE:
<223> OTHER INFORMATION: Specific forward primer

<400> SEQUENCE: 334
agtcatttgg cttattgtca cgttctgatt                                    30

<210> SEQ ID NO 335
<211> LENGTH: 28
<212> TYPE: DNA
<213> ORGANISM: Artificial sequence
<220> FEATURE:
<223> OTHER INFORMATION: Specific forward primer

<400> SEQUENCE: 335
cagtcatttg gccacgctca tgcacaca                                      28

<210> SEQ ID NO 336
<211> LENGTH: 23
<212> TYPE: DNA
<213> ORGANISM: Artificial sequence
<220> FEATURE:
<223> OTHER INFORMATION: Specific probe

<400> SEQUENCE: 336
ccgttttttt tttttacggg tgc                                           23

<210> SEQ ID NO 337
<211> LENGTH: 23
<212> TYPE: DNA
<213> ORGANISM: Artificial sequence
<220> FEATURE:
<223> OTHER INFORMATION: Specific probe

<400> SEQUENCE: 337
ccgttttttt tttttactca ccg                                           23

<210> SEQ ID NO 338
<211> LENGTH: 23
<212> TYPE: DNA
<213> ORGANISM: Artificial sequence
<220> FEATURE:
<223> OTHER INFORMATION: Specific probe

<400> SEQUENCE: 338
ccgttttttt tttttcacaa gtt                                           23

<210> SEQ ID NO 339
<211> LENGTH: 23
<212> TYPE: DNA
<213> ORGANISM: Artificial sequence
<220> FEATURE:
<223> OTHER INFORMATION: Specific probe

<400> SEQUENCE: 339
ccgttttttt tttttcacgc gag                                           23
```

<210> SEQ ID NO 340
<211> LENGTH: 23
<212> TYPE: DNA
<213> ORGANISM: Artificial sequence
<220> FEATURE:
<223> OTHER INFORMATION: Specific probe

<400> SEQUENCE: 340 ccgtttttttt tttttctcgg ggc                                          23

<210> SEQ ID NO 341
<211> LENGTH: 23
<212> TYPE: DNA
<213> ORGANISM: Artificial sequence
<220> FEATURE:
<223> OTHER INFORMATION: Specific probe

<400> SEQUENCE: 341 ccgtttttttt tttttctgaa acc                                          23

<210> SEQ ID NO 342
<211> LENGTH: 23
<212> TYPE: DNA
<213> ORGANISM: Artificial sequence
<220> FEATURE:
<223> OTHER INFORMATION: Specific probe

<400> SEQUENCE: 342 ccgtttttttt tttttggaaa tcc                                          23

<210> SEQ ID NO 343
<211> LENGTH: 23
<212> TYPE: DNA
<213> ORGANISM: Artificial sequence
<220> FEATURE:
<223> OTHER INFORMATION: Specific probe

<400> SEQUENCE: 343 ccgtttttttt tttttgtggg tgt                                          23

<210> SEQ ID NO 344
<211> LENGTH: 22
<212> TYPE: DNA
<213> ORGANISM: Artificial sequence
<220> FEATURE:
<223> OTHER INFORMATION: Specific probe

<400> SEQUENCE: 344
cgtttttttt ttttccaagt tc                                            22

<210> SEQ ID NO 345
<211> LENGTH: 22
<212> TYPE: DNA
<213> ORGANISM: Artificial sequence
<220> FEATURE:
<223> OTHER INFORMATION: Specific probe

<400> SEQUENCE: 345
cgtttttttt ttttccatca tt                                            22

<210> SEQ ID NO 346
<211> LENGTH: 22
<212> TYPE: DNA
<213> ORGANISM: Artificial sequence
<220> FEATURE:
<223> OTHER INFORMATION: Specific probe

```
<400> SEQUENCE: 346 cgttttttttt ttttcggcct ga                                        22

<210> SEQ ID NO 347
<211> LENGTH: 22
<212> TYPE: DNA
<213> ORGANISM: Artificial Sequence
<220> FEATURE:
<223> OTHER INFORMATION: Specific probe

<400> SEQUENCE: 347 cgttttttttt ttttgagccc tg                                        22
```

MIRNA EXPRESSION SIGNATURE IN THE CLASSIFICATION OF THYROID TUMORS

FIELD OF THE INVENTION

The present invention relates to methods for classification of thyroid tumors. Specifically the invention relates to microRNA molecules associated with specific thyroid tumors.

BACKGROUND OF THE INVENTION

The accurate diagnosis of thyroid nodules continues to challenge physicians managing patients with thyroid disease. Patients with cytologically indeterminate nodules are often referred for diagnostic surgery, though most of these nodules prove post-surgery to be benign. This limitation of FNA cytology in the pre-operative diagnosis leads to a clinical need for reliable pre-operative molecular markers to distinguish benign from malignant thyroid nodules. MicroRNAs (miRs) are an important class of regulatory RNAs, which have a profound impact on a wide array of biological processes. These small (typically 18-24 nucleotides long) non-coding RNA molecules can modulate protein expression pattern by promoting RNA degradation, inhibiting mRNA translation, and also by affecting gene transcription. miRs play pivotal roles in diverse processes such as development and differentiation, control of cell proliferation, stress response and metabolism. The expression of many miRs was found to be altered in numerous types of human cancer, and in some cases suggesting that such alterations may play a causative role in tumor progression.

The thyroid gland is formed of two main types of cells: the follicular cells and the C or parafollicular cells. Follicular cells produce thyroid hormones, which are regulators of human metabolism. Overproduction of thyroid hormone (hyperthyroidism) causes rapid or irregular heartbeat, trouble sleeping, nervousness, hunger, weight loss, and a feeling of being too warm. In counterpart, hypothyroidism causes metabolism slowdown, tiredness, and weight gain. Thyroid hormone release is regulated by the thyroid-stimulating hormone (TSH), produced by the pituitary gland. The C cells produce calcitonin, a hormone responsible for use of calcium. Lymphocytes and stromal cells are also found in the thyroid.

Thyroid cancer is the eighth most common cancer in the United States, and the most rapidly increasing cancer in the US, with more than 60,000 new cases diagnosed every year, and being the cause of about 1,800 deaths in 2014. Thyroid cancer usually presents itself as a palpable thyroid nodule. Different types of thyroid tumors develop from different cell types, which is a determinant for the gravity and the optimal treatment administered. Most of the growths and tumors in the thyroid gland are benign (non-cancerous) but others are malignant (cancerous).

Approximately 95% of thyroid cancers are differentiated thyroid carcinomas (DTC) that arise from thyroid follicular cells. There are two histological subtypes of DTC: papillary thyroid carcinoma (PTC) type (90-95%) and follicular thyroid carcinoma (FTC) type (5-10%).

The most commonly used method for thyroid cancer diagnosis is biopsy by fine-needle aspiration (FNA). FNA samples are routinely examined for cytology to determine whether the nodules are benign or cancerous. The sensitivity and specificity of the cytological examination of an FNA sample range from 68% to 98%, and 72% to 100%, respectively, depending on institutions and doctors. Unfortunately, in at least 25% of the cases the FNA specimens collected are either inadequate for diagnosis or indeterminable by cytology. In current medical practice, most patients with indeterminate results undergo surgery, and are subject to all risks and consequences of the surgical procedure. Follow-up results show that only 25% of the patients operated on are diagnosed with cancer, meaning that 75% of the patients underwent an unnecessary surgical procedure. Surgery entails significant cost and morbidity. One study has shown that adding molecular testing could have an overall positive impact on healthcare cost and patients' quality of life, reaching up to 74% fewer surgeries for benign nodules with no greater number of untreated cancers. Over a 5-year period, the study estimated a savings of almost $1,500 per patient [Li et al. 2011 J Clin Endocrinol. Metab 96(11): E1719-E1726].

When examining cytochemical or genetic markers, there is no unique marker that on its own is able to provide reliable results in order to replace the morphologic diagnosis of thyroid lesions. U.S. Pat. No. 7,319,011 describes the measuring the expression of any one of the genes DDIT3, ARG2, ITM1, C1orf24, TARSH, and ACO1 in a test follicular thyroid specimen for distinguishing between follicular adenoma (FA) from follicular carcinoma (FC). U.S. Pat. No. 7,670,775 describes the analysis of the expression of CCND2, PCSK2, and PLAB for identifying malignant thyroid tissue. U.S. Pat. No. 6,723,506 describes the molecular characterization of PAX8-PPAR1 molecules in connection with diagnosis and treatment of thyroid follicular carcinomas. U.S. Pat. No. 7,378,233 describes the occurrence of the T1796A mutation of the BRAF gene in 24 (69%) of papillary thyroid carcinomas.

Accumulated efforts have been invested in finding a molecular diagnostic test which will overcome the uncertainty of indeterminate cytology, and ultimately eliminate unnecessary surgery for non-cancer patients [Chen, Y. T. et. al. (2008) Mod. Pathol. 21, 1139-1146; He, H. et al. (2005) Proc. Natl Acad. Sci. USA 102, 19075-19080; Nikiforova, M. N. et al. (2009) Endocr. Pathol. 20, 85-91; Pallante, P. et al. (2006) Endocr. Relat. Cancer 13, 497-508; Nikiforova, M. N. et al. (2008) J. Clin. Endocrinol. Metab. 93, 1600-1608; Visone, R. et al. (2007) Endocr. Relat. Cancer 14(3): 791-8; US 2014/0030714 A1; U.S. Pat. No. 8,541,170; US 2012/0220474 A1; U.S. Pat. No. 8,465,914; U.S. Pat. No. 7,598,052; U.S. Pat. No. 8,202,692; WO 2013/066678; WO 2012/129378; US 2013/0237590; EP 2772 550 A1; Pallante et al. (2010) Endocrine-Related Cancer 17 F91-F104; Dettmer et al. (2014) J Mol Endocrinol. March 6; 52(2):181-9].

Nonetheless, numerous are the challenges that remain. It is of great necessity to develop a molecular assay with not only high sensitivity and specificity, but also that is able to deal with samples that failed the cytology analysis and that fall under the category of indeterminate samples. The present invention provides solutions for this challenge.

SUMMARY OF THE INVENTION

Thus, in a first aspect, the present invention provides a method of classifying a thyroid lesion sample as malignant or benign, the method comprising:

a. providing RNA extracted from a thyroid lesion sample obtained from a human subject;

b. obtaining an expression profile comprising expression levels of microRNAs comprising SEQ ID NOS. 1-37;

c. applying a classifier algorithm to the expression profile; wherein the classifier algorithm compares the expression profile to a reference value; and d. classifying said thyroid lesion as benign or malignant, or of a sub-type of benign or malignant tumor based on the result from the classifier algorithm.

In one embodiment of the method of the invention, following step (b) or (c) further comprising a step of obtaining the ratio between the expression levels of at least one pair of nucleic acids; and wherein in step (d) said classifier algorithm may be applied to any one of the nucleic acid expression profile, said ratio of at least one pair of nucleic acids, or to a combination thereof.

In a further embodiment of the method of the invention, said thyroid lesion sample is obtained by fine needle aspiration (FNA) biopsy. In one particular embodiment, said sample is a smear from a FNA biopsy.

In another further embodiment of the method of the invention, algorithm is a machine-learning algorithm. In one particular embodiment of said method of the invention, said algorithm further combines the microRNA expression profile with clinical or genetic data from said sample.

In another further embodiment of the method of the invention, following step (b) if at least one of said microRNA expression levels, or the ratio between the expression levels of at least one pair of microRNAs is below or above a threshold for thyroid cells, said sample is discarded based on the expression level of said microRNA.

In another further embodiment of the method of the invention, said measuring is performed by hybridization, amplification or next generation sequencing method.

In particular, an expression profile of microRNAs comprising SEQ ID NOS. 1-13, 17-22, 25, 26, 36 and 37 is determined.

In one particular embodiment of the method of the invention, said hybridization comprises contacting the sample with probes, wherein the probes comprise (i) DNA equivalents of the microRNAs, (ii) the complements thereof, (iii) sequences at least 80% identical to (i) or (ii) or (iv) a nucleic acid sequence that hybridizes with at least eight contiguous nucleotides of any one of SEQ ID NOs 1-37. In another particular embodiment of the invention, said probes are attached to a solid substrate.

In another further particular embodiment of the method of the invention, amplification is real-time polymerase chain reaction (RT-PCR), said RT-PCR amplification method comprising forward and reverse primers, and optionally further comprising hybridization with a probe.

Amplification by RT-PCR comprises contacting the RNA with forward and reverse primers for each of the miRNAs, wherein each forward primer comprises 15-21 nucleotides identical to one of the miRNAs. Forward primers are as defined in Table 8.

In another further embodiment, said method further comprises the step of administering a differential treatment to said subject if said thyroid lesion is benign or malignant.

In another further particular embodiment of the method of the invention, said lesion is malignant and said treatment is any one of surgery, chemotherapy, radiotherapy, hormone therapy, or any other recommended treatment.

In one embodiment, said probe is a general probe. In another embodiment said probe is a microRNA sequence-specific probe.

In another further aspect, the present invention provides an isolated nucleic acid, said nucleic acid comprising at least 12 contiguous nucleotides at least 80% identical to the sequence of any one of SEQ ID NOs. 27-29, 33, 34, 139, 140, 307 and 308.

In another further aspect, the present invention provides a pharmaceutical composition comprising as active agent the isolated nucleic acids described herein, and optionally adjuvants, carriers, diluents and excipients. Thus, said nucleic acid molecules may be comprised as an active agent in a pharmaceutical composition, a formulation or a medicament.

In another further aspect, the present invention provides a vector comprising the isolated nucleic acid described herein.

In another further aspect, the present invention provides a probe comprising the isolated nucleic acid described herein.

In another further aspect, the present invention provides a biochip comprising the isolated nucleic acid described herein.

In another further aspect, the present invention provides the use of an isolated nucleic acid as described herein in the preparation of a medicament.

BRIEF DESCRIPTION OF THE DRAWINGS

FIG. 1A shows the predicted secondary structure of two novel microRNAs, MD2-495 (top) and MD2-437 (bottom) detected in thyroid tissue. FIG. 1B shows the expression of the two novel microRNAs in each one of 11 resected thyroid samples.

FIG. 2A: The y and x axes show the median array expression levels of the miRs in FA (follicular adenoma) samples not documented as having Hurthle cells (n=22) versus FA samples with Hurthle cells (n=9). The dashed factor line=×1.5. BL=blood. NT, not tested. FIG. 2B: The y and x axes show the median PCR expression levels of the miRs in FA samples with no indication of Hurthle cells (n=21) versus FA samples with Hurthle cells (n=9). The dashed factor line=±0.6.

FIGS. 4A-4C: A Discriminant Analysis classifier was used to classify samples from the malignant+benign cohort as malignant (diamonds, M) or benign (squares, B). FIG. 4A: Classifier with two microRNAs (hsa-miR-551b-3p and hsa-miR-146b-5p), presented sensitivity of 84.8% and specificity of 68.9%. The grey shaded area marks the space in which a sample is classified as malignant, as determined by the classifier. FIG. 4B: Classifier with three microRNAs (hsa-miR-551b-3p, hsa-miR-146b-5p, and hsa-miR-31-5p) presenting sensitivity of 82.9% and specificity of 72.2%. Misclassified samples (miscl.) are represented by a dot. FIG. 4C: Classifier with eight microRNA (hsa-miR-551b-3p; hsa-miR-146b-5p; hsa-miR-31-5p; hsa-miR-222-3p; hsa-miR-375; hsa-miR-125b-5p; hsa-miR-152-3p; hsa-miR-181c-5p), presenting sensitivity of 83.5% and specificity of 81.5%. The figure shows a confusion matrix where the x-axis shows the classifier answer (Clas. Ans.) while the y-axis shows the true diagnosis (Real class=re.cl.).

FIG. 5A: Classifier with two microRNA ratios (hsa-miR-146b-5p:hsa-miR-342-3p and hsa-miR-31-5p:hsa-miR-342-3p), presented sensitivity of 78% and specificity of 79.5%. The grey shaded area marks the space in which a sample is classified as malignant, as determined by the classifier. FIG. 5B: Classifier with three microRNA ratios (hsa-miR-146b-5p:hsa-miR-342-3p; hsa-miR-31-5p:hsa-miR-342-3p; hsa-miR-125b-5p:hsa-miR-138-5p), presented sensitivity of 81.1% and specificity of 82.1%. Misclassified samples (miscl.) are represented by a dot. FIG. 5C: Classifier with 8 microRNA ratios (hsa-miR-146b-5p:hsa-miR-342-3p; hsa-miR-31-5p:hsa-miR-342-3p; hsa-miR-125b-5p:hsa-miR-138-5p; hsa-miR-125b-5p:hsa-miR-200c-3p; hsa-miR-222-3p:hsa-miR-486-5p; hsa-miR-200c-3p:hsa-miR-486-5p; MID-16582:hsa-miR-200c-3p; MID-16582:hsa-miR-138-5p) is shown as a confusion matrix where the x-axis shows the classifier answer (Clas. Ans.), while the y-axis shows the true diagnosis (Real class=re.cl.), and presented sensitivity of 74.4% and specificity of 84.1%.

FIG. 6A-6C: A Discriminant Analysis classifier was used to classify samples from the malignant+benign cohort as malignant (diamonds, M) or benign (squares, B), based on a combination of microRNAs and microRNA ratios. FIG. 6A: Classifier of one microRNA ratio and one microRNA (hsa-miR-146b-5p:hsa-miR-342-3p; hsa-miR-551b-3p) presented sensitivity of 82.9% and specificity of 82.8%. The grey shaded area marks the space in which a sample is classified as malignant, as determined by the classifier. FIG. 6B: Classifier of one microRNA ratio and two microRNAs (hsa-miR-146b-5p:hsa-miR-342-3p; hsa-miR-551b-3p; hsa-miR-146b-5p) presented sensitivity of 82.9% and specificity of 82.8%. FIG. 6C: Classifier of five microRNAs and three microRNA ratios (hsa-miR-146b-5p:hsa-miR-342-3p; hsa-miR-551b-3p; hsa-miR-146b-5p; hsa-miR-31-5p:hsa-miR-342-3p; hsa-miR-31-5p; hsa-miR-222-3p; hsa-miR-125b-5p:hsa-miR-138-5p; hsa-miR-375) as the features for the classification, is shown as a confusion matrix where the x-axis shows the classifier answer (Clas. Ans.), while the y-axis shows the true diagnosis (Real class=re.cl.) (Real class=re.cl.), and presented sensitivity of 93.3% and specificity of 42.4%.

FIG. 7A: Classifier using six microRNAs (hsa-miR-551b-3p; hsa-miR-146b-5p; hsa-miR-31-5p; hsa-miR-222-3p; hsa-miR-375; hsa-miR-125b-5p) is shown as a confusion matrix where the x-axis shows the classifier answer (Clas. Ans.), while the y-axis shows the true diagnosis (Real class=re.cl.), presented sensitivity of 82.3% and specificity of 68.2%. FIG. 7B: Classifier of eight microRNAs (hsa-miR-551b-3p; hsa-miR-146b-5p; hsa-miR-31-5p; hsa-miR-222-3p; hsa-miR-375; hsa-miR-125b-5p; hsa-miR-152-3p; hsa-miR-181c-5p) is shown in a confusion matrix where the x-axis shows the classifier answer (Clas. Ans.), while the y-axis shows the true diagnosis (Real class=re.cl.), and presenting sensitivity of 82.9% and of 74.2%. FIG. 7C: Classifier using twelve microRNAs (hsa-miR-551b-3p; hsa-miR-146b-5p; hsa-miR-31-5p; hsa-miR-222-3p; hsa-miR-375; hsa-miR-125b-5p; hsa-miR-152-3p; hsa-miR-181c-5p; hsa-miR-486-5p; hsa-miR-424-3p; hsa-miR-200c-3p; hsa-miR-346) is shown as a confusion matrix where the x-axis shows the classifier answer (Clas. Ans.), while the y-axis shows the true diagnosis (Real class=re.cl.), presenting sensitivity of 81.1% and specificity of 68.9%.

FIG. 8A: Classifier using six microRNA ratios (hsa-miR-146b-5p:hsa-miR-342-3p; hsa-miR-31-5p:hsa-miR-342-3p; hsa-miR-125b-5p:hsa-miR-138-5p; hsa-miR-125b-5p:hsa-miR-200c-3p; hsa-miR-222-3p:hsa-miR-486-5p; hsa-miR-200c-3p:hsa-miR-486-5p) as the features for the classification, is shown as a confusion matrix where the x-axis represents the classifier answer (Clas. Ans.), and the y-axis represents the true diagnosis (Real class=re.cl.), and presented sensitivity of 78% and specificity of 58.9%. FIG. 8B: Classifier using eight microRNA ratios (hsa-miR-146b-5p:hsa-miR-342-3p; hsa-miR-31-5p:hsa-miR-342-3p; hsa-miR-125b-5p:hsa-miR-138-5p; hsa-miR-125b-5p:hsa-miR-200c-3p; hsa-miR-222-3p:hsa-miR-486-5p; hsa-miR-200c-3p:hsa-miR-486-5p; MID-16582:hsa-miR-200c-3p; MID-16582:hsa-miR-138-5p) as the features for the classification, shown in a confusion matrix where the x-axis represents the classifier answer (Clas. Ans.), and the y-axis represents the true diagnosis (Real class=re.cl.), presented sensitivity of 80.5% and specificity of 65.6%.

FIG. 9A: Classifier using four microRNAs and two microRNA ratios (hsa-miR-31-5p; hsa-miR-222-3p; hsa-miR-551b-3p; hsa-miR-146b-5p; hsa-miR-146b-5p:hsa-miR-342-3p; hsa-miR-31-5p:hsa-miR-342-3p); as the features for the classification, is shown as a confusion matrix where the x-axis represents the classifier answer (Clas. Ans.), while the y-axis represents the true diagnosis (Real class=re.cl.), and presented sensitivity of 85.4% and specificity of 66.9%. FIG. 9B: Classifier using five microRNAs and three microRNA ratios (hsa-miR-551b-3p; hsa-miR-146b-5p; hsa-miR-375; hsa-miR-222-3p; hsa-miR-146b-5p:hsa-miR-342-3p; hsa-miR-31-5p:hsa-miR-342-3p; hsa-miR-31-5p; hsa-miR-125b-5p:hsa-miR-138-5p) as the features for the classification, is shown as a confusion matrix where the x-axis represents the classifier answer (Clas. Ans.), while the y-axis represents the true diagnosis (Real class=re.cl.), and presented sensitivity of 83.5% and specificity of 70.9%. FIG. 9C: Classifier using seven microRNAs and five microRNA ratios (hsa-miR-375; hsa-miR-551b-3p; hsa-miR-146b-5p; hsa-miR-152-3p; hsa-miR-125b-5p; hsa-miR-222-3p; hsa-miR-31-5p; hsa-miR-146b-5p:hsa-miR-342-3p; hsa-miR-31-5p:hsa-miR-342-3p; hsa-miR-125b-5p:hsa-miR-138-5p; hsa-miR-125b-5p:hsa-miR-200c-3p; hsa-miR-222-3p:hsa-miR-486-5p); as the features for the classification, is shown as a confusion matrix where the x-axis represents the classifier answer (Clas. Ans.), while the y-axis represents the true diagnosis (Real class=re.cl.), and presented sensitivity of 83.5% and specificity of 66.9%.

FIG. 10A-10C: A Discriminant Analysis classifier was used to classify samples from the Indeterminate sub-cohort as malignant (diamonds, M) or benign (squares, B). FIG. 10A: A classifier using two microRNAs (hsa-miR-146b-5p; hsa-miR-551b-3p) showed sensitivity of 80% and specificity of 56.3%. The grey shaded area marks the space in which a sample is classified as malignant, as determined by the classifier. FIG. 10B: A classifier of three microRNAs (hsa-miR-146b-5; hsa-miR-551b-3p; hsa-miR-222-3p) showed sensitivity of 82.6% and specificity of 59.5%. Misclassified samples (miscl.) are represented by a dot. FIG. 10C: A classifier of eight microRNAs (hsa-miR-146b-5p; hsa-miR-551b-3p; hsa-miR-222-3p; hsa-miR-125b-5p; hsa-miR-31-5p; hsa-miR-375; hsa-miR-152-3p; hsa-miR-181c-5p) is shown as a confusion matrix where the x-axis shows the classifier answer (Clas. Ans.), and the y-axis shows the true diagnosis (Real class=re.cl.). The sensitivity of this classifier is 81.7% and the specificity is 71.4%.

FIG. 11A: A classifier using two microRNA ratios (hsa-miR-146b-5p:hsa-miR-342-3p; hsa-miR-31-5p:hsa-miR-342-3p) as the features for the classification presented a sensitivity of classifier 80% and specificity of 72.2%. The grey shaded area marks the space in which a sample is classified as malignant. FIG. 11B: A classifier using three microRNA ratios (hsa-miR-146b-5p:hsa-miR-342-3p; hsa-miR-31-5p:hsa-miR-342-3p; hsa-miR-125b-5p:hsa-miR-200c-3p) as the features for the classification presented sensitivity of 80% and specificity of 69%. Misclassified samples (miscl.) are represented by a dot. FIG. 11C: A classifier using eight microRNA ratios (hsa-miR-146b-5p:hsa-miR-342-3p; hsa-miR-31-5p:hsa-miR-342-3p; hsa-miR-125b-5p:hsa-miR-200c-3p; hsa-miR-125b-5p:hsa-miR-138-5p; hsa-miR-222-3p:hsa-miR-486-5p; MID-16582:hsa-miR-200c-3p; MID-16582:hsa-miR-138-5p; hsa-miR-200c-3p:hsa-miR-486-5p) as the features for the classification, shown as a confusion matrix where the x-axis shows the classifier answer (Clas. Ans.), and the y-axis shows the true diagnosis (Real class=re.cl.), presented sensitivity of 80% and specificity of 66.7%.

FIG. 12A: A classifier using one microRNA and one microRNA ratio (hsa-miR-146b-5p; hsa-miR-146b-5p:hsa-miR-342-3p) as the features for the classification presented sensitivity of 80% and specificity of 73.8%. The grey shaded area marks the space in which a sample is classified as malignant, as determined by the classifier. FIG. 12B: A classifier using two microRNAs and one microRNA ratio (hsa-miR-146b-5p; hsa-miR-551b-3p; hsa-miR-146b-5p:hsa-miR-342-3p) as the features for the classification presented sensitivity of 79.1% and specificity of 73%. FIG. 12C: A classifier using five microRNAs and three microRNA ratios (hsa-miR-146b-5p; hsa-miR-551b-3p; hsa-miR-222-3p; hsa-miR-125b-5p; hsa-miR-31-5p; hsa-miR-146b-5p:hsa-miR-342-3p; hsa-miR-31-5p:hsa-miR-342-3p; hsa-miR-125b-5p:hsa-miR-200c-3p) as the features for the classification presented sensitivity of 87.8% and specificity of 67.5%, and it is shown as a confusion matrix where the x-axis shows the classifier answer (Clas. Ans.), while the y-axis shows the true diagnosis (Real class=re.cl.).

FIG. 13A: A classifier of six microRNAs (hsa-miR-146b-5p; hsa-miR-551b-3p; hsa-miR-222-3p; hsa-miR-125b-5p; hsa-miR-31-5p; hsa-miR-375) is shown as a confusion matrix where the x-axis shows the classifier answer (Clas. Ans.), while the y-axis shows the true diagnosis (Real class=re.cl.), presented sensitivity of 78.3% and specificity of 65.9%. FIG. 13B: A classifier using eight microRNAs (hsa-miR-146b-5p; hsa-miR-551b-3p; hsa-miR-222-3p; hsa-miR-125b-5p; hsa-miR-31-5p; hsa-miR-375; hsa-miR-152-3p; hsa-miR-181c-5p) as the features for classification is shown as a confusion matrix where the x-axis shows the classifier answer (Clas. Ans.), while the y-axis shows the true diagnosis (Real class=re.cl.), presented sensitivity of 82.6% and specificity of 73%. FIG. 13C: A classifier using 12 microRNAs (hsa-miR-551b-3p; hsa-miR-146b-5p; hsa-miR-222-3p; hsa-miR-125b-5p; hsa-miR-31-5p; hsa-miR-375; hsa-miR-152-3p; hsa-miR-181c-5p; hsa-miR-424-3p; hsa-miR-486-5p; hsa-miR-200c-3p; hsa-miR-346) as the features for the classification is shown as a confusion matrix where the x-axis shows the classifier answer (Clas. Ans.), while the y-axis shows the true diagnosis (Real class=re.cl.), presented sensitivity of 73.9% and specificity of 68.3%.

FIG. 14A: A classifier using six microRNA ratios (hsa-miR-146b-5p:hsa-miR-342-3p; hsa-miR-31-5p:hsa-miR-342-3p; hsa-miR-125b-5p:hsa-miR-200c-3p; hsa-miR-125b-5p:hsa-miR-138-5p; hsa-miR-222-3p:hsa-miR-486-5p; MID-16582:hsa-miR-200c-3p) as the features for classification is shown as a confusion matrix where the x-axis shows the classifier answer (Clas. Ans.), while the y-axis shows the true diagnosis (Real class=re.cl.), and presented sensitivity of 80.9% and specificity of 65.9%. FIG. 14B: A classifier using eight microRNA ratios (hsa-miR-146b-5p:hsa-miR-342-3p; hsa-miR-31-5p:hsa-miR-342-3p; hsa-miR-125b-5p:hsa-miR-200c-3p; hsa-miR-125b-5p:hsa-miR-138-5p; hsa-miR-222-3p:hsa-miR-486-5p; MID-16582:hsa-miR-200c-3p; MID-16582:hsa-miR-138-5p; hsa-miR-200c-3p:hsa-miR-486-5p) as the features for classification is shown as a confusion matrix where the x-axis shows the classifier answer (Clas. Ans.), while the y-axis shows the true diagnosis (Real class=re.cl.), presented sensitivity of 76.5% and specificity of 62.7%.

FIG. 15A: A classifier using three microRNAs and three microRNA ratios (hsa-miR-146b-5p; hsa-miR-551b-3p; hsa-miR-222-3p; hsa-miR-146b-5p:hsa-miR-342-3p; hsa-miR-31-5p:hsa-miR-342-3p; hsa-miR-125b-5p:hsa-miR-200c-3p) as the features for classification is shown as a confusion matrix where the x-axis shows the classifier answer (Clas. Ans.), while the y-axis shows the true diagnosis (Real class=re.cl.), and presented sensitivity of 76.5% and specificity of 57.9%. FIG. 15B: A classifier using five microRNAs and three microRNA ratios (hsa-miR-125b-5p; hsa-miR-31-5p; hsa-miR-551b-3p; hsa-miR-146b-5p; hsa-miR-222-3p; hsa-miR-146b-5p:hsa-miR-342-3p; hsa-miR-31-5p:hsa-miR-342-3p; hsa-miR-125b-5p:hsa-miR-200c-3p) as the features for classification is shown as a confusion matrix where the x-axis shows the classifier answer (Clas. Ans.), while the y-axis shows the true diagnosis (Real class=re.cl.), presented sensitivity of 78.3% and specificity of 64.3%

FIG. 15C: A classifier using seven microRNAs and five microRNA ratios (hsa-miR-146b-5p; hsa-miR-551b-3p; hsa-miR-222-3p; hsa-miR-125b-5p; hsa-miR-31-5p; hsa-miR-375; hsa-miR-152-3p; hsa-miR-146b-5p:hsa-miR-342-3p; hsa-miR-31-5p:hsa-miR-342-3p; hsa-miR-125b-5p:hsa-miR-200c-3p; hsa-miR-125b-5p:hsa-miR-138-5p; hsa-miR-222-3p:hsa-miR-486-5p); as the features for classification is shown as a confusion matrix where the x-axis shows the classifier answer (Clas. Ans.), while the y-axis shows the true diagnosis (Real class=re.cl.), presented sensitivity of 80.9% and specificity of 67.5%.

FIG. 16A: A classifier using three microRNAs (hsa-miR-146b-5p; hsa-miR-551b-3p; hsa-miR-222-3p) as the features for classification presented sensitivity of classifier 82.6% and specificity of 54.8%. Misclassified samples (miscl.) are represented by a dot. FIG. 16B: A classifier using sixmicroRNAs (hsa-miR-146b-5p; hsa-miR-551b-3p; hsa-miR-222-3p; hsa-miR-125b-5p; hsa-miR-31-5p; hsa-miR-375) as the features for the classification, is shown as a confusion matrix where the x-axis shows the classifier answer (Clas. Ans.), while the y-axis shows the true diagnosis (Real class=re.cl.), and presented sensitivity of 82.6% and specificity of 59.5%. FIG. 16C: A classifier using eight microRNAs (hsa-miR-146b-5p; hsa-miR-551b-3p; hsa-miR-222-3p; hsa-miR-125b-5p; hsa-miR-31-5p; hsa-miR-375; hsa-miR-152-3p; hsa-miR-181c-5p) as the features for the classification is shown as a confusion matrix where the x-axis shows the classifier answer (Clas. Ans.), while the y-axis shows the true diagnosis (Real class=re.cl.), and presented sensitivity of 90.4% and specificity of 60.3%.

FIG. 17A: A classifier using three microRNA ratios (hsa-miR-146b-5p:hsa-miR-342-3p; hsa-miR-31-5p:hsa-miR-342-3p; hsa-miR-125b-5p:hsa-miR-200c-3p) as the features for the classification presented sensitivity of 81.7% and specificity of 67.5%. Misclassified samples (miscl.) are represented by a dot. FIG. 17B: A classifier using six microRNA ratios (hsa-miR-146b-5p:hsa-miR-342-3p; hsa-miR-31-5p:hsa-miR-342-3p; hsa-miR-125b-5p:hsa-miR-200c-3p; hsa-miR-125b-5p:hsa-miR-138-5p; hsa-miR-222-3p:hsa-miR-486-5p; MID-16582:hsa-miR-200c-3p) as the features for the classification is shown as a confusion matrix where the x-axis shows the classifier answer (Clas. Ans.), while the y-axis shows the true diagnosis (Real class=re.cl.), and presented sensitivity of 88.7% and specificity of 63.5%. FIG. 17C: A classifier using eight microRNA ratios (hsa-miR-146b-5p:hsa-miR-342-3p; hsa-miR-31-5p:hsa-miR-342-3p; hsa-miR-125b-5p:hsa-miR-200c-3p; hsa-miR-125b-5p:hsa-miR-138-5p; hsa-miR-222-3p:hsa-miR-486-5p; MID-16582:hsa-miR-200c-3p; MID-16582:hsa-miR-138-5p; hsa-miR-200c-3p:hsa-miR-486-5p) as the features for the classification is shown as a confusion matrix where the x-axis shows the classifier answer (Clas. Ans.), while the y-axis shows the true diagnosis (Real class=re.cl.), and presented sensitivity of 87.8% and specificity of 58.7%.

FIG. 18A: A classifier using two microRNAs and one microRNA ratio (hsa-miR-146b-5p; hsa-miR-551b-3p; hsa-miR-146b-5p:hsa-miR-342-3p) as the features for the classification presented sensitivity of 80% and specificity of 71.4%. FIG. 18B: A classifier using threemicroRNAs and three microRNA ratios (hsa-miR-146b-5p; hsa-miR-551b-3p; hsa-miR-222-3p; hsa-miR-146b-5p:hsa-miR-342-3p; hsa-miR-31-5p:hsa-miR-342-3p; hsa-miR-125b-5p:hsa-miR-200c-3p) as the features for the classification is shown as a confusion matrix where the x-axis shows the classifier answer (Clas. Ans.), while the y-axis shows the true diagnosis (Real class=re.cl.), presented sensitivity of 89.9% and specificity of 51.6%. FIG. 18C: A classifier using five microRNAs and three microRNA ratios (hsa-miR-551b-3p; hsa-miR-146b-5p; hsa-miR-222-3p; hsa-miR-125b-5p; hsa-miR-31-5p; hsa-miR-146b-5p:hsa-miR-342-3p; hsa-miR-31-5p:hsa-miR-342-3p; hsa-miR-125b-5p:hsa-miR-200c-3p); as the features for the classification is shown as a confusion matrix where the x-axis shows the classifier answer (Clas. Ans.), while the y-axis shows the true diagnosis (Real class=re.cl.), and presented sensitivity of 84.3% and specificity of 68.3%.

FIG. 19A: A classifier using two microRNA (hsa-miR-146b-5p; hsa-miR-551b-3p) as the features for the classification presented sensitivity of 85.2% and specificity of 45.2%. The grey shaded area marks the space in which a sample is classified as malignant, as determined by the classifier. FIG. 19B: A classifier using three microRNAs (hsa-miR-551b-3p; hsa-miR-146b-5p; hsa-miR-222-3p) as the features for the classification presented sensitivity of 84.3% and specificity of 45.2%. Misclassified samples (miscl.) are represented by a dot. FIG. 19C: A classifier using eight microRNAs (hsa-miR-146b-5p; hsa-miR-551b-3p; hsa-miR-222-3p; hsa-miR-125b-5p; hsa-miR-31-5p; hsa-miR-375; hsa-miR-152-3p; hsa-miR-181c-5p) as the features for the classification is shown as a confusion matrix where the x-axis shows the classifier answer (Clas. Ans.), while the y-axis shows the true diagnosis (Real class=re.cl.), and presented sensitivity of 88.7% and specificity of 64.3%.

FIG. 20A-20C: A Discriminant analysis ensemble classifier was used to classify samples from the Indeterminate sub-cohort as malignant (diamonds, M) or benign (squares, B) FIG. 20A: A classifier using two microRNA ratios (hsa-miR-146b-5p:hsa-miR-342-3p; hsa-miR-31-5p:hsa-miR-342-3p) as the features for the classification presented sensitivity of 86.1% and specificity of 61.1%. The grey shaded area marks the space in which a sample is classified as malignant, as determined by the classifier. FIG. 20B: A classifier using three microRNA ratios (hsa-miR-146b-5p:hsa-miR-342-3p; hsa-miR-31-5p:hsa-miR-342-3p; hsa-miR-125b-5p:hsa-miR-200c-3p) as the features for the classification presented sensitivity of 87% and specificity of 57.1%. Misclassified samples (miscl.) are represented by a dot. FIG. 20C: A classifier using eight microRNA ratios (hsa-miR-146b-5p:hsa-miR-342-3p; hsa-miR-31-5p:hsa-miR-342-3p; hsa-miR-125b-5p:hsa-miR-200c-3p; hsa-miR-125b-5p:hsa-miR-138-5p; hsa-miR-222-3p:hsa-miR-486-5p; MID-16582:hsa-miR-200c-3p; MID-16582:hsa-miR-138-5p; hsa-miR-200c-3p:hsa-miR-486-5p) as the features for the classification is shown as a confusion matrix where the x-axis shows the classifier answer (Clas. Ans.), while the y-axis shows the true diagnosis (Real class=re.cl.), presented sensitivity of 89.6% and specificity of 65.1%.

FIG. 21A: A classifier using one microRNA and one microRNA ratio (hsa-miR-146b-5p:hsa-miR-342-3p; hsa-miR-146b-5p) as the features for the classification presented sensitivity of 83.5% and specificity of 58.7%. The grey shaded area marks the space in which a sample is classified as malignant, as determined by the classifier. FIG. 21B: A classifier using two microRNAs and one microRNA ratio (hsa-miR-146b-5p; hsa-miR-551b-3p; hsa-miR-146b-5p:hsa-miR-342-3p) as the features for the classification presented sensitivity of 85.2% and specificity of 65.9%. Misclassified samples (miscl.) are represented by a dot. FIG. 21C: A classifier using five microRNAs and 3 microRNA ratios (hsa-miR-146b-5p; hsa-miR-551b-3p; hsa-miR-222-3p; hsa-miR-125b-5p; hsa-miR-31-5p; hsa-miR-146b-5p:hsa-miR-342-3p; hsa-miR-31-5p:hsa-miR-342-3p; hsa-miR-125b-5p:hsa-miR-200c-3p) as the features for the classification is shown as a confusion matrix where the x-axis shows the classifier answer (Clas. Ans.), while the y-axis shows the true diagnosis (Real class=re.cl.), and presented sensitivity of 87.8% and specificity of 62.7%.

FIG. 22A-22C: A Discriminant analysis classifier was used to classify samples from the Bethesda IV sub-cohort as malignant (diamonds, M) or benign (squares, B). FIG. 22A: A classifier using two microRNAs (hsa-miR-125b-5p; hsa-miR-551b-3p) as the features for the classification presented sensitivity of 91.5% and specificity of 42.9%. The grey shaded area marks the space in which a sample is classified as malignant, as determined by the classifier. FIG. 22B: A classifier using three microRNAs (hsa-miR-125b-5p; hsa-miR-551b-3p; hsa-miR-222-3p) as the features for the classification presented sensitivity of 91.5% and specificity of 39.7%. Misclassified samples (miscl.) are represented by a dot. FIG. 22C: A classifier using eight microRNAs (hsa-miR-125b-5p; hsa-miR-551b-3p; hsa-miR-222-3p; hsa-miR-146b-5p; hsa-miR-375; hsa-miR-181c-5p; hsa-miR-31-5p; hsa-miR-138-5p) as the features for the classification is shown as a confusion matrix where the x-axis shows the classifier answer (Clas. Ans.), while the y-axis shows the true diagnosis (Real class=re.cl), and presented sensitivity of 89.4% and specificity of 47.6%.

FIG. 23A: Classifier using two microRNA ratios (hsa-miR-125b-5p:hsa-miR-200c-3p; hsa-miR-146b-5p:hsa-miR-342-3p) as the features for the classification presented sensitivity of 89.4% and specificity of 28.6%. The grey shaded area marks the space in which a sample is classified as malignant, as determined by the classifier. FIG. 23B: Classifier using three microRNA ratios (hsa-miR-125b-5p:hsa-miR-200c-3p; hsa-miR-146b-5p:hsa-miR-342-3p; hsa-miR-31-5p:hsa-miR-342-3p) as the features for the classification presented sensitivity of 91.5% and specificity of 30.2%. Misclassified samples (miscl.) are represented by a dot. FIG. 23C: Classifier using eight microRNA ratios (hsa-miR-125b-5p:hsa-miR-200c-3p; hsa-miR-146b-5p:hsa-miR-342-3p; hsa-miR-31-5p:hsa-miR-342-3p; MID-16582:hsa-miR-138-5p; hsa-miR-222-3p:hsa-miR-486-5p; MID-16582:hsa-miR-200c-3p; hsa-miR-125b-5p: hsa-miR-138-5p; hsa-miR-200c-3p:hsa-miR-486-5p) as the features for the classification, as shown as a confusion matrix where the x-axis shows the classifier answer (Clas. Ans.), while the y-axis shows the true diagnosis (Real class=re.cl.), and presented sensitivity of 80.9% and specificity of 57.1%.

FIG. 24A-24C: A Discriminant analysis classifier was used to classify samples from the Bethesda IV sub-cohort as malignant (diamonds, M) or benign (squares, B) using microRNAs and microRNA ratios. FIG. 24A: Classifier using one microRNA and one microRNA ratio (hsa-miR-125b-5p; hsa-miR-125b-5p:hsa-miR-200c-3p) as the features for the classification presented sensitivity of 93.6% and specificity of 33.3%. The grey shaded area marks the space in which a sample is classified as malignant, as determined by the classifier. FIG. 24B: Classifier using one microRNA and two microRNA ratios (hsa-miR-125b-5p; hsa-miR-125b-5p:hsa-miR-200c-3p; hsa-miR-146b-5p:hsa-miR-342-3p) as the features for the classification presented sensitivity of 89.4% and specificity of 41.3%. Misclassified samples (miscl.) are represented by a dot. FIG. 24C: Classifier using four microRNAs and four microRNA ratios (hsa-miR-125b-5p; hsa-miR-551b-3p; hsa-miR-222-3p; hsa-miR-146b-5p; hsa-miR-125b-5p:hsa-miR-200c-3p; hsa-miR-146b-5p:hsa-miR-342-3p; hsa-miR-31-5p:hsa-miR-342-3p; MID-16582:hsa-miR-138-5p) as the features for the classification is shown as a confusion matrix where the x-axis shows the classifier answer (Clas. Ans.), while the y-axis shows the true diagnosis (Real class=re.cl), and presented sensitivity of 87.2% and specificity of 46%.

FIG. 25A: Classifier using six microRNAs (hsa-miR-125b-5p; hsa-miR-551b-3p; hsa-miR-222-3p; hsa-miR-146b-5p; hsa-miR-375; hsa-miR-181c-5p) as the features for the classification presented sensitivity of 72.3% and specificity of 39.7%. FIG. 25B: Classifier using eight microRNAs (hsa-miR-125b-5p; hsa-miR-551b-3p; hsa-miR-222-3p; hsa-miR-146b-5p; hsa-miR-375; hsa-miR-181c-5p; hsa-miR-31-5p; hsa-miR-138-5p) as the features for the classification presented sensitivity of 66% and specificity of 61.9%. FIG. 25C: Classifier using twelve microRNAs (hsa-miR-125b-5p; hsa-miR-551b-3p; hsa-miR-222-3p; hsa-miR-146b-5p; hsa-miR-375; hsa-miR-181c-5p; hsa-miR-31-5p; hsa-miR-138-5p; hsa-miR-200c-3p; MID-16582; hsa-miR-346; hsa-miR-152-3p) as the features for the classification presented sensitivity of 66% and specificity of 61.9%.

FIG. 26A: Classifier using six microRNA ratios (hsa-miR-125b-5p:hsa-miR-200c-3p; hsa-miR-146b-5p:hsa-miR-342-3p; hsa-miR-31-5p:hsa-miR-342-3p; MID-16582:hsa-miR-138-5p; hsa-miR-222-3p:hsa-miR-486-5p; MID-16582:hsa-miR-200c-3p) as the features for the classification presented sensitivity of 78.7% and specificity of 61.9%. FIG. 26B: Classifier using eight microRNA ratios (hsa-miR-125b-5p:hsa-miR-200c-3p; hsa-miR-146b-5p:hsa-miR-342-3p; hsa-miR-31-5p:hsa-miR-342-3p; MID-16582:hsa-miR-138-5p; hsa-miR-222-3p:hsa-miR-486-5p; MID-16582:hsa-miR-200c-3p; hsa-miR-125b-5p:hsa-miR-138-5p; hsa-miR-200c-3p:hsa-miR-486-5p) as the features for the classification presented sensitivity of 80.9% and specificity of 50.8%.

FIG. 27A: Classifier using four microRNAs and two microRNA ratios (hsa-miR-551b-3p; hsa-miR-222-3p; hsa-miR-146b-5p; hsa-miR-125b-5p; hsa-miR-125b-5p:hsa-miR-200c-3p; hsa-miR-146b-5p:hsa-miR-342-3p) as the features for the classification, presented sensitivity of 63.8% and specificity of 46%. FIG. 27B: Classifier using four microRNAs and four microRNA ratios (hsa-miR-125b-5p; hsa-miR-551b-3p; hsa-miR-222-3p; hsa-miR-146b-5p; hsa-miR-125b-5p: hsa-miR-200c-3p; hsa-miR-146b-5p:hsa-miR-342-3p; hsa-miR-31-5p:hsa-miR-342-3p; MID-16582:hsa-miR-138-5p) as the features for the classification presented sensitivity of 68.1% and specificity of 49.2%. FIG. 27C: Classifier using six microRNAs and six microRNA ratios (hsa-miR-146b-5p; hsa-miR-125b-5p; hsa-miR-551b-3p; hsa-miR-375; hsa-miR-222-3p; hsa-miR-181c-5p; hsa-miR-125b-5p:hsa-miR-200c-3p; hsa-miR-146b-5p:hsa-miR-342-3p; hsa-miR-31-5p:hsa-miR-342-3p; MID-16582:hsa-miR-138-5p; hsa-miR-222-3p:hsa-miR-486-5p; MID-16582:hsa-miR-200c-

3p) as the features for the classification presented sensitivity of 74.5% and specificity of 58.7%.

Figure 28:
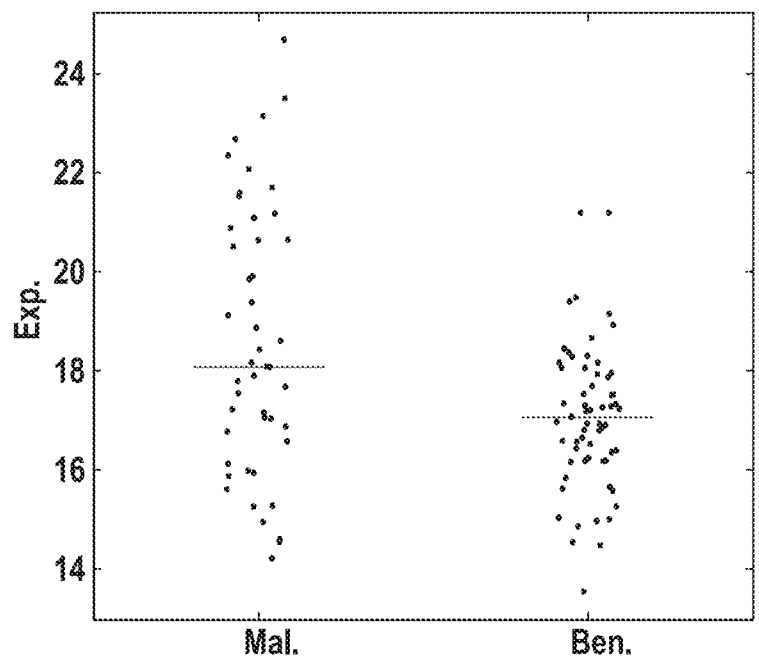

FIG. 28: The normalized expression (Exp.) levels of hsa-miR-146b-5p is shown as a dot plot for Bethesda IV non-medullary malignant ("Mal.") and for benign ("Ben.") samples. Lines represent the median values for each group. Within each group, dots are randomly distributed along the x-axis.

Figure 29:
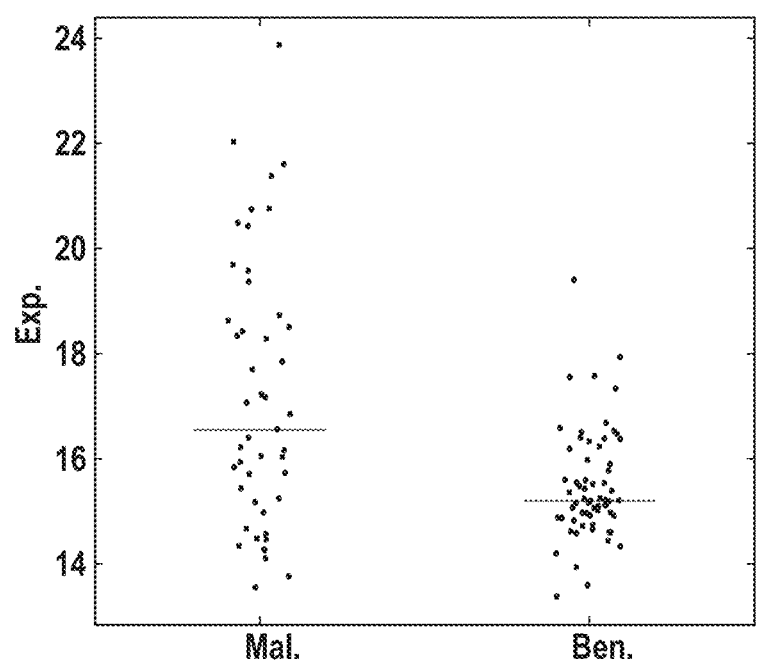

FIG. 29: The normalized expression (Exp.) levels of the microRNA ratio hsa-miR-146b-5p:hsa-miR-342-3p is shown as a dot plot for Bethesda IV non-medullary malignant ("Mal.") and for benign ("Ben.") samples. Lines represent the median values for each group. Within each group, dots are randomly distributed along the x-axis.

Figure 30:
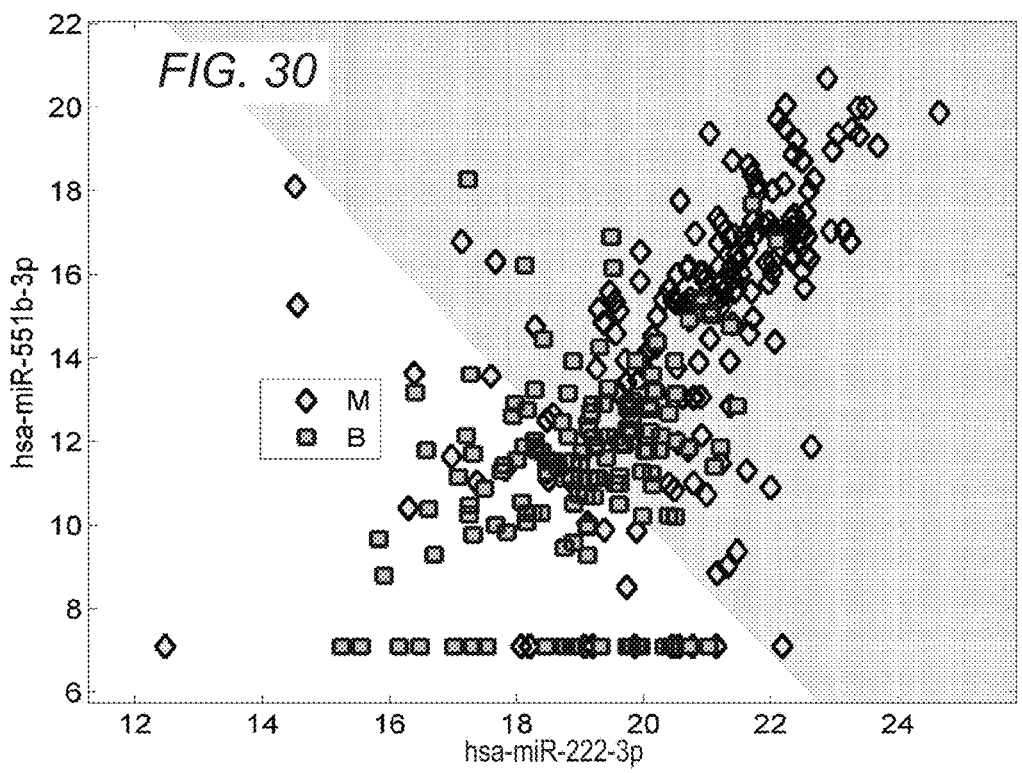

FIG. 30: A Discriminant Analysis classifier was used to classify malignant (diamonds, M) from benign (squares, B) samples, wherein the malignant group included samples of medullary tumor. The normalized values of two microRNA (hsa-miR-222-3p; hsa-miR-551b-3p) were used as features for the classification. The sensitivity of this classifier is 85.2% and the specificity is 53.6%. The grey shaded area marks the space in which a sample is classified as malignant, as determined by the classifier.

Figure 31:
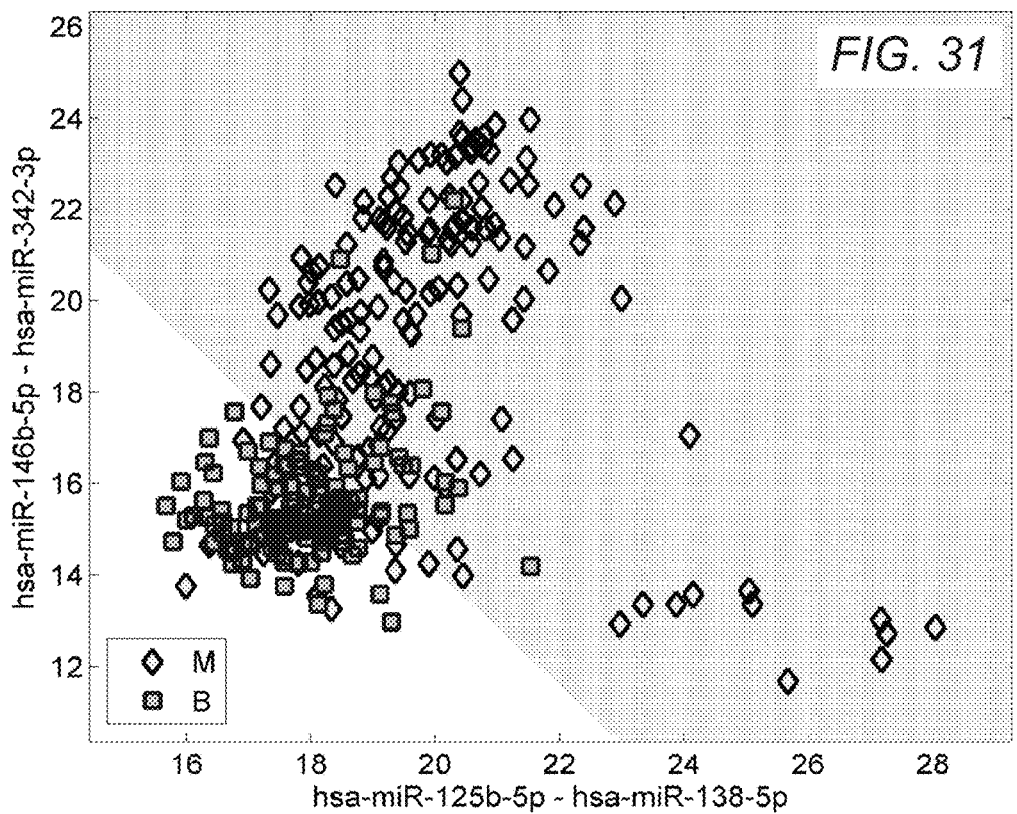

FIG. 31: A Discriminant Analysis classifier was used to classify malignant (diamonds, M) from benign (squares, B) samples, wherein the malignant group included samples of medullary tumor. The values of two microRNA ratios (hsa-miR-125b-5p:hsa-miR-138-5p; hsa-miR-146b-5p:hsa-miR-342-3p) were used as the features for the classification. The sensitivity of this classifier is 84.7% and the specificity is 80.8%. The grey shaded area marks the space in which a sample is classified as malignant, as determined by the classifier.

Figure 32:
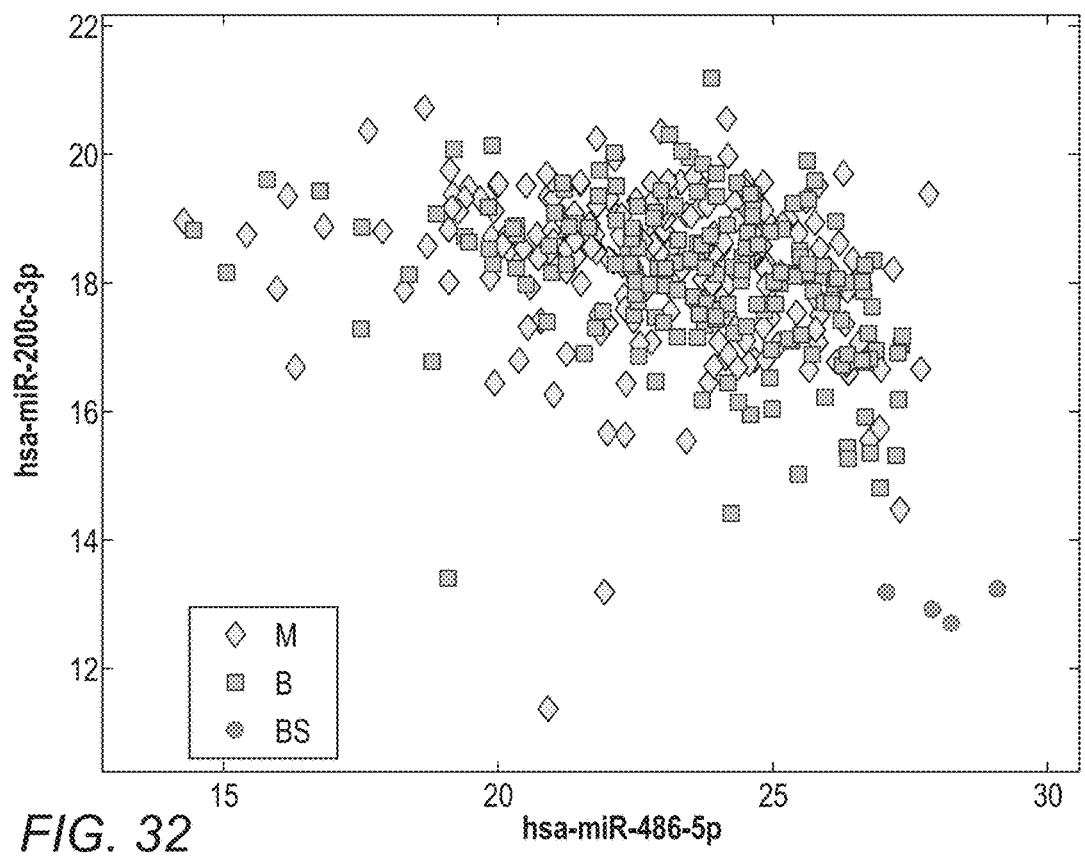

FIG. 32: Expression pattern of hsa-miR-486-5p and hsa-miR-200c-3p is determinant for the quality of the sample. Four samples of blood smears (BS) were analyzed for the expression of hsa-miR-486-5p (SEQ ID NO: 22) and hsa-miR-200c-3p (SEQ ID NO: 23 or 24) in comparison with their expression in malignant (M) and benign (B) thyroid samples. Normalized values for the two miRs are shown (normalized using all normalizers).

Figure 33:
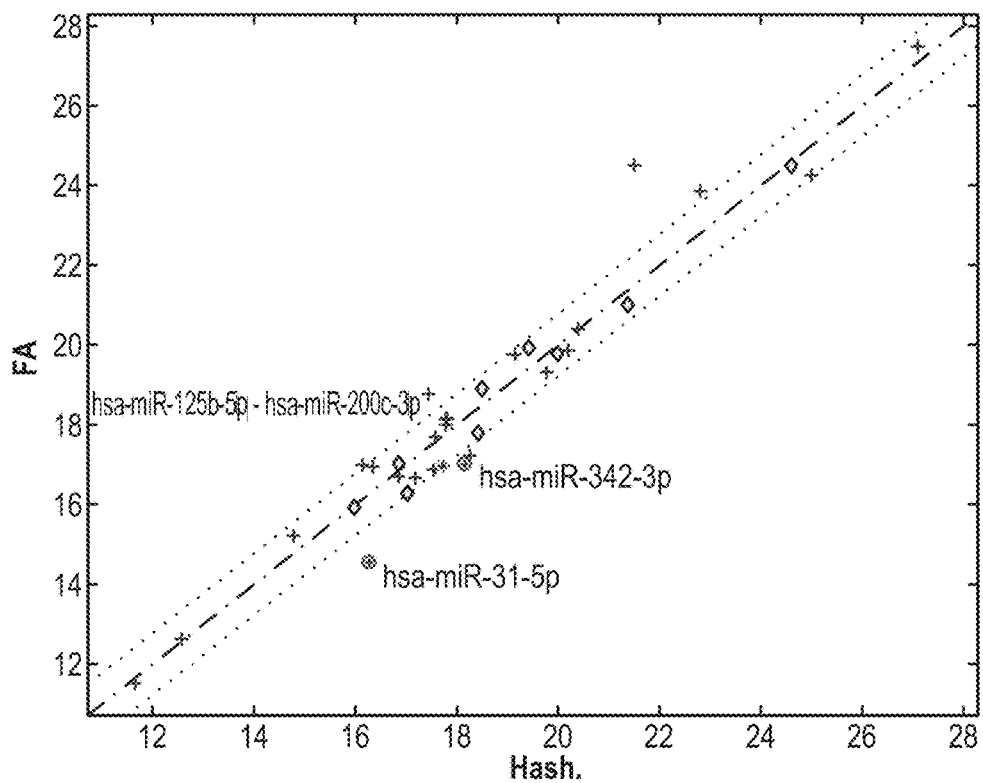

FIG. 33: Sub-typing of Benign Thyroid Tumors. microRNA expression profile (median) was established for two sub-types of benign tumors, Follicular Adenoma (FA, y axis, n=81) and Hashimoto (Hash., x axis, n=6). Each cross represents a microRNA or a microRNA ratio. The ratio hsa-miR-125b-5p:hsa-miR-200c-3p correlated to FA, while expression of hsa-miR-342-3p and hsa-miR-31-5p correlated with Hashimoto. Diamonds represent any one of the microRNAs of SEQ ID NOs. 26-37. Significant microRNAs (p-value for t-test <0.05) are represented by circles.

Figure 34:
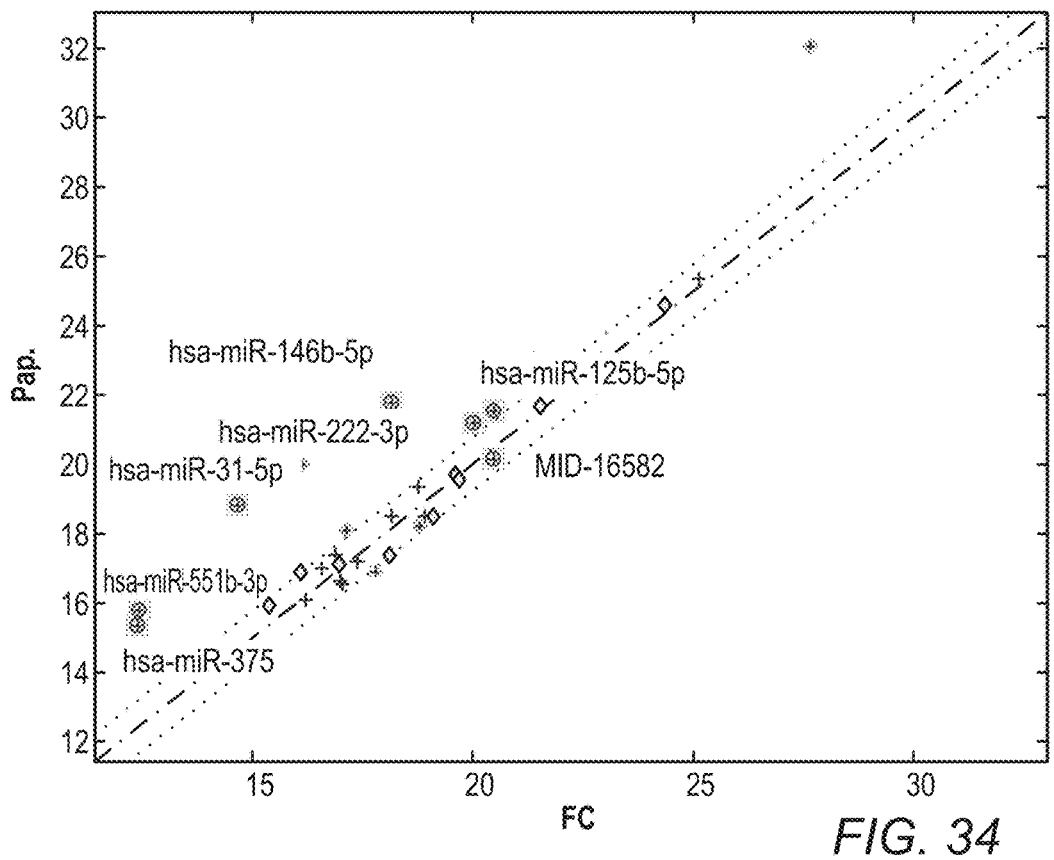

FIG. 34: Sub-typing of Malignant Thyroid Tumors. microRNA expression profile was established for two sub-types of malignant thyroid tumors, papillary carcinoma (Pap.; y-axis, n=161) and follicular carcinoma (FC; x-axis, n=16). Each cross represents a microRNA or a microRNA ratio. Diamonds are any one of the microRNAs of SEQ ID NOs. 26-37. Significant microRNAs (p-value for t-test <0.05) are encircled. Only normalized microRNA values are labeled. Unlabeled circles represent significant ratios.

Figure 35:
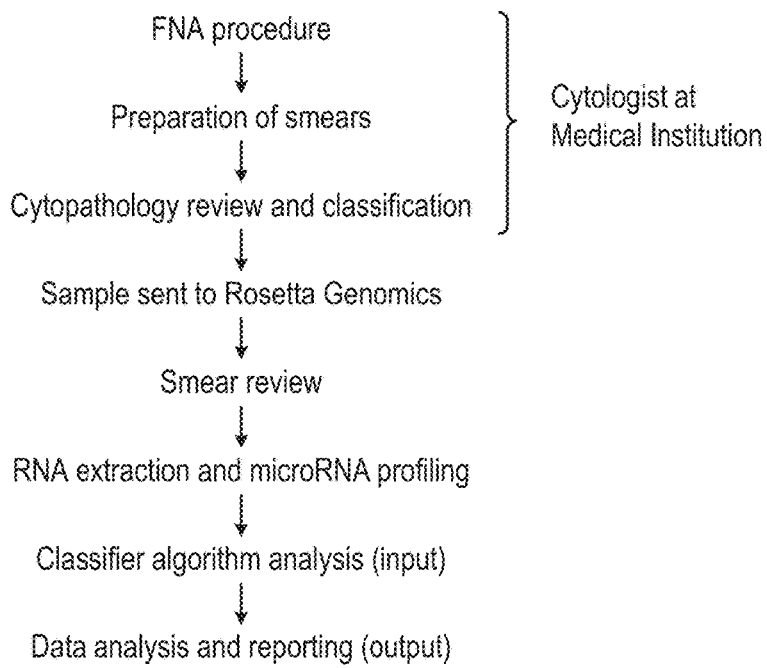

FIG. 35: Flowchart representing the protocol for diagnosis of indeterminate thyroid nodule samples obtained through FNA.

Figure 36:
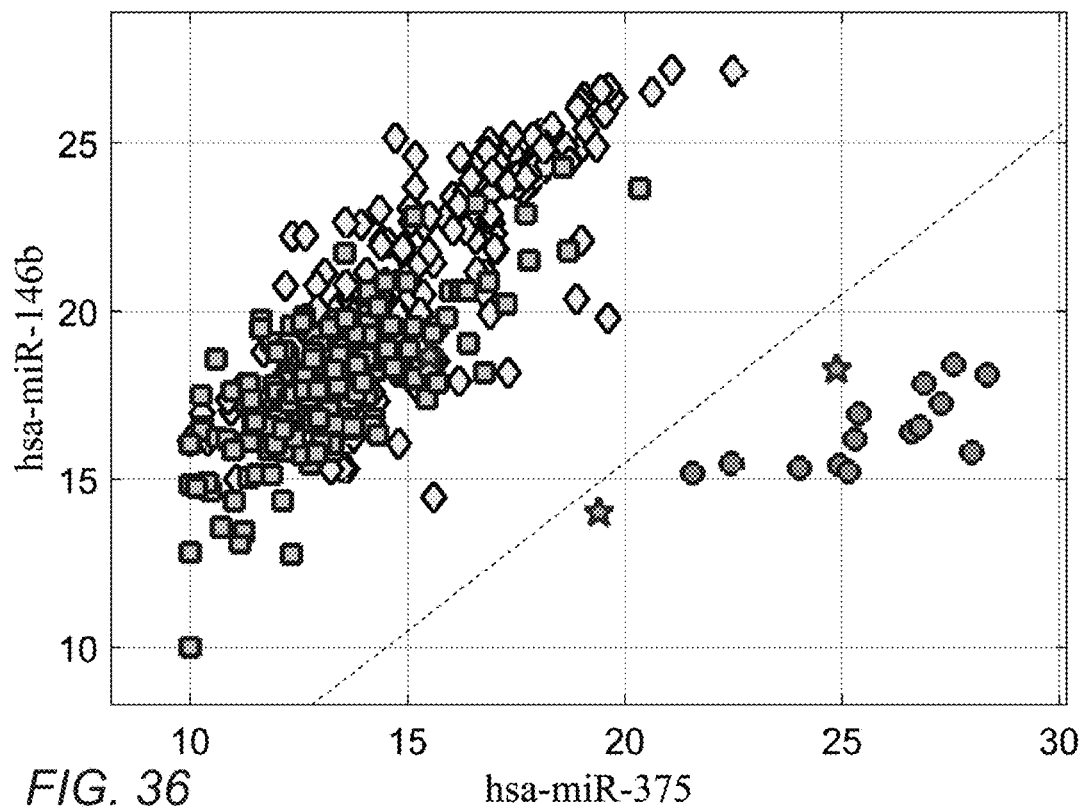

FIG. 36: Medullary carcinoma, Linear Discriminant Analysis step based on the expression of hsa-miR-375. All of the training medullary carcinoma stained smear samples and two of the three medullary validation samples demonstrate over-expression of hsa-miR-375 (x-axis shows hsa-miR-375 expression; y-axis shows hsa-miR-146b expression). Diamonds: malignant non-medullary training samples; squares, benign training samples; circles, medullary carcinoma training samples; stars, medullary carcinoma validation samples.

Figure 37:
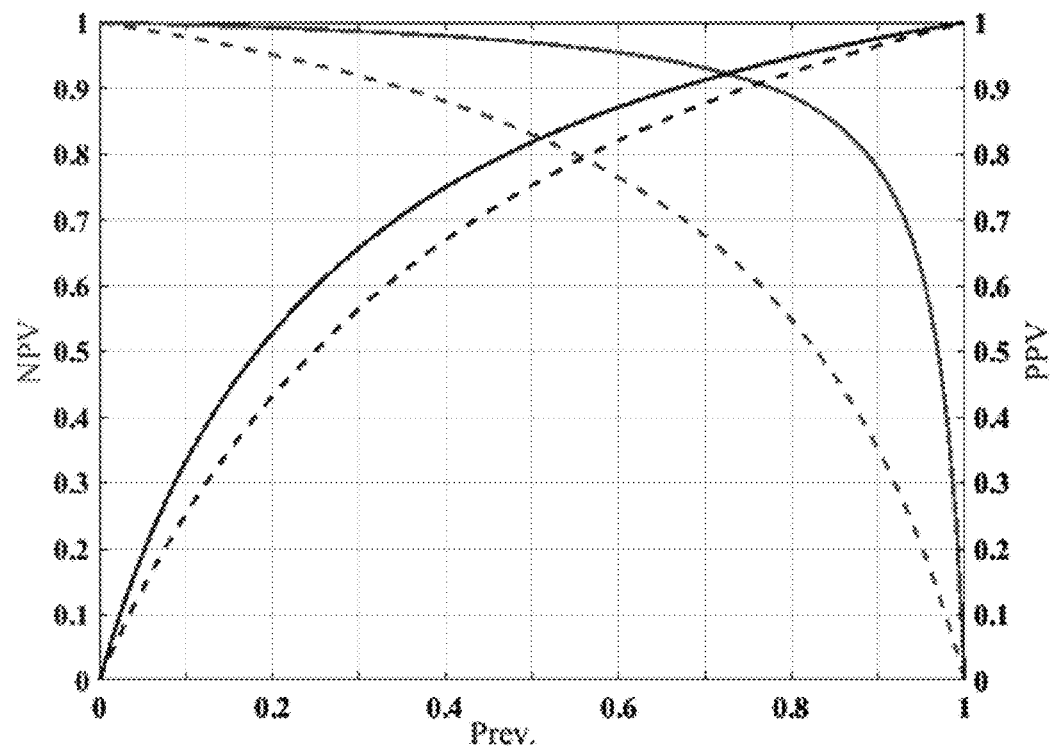

FIG. 37: Negative Predictive Value (NPV) and Positive Predictive Value (PPV) for varying prevalence values. NPV and PPV were calculated, based on the sensitivity and specificity of the entire validation set (85.2% and 71.9%, respectively; dashed lines) and the validation agreement set (97.5% and 78.2%, respectively; solid lines), for varying prevalence (Prev.) values. Calculated NPV: line starts on 1 on the left-hand side. Calculated PPV: lines starts on 1 on the right-hand side. Dotted, thick line: NPV=95%.

DETAILED DESCRIPTION OF THE INVENTION

Despite accumulated efforts in the search for accurate diagnosis of thyroid lesions, a great number of technical problems remain with no solution in sight. As a result of the quality of the material obtained, the diagnosis of thyroid lesions in fine needle aspiration (FNA) samples is still challenging. The low number of cells, the amount of blood, the ratio between thyroid tumor cells and non-thyroid tumor cells in the sample, make it challenging to extract enough material that will provide conclusive results.

The present inventors have developed a first-of-its-kind assay utilizing microRNA expression in FNA smears for distinguishing benign from malignant thyroid nodules. This assay offers a valuable tool for the classification of pre-operative thyroid samples, including those that are presently indeterminate to cytological evaluation.

The present invention provides a sensitive, specific and accurate methodology for distinguishing between malignant and benign thyroid tumors, as well as particular subtypes of thyroid tumors. Distinguishing between different subtypes of thyroid tumors is essential for providing the patient with the best and most suitable treatment. The present invention provides a significant improvement of the technologies currently available in the field of thyroid tumor classification and diagnosis.

The present inventors have developed an integrative platform for the classification of thyroid lesions, by profiling and characterizing microRNA expression in thyroid clinical samples obtained by FNA biopsies, while also overcoming hindrances such as low number of cells in the sample and the amount of blood in the sample by microRNA profiling. This technological platform was applied to stratify thyroid lesions into benign or malignant neoplasms, as well as subtypes of thyroid tumors, as an adjunctive tool in the pre-operative management of thyroid nodules. The inventors have exceptionally developed a method for classification of benign and malignant thyroid lesions, and specific subtypes of thyroid cancer and follicular lesions, while integrating steps for filtering out sub-optimal samples, by implementing specific algorithms based on microRNA profiling. The method is part of an overall protocol, in which existing or available clinical cytological slides having smears from FNA samples may be used, without the need to generate or collect additional material from the patients.

The present method further incorporates the analysis of microRNAs in minute amounts of RNA material from cytological samples. Once an FNA sample is collected, between one and several passes of material are smeared onto slides. Currently available methods usually require the use of several passes for having enough material for analysis. The present inventors developed a method in which even only one FNA slide provides sufficient material for microRNA detection. In addition, the method developed by the inventors allows for the analysis of samples having very small amounts of cells, such as samples having 50 cells, up to 120 cells and over.

The present method includes steps for eliminating or disqualifying samples that lack thyroid cells and/or in which non-thyroid cells, such as blood cells, are over-represented.

The assay developed by the present inventors accurately differentiates benign from malignant thyroid nodules in indeterminate FNA smears. The assay is advantageous over other previous diagnostic methods for thyroid nodules particularly in regard to its performance for cases in which all pathologists are in full agreement, showing 98% of sensitivity (95% confidence interval [CI], 87-100%); 78% of specificity (CI, 69-85%); a Negative Predictive Value (NPV) of 99% (CI, 94-100%); and a Positive Predictive Value (PPV) of 62% (CI, 49-74%). Performance for the overall validation sample set was 85% Sensitivity (CI, 74-93%); 72% Specificity (CI, 63-79%); 91% of NPV (CI, 84-96%); and 59% of PPV (CI, 48-69%).

Thus the present inventors have identified a unique microRNA expression signature for thyroid lesions through profiling the expression of the microRNAs denoted by SEQ ID NOs.1-308. A microRNA expression signature for classification of thyroid lesions is also obtained through profiling the expression of at least ten of the microRNAs denoted by SEQ ID NOs.1-37. Alternatively, a microRNA expression signature for classification of thyroid lesions is obtained through profiling the expression of at least seven of the microRNAs denoted by SEQ ID NOs.1-37.

More specifically, the present inventors have develop a platform for classification of thyroid clinical samples based on the levels of expression of a set of microRNAs, comprising at least two microRNAs, selected from the group consisting of hsa-miR-31-5p (SEQ ID NO: 5, 6, or 7), hsa-miR-424-3p (SEQ ID NO: 16), hsa-miR-222-3p (SEQ ID NO: 1 or 2), hsa-miR-146b-5p (SEQ ID NO: 10 or 11), hsa-miR-346 (SEQ ID NO: 14), MID-16582 (SEQ ID NO: 25), hsa-miR-342-3p (SEQ ID NO: 17 or 18), hsa-miR-181c-5p (SEQ ID NO: 15), hsa-miR-125b-5p (SEQ ID NO: 9), hsa-miR-375 (SEQ ID NO: 8), hsa-miR-486-5p (SEQ ID NO: 22), hsa-miR-551b-3p (SEQ ID NO: 3 or 4), hsa-miR-152-3p (SEQ ID NO: 12 or 13), hsa-miR-200c-3p (SEQ ID NO: 23 or 24) and hsa-miR-138-5p (SEQ ID NO: 19, 20, or 21); or a sequence at least 80%, at least 85%, or at least 90% identical thereto. The platform was established based on a training study with a robust cohort, and which also included the optional measurement of additional microRNAs that served as normalizers.

Variations of said platform for classification of thyroid clinical samples, particularly clinical samples classified as Bethesda III, IV and/or V, include determining the levels of expression of at least ten (10) microRNAs comprised in the group consisting of hsa-miR-375 (SEQ ID NO: 8), hsa-miR-146b-5p (SEQ ID NO: 10 or 11), hsa-miR-342-3p (SEQ ID NO: 17 or 18), hsa-miR-551b-3p (SEQ ID NO: 3 or 4), hsa-miR-31-5p (SEQ ID NO: 5, 6, or 7), hsa-miR-125b-5p (SEQ ID NO: 9), hsa-miR-138-5p (SEQ ID NO: 19, 20, or 21), hsa-miR-152-3p (SEQ ID NO: 12 or 13), hsa-miR-574-3p (SEQ ID NO: 36 or 37), hsa-miR-222-3p (SEQ ID NO: 1 or 2), hsa-miR-23a-3p (SEQ ID NO: 26), MID-16582 (SEQ ID NO: 25), and hsa-miR-486-5p (SEQ ID NO: 22); or a sequence at least 80%, at least 85%, at least 90%, or at least 95% identical thereto.

Alternatively, the classification of thyroid clinical samples, particularly FNA samples classified as Bethesda III, IV and/or V, include determining the levels of expression of eleven microRNAs comprised in the group consisting of hsa-miR-375 (SEQ ID NO: 8), hsa-miR-146b-5p (SEQ ID NO: 10 or 11), hsa-miR-342-3p (SEQ ID NO: 17 or 18), hsa-miR-551b-3p (SEQ ID NO: 3 or 4), hsa-miR-31-5p (SEQ ID NO: 5 or 7), hsa-miR-125b-5p (SEQ ID NO: 9), hsa-miR-138-5p (SEQ ID NO: 19, 20, or 21), hsa-miR-152-3p (SEQ ID NO: 12 or 13), hsa-miR-574-3p (SEQ ID NO: 36 or 37), hsa-miR-222-3p (SEQ ID NO: 1 or 2), hsa-miR-23a-3p (SEQ ID NO: 26), MID-16582 (SEQ ID NO: 25), and hsa-miR-486-5p (SEQ ID NO: 22); or a sequence at least 80%, at least 85%, at least 90%, or at least 95% identical thereto. Further to determining the level of expression of at least ten (10) microRNAs as denoted above, the method may comprise optionally determining the level of expression of two additional microRNAs as denoted above.

The present invention is particularly useful for the 25% of the cases in which FNA specimens present inconclusive results in cytopathology, usually referred to as "indeterminate", and which include thyroid lesion samples classified in Bethesda categories III, IV and V. In current medical practice, patients with specimens falling within this category undergo repeat FNA procedure, or surgery, including lobectomy and thyroidectomy.

Thus, in one embodiment, the present invention provides a method of classification for thyroid lesion samples that fall into the "indeterminate" cases, classified in categories III, IV and V of the Bethesda System (described further herein). In one particular embodiment, the present invention provides a method of classification for thyroid lesion samples classified in category IV of the Bethesda System, which relates to "Follicular Neoplasm" or "Suspicious of a Follicular Neoplasm", which is known to be the most difficult category to be classified.

Thus, the present invention presents primarily a protocol for management of thyroid lesion samples which failed to be classified by cytopathological analysis. Particular samples that are of interest are those obtained by FNA. In one embodiment, routine smears from FNA samples are used. In another embodiment, FNA samples in preservative solutions may be used. Total RNA is extracted from the FNA samples, and the expression of microRNAs is measured. In one embodiment, the expression of about 2200 microRNAs is measured. In another embodiment, the expression of 182 microRNAs, comprising the sequences of SEQ ID NO: 1-182 is measured. In a further embodiment, the expression of the microRNAs comprising the sequences of SEQ ID NO: 1-37 is measured. In another further embodiment, at least three, at least four, at least five, at least six, at least seven, at least eight, at least nine, at least ten, at least eleven, at least twelve, at least thirteen, at least fourteen, or all microRNAs from the group selected from hsa-miR-31-5p (SEQ ID NO: 5, 6, or 7), hsa-miR-424-3p (SEQ ID NO: 16), hsa-miR-222-3p (SEQ ID NO: 1 or 2), hsa-miR-146b-5p (SEQ ID NO: 10 or 11), hsa-miR-346 (SEQ ID NO: 14), MID-16582 (SEQ ID NO: 25), hsa-miR-342-3p (SEQ ID NO: 17 or 18), hsa-miR-181c-5p (SEQ ID NO: 15), hsa-miR-125b-5p (SEQ ID NO: 9), hsa-miR-375 (SEQ ID NO: 8), hsa-miR-486-5p (SEQ ID NO: 22), hsa-miR-551b-3p (SEQ ID NO: 3 or 4), hsa-miR-152-3p (SEQ ID NO: 12 or 13), hsa-miR-200c-3p (SEQ ID NO: 23 or 24), hsa-miR-138-5p (SEQ ID NO: 19, 20, or 21), hsa-miR-23a-3p (SEQ ID NO: 26), and hsa-miR-574-3p (SEQ ID NO: 36 or 37), or a sequence at least 80%, at least 85%, or at least 90% identical thereto, are measured and used in the classification.

In a further embodiment, classification of the thyroid sample as malignant or benign comprises measuring the expression levels of hsa-miR-222-3p (SEQ ID NO: 1 or 2), hsa-miR-551b-3p (SEQ ID NO: 3 or 4), hsa-miR-31-5p (SEQ ID NO: 5, 6, or 7), hsa-miR-375 (SEQ ID NO: 8), hsa-miR-125b-5p (SEQ ID NO: 9), hsa-miR-146b-5p (SEQ ID NO: 10 or 11), hsa-miR-152-3p (SEQ ID NO: 12 or 13), hsa-miR-346 (SEQ ID NO: 14), hsa-miR-181c-5p (SEQ ID NO: 15), hsa-miR-424-3p (SEQ ID NO: 16), hsa-miR-342-3p (SEQ ID NO: 17 or 18), hsa-miR-138-5p (SEQ ID NO: 19, 20, or 21), hsa-miR-486-5p (SEQ ID NO: 22), hsa-miR-200c-3p (SEQ ID NO: 23 or 24), MID-16582 (SEQ ID NO: 25), or any combination thereof, or a sequence at least 80%, at least 85%, or at least 90% identical thereto, providing the levels of expression to a classifier which analyzes and classifies the sample as malignant or benign.

Thus, the present invention provides a method for distinguishing between malignant and benign thyroid tumor lesions in a subject in need, said method comprising obtaining a thyroid tumor lesion sample from said subject, or provided a biological sample obtained from said subject, determining an expression profile in said sample of one or more, or at least four, at least eight, at least eleven, at least thirteen microRNAs comprising SEQ ID NOS: 1-37, or a sequence at least 80%, at least 85%, at least 90%, or at least 95% identical thereto, or any combination of said microRNAs, by hybridization or by amplification, comparing said expression profile to a reference threshold value by using a classifier algorithm; and determining whether the thyroid lesion is malignant or benign. In one particular embodiment, the method of the invention is for distinguishing sub-types of malignant or benign thyroid tumor lesions.

In one embodiment, the method of the invention comprises measuring the expression of at least four of the microRNAs comprising SEQ ID NOS: 1-37, obtaining the microRNA expression profile value of said sample, and using a classifier to establish, based on said value, whether the thyroid lesion is malignant or benign, and optionally further classifying the sample into one of the malignant or benign subtypes.

In one particular embodiment, said determining an expression profile by hybridization comprises contacting the sample with probes that hybridize to each of SEQ ID NOS: 1-37, or to a sequence at least 80%, at least 85%, or at least 90% identical thereto. In another embodiment, said determining an expression profile by hybridization comprises contacting the sample with probes that hybridize with at least eight, at least ten, at least twelve, at least fourteen, or at least sixteen contiguous nucleotides of said microRNA comprising SEQ ID NOS: 1-37.

The present invention further provides a method of classifying a sample as malignant or benign, and/or sub-typing said sample, whereby, further to measuring the expression levels of microRNAs in the sample, obtaining an expression profile and optionally calculating microRNA ratios, applying a multi-step analysis of the expression data. Said multi-step analysis comprising applying one or more algorithms, in parallel or sequentially, to at least one of the microRNA expression profiles, microRNA ratios, or a combination thereof. Said multi-step analysis may also further include analyzing the expression of one or more single microRNA levels which may be indicative of the overall quality of the sample.

Examples of criteria that may be included in the multi-step analysis, in any order and in any combination, are: the expression of non-malignant cell markers, the expression of microRNAs that correlate with a specific sub-type of thyroid tumor, and the like. Thus for example, one step may be examining whether the expression of non-thyroid cell markers is higher or lower than the threshold established in the data set, e.g. the training data set, in which case the sample may be disqualified. Another further step may be examining the expression of a microRNA or microRNA ratio that correlates with a thyroid tumor sub-type, e.g. if the expression of hsa-miR-342-3p (SEQ ID NO: 17 or 18) is very high compared to the threshold established in the data set, e.g. the training data set, the sample may be classified as benign, and further sub-typed as being Hashimoto. Alternatively, if the expression of hsa-miR-342-3p (SEQ ID NO: 17 or 18) is very high compared to the threshold established in the data set, e.g. the training data set, the sample may be disqualified for lack of sufficient thyroid cells. Another further optional step may relate to the level of expression of MID-16582 (SEQ ID NO: 25), may be used to determine whether the sample may be discarded, or analyzed using a classifier specific for these samples in which MID-16582 (SEQ ID NO: 25) is high (compared to the threshold established in the training set).

In one particular embodiment of the invention, said non-thyroid cell marker is a blood cell marker.

In another particular embodiment of the invention, said cell marker is an epithelial cell marker.

In a further particular embodiment of the invention, said cell marker is a blood cell marker, a white blood cell marker or an epithelial cell marker. Examples of blood cell markers are hsa-miR-486-5p (SEQ ID NO: 22), hsa-miR-320a (SEQ ID NO: 173), hsa-miR-106a-5p (SEQ ID NO: 150), hsa-miR-93-5p (SEQ ID NO: 182), hsa-miR-17-3p (SEQ ID NO: 160), hsa-let-7d-5p (SEQ ID NO: 144), hsa-miR-107 (SEQ ID NO: 152), hsa-miR-103a-3p (SEQ ID NO: 149), hsa-miR-17-5p (SEQ ID NO: 161), hsa-miR-191-5p (SEQ ID NO: 163), hsa-miR-25-3p (SEQ ID NO: 167), hsa-miR-106b-5p (SEQ ID NO: 151), hsa-miR-20a-5p (SEQ ID NO: 166), hsa-miR-18a-5p (SEQ ID NO: 40), hsa-miR-144-3p (SEQ ID NO: 154), hsa-miR-140-3p (SEQ ID NO: 51), hsa-miR-15b-5p (SEQ ID NO: 157), hsa-miR-16-5p (SEQ ID NO: 159), hsa-miR-92a-3p (SEQ ID NO: 181), hsa-miR-484 (SEQ ID NO: 179), hsa-miR-151a-5p (SEQ ID NO: 156), hsa-let-7f-5p (SEQ ID NO: 145), hsa-let-7a-5p (SEQ ID NO: 141), hsa-let-7c-5p (SEQ ID NO: 143), hsa-let-7b-5p (SEQ ID NO: 142), hsa-let-7g-5p (SEQ ID NO: 146), hsa-let-7i-5p (SEQ ID NO: 147), hsa-miR-185-5p (SEQ ID NO: 162), hsa-miR-30d-5p (SEQ ID NO: 172), hsa-miR-30b-5p (SEQ ID NO: 170), hsa-miR-30c-5p (SEQ ID NO: 171), hsa-miR-19b-3p, hsa-miR-26a-5p (SEQ ID NO: 168), hsa-miR-26b-5p (SEQ ID NO: 169), hsa-miR-425-5p (SEQ ID NO: 176), MID-19433 (SEQ ID NO: 133), and hsa-miR-4306 (SEQ ID NO: 177). Examples of white blood cell markers are hsa-miR-342-3p (SEQ ID NO: 17 or 18), hsa-miR-146a-5p and hsa-miR-150-5p (SEQ ID NO: 59). Examples of epithelial markers are hsa-miR-200c-3p (SEQ ID NO: 23 or 24), hsa-miR-138-5p (SEQ ID NO: 19, 20, or 21), hsa-miR-3648 (SEQ ID NO: 174), hsa-miR-125b-5p (SEQ ID NO: 9), hsa-miR-125a-5p (SEQ ID NO: 153), hsa-miR-192-3p (SEQ ID NO: 164), hsa-miR-4324 (SEQ ID NO: 178), hsa-miR-376a-3p (SEQ ID NO: 175).

Thus, quality assessment (QA) or quality control (QC) of the sample may be one of the steps of the multi-step analysis of the expression data, or one of the steps of the method of the invention. In the context of the method of the invention, QC relates to the expression profile of microRNAs of any one of SEQ ID NOS. 1-37, or to the ratio of the expression level of at least one pair of microRNAs of any one of SEQ ID NOS. 1-37. Therefore, the expression profile or the ratio of the expression levels of microRNAs are optionally used indicators of sample quality.

As referred to herein, said microRNA ratio is the ratio between the normalized or non-normalized expression level of a pair of microRNAs, wherein the expression level of one microRNA is used as the numerator and the expression level of a second microRNA is the denominator.

Examples of pairs of microRNAs whose expression level ratios are used in the classifier are hsa-miR-125b-5p:hsa-miR-138-5p; hsa-miR-146b-5p:hsa-miR-342-3p; hsa-miR-125b-5p:hsa-miR-200c-3p; hsa-miR-375:hsa-miR-146b; hsa-miR-551b-3p:hsa-miR-23a-3p; hsa-miR-31-5p:hsa-miR-342-3p; hsa-miR-222-3p:hsa-miR-486-5p; hsa-miR-200c-3p:hsa-miR-486-5p; MID-16582:hsa-miR-200c-3p; MID-16582:hsa-miR-138-5p; hsa-miR-222-3p:MID-16582; and the like.

In another particular embodiment, said determining an expression profile comprises contacting the sample with RT-PCR reagents, including forward and reverse primers as exemplified herein in the Examples, and generating RT-PCR products.

In a further particular embodiment, said method comprises contacting RT-PCR products with specific or general probes, or a combination thereof, as exemplified herein in the Examples, detecting and measuring the PCR products.

In a further embodiment, said determining an expression profile comprises measuring microRNA expression by hybridization, using microarrays and the like. In another further embodiment, said determining an expression profile comprises measuring microRNA expression by next-generation sequencing.

The method of the invention further comprises optionally determining the expression profile of at least one microRNA to be used as normalizer. In this context, any microRNA as described in Table 1 may be used as a normalizer. In one particular embodiment, any of the microRNAs comprising SEQ ID NO: 26-37, or a sequence at least 80%, 85%, 90%, or 95% identical thereto, are used as normalizers.

The present inventors have surprisingly found that the classification of a thyroid tumor sample is improved when a number of markers, from different categories as defined and exemplified herein are used. Said markers may be any one of malignant markers, secondary markers and cell-type markers, or any combination thereof, comprising SEQ ID NOS: 1-25, or a sequence at least 80%, 85%, 90%, or 95% identical thereto. In order to perform the method of the invention, the full set of markers may be used. Alternatively, any combination of malignant, secondary and cell-type markers may be used. Thus, the method may comprise at least one malignant marker, in association with at least one secondary marker and/or at least one cell-type marker.

Depending on the analysis of the data, each of the cell type markers may be used as in the form of raw or normalized signals. Alternatively, the cell type markers may be used as a preliminary test prior to performing the classification, in order to determine whether the sample has sufficient relevant material to perform classification, or whether the sample should be discarded. Yet another option is to use the cell-type markers as part of the final classifier, where the signal of the cell type marker is used by the classifier. A further option is to use the cell-type markers as the denominator of a miR ratio optionally used by the classifier. For example, the expression level of a malignant or a secondary marker may be divided by the expression level of a cell-type marker, and the resulting miR ratio used in the classifier.

Thus, in a further embodiment of the method for distinguishing between malignant and benign thyroid tumor lesions in a subject in need, said classifier may be any one of a single classifier, a multi-step classifier, a classifier which uses all the malignant markers, a classifier which uses a subset of the malignant markers, a classifier which uses all the malignant markers and the secondary markers, a classifier which uses a subset of the malignant markers and a subset of the secondary markers, a classifier which uses all the malignant markers and the secondary markers and the cell type markers, a classifier which employs a subset of all the malignant markers and the secondary markers and the cell type markers, a classifier which uses all or a subset of the malignant markers and all or a subset of the cell type markers.

In another further embodiment of the method or the protocol of the invention, the performance of the classification may be improved by further combining the result from the algorithm classifier with additional clinical or molecular data available for the thyroid sample being analyzed. Additional data available may be related to the thyroid lesion, such as the size of the nodule, the number of nodules; it may relate to other clinical information available for the subject from whom the sample was obtained, such as molecular test results, like the expression of other molecular markers, genetic markers, biochemical test results, blood test results, urine test results, recurrence, prognosis data, family history, patient medical history, and the like. Other data that may also be combined is thyroid genetic data, such as mutation analysis, gene fusions, chromosomal rearrangements, gene expression, protein expression, and the like.

Therapeutic indications may vary according to the diagnostic obtained with the method or protocol of the invention. Typically there are five types of therapy that may be administered to a thyroid cancer patient: surgery, radiation therapy, chemotherapy, thyroid hormone therapy and targeted therapy.

Surgery is the most common treatment of thyroid cancer. One of the following procedures may be used:

Lobectomy: Removal of the lobe in which thyroid cancer is found. Biopsies of lymph nodes in the area may be done to see if they contain cancer.

Near-total thyroidectomy: Removal of all but a very small part of the thyroid.

Total thyroidectomy: Removal of the whole thyroid.

Lymphadenectomy: Removal of lymph nodes in the neck that contain cancer.

Thyroidectomy is a surgical procedure that has several potential complications or sequela including: temporary or permanent change in voice, temporary or permanently low calcium, need for lifelong thyroid hormone replacement, bleeding, infection, and the remote possibility of airway obstruction due to bilateral vocal cord paralysis. Therefore, accurate diagnosis which would prevent the unnecessary removal of the thyroid gland is very desirable.

Radiation therapy uses high-energy x-rays or other types of radiation to eliminate cancer cells or inhibit their proliferation. There are two types of radiation therapy. External radiation therapy uses a machine outside the body to send radiation toward the cancer. Internal radiation therapy uses a radioactive substance sealed in needles, seeds, wires, or catheters that are placed directly into or near the cancer. The radiation therapy of choice will be dependent on the type and stage of the thyroid cancer. Radiation therapy may be supplementary to surgery in order to eliminate cancer cells that were not successfully removed. Follicular and papillary thyroid cancers may be treated with radioactive iodine (RAI)

therapy. RAI is administered orally and collects in any remaining thyroid tissue, including thyroid cancer cells that have spread to other places in the body. Since only thyroid tissue takes up iodine, the RAI destroys thyroid tissue and thyroid cancer cells without harming other tissues. Before a full treatment dose of RAI is given, a small test-dose is given to see if the tumor takes up the iodine.

Chemotherapy is another option for thyroid cancer treatment. Chemotherapy may be administered orally or by injection, intravenous or intramuscular. Chemotherapy may also be administered directly into the cancer affected area instead of systemically. The choice of administration will depend on the type and stage of the cancer. A few examples of drugs that have been approved for thyroid cancer treatment are: Adriamycin PFS (Doxorubicin Hydrochloride), Adriamycin RDF (Doxorubicin Hydrochloride), Cabozantinib-S-Malate, Caprelsa (Vandetanib), Cometriq (Cabozantinib-S-Malate), Doxorubicin Hydrochloride, Nexavar (Sorafenib Tosylate), Sorafenib Tosylate and Vandetanib.

Thyroid hormone therapy http://www.cancer.gov/Common/PopUps/ popDefinition.aspx?id=45110&version=Patient&language=English is a cancer treatment that removes hormones or blocks their action and inhibits cancer cell proliferation. In the treatment of thyroid cancer, drugs may be given to prevent thyroid-stimulating hormone (TSH) production, in order to avoid that the hormone would induce the growth or recurrence of the thyroid cancer.

Also, because thyroid cancer treatment specifically targets thyroid cells, the thyroid is not able to make enough thyroid hormone. Patients are given thyroid hormone replacement pills.

Targeted therapy uses drugs or other substances to identify and attack specific cancer cells without harming normal cells. Tyrosine kinase inhibitor (TKI) therapy blocks signal transduction in thyroid cancer cells, inhibiting their growth. Vandetanib is a TKI used to treat thyroid cancer.

Dosage and duration of any therapy will depend on individual evaluation of the patient and on standard practice known by the health care provider. The duration of treatment is the period of time during which doses of a pharmaceutical agent or pharmaceutical composition are administered.

The identification and differentiation of the thyroid tumor, firstly as benign or malignant, and subsequently its classification into the various subtypes through the analysis of differentially expressed microRNAs can provide further clues to the biological differences between the subtypes, their diverging oncogenetic processes and possible new targets for type-specific target therapy.

The present invention provides diagnostic assays and methods, both quantitative and qualitative, for detecting, diagnosing, monitoring, staging and prognosticating thyroid cancers by comparing levels of the specific microRNA molecules as described herein. Such levels are measured in a patient sample, which may be from a biopsy, tumor samples, cells, tissues and/or bodily fluids.

Thus, the method of the invention is particularly useful for discriminating between different subtypes of malignant thyroid tumors, such types being follicular carcinoma, papillary carcinoma, follicular variant of papillary carcinoma (FVPC or FVPTC), encapsulated FVPC (or encapsulated FVPTC), medullary carcinoma, anaplastic thyroid cancer, poorly differentiated thyroid cancer, and for determining the therapeutic course to be followed after diagnosis. In a further embodiment, the present invention provides a method for classifying sub-types of benign thyroid tumor, e.g. follicular adenoma, Hashimoto thyroiditis, hyperplasia (Goiter).

The present invention also provides a method of treatment of thyroid cancer, said method comprising the method of distinguishing between benign or malignant thyroid tumor as described herein, optionally subtyping the thyroid tumor type, and administering the treatment according to the diagnosis provided by the present method.

All the methods of the present invention may optionally further include measuring levels of other cancer markers. Other cancer markers, in addition to said microRNA molecules useful in the present invention, will depend on the cancer being tested and are known to those of skill in the art.

Assay techniques that can be used to determine levels of gene expression, such as the nucleic acid sequence of the present invention, in a sample derived from a patient are well known to those of skill in the art. Such assay methods include, but are not limited to, reverse transcriptase PCR (RT-PCR) assays, in situ hybridization assays, competitive-binding assays, Northern blot analyses, nucleic acid microarrays and biochip analysis.

An arbitrary threshold on the expression level of one or more nucleic acid sequences can be set for assigning a sample or tumor sample to one of two groups. Alternatively, in a preferred embodiment, expression levels of one or more nucleic acid sequences of the invention are combined by taking ratios of expression levels of two nucleic acid sequences and/or by a method such as logistic regression to define a metric which is then compared to previously measured samples or to a threshold. The threshold for assignment is treated as a parameter, which can be used to quantify the confidence with which samples are assigned to each class. The threshold for assignment can be scaled to favor sensitivity or specificity, depending on the clinical scenario. The correlation value to the reference data generates a continuous score that can be scaled and provides diagnostic information on the likelihood that a samples belongs to a certain class of thyroid subtype. In multivariate analysis, the microRNA signature provides a high level of prognostic information.

The present invention also provides novel microRNA molecules, comprising nucleic acids denoted by SEQ ID NOS.27-29, 33, 34, 139, 140, 307 and 308. It is to be understood, that the cDNA, complement sequence, and anti-miR corresponding to any one of SEQ ID NOS.27-29, 33, 34, 139, 140, 307 and 308 are also encompassed by the present invention.

Further, the present application provides compositions, formulations and medicaments comprising the microRNAs described herein. In one particular embodiment, the present invention provides compositions, formulations and medicaments comprising as an active agent the microRNA comprising any one of SEQ ID NOS.27-29, 33, 34, 139, 140, 307 and 308, variants thereof, or a sequence at least 80%, at least 85%, or at least 90% identical thereto. Said compositions, formulations and medicaments may further optionally comprise any one of adjuvants, carriers, diluents and excipients. The microRNAs described herein can be formulated into compositions, formulations and medicaments by combination with appropriate, pharmaceutically acceptable carriers or diluents, and can be formulated into preparations in solid, semi-solid, liquid or gaseous forms, such as tablets, capsules, powders, granules, ointments, solutions, suppositories, injections, inhalants and aerosols. As such, administration of the microRNA or a pharmaceutical composition comprising thereof can be achieved in various ways, including oral, buccal, rectal, parenteral, intraperitoneal, intradermal, transdermal, intratracheal, etc.

In certain embodiments, pharmaceutical compositions of the present invention comprise one or more nucleic acids of the invention and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition of the present invention is prepared using known techniques, including, but not limited to mixing, dissolving, granulating, dragee-making, levigating, emulsifying, encapsulating, entrapping or tabletting processes. Methods for the preparation of pharmaceutical compositions may be found in the literature, e.g. in Gennaro, A. R. (2000) Remington: The Science and Practice of Pharmacy, $20^{th}$ ed.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition of the present invention is a solid (e.g., a powder, tablet, and/or capsule). In certain of such embodiments, a solid pharmaceutical composition comprising one or more nucleic acids of the invention is prepared using ingredients known in the art, including, but not limited to, starches, sugars, diluents, granulating agents, lubricants, binders, and disintegrating agents.

Further, the present application provides vectors and probes comprising the compounds (the nucleic acids) disclosed herein. In one particular embodiment, the present application provides vectors and probes comprising nucleic acids denoted by SEQ ID NOS.27-29, 33, 34, 139, 140, 307 and 308, variants thereof or a sequence at least 80%, at least 85%, or at least 90% identical thereto.

It is to be understood that the terminology used herein is for the purpose of describing particular embodiments only and it is not intended to be limiting. It must be noted that, as used in the specification and the appended claims, the singular forms "a," "an" and "the" include plural referents unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0 for example, the numbers 6.0, 6.1, 6.2, 6.3, 6.4, 6.5, 6.6, 6.7, 6.8, 6.9 and 7.0 are explicitly contemplated.

As used herein, the term "aberrant proliferation" means cell proliferation that deviates from the normal, proper, or expected course. Aberrant cell proliferation may include cell proliferation whose characteristics are associated with an indication caused by, mediated by, or resulting in inappropriately high levels of cell division, inappropriately low levels of apoptosis, or both. Such indications may be characterized, for example, by single or multiple local abnormal proliferations of cells, groups of cells, or tissue(s), whether cancerous or non-cancerous, benign or malignant. Aberrant proliferation is one of the main features of cancer.

As used herein, the term "about" refers to +/−10%.

"Attached" or "immobilized", as used herein to refer to a probe and a solid support, means that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

"Biological sample" or "sample", as used herein, means a sample of biological tissue or fluid that comprises nucleic acids, microRNA in particular. Such samples include, but are not limited to, tissue or fluid isolated from subjects. Biological samples also include sections of tissues such as biopsy and autopsy samples, fine-needle aspiration (FNA) samples, frozen sections taken for histological purposes, blood, blood fraction, plasma, serum, and the like. A biological sample may be provided by removing a sample of cells from a subject, but can also be accomplished by using previously isolated cells (e.g., isolated by another person, at another time, and/or for another purpose), which may then be cultured or not. Archival tissues, such as those having treatment or outcome history, may also be used.

In another embodiment of the invention, the FNA biopsy is prepared as a smear.

The term "classification" refers to a procedure and/or algorithm in which individual items are placed into groups or classes based on quantitative information on one or more characteristics inherent in the items (referred to as traits, variables, characters, features, etc.) and based on a statistical model and/or a training set of previously labeled items.

As used herein, the term "classifying thyroid tumors" refers to the identification of one or more properties of a thyroid tissue sample (e.g., including but not limited to, the presence of microRNAs expressed in cancerous tissue, the presence of microRNAs expressed in pre-cancerous tissue that is likely to become cancerous, and the presence of microRNAs expressed in cancerous tissue that is likely to metastasize).

The term "classifier" as used herein refers to an algorithm used to classify, distinguish or identify thyroid tumors (or lesions) as benign or malignant, or to classify, distinguish or identify sub-types of thyroid tumor. Once the microRNA expression profile of the samples of any study cohort is acquired, for example from the training cohort, a database is generated in which the expression levels of all the microRNAs in the samples of the cohorts are stored. This database is also referred to as "the training data" and it is used to choose an optimal algorithm for classification. Nucleic acid (or microRNA) ratios, alone or in combination with nucleic acid (or microRNA) levels may also be used by the algorithm for the classification of thyroid samples.

In one embodiment, the algorithm to be used in the method or protocol of the invention is a machine-learning algorithm. Examples of machine-learning algorithms are discriminant analysis, K-nearest neighbor classifier (KNN), Support Vector Machine (SVM) classifier, logistic regression classifier, neural network classifier, Gaussian mixture model (GMM), nearest centroid classifier, linear regression classifier, decision tree classifier, and random forest classifier, ensemble of classifiers, or any combination thereof.

Thus, the classifier may comprise a combination of algorithms, such as for example a discriminant analysis and a KNN classifier, a KNN classifier and a SVM classifier, a discriminant analysis and a logistic regression classifier, and so forth with any of the machine-learning algorithms.

When a discriminant analysis classifier is used, the discriminant may be any one of a linear, quadratic, a diagonal of the linear covariance matrix, diagonals of the quadratic covariance matrices, pseudoinverse of the linear covariance matrix, and pseudoinverse of the quadratic covariance matrices. When a KNN classifier is used, the k may be altered and the distance metric can be either Pearson correlation, spearman correlation, Euclidean or cityblock (Manhattan) distance. A KNN classifier uses a number of neighboring samples for the classification of each sample, which may be 5 neighboring samples, 6 neighboring samples, 7 neighboring samples, 8 neighboring samples, 9 neighboring samples, 10 neighboring samples, and the like.

When a SVM classifier is used, the kernel may be linear, Gaussian or polynomial. When an ensemble method classifier is used, it usually applies algorithms such as classification trees, KNN or discriminate analysis classifiers. The ensembles can be either created using boosting or bagging algorithms and the number of ensemble learning cycles can range from two up to a few thousand.

One such combination of algorithms may comprise one linear discriminant analysis (LDA) and one KNN, two LDA algorithms and one KNN, three LDA algorithms and one KNN, four LDA algorithms and one KNN, or five LDA algorithms and one KNN.

Thus, a classifier for the classification of thyroid tumor samples and its use are provided herein, said classifier comprising a combination of algorithms, particularly machine-learning algorithms, which utilize (as an input) the expression levels of nucleic acids of SEQ ID NOS:1-37, or the ratios between pairs of expression levels of said nucleic acids of SEQ ID NOS:1-37, in a series of steps which result in the classification of a thyroid tumor sample as benign or malignant (as the output).

As used herein, "confusion matrix" refers to a specific table layout that allows visualization of the performance of an algorithm, typically a supervised learning one. A "confusion matrix" may also be referred to as a contingency table or an error matrix.

"Complement" or "complementary", as used herein to refer to a nucleic acid, may mean Watson-Crick (e.g., A-T/U and C-G) or Hoogsteen base pairing between nucleotides or nucleotide analogs of nucleic acid molecules. A full complement or fully complementary means 100% complementary base pairing between nucleotides or nucleotide analogs of nucleic acid molecules. In some embodiments, the complementary sequence has a reverse orientation (5'-3'). The present invention also provides the complement of the nucleic acids denoted by SEQ ID NOS. 7-29, 33, 34, 139, and 140.

As used herein, "$C_T$ signals" or "$C_T$" represent the first cycle of PCR where amplification crosses a threshold (cycle threshold) of fluorescence. Accordingly, low values of $C_T$ represent high abundance or expression levels of the microRNA. In some embodiments the PCR $C_T$ signal is normalized such that the normalized $C_T$ is inversed from the expression level. In other embodiments the PCR $C_T$ signal may be normalized and then inverted such that low normalized-inverted $C_T$ represents low abundance or expression levels of the microRNA.

As used herein, a "data processing routine" refers to a process that can be embodied in software that determines the biological significance of acquired data (i.e., the ultimate results of an assay or analysis) with respect to one or more samples. For example, the data processing routine can make determination of whether a thyroid lesion from which a sample was collected or obtained is benign or malignant, or of a specific sub-type, based upon the data collected. In the systems and methods herein, the data processing routine can also control the data collection routine based upon the results determined. The data processing routine and the data collection routines can be integrated and provide feedback to operate the data acquisition, and hence provide assay-based judging methods.

"Detection" means detecting the presence of a component in a sample. Detection also means detecting the absence of a component. Detection also means determining the level of a component, either quantitatively or qualitatively.

"Differential expression" or a "difference in expression levels" means qualitative or quantitative differences in the microRNA expression patterns in thyroid samples. Thus, a differentially expressed microRNA may qualitatively have its expression altered, including an activation or inactivation, in, e.g., normal versus diseased thyroid tissue. A qualitatively regulated microRNA may exhibit an expression pattern within a thyroid sample or cell type which may be detectable by standard techniques. Some microRNAs may be expressed in one thyroid sample or cell type, and not in other, or expressed at different levels between different cell types or different samples. Thus, the difference in expression may be quantitative, e.g., in that expression is modulated, up-regulated, resulting in an increased amount of microRNA, or down-regulated, resulting in a decreased amount of microRNA. The degree to which expression differs needs only be large enough to quantify via standard characterization techniques such as expression arrays, next generation sequencing (NGS), quantitative reverse transcriptase PCR, northern blot analysis, real-time PCR, in situ hybridization and RNase protection.

The term "expression profile" is used broadly to include a genomic expression profile, as well as an expression profile of microRNAs, for example. As used herein, expression profile means the set of data obtained for the nucleic acid (or microRNA) expression. It may refer to the raw data or to the normalized expression values. Expression profiles may be generated by any convenient means for determining a level of a nucleic acid sequence e.g. quantitative hybridization of microRNA, labeled microRNA, amplified microRNA, cDNA, etc., quantitative PCR, and the like. Further to measuring nucleic acid sequence levels, the data obtained may be normalized—normalization of data has been discussed somewhere else in this application. Expression profiles allow the analysis of differential gene expression between two or more samples, as well as between samples and thresholds. Further, classifiers may be applied to expression profiles in order to obtain information about the sample, such as classification, diagnosis, sub-typing of the sample, and the like. Nucleic acid sequences of interest are nucleic acid sequences that are found to be predictive, including the nucleic acid sequences provided herein in Table 1, where the expression profile may include expression data for 5, 10, 20, 25, 50, 100 or more of, including all of the listed nucleic acid sequences. According to some embodiments, the term "expression profile" means measuring the abundance of the nucleic acid sequences in the measured samples. In a specific embodiment, microRNA expression profiles are characterized in each thyroid sample.

"Expression ratio", as used herein, refers to relative expression levels of two or more nucleic acids, i.e. microRNAs, as determined by detecting the relative expression levels of the corresponding nucleic acids in a biological sample, such as a thyroid sample. Since microRNA expression levels are expressed as $C_T$s, which are obtained in log scale, in practice expression ratios are obtained by subtraction of the $C_T$s, rather than by division.

As used herein, "FDR" or "False Discovery Rate", is a statistical method used in multiple hypothesis testing to correct for multiple comparisons. When performing multiple statistical tests, for example in comparing the signal between two groups in multiple data features, there is an increasingly high probability of obtaining false positive results, by random differences between the groups that can reach levels that would otherwise be considered as statistically significant. In order to limit the proportion of such false discoveries, statistical significance is defined only for data features in which the differences reached a p-value (by two-sided t-test) below a threshold, which is dependent on the number of tests performed and the distribution of p-values obtained in these tests.

As used herein, "FNA" relates to "fine needle aspiration". Fine-needle aspiration biopsy (FNAB, FNA or NAB), or fine-needle aspiration cytology (FNAC), is a diagnostic procedure used to investigate superficial (just under the skin) lumps or masses, and it is particularly useful for thyroid lesion biopsies. A biopsy is collected by inserting a thin, hollow needle into the mass for sampling of cells that, after being stained, will be examined under a microscope. There could be cytology exam of aspirate (cell specimen evaluation, FNAC) or histological (biopsy—tissue specimen evaluation, FNAB). FNA is a popular biopsy method used for thyroid nodules since a major surgical (excisional or open) biopsy can be avoided by performing a needle aspiration biopsy instead. A detailed description of specimen collection and preparation may be found in "Atlas of Fine Needle Aspiration Cytology" by Henryk A. Domanski (2014), the contents of which are incorporated herein by reference. The preparation of aspiration specimens has been well described in the art. Usually, a suitable amount of aspirate (usually about one drop) is spread thinly and evenly over a microscopic slide which is then stained and mounted. FNA specimen prepared in this manner are also referred to as "smear". The result should be compatible to a sectioned histological slide with regard to specimen thickness and evenness. Fixation of FNA smears is usually by air drying (generally referred to as "routine air dried FNAB") or wet fixing using either 95% ethanol or cyto-spray as fixative. Other suitable liquid fixatives are methanol, acetone, isopropyl alcohol, acetone/methanol and the like. Alternatively, FNA samples may be added to or mixed with preservatives in a tube.

As referred to herein, a "follicular" lesion may be any one of follicular adenoma (FA), follicular carcinoma (FC) and follicular variant of papillary thyroid carcinoma (FVPTC).

"Fragment" is used herein to indicate a non-full-length part of a nucleic acid. Thus, a fragment is itself also a nucleic acid.

"Groove binder" and/or "minor groove binder" (MGB), as used herein, may be used interchangeably and refer to small molecules that fit into the minor groove of double-stranded DNA, typically in a sequence-specific manner. Minor groove binders may be long, flat molecules that can adopt a crescent-like shape and thus, fit snugly into the minor groove of a double helix, often displacing water. Minor groove binding molecules may typically comprise several aromatic rings connected by bonds with torsional freedom such as furan, benzene, or pyrrole rings. Minor groove binders may be antibiotics such as netropsin, distamycin, berenil, pentamidine and other aromatic diamidines, Hoechst 33258, SN 6999, aureolic anti-tumor drugs such as chromomycin and mithramycin, CC-1065, dihydrocyclopyrroloindole tripeptide ($DPI_3$), 1,2-dihydro-(3H)-pyrrolo[3,2-e]indole-7-carboxylate ($CDPI_3$), and related compounds and analogues, including those described in Nucleic Acids in Chemistry and Biology, 2d ed., Blackburn and Gait, eds., Oxford University Press, 1996, and PCT Published Application No. WO 03/078450, the contents of which are incorporated herein by reference. A minor groove binder may be a component of a primer, a probe, a hybridization tag complement, or combinations thereof. Minor groove binders may increase the $T_m$ of the primer or a probe to which they are attached, allowing such primers or probes to effectively hybridize at higher temperatures.

"Identical" or "identity", as used herein in the context of two or more nucleic acid sequences, mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA sequences, thymine (T) and uracil (U) may be considered equivalent. Identity may be performed manually or by using a computer sequence algorithm such as BLAST, BLAST 2.0, and the like.

"In situ detection", as used herein, means the detection of expression or expression levels in the original site hereby meaning in a tissue sample such as biopsy.

"Label", as used herein, means a composition detectable by spectroscopic, photochemical, biochemical, immunochemical, chemical, or other physical means. The label may be any entity that does not naturally occur in a protein or nucleic acid and allows the nucleic acid or protein to be detectable. For example, useful labels include $^{32}P$, fluorescent dyes, electron-dense reagents, enzymes, biotin, digoxigenin, or haptens and other entities which can be made detectable, and the like. A label may be incorporated into nucleic acids and proteins at any position.

"Logistic regression" is part of a category of statistical models called generalized linear models. Logistic regression allows one to predict a discrete outcome, such as group membership, from a set of variables that may be continuous, discrete, dichotomous, or a mix of any of these. The dependent or response variable can be dichotomous, for example, one of two possible types of cancer. Logistic regression models the natural log of the odds ratio, i.e. the ratio of the probability of belonging to the first group (P) over the probability of belonging to the second group (1−P), as a linear combination of the different expression levels (in log-space). The logistic regression output can be used as a classifier by prescribing that a case or sample will be classified into the first type is P is greater than 0.5 or 50%. Alternatively, the calculated probability P can be used as a variable in other contexts such as a 1D or 2D threshold classifier.

As used herein, the term "prior" refers to a probability for each class, e.g., given to the different classes, and used by the likelihood that a sample is malignant or benign, without any additional knowledge regarding the expression profile of the sample in a classification. Priors may be set at different ratios, such as for example 80%-20% malignant-benign, 75%-25% malignant-benign, 70%-30% malignant-benign, 65%-35% malignant-benign, 60%-40% malignant-benign, 50%-50% malignant-benign (i.e., uniform). In addition, priors may be empirical, i.e., based on the distribution of the samples in training cohort. Priors may be adjusted in order to achieve a predetermined sensitivity or specificity.

As used herein, a "marker" is a microRNA, or a nucleic acid sequence, whose presence and abundance is measured in a sample. A "marker" further provides an indication of the status of the sample.

As used herein, "malignant marker" is a microRNA, or a nucleic acid sequence which is present at higher levels in malignant samples versus benign samples. A malignant marker may or may not be present in test samples.

As used herein, "secondary marker" is a microRNA, or a nucleic acid sequence, which is used to differentiate between malignant and benign samples, and for which the difference, or the ratio, in the expression levels of said secondary marker in malignant and benign samples is less than the difference, or the ratio, in the expression levels of malignant markers. A secondary marker may or may not be present in test samples.

As used herein, "cell type marker" refers to a microRNA, or nucleic acid sequence, whose expression correlates with certain cell types. Said cell types may generally be found in a sample, e.g. blood cells, white blood cells, red blood cells, epithelial cells, Hurthle cells, mitochondrial-rich cells, lymphocytes, follicular cells, parafollicular cells (C cells), metastatic cells, immune cells, macrophages and the like. Other markers included as "cell type markers" may be species-specific markers, such as markers from bacteria, fungi, and the like.

"Normalizer", as used herein, means a microRNA or a nucleic acid sequence whose signal (i.e., level of expression) is used in order to normalize each sample. A normalizer may be used alone (one microRNA as normalizer), or as part of a set of normalizers (more than one microRNA as normalizer, for example two, three, four, five, six, seven eight, nine, ten eleven, twelve, thirteen fourteen, sixteen or seventeen microRNAs may be used as normalizers in a set). As referred to herein, any microRNA detected in the sample may be used as a normalizer. Essentially, any microRNA may be used as a normalizer. MicroRNAs denoted by any one of SEQ ID NOs 1-182 may be used as normalizers. MicroRNAs denoted by any one of SEQ ID NOs. 1-37 may be used as normalizers. Particular examples of microRNAs that may be used as normalizers are hsa-miR-23a-3p, MID-20094, MID-50969, hsa-miR-345-5p, hsa-miR-3074-5p, MID-50976, MID-50971, hsa-miR-5701 and hsa-miR-574-3p.

"Normalization" of data values refers to mapping the original data range into another scale. Normalization may be done by subtracting the mean expression of the set of normalizers, subtracting the median expression of the set of normalizers, fitting the expression values of the normalizers to a reference set of values (using a polynomial fit) and applying this fit to all signals. All the normalizers, or a subset of the normalizers may be used.

"Nucleic acid" or "oligonucleotide" or "polynucleotide", as used herein, means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand may provide a probe that hybridizes to a target sequence under stringent hybridization conditions. Thus, a nucleic acid also encompasses a probe that hybridizes under stringent hybridization conditions.

Nucleic acids may be single-stranded or double-stranded, or may contain portions of both double-stranded and single-stranded sequences. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine, hypoxanthine, isocytosine and isoguanine. Nucleic acids may be obtained by chemical synthesis methods or by recombinant methods.

A nucleic acid will generally contain phosphodiester bonds, although nucleic acid analogs may be included. The analog may include a non-naturally occurring linkage, backbone, or nucleotide. The analog may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. No. 5,235,033 and U.S. Pat. No. 5,034,506, which are incorporated herein by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e., ribonucleotides containing a non-naturally occurring nucleobase instead of a naturally occurring nucleobase such as uridines or cytidines modified at the 5-position, e.g., 5-(2-amino) propyl uridine, 5-bromo uridine; adenosines and guanosines modified at the 8-position, e.g., 8-bromo guanosine; deaza nucleotides, e.g., 7-deaza-adenosine; 0- and N-alkylated nucleotides, e.g., N6-methyl adenosine are suitable. The 2'-OH-group may be replaced by a group selected from H, OR, R, halo, SH, SR, $NH_2$, NHR, $NR_2$ or CN, wherein R is C1-C6 alkyl, alkenyl or alkynyl and halo is F, Cl, Br or I. Modified nucleotides also include nucleotides conjugated with cholesterol through, e.g., a hydroxyprolinol linkage as described in Krutzfeldt et al. (Nature 2005; 438:685-689), Soutschek et al. (Nature 2004; 432:173-178), and WO 2005/079397, which are incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver and thyroid. Mixtures of naturally occurring nucleic acids and analogs may be made. Alternatively, mixtures of different nucleic acid analogs, and mixtures of naturally occurring nucleic acids and analogs may be made.

Thus, novel isolated nucleic acids are provided herein. The nucleic acids provided herein may be non-naturally occurring, synthesized nucleic acids. Thus, the nucleic acid provided herein may be a synthetic nucleic acid. Methods of synthesizing nucleic acids are known to the man skilled in the art, and are described, e.g., in U.S. Pat. No. 7,579,451, the contents of which are incorporated herein by reference. The nucleic acids may comprise at least one of the sequences of SEQ ID NOS: 1-308 or a variant thereof. In one embodiment, the nucleic acids comprise at least one of the sequences of SEQ ID NOS: 1-182. The variant may be a complement of the referenced nucleotide sequence. The variant may be a nucleotide sequence that is 70%, 75%, 80%, 85%, 90% or 95% identical to the referenced nucleotide sequence or the complement thereof. The variant may be a nucleotide sequence which hybridizes under stringent conditions to the referenced nucleotide sequence, complements thereof, or nucleotide sequences substantially identical thereto.

A nucleic acid as described herein may have a length of from about 10 to about 250 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 125, 150, 175, 200 or 250 nucleotides. The nucleic acid may be synthesized or expressed in a cell (in vitro or in vivo) using a synthetic gene. The nucleic acid may be synthesized as a single strand molecule and hybridized to a substantially complementary nucleic acid to form a duplex. The nucleic acid may be introduced to a cell, tissue or organ in a single- or double-stranded form or capable of being expressed by a synthetic gene using methods well known to those skilled in the art, including as described in U.S. Pat. No. 6,506,559, the contents of which are incorporated by reference herein.

The nucleic acid may comprise a microRNA sequence shown in Table 1, or a variant thereof. In some instances, variants of the same microRNA are also provided in Table 1. It is to be noted that SEQ ID NOs.1-180 in Table 1 present the cDNA corresponding to the sequence of the naturally occurring microRNA, i.e., the sequences present thymine (T) instead of uracil (U).

It is to be understood that nucleic acid refers to deoxyribonucleotides, ribonucleotides, or modified nucleotides, and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs) and unlocked nucleic acids (UNAs; see, e.g., Jensen et al. Nucleic Acids Symposium Series 52: 133-4), and derivatives thereof.

Nucleotide is used as recognized in the art, to include those with natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, also referred to interchangeably as nucleotide analogs, modified nucleotides, non-natural nucleotides, non-standard nucleotides and other (see, e.g., WO 92/07065; WO 93/15187; the contents of which are incorporated herein by reference). There are several examples of modified nucleic acid bases known in the art as summarized by Limbach, et al, Nucleic Acids Res. 22:2183, 1994. Some of the non-limiting examples of base modifications that can be introduced into nucleic acid molecules include, hypoxanthine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others (Burgin, et al., Biochemistry 35:14090, 1996). By "modified bases" in this aspect is meant nucleotide bases other than adenine, guanine, cytosine and uracil at 1' position or their equivalents.

Modified nucleotide refers to a nucleotide that has one or more modifications to the nucleoside, the nucleobase, pentose ring, or phosphate group. Modifications include those naturally occurring that result from modification by enzymes that modify nucleotides, such as methyltransferases. Modified nucleotides also include synthetic or non-naturally occurring nucleotides. Synthetic or non-naturally occurring modifications in nucleotides include those with 2' modifications, e.g., 2'-methoxyethoxy, 2'-fluoro, 2'-allyl, 2'-O-[2-(methylamino)-2-oxoethyl], 4'-thio, 4'-CH$_2$—O-2'-bridge, 4'-(CH$_2$)$_2$—O-2'-bridge, 2'-LNA or other bicyclic or "bridged" nucleoside analog, and 2'-O—(N-methylcarbamate) or those comprising base analogs. In connection with 2'-modified nucleotides as described for the present disclosure, by "amino" is meant 2'-NH$_2$ or 2'-O—NH$_2$, which can be modified or unmodified. Such modified groups are described, e.g., in U.S. Pat. No. 5,672,695 and U.S. Pat. No. 6,248,878. "Modified nucleotides" of the instant invention can also include nucleotide analogs as described above.

As used herein, "base analog" refers to a heterocyclic moiety which is located at the 1' position of a nucleotide sugar moiety in a modified nucleotide that can be incorporated into a nucleic acid duplex (or the equivalent position in a nucleotide sugar moiety substitution that can be incorporated into a nucleic acid duplex). A base analog may be generally a purine or a pyrimidine base, excluding the common bases guanine (G), cytosine (C), adenine (A), thymine (T), and uracil (U). Base analogs can duplex with other bases or base analogs in dsRNAs. Base analogs include those useful in the compounds and methods of the invention, e.g., those disclosed in U.S. Pat. No. 5,432,272, U.S. Pat. No. 6,001,983 and U.S. Pat. No. 7,579,451, which are herein incorporated by reference. Non-limiting examples of bases include hypoxanthine (I), xanthine (X), 313-D-ribofuranosyl-(2,6-diaminopyrimidine) (K), 3-gamma-D-ribofuranosyl-(1-methyl-pyrazolo[4,3-d]pyrimidine-5,7(4H, 6H)-dione) (P), iso-cytosine (iso-C), iso-guanine (iso-G), 1-gamma-D-ribofuranosyl-(5-nitroindole), 1-gamma-D-ribofuranosyl-(3-nitropyrrole), 5-bromouracil, 2-aminopurine, 4-thio-dT, 7-(2-thienyl)-imidazo[4,5-b]pyridine (Ds) and pyrrole-2-carbaldehyde (Pa), 2-amino-6-(2-thienyl)purine (S), 2-oxopyridine (Y), difluorotolyl, 4-fluoro-6-methylbenzimidazole, 4-methylbenzimidazole, 3-methyl isocarbostyrilyl, 5-methyl isocarbostyrilyl, and 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylindolyl, 4,6-dimethylindolyl, phenyl, napthalenyl, anthracenyl, phenanthracenyl, pyrenyl, stilbenzyl, tetracenyl, pentacenyl, and structural derivates thereof (Schweitzer et al., J. Org. Chem., 59:7238-7242 (1994); Berger et al., Nucleic Acids Research, 28(15):2911-2914 (2000); Moran et al., J. Am. Chem. Soc., 119:2056-2057 (1997); Morales et al., J. Am. Chem. Soc., 121:2323-2324 (1999); Guckian et al., J. Am. Chem. Soc., 118:8182-8183 (1996); Morales et al., J. Am. Chem. Soc., 122(6):1001-1007 (2000); McMinn et al., J. Am. Chem. Soc., 121:11585-11586 (1999); Guckian et al., J. Org. Chem., 63:9652-9656 (1998); Moran et al., Proc. Natl. Acad. Sci., 94:10506-10511 (1997); Das et al., J. Chem. Soc., Perkin Trans., 1:197-206 (2002); Shibata et al., J. Chem. Soc., Perkin Trans., 1: 1605-1611 (2001); Wu et al., J. Am. Chem. Soc., 122(32):7621-7632 (2000); O'Neill et al., J. Org. Chem., 67:5869-5875 (2002); Chaudhuri et al., J. Am. Chem. Soc., 117:10434-10442 (1995); and U.S. Pat. No. 6,218,108.). Base analogs may also be a universal base.

"Universal base" refers to a heterocyclic moiety located at the 1' position of a nucleotide sugar moiety in a modified nucleotide, or the equivalent position in a nucleotide sugar moiety substitution, that, when present in a nucleic acid duplex, can be positioned opposite more than one type of base without altering the double helical structure (e.g., the structure of the phosphate backbone). Additionally, the universal base does not destroy the ability of the single stranded nucleic acid in which it resides to duplex to a target nucleic acid.

TABLE 1

The microRNAs of the invention

| miR name | SEQ ID NO. | Sequence |
|---|---|---|
| hsa-miR-222-3p | 1 | AGCTACATCTGGCTACTGGGT |
|  | 2 | AGCTACATCTGGCTACTGGGTCTC |
| hsa-miR-551b-3p | 3 | GACCCATACTTGGTTTCAGAGG |
|  | 4 | GCGACCCATACTTGGTTTCAG |
| hsa-miR-31-5p | 5 | AGGCAAGATGCTGGCATAGCT |
|  | 6 | AGGCAAGATGCTGGCATAGCTGT |
|  | 7 | GGCAAGATGCTGGCATAGCTG |
| hsa-miR-375 | 8 | TTTGTTCGTTCGGCTCGCGTGA |
| hsa-miR-125b-5p | 9 | TCCCTGAGACCCTAACTTGTGA |
| hsa-miR-146b-5p | 10 | TGAGAACTGAATTCCATAGGCT |
|  | 11 | TGAGAACTGAATTCCATAGGCTGT |
| hsa-miR-152-3p | 12 | TCAGTGCATGACAGAACTTGG |
|  | 13 | TCAGTGCATGACAGAACTTGGG |
| hsa-miR-346 | 14 | TGTCTGCCCGCATGCCTGCCTCT |
| hsa-miR-181c-5p | 15 | AACATTCAACCTGTCGGTGAGT |
| hsa-miR-424-3p | 16 | CAAAACGTGAGGCGCTGCTAT |
| hsa-miR-342-3p | 17 | TCTCACACAGAAATCGCACCCGT |
|  | 18 | TCTCACACAGAAATCGCACCCGTC |
| hsa-miR-138-5p | 19 | AGCTGGTGTTGTGAATC |
|  | 20 | AGCTGGTGTTGTGAATCAGGCCG |
|  | 21 | AGCTGGTGTTGTGAATCAGGCCGT |
| hsa-miR-486-5p | 22 | TCCTGTACTGAGCTGCCCCGAG |
| hsa-miR-200c-3p | 23 | TAATACTGCCGGGTAATGATGG |
|  | 24 | TAATACTGCCGGGTAATGATGGA |
| MID-16582 | 25 | AGTGAAGCATTGGACTGTA |
| hsa-miR-23a-3p | 26 | ATCACATTGCCAGGGATTTCC |
| MID-20094 | 27 | TAAGCCAGTTTCTGTCTGATA |
|  | 28 | TTTCTAAGCCAGTTTCTGTCTGATA |
| MID-50969 | 29 | ATGACAGATTGACATGGACAATT |
| hsa-miR-345-5p | 30 | GCTGACTCCTAGTCCAGGGCTC |
|  | 31 | TGCTGACTCCTAGTCCAGGGC |
| hsa-miR-3074-5p | 32 | GTTCCTGCTGAACTGAGCCAG |

TABLE 1-continued

The microRNAs of the invention

| miR name | SEQ ID NO. | Sequence |
|---|---|---|
| MID-50976 | 33 | CTGTCTGAGCGCCGCTC |
| MID-50971 | 34 | ATACTCTGGTTTCTTTTC |
| hsa-miR-5701 | 35 | TTATTGTCACGTTCTGATT |
| hsa-miR-574-3p | 36 | CACGCTCATGCACACACCCAC |
|  | 37 | CACGCTCATGCACACACCCACA |
| hsa-miR-7-5p | 38 | TGGAAGACTAGTGATTTTGTTGT |
| hsa-miR-10a-5p | 39 | TACCCTGTAGATCCGAATTTGTG |
| hsa-miR-18a-5p | 40 | TAAGGTGCATCTAGTGCAGATAG |
| hsa-miR-21-3p | 41 | CAACACCAGTCGATGGGCTGT |
| hsa-miR-21-5p | 42 | TAGCTTATCAGACTGATGTTGA |
| hsa-miR-30e-5p | 43 | TGTAAACATCCTTGACTGGAAG |
| hsa-miR-31-3p | 44 | TGCTATGCCAACATATTGCCAT |
| hsa-miR-34a-5p | 45 | TGGCAGTGTCTTAGCTGGTTGTT |
| hsa-miR-92b-5p | 46 | AGGGACGGGACGCGGTGCAGTG |
| hsa-miR-96-5p | 47 | TTTGGCACTAGCACATTTTTGCT |
| hsa-miR-100-5p | 48 | AACCCGTAGATCCGAACTTGTG |
| hsa-miR-126-3p | 49 | TCGTACCGTGAGTAATAATGCG |
| hsa-miR-138-1-3p | 50 | GCTACTTCACAACACCAGGGCC |
| hsa-miR-140-3p | 51 | TACCACAGGGTAGAACCACGG |
| hsa-miR-141-3p | 52 | TAACACTGTCTGGTAAAGATGG |
| hsa-miR-142-3p | 53 | TGTAGTGTTTCCTACTTTATGGA |
| hsa-miR-142-5p | 54 | CATAAAGTAGAAAGCACTACT |
| hsa-miR-146b-3p | 55 | TGCCCTGTGGACTCAGTTCTGG |
| hsa-miR-146a-5p | 56 | TGAGAACTGAATTCCATGGGTT |
| hsa-miR-148a-3p | 57 | TCAGTGCACTACAGAACTTTGT |
| hsa-miR-150-3p | 58 | CTGGTACAGGCCTGGGGGACAG |
| hsa-miR-150-5p | 59 | TCTCCCAACCCTTGTACCAGTG |
| hsa-miR-155-5p | 60 | TTAATGCTAATCGTGATAGGGGT |
| hsa-miR-181a-5p | 61 | AACATTCAACGCTGTCGGTGAGT |
| hsa-miR-181b-5p | 62 | AACATTCATTGCTGTCGGTGGGT |
| hsa-miR-182-5p | 63 | TTTGGCAATGGTAGAACTCACACT |
| hsa-miR-187-3p | 64 | TCGTGTCTTGTGTTGCAGCCGG |
| hsa-miR-193a-3p | 65 | AACTGGCCTACAAAGTCCCAGT |
| hsa-miR-195-5p | 66 | TAGCAGCACAGAAATATTGGC |
| hsa-miR-197-5p | 67 | CGGGTAGAGAGGGCAGTGGGAGG |
| hsa-miR-199a-3p | 68 | ACAGTAGTCTGCACATTGGTTA |
| hsa-miR-200a-3p | 69 | TAACACTGTCTGGTAACGATGTT |
| hsa-miR-200b-3p | 70 | TAATACTGCCTGGTAATGATGA |

TABLE 1-continued

The microRNAs of the invention

| miR name | SEQ ID NO. | Sequence |
|---|---|---|
| hsa-miR-199a-5p | 71 | CCCAGTGTTCAGACTACCTGTTC |
| hsa-miR-199b-5p | 72 | CCCAGTGTTTAGACTATCTGTTC |
| hsa-miR-205-5p | 73 | TCCTTCATTCCACCGGAGTCTG |
| hsa-miR-210-3p | 74 | CTGTGCGTGTGACAGCGGCTGA |
| hsa-miR-214-3p | 75 | ACAGCAGGCACAGACAGGCAGT |
| hsa-miR-221-3p | 76 | AGCTACATTGTCTGCTGGGTTTC |
| hsa-miR-221-5p | 77 | ACCTGGCATACAATGTAGATTT |
| hsa-miR-223-3p | 78 | TGTCAGTTTGTCAAATACCCCA |
| hsa-miR-222-5p | 79 | CTCAGTAGCCAGTGTAGATCCT |
| hsa-miR-224-5p | 80 | CAAGTCACTAGTGGTTCCGTTTAG |
| hsa-miR-342-5p | 81 | AGGGGTGCTATCTGTGATTGA |
| hsa-miR-429 | 82 | TAATACTGTCTGGTAAAACCGT |
| hsa-miR-455-3p | 83 | GCAGTCCATGGGCATATACAC |
| hsa-miR-483-5p | 84 | AAGACGGGAGGAAAGAAGGGAG |
| hsa-miR-487b-3p | 85 | AATCGTACAGGGTCATCCACTT |
| hsa-miR-497-5p | 86 | CAGCAGCACACTGTGGTTTGT |
| hsa-miR-513a-5p | 87 | TTCACAGGGAGGTGTCATTTAT |
| hsa-miR-542-5p | 88 | TCGGGGATCATCATGTCACGAGA |
| hsa-miR-625-5p | 89 | AGGGGGAAAGTTCTATAGTCC |
| hsa-miR-650 | 90 | AGGAGGCAGCGCTCTCAGGAC |
| hsa-miR-658 | 91 | GGCGGAGGGAAGTAGGTCCGTTGGT |
| hsa-miR-664b-5p | 92 | TGGGCTAAGGGAGATGATTGGGTA |
| hsa-miR-708-5p | 93 | AAGGAGCTTACAATCTAGCTGGG |
| hsa-miR-765 | 94 | TGGAGGAGAAGGAAGGTGATG |
| hsa-miR-1229-5p | 95 | GTGGGTAGGGTTTGGGGGAGAGCG |
| hsa-miR-2392 | 96 | TAGGATGGGGGTGAGAGGTG |
| hsa-miR-3141 | 97 | GAGGGCGGGTGGAGGAGGA |
| hsa-miR-3162-5p | 98 | TTAGGGAGTAGAAGGGTGGGGAG |
| hsa-miR-3679-5p | 99 | TGAGGATATGGCAGGGAAGGGA |
| hsa-miR-3687 | 100 | CCCGGACAGGCGTTCGTGCGACGT |
| hsa-miR-3940-5p | 101 | GTGGGTTGGGGCGGGCTCTG |
| hsa-miR-4270 | 102 | TCAGGGAGTCAGGGGAGGGC |
| hsa-miR-4284 | 103 | GGGCTCACATCACCCCAT |
| hsa-miR-4443 | 104 | TTGGAGGCGTGGGTTTT |
| hsa-miR-4447 | 105 | GGTGGGGGCTGTTGTTT |
| hsa-miR-4448 | 106 | GGCTCCTTGGTCTAGGGGTA |
| hsa-miR-4454 | 107 | GGATCCGAGTCACGGCACCA |
| hsa-miR-4534 | 108 | GGATGGAGGAGGGGTCT |
| hsa-miR-4538 | 109 | GAGCTTGGATGAGCTGGGCTGA |
| hsa-miR-4539 | 110 | GCTGAACTGGGCTGAGCTGGGC |
| hsa-miR-4689 | 111 | TTGAGGAGACATGGTGGGGGCC |
| hsa-miR-4690-5p | 112 | GAGCAGGCGAGGCTGGGCTGAA |
| hsa-miR-4739 | 113 | AAGGGAGGAGGAGCGGAGGGGCCCT |
| hsa-miR-5001-5p | 114 | AGGGCTGGACTCAGCGGCGGAGCT |
| hsa-miR-5100 | 115 | TTCAGATCCCAGCGGTGCCTCT |
| hsa-miR-5684 | 116 | AACTCTAGCCTGAGCAACAG |
| hsa-miR-5698 | 117 | TGGGGGAGTGCAGTGATTGTGG |
| hsa-miR-5739 | 118 | GCGGAGAGAGAATGGGGAGC |
| hsa-miR-6076 | 119 | AGCATGACAGAGGAGAGGTGG |
| hsa-miR-6086 | 120 | GGAGGTTGGGAAGGGCAGAG |
| hsa-miR-6127 | 121 | TGAGGGAGTGGGTGGGAGG |
| MID-00078 | 122 | AAGTGATTGGAGGTGGGTGGG |
| MID-00321 | 123 | CCTGTCTGAGCGACGCT |
| MID-00387 | 124 | GAGACTCTCCTGTGCAG |
| MID-00671 | 125 | TGCAGATTGTGGGTGGGAGGAC |
| MID-00672 | 126 | TGCAGCTGGTGGAGTCTGGGGG |
| MID-00690 | 127 | TGGAGAAGACTGGAGAGGGTAT |
| MID-15965 | 128 | ACTACCCCAGGATGCCAGCATAGTT |
| MID-16318 | 129 | AGCTGGTTTGATGGGGAGCCAT |
| MID-17144 | 130 | CACTGATTATCGAGGCGATTCT |
| MID-17866 | 131 | CGCCTGTGAATAGTCACTGCAC |
| MID-18468 | 132 | GACGTGAGGGGTGCTACATAC |
| MID-19433 | 133 | GGCTGGTCCGAAGGTAGTGAGTT |
| MID-19434 | 134 | GGCTGGTCCGAGTGCAGTGGTGTTT |
| MID-23168 | 135 | TGTCCAAAGTAAACGCCCTGACGCA |
| MID-23794 | 136 | TTCCCGGCCAATGCATTA |
| MID-24496 | 137 | TTTGGAGGGGCCGTGACAGATG |
| MID-24705 | 138 | CTCCCACTGCTTCACTTGACTA |
| MD2-495 | 139 | NGGGCCGAGGGAGCGAGAG[1] |
| MD2-437 | 140 | AGUGCUUGGCUGAGGAGCU |
| hsa-let-7a-5p | 141 | TGAGGTAGTAGGTTGTATAGTT |
| hsa-let-7b-5p | 142 | TGAGGTAGTAGGTTGTGTGGTT |
| hsa-let-7c-5p | 143 | TGAGGTAGTAGGTTGTATGGTT |
| hsa-let-7d-5p | 144 | AGAGGTAGTAGGTTGCATAGTT |
| hsa-let-7f-5p | 145 | TGAGGTAGTAGATTGTATAGTT |
| hsa-let-7g-5p | 146 | TGAGGTAGTAGTTTGTACAGTT |

TABLE 1-continued

The microRNAs of the invention

| miR name | SEQ ID NO. | Sequence |
|---|---|---|
| hsa-let-7i-5p | 147 | TGAGGTAGTAGTTTGTGCTGTT |
| hsa-miR-103a-2-5p | 148 | AGCTTCTTTACAGTGCTGCCTTG |
| hsa-miR-103a-3p | 149 | AGCAGCATTGTACAGGGCTATGA |
| hsa-miR-106a-5p | 150 | AAAAGTGCTTACAGTGCAGGTAGC |
| hsa-miR-106b-5p | 151 | TAAAGTGCTGACAGTGCAGAT |
| hsa-miR-107 | 152 | AGCAGCATTGTACAGGGCTATCA |
| hsa-miR-125a-5p | 153 | TCCCTGAGACCCTTTAACCTGTGA |
| hsa-miR-144-3p | 154 | TACAGTATAGATGATGTACT |
| hsa-miR-149-5p | 155 | TCTGGCTCCGTGTCTTCACTCCC |
| hsa-miR-151a-5p | 156 | TCGAGGAGCTCACAGTCTAGTA |
| hsa-miR-15b-5p | 157 | TAGCAGCACATCATGGTTTACA |
| hsa-miR-16-1-3p | 158 | CCAGTATTAACTGTGCTGCTGA |
| hsa-miR-16-5p | 159 | TAGCAGCACGTAAATATTGGCG |
| hsa-miR-17-3p | 160 | ACTGCAGTGAAGGCACTTGTAG |
| hsa-miR-17-5p | 161 | CAAAGTGCTTACAGTGCAGGTAGT |
| hsa-miR-185-5p | 162 | TGGAGAGAAAGGCAGTTCCTGA |
| hsa-miR-191-5p | 163 | CAACGGAATCCCAAAAGCAGCTG |
| hsa-miR-192-3p | 164 | CTGCCAATTCCATAGGTCACAG |
| hsa-miR-19b-3p | 165 | TGTGCAAATCCATGCAAAACTGA |
| hsa-miR-20a-5p | 166 | TAAAGTGCTTATAGTGCAGGTAG |
| hsa-miR-25-3p | 167 | CATTGCACTTGTCTCGGTCTGA |
| hsa-miR-26a-5p | 168 | TTCAAGTAATCCAGGATAGGCT |
| hsa-miR-26b-5p | 169 | TTCAAGTAATTCAGGATAGGT |
| hsa-miR-30b-5p | 170 | TGTAAACATCCTACACTCAGCT |
| hsa-miR-30c-5p | 171 | TGTAAACATCCTACACTCTCAGC |
| hsa-miR-30d-5p | 172 | TGTAAACATCCCCGACTGGAAG |
| hsa-miR-320a | 173 | AAAAGCTGGGTTGAGAGGGCGAA |
| hsa-miR-3648 | 174 | AGCCGCGGGGATCGCCGAGGG |
| hsa-miR-376a-3p | 175 | ATCATAGAGGAAAATCCACGT |
| hsa-miR-425-5p | 176 | AATGACACGATCACTCCCGTTGA |
| hsa-miR-4306 | 177 | TGGAGAGAAAGGCAGTA |
| hsa-miR-4324 | 178 | CCCTGAGACCCTAACCTTAA |
| hsa-miR-484 | 179 | TCAGGCTCAGTCCCCTCCCGAT |
| hsa-miR-624-5p | 180 | TAGTACCAGTACCTTGTGTTCA |
| hsa-miR-92a-3p | 181 | TATTGCACTTGTCCCGGCCTGT |
| hsa-miR-93-5p | 182 | CAAAGTGCTGTTCGTGCAGGTAG |

[1] "N" may be any one of G, C, A, T/U.
miR name is the miRBase registry name (release 20), except for the miR names represented by MID-[numeral] or MD2-[numeral]. MID-00078, MID-00321, MID-00387, MID-00671, MID-00672, MID-00690, MID-15965, MID-16318, MID-17144, MID-17866, MID-18468, MID-19433, MID-19434, MID-23168, MID-23794, MID-24496, MID-24705, MD2-495 and MD2-437 are putative microRNAs, which were predicted and/or cloned at Rosetta Genomics.

The nucleic acid may also comprise a miR hairpin sequence shown in Table 2, or a variant thereof.

TABLE 2

Hairpins of the microRNAs of the invention

| miR name | Hairpin SEQ ID NO. | Hairpin Sequence |
|---|---|---|
| hsa-mir-7 | 183 | GTGGACCGGCTGGCCCCATCTGGAAGACTAGTGATTTTGTTGTTGTCTTACTGCGCTCAACAACAAATCCCAGTCTACCTAATGGTGCCAGCCATCGC |
| hsa-mir-10a | 184 | GTCTTCTGTATATACCCTGTAGATCCGAATTTGTGTAAGGAATTTTGTGGTCACAAATTCGTATCTAGGGGAATATGTAGTTGAC |
| hsa-mir-18a | 185 | GTTCTAAGGTGCATCTAGTGCAGATAGTGAAGTAGATTAGCATCTACTGCCCTAAGTGCTCCTTCTGGC |
| hsa-mir-21 | 186 | GTACCACCTTGTCGGGTAGCTTATCAGACTGATGTTGACTGTTGAATCTCATGGCAACACCAGTCGATGGGCTGTCTGACATTTTGGTAT |
| hsa-mir-23a | 187 | GGCCGGCTGGGGTTCCTGGGGATGGGATTTGCTTCCTGTCACAAATCACATTGCCAGGGATTTCCAACCGACC |
| hsa-mir-30e | 188 | GGCAGTCTTTGCTACTGTAAACATCCTTGACTGGAAGCTGTAAGGTGTTCAGAGGAGCTTTCAGTCGGATGTTTACAGCGGCAGGCTGCC |
| hsa-mir-31 | 189 | GGAGAGGAGGCAAGATGCTGGCATAGCTGTTGAACTGGGAACCTGCTATGCCAACATATTGCCATCTTTCC |
| hsa-mir-34a | 190 | GTGAGTGTTTCTTTGGCAGTGTCTTAGCTGGTTGTTGTGAGCAATAGTAAGGAAGCAATCAGCAAGTATACTGCCCTAGAAGTGCTGCAC |

TABLE 2-continued

Hairpins of the microRNAs of the invention

| miR name | Hairpin SEQ ID NO. | Hairpin Sequence |
| --- | --- | --- |
| hsa-mir-92b | 191 | GGGGAGCGGGATCCCGGGCCCCGGGCGGGCGGGAGGGACGGGACGCGGTG CAGTGTTGTTTTTTCCCCCGCCAATATTGCACTCGTCCCGGCCTCCGGCC CCCCCGGCCCCCCGGCCTCCCCGCTACCCC |
| hsa-mir-96 | 192 | TCTGCTTGGCCGATTTTGGCACTAGCACATTTTTGCTTGTGTCTCTCCGC TCTGAGCAATCATGTGCAGTGCCAATATGGGAAAAGCAGG |
| hsa-mir-100 | 193 | GCCTGTTGCCACAAACCCGTAGATCCGAACTTGTGGTATTAGTCCGCACA AGCTTGTATCTATAGGTATGTGTCTGTTAGGC |
| hsa-mir-126 | 194 | GCTGGCGACGGGACATTATTACTTTTGGTACGCGCTGTGACACTTCAAAC TCGTACCGTGAGTAATAATGCGCCGTCCACGGC |
| hsa-mir-125b-1 | 195 | TGCGCTCCTCTCAGTCCCTGAGACCCTAACTTGTGATGTTTACCGTTTAA ATCCACGGGTTAGGCTCTTGGGAGCTGCGAGTCGTGCT |
| hsa-mir-125b-2 | 196 | ACCAGACTTTTCCTAGTCCCTGAGACCCTAACTTGTGAGGTATTTTAGTA ACATCACAAGTCAGGCTCTTGGGACCTAGGCGGAGGGGA |
| hsa-mir-138-1 | 197 | TGGTGTGGTGGGCAGCTGGTGTTGTGAATCAGGCCGTTGCCAATCAGAG AACGGCTACTTCACAACACCAGGGCCACACCACACTA |
|  | 198 | CCCTGGCATGGTGTGGTGGGCAGCTGGTGTTGTGAATCAGGCCGTTGCC AATCAGAGAACGGCTACTTCACAACACCAGGGCCACACCACACTACAGG |
| hsa-mir-138-2 | 199 | CGTTGCTGCAGCTGGTGTTGTGAATCAGGCCGACGAGCAGCGCATCCTCT TACCCGGCTATTTCACGACACCAGGGTTGCATCA |
|  | 200 | GAGGAAGCCGGCGGAGTTCTGGTATCGTTGCTGCAGCTGGTGTTGTGAAT CAGGCCGACGAGCAGCGCATCCTCTTACCCGGCTATTTCACGACACCAGG GTTGCATCATACCCATCCTCTCCAGGCGAGCCTC |
| hsa-mir-140 | 201 | GCGCCCTGTGTGTGTCTCTCTGTGTCCTGCCAGTGGTTTTACCCTATG GTAGGTTACGTCATGCTGTTCTACCACAGGGTAGAACCACGGACAGGATA CCGGGGCACCCTCTGCGT |
| hsa-mir-141 | 202 | GTCGGCCGGCCCTGGGTCCATCTTCCAGTACAGTGTTGGATGGTCTAATT GTGAAGCTCCTAACACTGTCTGGTAAAGATGGCTCCCGGGTGGGTTCTCT CGGC |
| hsa-mir-142 | 203 | ACAGTGCAGTCACCCATAAAGTAGAAAGCACTACTAACAGCACTGGAGGG TGTAGTGTTTCCTACTTTATGGATGAGTGTACTGT |
| hsa-mir-146b | 204 | CCTGGCACTGAGAACTGAATTCCATAGGCTGTGAGCTCTAGCAATGCCCT GTGGACTCAGTTCTGGTGCCCGG |
| hsa-mir-146a | 205 | GTATCCTCAGCTTTGAGAACTGAATTCCATGGGTTGTGTCAGTGTCAGAC CTCTGAAATTCAGTTCTTCAGCTGGGATAT |
| hsa-mir-148a | 206 | GGTCTTTTGAGGCAAAGTTCTGAGACACTCCGACTCTGAGTATGATAGAA GTCAGTGCACTACAGAACTTTGTCTCTAGAGGCT |
| hsa-mir-150 | 207 | TCCCCATGGCCCTGTCTCCCAACCCTTGTACCAGTGCTGGGCTCAGACCC TGGTACAGGCCTGGGGGACAGGGACCTGGGA |
| hsa-mir-152 | 208 | GTCCCCCCCGGCCCAGGTTCTGTGATACACTCCGACTCGGGCTCTGGAGC AGTCAGTGCATGACAGAACTTGGGCCCGGAAGGAC |
|  | 209 | TGTCCCCCCGGCCCAGGTTCTGTGATACACTCCGACTCGGGCTCTGGAG CAGTCAGTGCATGACAGAACTTGGGCCCGGAAGGACC |
| hsa-mir-155 | 210 | TAGGCTGTATGCTGTTAATGCTAATCGTGATAGGGGTTTTTGCCTCCAAC TGACTCCTACATATTAGCATTAACAGTGTATGATGCCTG |
| hsa-mir-181a | 211 | GGTTGCTTCAGTGAACATTCAACGCTGTCGGTGAGTTTGGAATTAAAATC AAAACCATCGACCGTTGATTGTACCCTATGGCTAACC |
| hsa-mir-181b | 212 | GGTCACAATCAACATTCATTGCTGTCGGTGGGTTGAACTGTGTGGACAAG CTCACTGAACAATGAATGCAACTGTGGCC |
| hsa-mir-181c | 213 | CGGAAAATTTGCCAAGGGTTTGGGGGAACATTCAACCTGTCGGTGAGTTT GGGCAGCTCAGGCAAACCATCGACCGTTGAGTGGACCCTGAGGCCTGGAA TTGCCATCCT |
| hsa-mir-182 | 214 | CCTCCCCCCGTTTTTGGCAATGGTAGAACTCACACTGGTGAGGTAACAGG ATCCGGTGGTTCTAGACTTGCCAACTATGGGGCGAGG |

TABLE 2-continued

Hairpins of the microRNAs of the invention

| miR name | Hairpin SEQ ID NO. | Hairpin Sequence |
| --- | --- | --- |
| hsa-mir-187 | 215 | CCTCGGGCTACAACACAGGACCCGGGCGCTGCTCTGACCCCTCGTGTCTT GTGTTGCAGCCGGAGG |
| hsa-mir-193a | 216 | GGGAGCTGAGGGCTGGGTCTTTGCGGGCGAGATGAGGGTGTCGGATCAAC TGGCCTACAAAGTCCCAGTTCTCGGCCCC |
| hsa-mir-195 | 217 | CCTGGCTCTAGCAGCACAGAAATATTGGCACAGGGAAGCGAGTCTGCCAA TATTGGCTGTGCTGCTCCAGG |
| hsa-mir-197 | 218 | TGTGCTCTGGGGGCTGTGCCGGGTAGAGAGGGCAGTGGGAGGTAAGAGCT CTTCACCCTTCACCACCTTCTCCACCCAGCATGGCCGGCACA |
| hsa-mir-199a | 219 | GGCCCCGCCAACCCAGTGTTCAGACTACCTGTTCAGGAGGCTCTCAATGT GTACAGTAGTCTGCACATTGGTTAGGCTGGGCT |
| hsa-mir-200a | 220 | GAGCATCTTACCGGACAGTGCTGGATTTCCCAGCTTGACTCTAACACTGT CTGGTAACGATGTTC |
| hsa-mir-200b | 221 | GCTCGGGCAGCCGTGGCCATCTTACTGGGCAGCATTGGATGGAGTCAGGT CTCTAATACTGCCTGGTAATGATGACGGCGGAGCCCTGC |
| hsa-mir-200c | 222 | GGGCGGGGCCCTCGTCTTACCCAGCAGTGTTTGGGTGCGGTTGGGAGTC TCTAATACTGCCGGGTAATGATGGAGGCCCCTGTCC |
| | 223 | CCCTCGTCTTACCCAGCAGTGTTTGGGTGCGGTTGGGAGTCTCTAATACT GCCGGGTAATGATGGAGG |
| hsa-mir-199a | 224 | GGCCCCGCCAACCCAGTGTTCAGACTACCTGTTCAGGAGGCTCTCAATGT GTACAGTAGTCTGCACATTGGTTAGGCTGGGCT |
| hsa-mir-199b | 225 | GTCTACCCAGTGTTTAGACTATCTGTTCAGGACTCCCAAATTGTACAGTA GTCTGCACATTGGTTAGGC |
| hsa-mir-205 | 226 | TCCATGTGCTTCTCTTGTCCTTCATTCCACCGGAGTCTGTCTCATACCCA ACCAGATTTCAGTGGAGTGAAGTTCAGGAGGCATGGA |
| hsa-mir-210 | 227 | CCAGGCGCAGGGCAGCCCCTGCCCACCGCACACTGCGCTGCCCCAGACCC ACTGTGCGTGTGACAGCGGCTGATCTGTGCCTGG |
| hsa-mir-214 | 228 | GGCTGGACAGAGTTGTCATGTGTCTGCCTGTCTACACTTGCTGTGCAGAA CATCCGCTCACCTGTACAGCAGGCACAGACAGGCAGTCACATGACAACCC AGCC |
| hsa-mir-221 | 229 | GAACATCCAGGTCTGGGGCATGAACCTGGCATACAATGTAGATTTCTGTG TTCGTTAGGCAACAGCTACATTGTCTGCTGGGTTTCAGGCTACCTGGAAA CATGTTC |
| hsa-mir-222 | 230 | CAGCTGCTGGAAGGTGTAGGTACCCTCAATGGCTCAGTAGCCAGTGTAGA TCCTGTCTTTCGTAATCAGCAGCTACATCTGGCTACTGGGTCTCTGATGG CATCTTCTAGCTTCTG |
| | 231 | GCTGCTGGAAGGTGTAGGTACCCTCAATGGCTCAGTAGCCAGTGTAGATC CTGTCTTTCGTAATCAGCAGCTACATCTGGCTACTGGGTCTCTGATGGCA TCTTCTAGCT |
| hsa-mir-223 | 232 | GCTCTTGGCCTGGCCTCCTGCAGTGCCACGCTCCGTGTATTTGACAAGCT GAGTTGGACACTCCATGTGGTAGAGTGTCAGTTTGTCAAATACCCCAAGT GCGGCACATGCTTACCAGCTCTAGGCCAGGGC |
| hsa-mir-224 | 233 | GGGGCTTTCAAGTCACTAGTGGTTCCGTTTAGTAGATGATTGTGCATTGT TTCAAAATGGTGCCCTAGTGACTACAAAGCCCC |
| hsa-mir-342 | 234 | GTGAAACTGGGCTCAAGGTGAGGGGTGCTATCTGTGATTGAGGGACATGG TTAATGGAATTGTCTCACACAGAAATCGCACCCGTCACCTTGGCCTACTT ATCAC |
| | 235 | GAAACTGGGCTCAAGGTGAGGGGTGCTATCTGTGATTGAGGGACATGGTT AATGGAATTGTCTCACACAGAAATCGCACCCGTCACCTTGGCCTACTTA |
| hsa-mir-345 | 236 | ACCCAAACCCTAGGTCTGCTGACTCCTAGTCCAGGGCTCGTGATGGCTGG TGGGCCCTGAACGAGGGGTCTGGAGGCCTGGGTTTGAATATCGACAGC |
| hsa-mir-346 | 237 | GGTCTCTGTGTTGGGCGTCTGTCTGCCCGCATGCCTGCCTCTCTGTTGCT CTGAAGGAGGCAGGGGCTGGGCCTGCAGCTGCCTGGGCAGAGCGG |

TABLE 2-continued

Hairpins of the microRNAs of the invention

| miR name | Hairpin SEQ ID NO. | Hairpin Sequence |
| --- | --- | --- |
| hsa-mir-375 | 238 | CGCTCCCGCCCCGCGACGAGCCCCTCGCACAAACCGGACCTGAGCGTTTT GTTCGTTCGGCTCGCGTGAGGCAGGGGCG |
|  | 239 | CCCCGCGACGAGCCCCTCGCACAAACCGGACCTGAGCGTTTTGTTCGTTC GGCTCGCGTGAGGC |
| hsa-mir-424 | 240 | CGAGGGGATACAGCAGCAATTCATGTTTTGAAGTGTTCTAAATGGTTCAA AACGTGAGGCGCTGCTATACCCCCTCGTGGGGAAGGTAGAAGGTGGGG |
| hsa-mir-429 | 241 | GATGGGCGTCTTACCAGACATGGTTAGACCTGGCCCTCTGTCTAATACTG TCTGGTAAAACCGTCCATC |
| hsa-mir-455 | 242 | GGCGTGAGGGTATGTGCCTTTGGACTACATCGTGGAAGCCAGCACCATGC AGTCCATGGGCATATACACTTGCCTCAAGGCC |
| hsa-mir-483 | 243 | ACCCCAAGGTGGAGCCCCAGCGACCTTCCCCTTCCAGCTGAGCATTGCT GTGGGGAGAGGGGGAAGACGGGAGGAAAGAAGGGAGTGGTTCCATCACG CCTCCTCACTCCTCTCCTCCCGTCTTCTCCTCTCCTGCCCTTGTCTCCCT GTCTCAGCAGCTCCAGGGGTGGTGTGGGCCCCTCCAGCCTCCTAGGTGGT |
| hsa-mir-487b | 244 | GTGCTAACCTTTGGTACTTGGAGAGTGGTTATCCCTGTCCTGTTCGTTTT GCTCATGTCGAATCGTACAGGGTCATCCACTTTTTCAGTATCAAGAGCGC |
| hsa-mir-486 | 245 | CTGATCTCCATCCTCCCTGGGGCATCCTGTACTGAGCTGCCCCGAGGCCC TTCATGCTGCCCAGCTCGGGGCAGCTCAGTACAGGATACTCGGGGTGGGA GTCAGCAGGAGGTGAG |
|  | 246 | GCATCCTGTACTGAGCTGCCCCGAGGCCCTTCATGCTGCCCAGCTCGGGG CAGCTCAGTACAGGATAC |
| hsa-mir-486-2 | 247 | TCCTGTACTGAGCTGCCCCGAGCTGGGCAGCATGAAGGGCCTCGGGGCAG CTCAGTACAGGATG |
| hsa-mir-497 | 248 | CGGTCCTGCTCCCGCCCCAGCAGCACACTGTGGTTTGTACGGCACTGTGG CCACGTCCAAACCACACTGTGGTGTTAGAGCGAGGGTGGGGGAGGCACCG |
| hsa-mir-513a | 249 | GGGATGCCACATTCAGCCATTCAGCGTACAGTGCCTTTCACAGGGAGGTG TCATTTATGTGAACTAAAATATAAATTTCACCTTTCTGAGAAGGGTAATG TACAGCATGCACTGCATATGTGGTGTCCC |
| hsa-mir-542 | 250 | GGATGCACAGATCTCAGACATCTCGGGGATCATCATGTCACGAGATACCA GTGTGCACTTGTGACAGATTGATAACTGAAAGGTCTGGGAGCCACTCATC T |
| hsa-mir-551b | 251 | TGCCAGATGTGCTCTCCTGGCCCATGAAATCAAGCGTGGGTGAGACCTGG TGCAGAACGGGAAGGCGACCCATACTTGGTTTCAGAGGCTGTGAGAATAA CTGCA |
|  | 252 | AGATGTGCTCTCCTGGCCCATGAAATCAAGCGTGGGTGAGACCTGGTGCA GAACGGGAAGGCGACCCATACTTGGTTTCAGAGGCTGTGAGAATAA |
| hsa-mir-574 | 253 | GGGACCTGCGTGGGTGCGGGCGTGTGAGTGTGTGTGTGAGTGTGTGTC GCTCCGGGTCCACGCTCATGCACACACCCACACGCCCACACTCAGG |
| hsa-mir-625 | 254 | TGGTAAGGGTAGAGGGATGAGGGGGAAAGTTCTATAGTCCTGTAATTAGA TCTCAGGACTATAGAACTTTCCCCCTCATCCCTCTGCCCTCTACCA |
| hsa-mir-650 | 255 | TCTCAGGAGGCAGCGCTCTCAGGACGTCACCACCATGGCCTGGGCTCTGC TCCTCCTCA |
| hsa-mir-658 | 256 | CTCGGTTGCCGTGGTTGCGGGCCCTGCCCGCCCGCCAGCTCGCTGACAGC ACGACTCAGGGCGGAGGGAAGTAGGTCCGTTGGTCGGTCGGGAACGAG |
| hsa-mir-664b | 257 | GTTCAGTCCAGGGCAGCTTCCCTGTTCTGTTAATTAAACTTTGGGACATT AAAATGGGCTAAGGGAGATGATTGGGTAGAAAGTATTATTCTATTCATTT GCCTCCCAGCCTACAAAAATGCCTGCTTGGGGTCTAATACTTCAACGGTT AAAGATGCCTGGAAGAGGGC |
| hsa-mir-708 | 258 | GGTAACTGCCCTCAAGGAGCTTACAATCTAGCTGGGGGTAAATGACTTGC ACATGAACACAACTAGACTGTGAGCTTCTAGAGGGCAGGGACC |
| hsa-mir-765 | 259 | TTAGGCGCTGATGAAAGTGGAGTTCAGTAGACAGCCCTTTTCAAGCCCTA CGAGAAACTGGGGTTTCTGGAGGAGAAGGAAGGTGATGAAGGATCTGTTC TCGTGAGCCTGA |
| hsa-mir-1229 | 260 | GTGGGTAGGGTTTGGGGGAGAGCGTGGGCTGGGGTTCAGGGACACCCTCT CACCCACTGCCCTCCCACAG |

TABLE 2-continued

Hairpins of the microRNAs of the invention

| miR name | Hairpin SEQ ID NO. | Hairpin Sequence |
|---|---|---|
| hsa-mir-2392 | 261 | TGGTCCCTCCCAATCCAGCCATTCCTCAGACCAGGTGGCTCCCGAGCCACCCCAGGCTGTAGGATGGGGGTGAGAGGTGCTA |
| hsa-mir-3074 | 262 | GCTCGACTCCTGTTCCTGCTGAACTGAGCCAGTGTGTAAAATGAGAACTGATATCAGCTCAGTAGGCACCGGAGGGCGGGT |
| hsa-mir-3141 | 263 | CCCGGTGAGGGCGGGTGGAGGAGGAGGGTCCCCACCATCAGCCTTCACTGGGACGGG |
| hsa-mir-3162 | 264 | AAGTTAATTTTGAAGCTGACTTTTTTAGGGAGTAGAAGGGTGGGGAGCATGAACAATGTTTCTCACTCCCTACCCCTCCACTCCCCAAAAAAGTCAGCTTCTCTTGTTAACTT |
| hsa-mir-3679 | 265 | GGCCCCACGTGGTGAGGATATGGCAGGGAAGGGGAGTTTCCCTCTATTCCCTTCCCCCCAGTAATCTTCATCATGCGGTGTC |
| hsa-mir-3687 | 266 | GCGCGTGCGCCCGAGCGCGGCCCGGTGGTCCCTCCCGGACAGGCGTTCGTGCGACGTGT |
| hsa-mir-3940 | 267 | GAGGAAAAGATCGAGGTGGGTTGGGGCGGGCTCTGGGGATTTGGTCTCACAGCCCGGATCCCAGCCCACTTACCTTGGTTACTCTCCTT |
| hsa-mir-4270 | 268 | CAAATAGCTTCAGGGAGTCAGGGGAGGGCAGAAATAGATGGCCTTCCCCTGCTGGGAAGAAAGTG |
| hsa-mir-4284 | 269 | TTCTGTGAGGGGCTCACATCACCCCATCAAAGTGGGGACTCATGGGGAGAGGGGGTAGTTAGGAGCTTTGATAGAG |
| hsa-mir-4443 | 270 | GGTGGGGGTTGGAGGCGTGGGTTTTAGAACCTATCCCTTTCTAGCCCTGAGCA |
| hsa-mir-4447 | 271 | GTTCTAGAGCATGGTTTCTCATCATTTGCACTACTGATACTTGGGGTCAGATAATTGTTTGTGGTGGGGCTGTTGTTTGCATTGTAGGAT |
| hsa-mir-4448 | 272 | GGAGTGACCAAAAGACAAGAGTGCGAGCCTTCTATTATGCCCAGACAGGGCCACCAGAGGGCTCCTTGGTCTAGGGGTAATGCC |
| hsa-mir-4454 | 273 | CCGGATCCGAGTCACGGCACCAAATTTCATGCGTGTCCGTGTGAAGAGACCACCA |
| hsa-mir-4534 | 274 | GTGAATGACCCCCTTCCAGAGCCAAAATCACCAGGGATGGAGGAGGGGTCTTGGGTAC |
| hsa-mir-4538 | 275 | AACTGGGCTGGGCTGAACTGGGCTGGGCTGAGCTGAGCTTGGATGAGCTGGGCTGAACTGGGCTGGGTTGAGCTGGGCTGGGCTGAGTTGAGCCAGGCTGATCTGGGCTGAGCCGAGCTGGGTTAAGCCGAGCTGGGTT |
| hsa-mir-4539 | 276 | GGCTGGGCTGGGCTGGGCTCTGCTGTGCTGTGCTGAACAGGGCTGAGCTGAACTGAGCTGAGCTGGGCTGAGCTGGGCTCTGCTGTGCTGTGCTGAGCAGGGCTGAGCTGAACTGGGCTGAGCTGGGCTGAGCTGGGCTGAGTTGAGCAGAGCTGGGTTGAGCAGAGCTGGGCTGGGCTGGGCTGAGTTGAGCC |
| hsa-mir-4689 | 277 | CGGTTTCTCCTTGAGGAGACATGGTGGGGCCGGTCAGGCAGCCCATGCCATGTGTCCTCATGGAGAGGCCG |
| hsa-mir-4690 | 278 | GGCAGGTGAGCAGGCGAGGCTGGGCTGAACCCGTGGGTGAGGAGTGCAGCCCAGCTGAGGCCTCTGCTGTCTTATCTGTC |
| hsa-mir-4739 | 279 | GTGGGCAGGGGAGGAAGAAGGGAGGAGGAGCGGAGGGGCCCTTGTCTTCCCAGAGCCTCTCCCTTCCTCCCCTCCCCCTCCCTCTGCTCAT |
| hsa-mir-5001 | 280 | GGGCGGCTGCGCAGAGGGCTGGACTCAGCGGCGGAGCTGGCTGCTGGCCTCAGTTCTGCCTCTGTCCAGGTCCTTGTGACCCGCCC |
| hsa-mir-5100 | 281 | CTGGGGGTAGGAGCGTGGCTTCTGGAGCTAGACCACATGGGTTCAGATCCCAGCGGTGCCTCTAACTG |
| hsa-mir-5684 | 282 | GAGCTATGATTGTGTAGCTGAACTCTAGCCTGAGCAACAGAGTGAGATGGTCTTGTTTTGTTGCCAGGCTGGAGTCCAGTGTCAAGATCATGGCTC |
| hsa-mir-5698 | 283 | GAGCTCCAAATCTGTGCACCTGGGGGAGTGCAGTGATTGTGGAATGCAAAGTCCCACAATCACTGTACTCCCCAGGTGCACAGATTCTCTCTC |

TABLE 2-continued

Hairpins of the microRNAs of the invention

| miR name | Hairpin SEQ ID NO. | Hairpin Sequence |
| --- | --- | --- |
| hsa-mir-5701-1 | 284 | GATTGGACTTTATTGTCACGTTCTGATTGGTTAGCCTAAGACTTGTTCTG ATCCAATCAGAACATGAAAATAACGTCCAATC |
| hsa-mir-5701-2 | 285 | GATTGGACTTTATTGTCACGTTCTGATTGGTTAGCCTAAGACTTGTTCTG ATCCAATCAGAACATGAAAATAACGTCCAATC |
| hsa-mir-5739 | 286 | TTGGCTATAACTATCATTTCCAAGGTTGTGCTTTTAGGAAATGTTGGCTG TCCTGCGGAGAGAGAATGGGGAGCCAG |
| hsa-mir-6076 | 287 | AGCATGACAGAGGAGAGGTGGAGGTAGGCGAGAGTAATATAATTTCTCCA GGAGAACATCTGAGAGGGGAAGTTGCTTTCCTGCCCTGGCCCTTTCACCC TCCTGAGTTTGGG |
| hsa-mir-6086 | 288 | AGGAGGTTGGGAAGGGCAGAGATGAGCATAAAGTTTTTGCCTTGTTTTTC TTTTT |
| hsa-mir-6127 | 289 | AAGATGAGGGAGTGGGTGGGAGGTGGGAAGGCTGCCCCAAATGGCCTCTA ACATCCCTTCCAGTCTCCTCCTCCTCCTCCTCCTTCTTCTT |
| MID-00078 | 290 | TATGTACCCGGAGCCAAAAGTGATTGGAGGTGGGTGGGGTTAATGAATAG ACAAGTGTTAAAACTAAAAGTCACGTCTCTCTCTCCTTCCTCCTCAGTTT TGGCTTGATTTTTCATG |
| MID-00321 | 291 | CTTACCTAGAAATTGTTGCCTGTCTGAGCGACGCTTCAAACTCAGCTTCA GCAGGTCTGCAGGGACATCAGGTAGG |
| MID-00387 | 292 | GTGTCTCTGTGTTTGCAGGTGTCCAGTGTGAGGTGCAGCTGGTGGAGTCT GGGGGAGGCTTGGTACAGCCTGGGGGATCCCTGAGACTCTCCTGTGCAGC CTCTGGATTCACCTTCAGTAACAGTGACAT |
| MID-00671 | 293 | GTCAGCCTGCAATTAGTGAAATGGAGGCACACATGCTGGTTTGCAGATTG TGGGTGGGAGGAC |
| MID-00672 | 294 | GTGTCTCTGTGTTTGCAGGTGTCCAGTGTGAGGTGCAGCTGGTGGAGTCT GGGGGAGGCTTGGTACAGCCTGGGGGATCCCTGAGACTCTCCTGTGCAGC CTCTGGATTCACCTTCAGTAACAGTGACAT |
| MID-00690 | 295 | GGCCTTGGATGGAGAAGACTGGAGAGGGTATGGAAGTGCTTGGACGTAGG ACATCTGCCTCTCTGGTCTTTGTCCATCCCACAGGGCC |
| MID-15965 | 296 | AGCTGGTTGGCATTCTGGCCCTGGTTCATGCCAACTCTTGTGTTGACTAC CCCAGGATGCCAGCATAGTTG |
| MID-16318 | 297 | CTGCCAAAGAGCAGCAAGATGAGCTGGTTTGATGGGGAGCCATCCCTTGA TGAGGAGAACCCTTCCCACTCTCACTCAGCCTCACCCAGCTGCCCTGAGG CAG |
| MID-17144 | 298 | GCTCAGAAGTGATGAATTGATCAGATAGACGAGGCCGGGCTTGTCCCCGG CCACTGATTATCGAGGCGATTCTGATCTGGGC |
| MID-17866 | 299 | GCTGGGTGCAGTAGCTTATGTCTGTAGTCCCAGCTACTTGGGAGGCTGAG GTGGGAGGATCACCTGAGGTCAGGAGTTTGGGTCTGCCGTGAGCTGTGAT TGCGCCTGTGAATAGTCACTGCACTCCAGC |
| MID-18468 | 300 | GACGTGAGGGGGTGCTACATACAGCAGCTGTGTGTAGTATGTGCCTTTCT CTGTT |
| MID-19433 | 301 | TAGGAATTCTGGACCAGGCTTAAAAGACTGGGATGAGGCTGGTCCGAAGG TAGTGAGTTATCTCCATTGATAGTTCAGTCTGTAACAGATCAAACTCCTT GTTCTACTCTTTTTTTTTTTTTTAGACAGA |
| MID-19434 | 302 | TGGGCTGGTCCGAGTGCAGTGGTGTTTACAAGTATTTGATTATAACTAGT TACAGATTTCTTTGTTTCCTTCTCCACTCCCACTGCCTCACTTGACTGGC CTA |
| MID-23168 | 303 | GCTCTGTCCAAAGTAAACGCCCTGACGCACTGTGGGAAGGGTGAGATGGG CACCGC |
| MID-23794 | 304 | GTGAGTGGGAGGGGGCTGCAGCCCAAAGAGGCAACAAAGGCCCTTCCCG GCCAATGCATTAC |

TABLE 2-continued

Hairpins of the microRNAs of the invention

| miR name | Hairpin SEQ ID NO. | Hairpin Sequence |
|---|---|---|
| MID-24496 | 305 | TGTCCTCAGGCCTGCTACTGATCCTGCAGCCAGAAGTTCCAGAAAGTGAAGGGATTTGGAGGGGCCGTGACAGATGCAGGTGCCCTCAACATCCTTGCCCTGTCACCCCCTGCCCAGAATTTGCTACTTAAATGGTACTTCTCTGAAGAAGATGAGGAGGAAGGGGACA |
| MID-24705 | 306 | ACAGAATTCCTCTTCTCCCTTCTCCTATAACCTGTTTTATTTAATTAATTAATTTTTTAGGCTAGTCAAGTGAAGCAGTGGGAGTGGAAGGAACAAAGAAATCTGT |
| MD2-495 | 307 | UGAGCUCUGCGGCGCCAAGGGACCGAGGGGCCGAGGGAGCGAGAG |
| MD2-437 | 308 | AGUGCUUGGCUGAGGAGCUGGGGCCAAGGGGGAACACAAAUAUGGUCCUGACCCUACAUUCCCAGCCCUGCCUCU |

It is to be noted that SEQ ID NOs.183-306 in Table 2 present the cDNA corresponding to the sequence of the naturally occurring pre-miR, i.e., the sequences present thymine (T) instead of uracil (U).

The nucleic acid may be in the form of a nucleic acid complex, and may further comprise one or more of the following: a peptide, a protein, a RNA-DNA hybrid, an antibody, an antibody fragment, a Fab fragment, or an aptamer.

The nucleic acid may also comprise a sequence of a pre-miRNA or a variant thereof. The pre-miRNA sequence may comprise from 45-90, 60-80 or 60-70 nucleotides. The sequence of the pre-miRNA may comprise a miRNA and a miRNA* as set forth herein. The sequence of the pre-miRNA may comprise the sequence of SEQ ID NOS: 183-308 or variants thereof.

As described herein, the nucleic acid may be at least 70%, 75%, 80%, 85%, 90%, 95%, 97%, 98% or 99% identical to the nucleic acid sequences in Tables 1 or 2 (with increments of 1% from 80 to 99%), over a region of 8, 9, 10, 11, 12, 13, 14, 15, 16, 17, 18, 19, 20, 21, 22, 23, 24, 25, 30, 35, 40, 45, 50 or more nucleotides.

The nucleic acid may also comprise a sequence of a microRNA (including a miRNA*) or a variant thereof, including those putative microRNAs represented by MID-[numeral]. As referred to herein, microRNAs include those miRs which have been listed in the miRBase registry name (release 20), as well as putative microRNAs which have been predicted and/or cloned by Rosetta Genomics and which are represented by MID-[numeral]. The microRNA sequence may comprise from 13-33, 18-24 or 21-23 nucleotides. The microRNA may also comprise a total of at least 5, 67, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the microRNA may be the first 13-33 nucleotides of the pre-miRNA. The sequence of the microRNA may also be the last 13-33 nucleotides of the pre-miRNA. The sequence of the microRNA may comprise the sequence of any one of SEQ ID NOS: 1-182 or a variant thereof. The present invention employs microRNAs for the identification, classification and diagnosis of thyroid nodules.

"Variant", as used herein referring to a nucleic acid, means (i) a portion of a referenced nucleotide sequence; (ii) the complement of a referenced nucleotide sequence or portion thereof; (iii) a nucleic acid that differs from the referenced nucleotide sequence by a point-mutation or the complement thereof; (iv) a naturally-occurring variant of the referenced nucleotide sequence present in the general population or the complement thereof; or (iv) a nucleic acid that hybridizes under stringent conditions to the referenced nucleic acid, of the complement thereof.

"Probe", as used herein, means an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. For example, for hybridization assays, the probe may be complementary to at least 8, at least 9, at least 10, at least 11, at least 12, at least 13, at least 14, at least 15, at least 16, at least 17, at least 18, at least 19, at least 20 contiguous nucleotides of the sequence of the microRNA being detected. Alternatively, for PCR assays, the probe may be complementary to at least 8, at least 9, at least 10, at least 11, at least 12, at least 13, at least 14, at least 15, at least 16, at least 17, at least 18, at least 19, at least 20 contiguous nucleotides of the sequence of the PCR product being detected.

Thus, a probe may be complementary to, or may hybridize to at least 60%, 65%, 70%, 75%, 80%, 85%, 90%, 95%, 97%, 98% or 99% of its target nucleic acid.

A probe may be single-stranded or partially single- and partially double-stranded. The strandedness of the probe is dictated by the structure, composition and properties of the target sequence. Probes may include a label, an attachment, or a nucleotide sequence that does not naturally occur in a nucleic acid described herein. Probes may be directly labeled or indirectly labeled such as with biotin to which a streptavidin complex may bind.

"Probe" may be an agent for detecting the nucleic acid sequences described herein. Probe may be a labeled nucleic acid probe capable of hybridizing to a portion of the nucleic acid sequence of the invention, or amplification products derived therefrom. In some embodiments, the nucleic acid probe is reverse complementary nucleic acid molecule of the nucleic acid sequence disclosed herein. A probe may be a nucleic acid sequence which sufficiently specifically hybridizes under stringent conditions to the nucleic acid disclosed herein. A probe is optionally labeled with a fluorescent molecule such as a fluorescein, e.g. 6-carboxyfluorescein (FAM), an indocarbocyanine, e.g. QUASAR-670 (QUA), a hexafluorocine, such as 6-carboxyhexafluorescein (HEX), or other fluorophore molecules and optionally a quencher. A quencher is appreciated to be matched to a fluorophore. Illustrative examples of a quencher include the black hole quenchers BHQ1, and BHQ2, or minor groove binders (MGB), e.g. dihydrocyclopyrroloindole tripeptide. Other fluorophores and quenchers are known in the art and are similarly operable herein.

Thus, the present invention also provides a probe, said probe comprising the novel nucleic acid sequences described herein, defined by any one of SEQ ID NOs. 27-29, 33, 34, 139, 140, 307 and 308, or variants thereof. Probes may be used for screening and diagnostic methods. The probe may be attached or immobilized to a solid substrate, such as a biochip. The probe may have a length of from 8 to 500, 10 to 100 or 20 to 60 nucleotides. The probe may have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may further comprise a linker sequence of from 10-60 nucleotides. The probe may further comprise a linker. The linker may comprise a sequence that does not occur naturally in a nucleic acid described herein. The linker may be 10-60 nucleotides in length. The linker may be 20-27 nucleotides in length. The linker may be of sufficient length to allow the probe to be a total length of 45-60 nucleotides. The linker may not be capable of forming a stable secondary structure, or may not be capable of folding on itself, or may not be capable of folding on a non-linker portion of a nucleic acid contained in the probe. The sequence of the linker is heterogeneous, and it may not appear in the genome of the animal from which the probe non-linker nucleic acid is derived.

As used herein, the term "reference value" means a value that statistically correlates to a particular outcome when compared to an assay result. In one embodiment, the reference value is determined from statistical analysis of studies that compare microRNA expression with known clinical outcomes. In another embodiment, the reference value may vary according to the classifier (i.e. the algorithm) used. Hence, the reference value may be the expression levels (or values) of all the microRNAs in the training data. The reference value may be one or more thresholds established by the classifier. The reference value may further be a coefficient or set of coefficients. Essentially the reference value refers to any parameter needed or used by the algorithm.

"Sensitivity", as used herein, may mean a statistical measure of how well a classification test correctly identifies a condition or conditions, for example, how frequently it correctly classifies a cancer into the correct type out of two or more possible types. In a binary classification test, sensitivity means how frequently the test correctly classifies a cancer into the correct type out of two possible types. The sensitivity for class A is the proportion of cases that are determined to belong to class "A" by the test out of the cases that are in class "A", as determined by some absolute or gold standard.

"Smear", as used herein, refers to a sample of thyroid tissue spread thinly on a microscope slide for examination, typically for medical diagnosis. Smears from FNAs usually have very small amounts of cells, which results in small amounts of RNA, which may range from 1-1000 ng, 1-100 ng, 1-50 ng, 1-40 ng, 5-100 ng, 5-50 ng, 5-40 ng, accordingly. Smears may be stained with any stain known to the man skilled in the art of cytology, histology or pathology, such as any stain used to differentiate cells in pathologic specimens. Examples of stains are multichromatic stains, like Papanicolaou, which are a combination of nuclear stain and cytoplasm stain; cellular structure stains such as Wright, Giemsa, Romanowsky and the like; nuclear stains, such as Hoescht stains and the like; cell viability stains, such as Trypan blue, and the like, enzyme activity, such as benzidine for HRP to form visible precipitate and the like.

"Specificity", as used herein, may mean a statistical measure of how well a binary classification test correctly identifies cases that do not have a specific condition, for example, how frequently it correctly classifies a sample as non-cancer when indeed it is a non-cancerous sample. The specificity for class A is the proportion of cases that are determined to belong to class "not A" by the test out of the cases that are in class "not A", as determined by some absolute or gold standard.

"Specificity", as used herein, may mean a statistical measure of how well a classification test correctly identifies cases that do not have a specific condition. The specificity for class A is the proportion of cases that are determined by the test not to belong to class A out of the cases that are not in class A, as determined by some absolute or gold standard.

As used herein, the term "stage of cancer" refers to a numerical measurement of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

"Stringent hybridization conditions", as used herein, mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C., DMSO, 6×SSPE+0.005% N-Lauroylsarcosine+0.005% Triton X-102, 0.06×SSPE+0.005% N-Lauroylsarcosine+ 0.005% Triton X-102.

As used herein, the term "subject" refers to a mammal, including both human and other mammals. The methods of the present invention are preferably applied to human subjects.

As used herein, the term "subtype of cancer" refers to different types of cancer that affect the same organ (e.g., papillary, follicular carcinoma and follicular variant papillary carcinoma of the thyroid).

"Thyroid lesion" as used herein, may mean a thyroid tumor, including sub-types of thyroid tumors, such as Hashimoto disease, follicular carcinoma, papillary carcinoma, follicular variant of papillary carcinoma (FVPC or FVPTC), encapsulated FVPC (or encapsulated FVPTC), non-encapsulated (infiltrative/diffuse) FVPC or FVPTC, medullary carcinoma, anaplastic thyroid cancer, or poorly differentiated thyroid cancer.

As used herein, the phrase "threshold expression profile" refers to a criterion expression profile to which measured values are compared in order to classify a tumor.

As used herein, a tissue sample is tissue obtained from a tissue biopsy using methods well known to those of ordinary skill in the related medical arts. The phrase "suspected of being cancerous", as used herein, means a cancer tissue sample believed by one of ordinary skill in the medical arts to contain cancerous cells. Methods for obtaining the sample from the biopsy include gross apportioning of a mass, microdissection, laser-based microdissection, or other art-known cell-separation methods.

"Tumor", as used herein, refers to all neoplastic cell growth and proliferation, whether malignant or benign, and all pre-cancerous and cancerous cells and tissues. The cytological classification of the thyroid lesions or tumor samples used herein is based on "The Bethesda System for Reporting Thyroid Cytopathology", the "BSRTC" (Syed, Z. Ali and Edmund S. Cibas, eds.; DOI 10.1007/978-0-387-87666-5_1; Springer Science+Business Media, LLC 2010). The BSRTC recommends that each thyroid FNA report be accompanied by a general diagnostic category, in which each category has an implied cancer risk.

Recommended nomenclature for the Bethesda categories are as follows:
I. Non-diagnostic or Unsatisfactory
    Cyst fluid only
    Virtually acellular specimen
    Other (obscuring blood, clotting artifact, etc.)
II. Benign
    Consistent with a benign follicular nodule (includes adenomatoid nodule, colloid nodule, etc.)
    Consistent with lymphocytic (Hashimoto) thyroiditis in the proper clinical context
    Consistent with granulomatous (subacute) thyroiditis
    Other
III. Atypia of Undetermined Significance or Follicular Lesion of Undetermined Significance
IV. Follicular Neoplasm or suspicious of a Follicular Neoplasm
    Specific in Hurthle cell (oncocytic) type
V. Suspicious for Malignancy
    Suspicious for papillary carcinoma
    Suspicious for medullary carcinoma
    Suspicious for metastatic carcinoma
    Suspicious for lymphoma
    Other
VI. Malignant
    Papillary thyroid carcinoma
    Poorly differentiated carcinoma
    Medullary thyroid carcinoma
    Undifferentiated (anaplastic) carcinoma
    Squamous cell carcinoma
    Carcinoma with mixed features
    Metastatic carcinoma
    Non-Hodgkin lymphoma
    Other As used herein, "Indeterminate" refers to thyroid lesions or tumor samples examined for cytology and classified according to the Bethesda classification in categories III, IV and V.

The present invention further provides a method for identifying subtypes of thyroid lesions in a subject, said subtypes of thyroid lesions being said subtypes of malignant or benign thyroid tumor. Subtype is any one of follicular carcinoma, papillary carcinoma, follicular variant of papillary carcinoma (FVPC or FVPTC), encapsulated FVPC (or encapsulated FVPTC), non-encapsulated FVPC (or non-encapsulated FVPTC), medullary carcinoma, anaplastic thyroid cancer or poorly differentiated thyroid cancer.

In another further embodiment, said subtype is any one of Hashimoto thyroiditis, follicular adenoma or hyperplasia.

In another further embodiment, said subtype is Hurthle cell carcinoma.

In another aspect, the present invention provides a method for distinguishing between follicular adenoma and follicular carcinoma.

In another further aspect, the present invention provides a method for distinguishing follicular adenoma from papillary carcinoma.

In another further aspect, the present invention provides a method for distinguishing follicular adenoma from follicular variant of papillary carcinoma.

In another further aspect, the present invention provides a method for distinguishing non-encapsulated follicular variant of papillary carcinoma from benign lesions.

In another further aspect the present invention provides a method for distinguishing papillary carcinoma and Hashimoto thyroiditis.

"Vector" refers to any known vector such as a plasmid vector, a phage vector, a phagemid vector, a cosmid vector, or a virus vector. The nucleic acid described herein may be comprised in a vector. The vector may be used for delivery of the nucleic acid. The vector preferably contains at least a promoter that enhances expression of the nucleic acid carried, and in this case the nucleic acid is preferably operably linked to such a promoter. The vector may or may not be replicable in a host cell, and the transcription of a gene may be carried out either outside the nucleus or within the nucleus of a host cell. In the latter case, the nucleic acid may be incorporated into the genome of a host cell. A vector may be a DNA or RNA vector. A vector may be either a self-replicating extrachromosomal vector or a vector that integrates into a host genome.

In one embodiment of the method or protocol of the invention, the levels of microRNAs are measured by reverse transcription polymerase chain reaction (RT-PCR). Target sequences of a cDNA are generated by reverse transcription of a target RNA, which may be a nucleic acid described herein (comprising a sequence provided in Tables 1 and 2). Known methods for generating cDNA involve reverse transcribing either polyadenylated RNA or alternatively, RNA with a ligated adaptor sequence.

RNA may be ligated to an adaptor sequence prior to reverse transcription. A ligation reaction may be performed by T4 RNA ligase to ligate an adaptor sequence at the 3' end of the RNA. Reverse transcription (RT) reaction may then be performed using a primer comprising a sequence that is complementary to the 3' end of the adaptor sequence.

Alternatively, polyadenylated RNA may be used in a reverse transcription (RT) reaction using a poly(T) primer comprising a 5' adaptor sequence. The poly(T) sequence may comprise 8, 9, 10, 11, 12, 13, or 14 consecutive thymines.

The reverse transcript of the RNA may then be amplified by real-time PCR, using a specific forward primer comprising at least 15 nucleic acids complementary to the target nucleic acid and a 5' tail sequence; a reverse primer that is complementary to the 3' end of the adaptor sequence; and a probe comprising at least 8 nucleic acids complementary to the target nucleic acid. The probe may be partially complementary to the 5' end of the adaptor sequence.

The amplification of the reverse transcripts of the target nucleic acids (microRNAs, including herein described putative microRNAs) may be by PCR or the like. The first cycles of the PCR reaction may have an annealing temperature of 56° C., 57° C., 58° C., 59° C., or 60° C. The first cycles may comprise 1-10 cycles. The remaining cycles of the PCR reaction may be 60° C. The remaining cycles may comprise 2-40 cycles.

The PCR reaction comprises a forward primer. In one embodiment, the forward primer may comprise 15, 16, 17, 18, 19, 20, or 21 nucleotides identical to the target nucleic acid. The 3' end of the forward primer may be sensitive to differences in sequence between a target nucleic acid and highly similar sequences.

The forward primer may also comprise a 5' overhanging tail. The 5' tail may increase the melting temperature of the forward primer. The sequence of the 5' tail may comprise a sequence that is non-identical to the target nucleic acid. The sequence of the 5' tail may also be synthetic. The 5' tail may comprise 8, 9, 10, 11, 12, 13, 14, 15, or 16 nucleotides. Examples of forward primers used in the invention are provided in Table 8.

The PCR reaction comprises a reverse primer. The reverse primer may be complementary to a target nucleic acid. The reverse primer may also comprise a sequence complementary to an adaptor sequence. Examples of reverse primers used in the invention are provided in Example 8.

The probes used to detect products of RT-PCR amplification may be general probes or sequence-specific probes. General probes are designed to detect (or hybridize with) RT-PCR amplification products in a non-sequence specific manner. Said probes are between 16 and 20 nucleotides long, preferably 18 nucleotides long, and comprise a sequence which is the reverse complement of the RT primer, including 4 adenines (As) at the 5' end. Sequence-specific probes are designed to detect (or hybridize with) RT-PCR amplification products based on total or partial complementarity between the sequence of the probe and the sequence of the RT-PCR product. Said probes are between 20 and 28 nucleotides longs, preferably 24 nucleotides long, and comprising at the 5' end three nucleotides from each at least two are complementary to the RT primer, followed by between 10 to 14, preferably 12 thymines (Ts), followed by between 6 to 10, preferably 8 contiguous nucleotides which correspond to the reverse complementary sequence of the specific corresponding microRNA.

A biochip comprising novel nucleic acids described herein is provided. In one embodiment, the biochip may comprise probes that recognize the novel nucleic acids described herein. Said nucleic acids are isolated nucleic acids comprising at least 12 contiguous nucleotides at least 80% identical to the sequence of any one of SEQ ID NOs. 27-29, 33, 34, 139, 140, 307 and 308. In one embodiment, said isolated nucleic acid comprises at least 13, at least 14, at least 15, at least 16, at least 17, at least 18, at least 19, or at least 20 contiguous nucleotides identical to the sequence of any one of SEQ ID NOs. 27-29, 33, 34, 139, 140, 307 and 308. The biochip may comprise a solid substrate comprising an attached nucleic acid, probe or plurality of probes described herein. The probes may be capable of hybridizing to a target sequence under stringent hybridization conditions. The probes may be attached at spatially defined addresses on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as flexible foam, including closed cell foams made of particular plastics.

The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

In a further embodiment of the invention, measuring the microRNAs for classification of thyroid lesions may be effected by high throughput sequencing. High throughput sequencing can involve sequencing-by-synthesis, sequencing-by-ligation, and ultra-deep sequencing. Sequence-by-synthesis can be initiated using sequencing primers complementary to the sequencing element on the nucleic acid tags. The method involves detecting the identity of each nucleotide immediately after (substantially real-time) or upon (real-time) the incorporation of a labeled nucleotide or nucleotide analog into a growing strand of a complementary nucleic acid sequence in a polymerase reaction. After the successful incorporation of a label nucleotide, a signal is measured and then nulled by methods known in the art. Examples of sequence-by-synthesis methods are known in the art, and are described for example in U.S. Pat. No. 7,056,676, U.S. Pat. No. 8,802,368 and U.S. Pat. No. 7,169,560, the contents of which are incorporated herein by reference. Examples of labels that can be used to label nucleotide or nucleotide analogs for sequencing-by-synthesis include, but are not limited to, chromophores, fluorescent moieties, enzymes, antigens, heavy metal, magnetic probes, dyes, phosphorescent groups, radioactive materials, chemiluminescent moieties, scattering or fluorescent nanoparticles, Raman signal generating moieties, and electrochemical detection moieties. Sequencing-by-synthesis can generate at least 1,000, at least 5,000, at least 10,000, at least 20,000, 30,000, at least 40,000, at least 50,000, at least 100,000 or at least 500,000 reads per hour. Such reads can have at least 40, at least 45, at least 50, at least 60, at least 70, at least 80, at least 90, at least 100, at least 120 or at least 150 bases per read.

Sequencing-by-synthesis may be performed on a solid surface (or a chip) using fold-back PCR and anchored primers. Since microRNAs occur as small nucleic acid fragments—adaptors are added to the 5' and 3' ends of the fragments. Nucleic acid fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded nucleic acid molecules of the same template in each channel of the flow cell. Primers, polymerase and four fluorophore-labeled, reversibly terminating nucleotides are used to perform sequential sequencing. After nucleotide incorporation, a laser is used to excite the fluorophores, an image is captured and the identity of the first base is recorded. The 3' terminators and fluorophores from each incorporated base are removed and the incorporation, detection and identification steps are repeated. This technology is used, for example, in the Illumina® sequencing platform.

Another sequencing method involves hybridizing the amplified regions to a primer complementary to the sequence element in an LST (a file listing the names of fasta files). This hybridization complex is incubated with a polymerase, ATP sulfurylase, luciferase, apyrase, and the substrates luciferin and adenosine 5' phosphosulfate. Next, deoxynucleotide triphosphates corresponding to the bases A, C, G, and T (U) are added sequentially. Each base incorporation is accompanied by release of pyrophosphate, converted to ATP by sulfurylase, which drives synthesis of oxyluciferin and the release of visible light. Since pyrophosphate release is equimolar with the number of incorporated bases, the light given off is proportional to the number of nucleotides adding in any one step. The process is repeated until the entire sequence is determined. Yet another sequencing method involves a four-color sequencing by ligation scheme (degenerate ligation), which involves hybridizing an anchor primer to one of four positions. Then an enzymatic ligation reaction of the anchor primer to a population of degenerate nonamers that are labeled with fluorescent dyes is performed. At any given cycle, the population of nonamers that is used is structure such that the identity of one of its positions is correlated with the identity of the fluorophore attached to that nonamer. To the extent that the ligase discriminates for complementarily at that queried position, the fluorescent signal allows the inference of the identity of the base. After performing the ligation and four-color imaging, the anchor primer:nonamer complexes are stripped and a new cycle begins. Methods to image sequence information after performing ligation are known in the art. In some cases, high throughput sequencing involves the use of ultra-deep sequencing, such as described in Marguiles et al., Nature 437 (7057): 376-80 (2005).

MicroRNA sequencing (miRNA-seq) is a type of RNA Sequencing (RNA-Seq) which uses next-generation sequencing or massively parallel high-throughput DNA sequencing to sequence microRNAs. miRNA-seq differs from other forms of RNA-Seq in that input material is often enriched for small RNAs. miRNA-seq provides tissue specific expression patterns, which may lead to disease associations and microRNAs isoforms. miRNA-seq is also used for the discovery of previously uncharacterized microRNAs, such as the nucleic acid sequences denoted by SEQ ID NOs 139-140 and 307-308.

As used herein, the term "diagnosing" refers to classifying pathology, or a symptom, determining a severity of the pathology (grade or stage), monitoring pathology progression, forecasting an outcome of pathology and/or prospects of recovery.

As used herein, the phrase "subject in need thereof" refers to an human subject who is known to have cancer, at risk of having cancer (e.g., a genetically predisposed subject, a subject with medical and/or family history of cancer, a subject who has been exposed to carcinogens, occupational hazard, environmental hazard) and/or a subject who exhibits suspicious clinical signs of cancer (e.g., nodules in the thyroid). Additionally or alternatively, the subject in need thereof can be a healthy human subject undergoing a routine well-being check-up.

Analyzing presence of malignant or pre-malignant cells can be effected in vivo or ex vivo, whereby a biological sample (e.g., biopsy) is retrieved. Such biopsy samples comprise cells and may be an incisional or excisional biopsy. The sample may be retrieved from the thyroid of the subject, and may be retrieved using FNA. Alternatively the cells may be retrieved from a complete resection.

While employing the present teachings, additional information may be gleaned pertaining to the determination of treatment regimen, treatment course and/or to the measurement of the severity of the disease.

As used herein, the phrase "treatment regimen" refers to a treatment plan that specifies the type of treatment, dosage, schedule and/or duration of a treatment provided to a subject in need thereof (e.g., a subject diagnosed with a pathology). The selected treatment regimen can be an aggressive one which is expected to result in the best clinical outcome (e.g., complete cure of the pathology) or a more moderate one which may relieve symptoms of the pathology yet results in incomplete cure of the pathology. It will be appreciated that in certain cases the treatment regimen may be associated with some discomfort to the subject or adverse side effects (e.g., damage to healthy cells or tissue). The type of treatment can include a surgical intervention (e.g., removal of lesion, diseased cells, tissue, or organ), a cell replacement therapy, an administration of a therapeutic drug (e.g., receptor agonists, antagonists, hormones, chemotherapy agents) in a local or a systemic mode, an exposure to radiation therapy using an external source (e.g., external beam) and/or an internal source (e.g., brachytherapy) and/or any combination thereof. The dosage, schedule and duration of treatment can vary, depending on the severity of pathology and the selected type of treatment, and those of skills in the art are capable of adjusting the type of treatment with the dosage, schedule and duration of treatment.

A method of diagnosis is also provided. The method comprises detecting an expression level of a specific cancer-associated nucleic acid in a biological sample. Diagnosis of a specific cancer state in a patient may allow for prognosis and selection of therapeutic strategy. Further, the developmental stage of cells may be classified by determining temporarily expressed specific cancer-associated nucleic acids.

In situ hybridization of labeled probes to tissue sections or FNA smears may be performed. When comparing the fingerprints between individual samples the skilled artisan can make a diagnosis, a prognosis, or a prediction based on the findings. It is further understood that the nucleic acid sequence which indicate the diagnosis may differ from those which indicate the prognosis and molecular profiling of the condition of the cells may lead to distinctions between responsive or refractory conditions or may be predictive of outcomes.

A kit is also provided and may comprise a nucleic acid described herein together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods described herein. The kit may further comprise a software package for data analysis of expression profiles.

For example, the kit may be a kit for the amplification, detection, identification or quantification of a target nucleic acid sequence. The kit may comprise a poly (T) primer, a forward primer, a reverse primer, and a probe. Specifically, it is provided a kit for thyroid tumor classification, said kit comprising: (a) probes for performing thyroid tumor classification, wherein said probes comprise any one of (i) DNA equivalents of microRNAs comprising at least one of SEQ ID NOs 1-37, (ii) the complements thereof, (iii) sequences at least 80% identical to (i) or (ii), (iv) a nucleic acid sequence that hybridizes with at least eight contiguous nucleotides of any one of SEQ ID NOs 1-37, or (v) a nucleic acid sequence that hybridizes with RT-PCR products; and optionally (b) an instruction manual for using said probes.

Any of the compositions described herein may be comprised in a kit. In a non-limiting example, reagents for isolating microRNA, labeling microRNA, and/or evaluating a microRNA population using an array are included in a kit. The kit may further include reagents for creating or synthesizing microRNA probes. The kits will thus comprise, in suitable container means, an enzyme for labeling the microRNA by incorporating labeled nucleotide or unlabeled nucleotides that are subsequently labeled. It may also include one or more buffers, such as reaction buffer, labeling buffer, washing buffer, or a hybridization buffer, compounds for preparing the microRNA probes, components for in situ hybridization and components for isolating microRNA. Other kits of the invention may include components for making a nucleic acid array comprising microRNA, and thus, may include, for example, a solid support.

The following examples are presented in order to more fully illustrate some embodiments of the invention. They should in no way be construed, however, as limiting the broad scope of the invention.

EXAMPLES

Materials and Methods 1. microRNA Analysis

The presence and/or level of microRNAs in thyroid tumor samples may be evaluated using methods known in the art, e.g., Northern blot, RNA expression assays, e.g., microarray analysis, RT-PCR, high throughput sequencing (next generation sequencing), cloning, and quantitative real time polymerase chain reaction (qRT-PCR). Analytical techniques to determine RNA expression are known in the art, see e.g. Sambrook et al., Molecular Cloning: A Laboratory Manual, 3rd Ed., Cold Spring Harbor Press, Cold Spring Harbor, N.Y. (2001). Examples of specific methods used herein are described in more detail below.

2. RNA Extraction

FNA Cell Block Samples

Total RNA was isolated from seven to ten 10 µm-thick tissue sections. Sections were incubated a few times (1-3 times) in xylene at 57° C. for 5 minutes in order to remove excess paraffin, followed by centrifugation at ambient temperature for 2 minutes at 10,000 g. The specimen was then washed several times (about 3 times) with 1 ml 100% ethanol in order to wash the xylene out of the tissue, followed by centrifugation at ambient temperature for 10 minutes at 10,000 g. The supernatant was discarded and the tissue dried at 65° C. for 5 minutes. Proteins were degraded by proteinase K solution (5-12 µl Proteinase K (e.g., Sigma or ABI) in 500 µl of Buffer B (10 mM NaCl, 500 mM Tris pH 7.5, 20 mM EDTA pH 8, 1% SDS), at 45° C. for a few hours (about 16 hours). Proteinase K was inactivated by incubation at 95° C. for 7 minutes. After the tubes were chilled 10 µl of RNA synthetic spikes was added (e.g., 2 spikes of 0.15 fmol/µl). RNA was extracted using acid phenol/chloroform equal volume, vortexing, followed by centrifugation at 4° C. for 15 minutes at 12000 g. RNA was then precipitated using 8 µl linear acrylamide, 0.1 volumes of 3M NaOAc pH 5.2, and 3 volumes of absolute 100% ethanol, for 30 minutes to 16 hours followed by centrifugation at 4° C. for at least 40 minutes at 20000 g (14,000 rpm). The pellet was washed by adding 1 ml 85% cold Ethanol. DNAses were introduced at 37° C. for 60 minutes to digest DNA (e.g. 10 µl Turbo™ DNase), followed by extraction using acid phenol/chloroform and ethanol precipitated as described above.

FNA Smears Samples (e.g.)

Total RNA was isolated from FNA smear samples in slides, either non-stained or stained (e.g. by Papanicolaou, Giemsa or Diff-Quick) after removal of the coverslip (when present) by dipping the slides for several hours (about 2-20 hours, usually about 16 hours) in xylene at ambient temperature, in order to remove excess paraffin or glue. Further the slides were washed several times (about 3 times) with 100% ethanol in order to wash the xylene out. Slides were dipped for 1 minute in double-distilled water (DDW). The cells were scraped from the slide using a scalpel. The slide was then washed with 500 µl buffer B (10 mM NaCl, 500 mM Tris pH 7.5, 20 mM EDTA pH 8, 1% SDS), and transferred to a 1.7 ml tube. Proteins were degraded by proteinase K (e.g., 5-12 µl Sigma or ABI) at 45° C. for a few hours (about 16 hours). Proteinase K was inactivated by incubating the tubes at 95° C. for 7 minutes. After chilling the tubes, 10 µl of RNA synthetic spikes (e.g., 2 spikes of 0.15 fmol/µl) was added. RNA was extracted using acid phenol/chloroform equal volume, vortexing, spinning down at 4° C. for 15 minutes at 12000 g. RNA was then precipitated using 8 µl linear acrylamide, 0.1 volumes of 3M NaOAc pH 5.2, and 3 volumes of absolute ethanol from 30 minutes to 16 hours. The tubes were then spun down at 4° C. for at least 40 minutes at 20000 g (14,000 rpm). The pellet was washed with about 1 ml 85% cold ethanol. DNAses were introduced at 37° C. for 60 minutes to digest DNA (e.g. 10 µl Turbo™ DNase, Ambion, Life Technologies), followed by extraction using acid phenol/chloroform and ethanol precipitation as described above.

3. Total RNA Quantification

Total RNA quantification was performed by fluorospectrometry in a NanoDrop 3300 (ND3300) fluorospectrometer using the RiboGreen® dye (Thermo Fisher Scientific®, Wilmington, Del.). The ND3300 RNA detection range is of 25 ng/ml-1000 ng/ml when using a high concentration of RiboGreen® dye (1:200 dilution), and 5 ng/ml-50 ng/ml when using a 1:2000 dilution of RiboGreen® dye. The RNA amounts which were determined by ND3300 were highly correlated to the detected expressed microRNA.

4. MicroRNA Profiling in Microarray

Custom microarrays (Agilent Technologies, Santa Clara, Calif.) were generated by printing DNA oligonucleotide probes to: 2172 miRs sequences, 17 negative controls, 23 spikes, and 10 positive controls (total of 2222 probes). Each microRNA probe, printed in triplicate, carried up to 28-nucleotide (nt) linker at the 3' end of the microRNAs' complement sequence. Negative spikes and positive probes were printed from 3 to 200 times. Seventeen (17) negative control probes were designed using sequences that do not match the genome. Two groups of positive control probes were designed to hybridize to the microRNA array: (i) synthetic small RNAs were spiked to the RNA before labeling to verify the labeling efficiency; and (ii) probes for abundant small RNA, e.g., small nuclear RNAs (U43, U24, Z30, U6, U48, U44), 5.8s and 5s ribosomal RNA were spotted on the array to verify RNA quality.

5. Cy-Dye Labeling of microRNA for Microarray

Total RNA (20-1000 ng) was labeled by ligation (Thomson et al. Nature Methods 2004; 1:47-53) with an RNA linker, p-rCrU-Cy/dye or several sequential Cys (BioSpring GmbH, IBA GmbH or equivalent), to the 3' end with Cy3 or Cy5. The labeling reaction contained total RNA, spikes (0.1-100 fmoles), 250-400 ng RNA-linker-dye, 15% DMSO, 1x ligase buffer and 20 units of T4 RNA ligase (NEB or equivalent), and proceeded at 4° C. for 1 hour, followed by 1 hour at 37° C., followed by 4° C. up to 40 minutes.

The labeled RNA was mixed with 30 µl hybridization mixture (mixture of 45 µL of the 10×GE Agilent Blocking Agent and 246 µL of 2× Hi-RPM Hybridization). The labeling mixture was incubated at 100° C. for 5 minutes followed by ice incubation in water bath for 5 minutes. Slides were hybridized at 54-55° C. for 16-20 hours, followed by two washes. The first wash was conducted at room temperature with Agilent GE Wash Buffer 1 (e.g. 6×SSPE+ 0.005% N-Lauroylsarcosine+0.005% Triton X-102), for 5 minutes followed by a second wash with Agilent GE Wash Buffer 2 at 37° C. for 5 minutes (e.g. 0.06×SSPE+0.005% N-Lauroylsarcosine+0.005% Triton X-102).

Arrays were scanned using a microarray scanner (Agilent Microarray Scanner Bundle G2565BA, resolution of 5 µm at XDR Hi 100%, XDR Lo 10%). Array images were analyzed using appropriate software (Feature Extraction 10.7 software, Agilent).

6. RT-PCR

Poly-adenylation and reverse transcription was performed on 1-500 ng of total RNA. RNA was incubated in the presence of poly (A) polymerase (Poly (A) Polymerase NEB-M0276L), ATP, an oligodT primer harboring a consensus sequence and reverse transcriptase (SuperScript® II RT, Invitrogen, Carlsbad, Calif.) for 1 hour at 37° C. Next, the cDNA was amplified by RT-PCR. The amplification reaction included a microRNA-specific forward primer, being a TaqMan® (MGB) probe complementary to the 3' of the specific microRNA sequence and or to part of the polyA adaptor sequence, and a universal reverse primer complementary to the consensus 3' sequence of the oligodT tail. Detailed description of the RT-PCR methodology may be found in publication WO 2008/029295, the contents of which are incorporated herein by reference.

The cycle threshold (CT, the PCR cycle at which probe signal reaches the threshold) was determined for each microRNA.

In order to allow comparison between microRNA expression results from RT-PCR with microRNA expression results from microarray, each value obtained by RT-PCR was subtracted from 50 (50-CT). The 50-$C_T$ expression for each microRNA for each patient was compared with the signal obtained by the microarray method.

7. Array Data Normalization

The initial data set consisted of signals measured for multiple probes for every sample. For the analysis, signals were used only for probes that were designed to measure the expression levels of known or validated human microRNAs.

Triplicate spots were combined into one signal by taking the logarithmic mean of the reliable spots. All data was log-transformed and the analysis was performed in log-space. A reference data vector for normalization, R, was calculated by taking the mean expression level for each probe in two representative samples, one from each tumor type.

For each sample k with data vector $S^k$, a 2nd degree polynomial $F^k$ was found so as to provide the best fit between the sample data and the reference data, such that $R \approx F^k(S^k)$. Remote data points ("outliers") were not used for fitting the polynomials F. For each probe in the sample (element $S_i^k$ in the vector $S^k$), the normalized value (in log-space) $M_i^k$ is calculated from the initial value $S_i^k$ by transforming it with the polynomial function $F^k$, so that $M_i^k = F^k(S_i^k)$. Statistical analysis is performed in log-space. For presentation and calculation of fold-change, data is translated back to linear-space by taking the exponent.

8. miRNA-Seq Sequence Library Construction

Sequence library construction may be performed using a variety of different kits depending on the high-throughput sequencing platform being employed. However, there are several common steps for small RNA sequencing preparation. The ligation step adds DNA adaptors to both ends of the small RNAs, which act as primer binding sites during reverse transcription and PCR amplification. An adenylated single strand DNA 3' adaptor followed by a 5' adaptor is ligated to the small RNAs using a ligating enzyme such as T4 RNA ligase or adding 5' adaptor using 5' RACE reaction 2. The adaptors are also designed to capture small RNAs with a 5' phosphate group, characteristic microRNAs, rather than RNA degradation products with a 5' hydroxyl group. Reverse transcription and PCR amplification steps convert the small adaptor ligated RNAs into cDNA clones used in the sequencing reaction. PCR is then carried out to amplify the pool of cDNA sequences. Primers designed with unique nucleotide tags may also be used in this step to create ID tags in pooled library multiplex sequencing.

9. Next Generation Sequencing (NGS)

500 ng of RNA from each FFPE sample were used for small RNA deep sequencing (miRSeq). Libraries were loaded on two lanes of the sequence analyzer (Illumina® HiSeq™ 2000 DNA). An average of about 6.3 million reads per library were obtained. To find novel microRNAs, sequence analysis software (miRDeep2, Friedlander M R et al. Nucleic Acids Res. 2012 January; 40(1):37-52) was applied on the raw sequencing data (primer-adapter sequences were trimmed).

10. Statistical Analysis

P-values were calculated using a two-sided (unpaired) Student's t-test on the log-transformed normalized fluorescence signal. The threshold for significant differences was determined by setting a false discovery rate (FDR) of 0.05 to 0.1, to correct for effects of multiple hypothesis testing, resulting in p-value cutoffs in the range of 0.01-0.06. For each differentially expressed microRNA, the fold-difference (ratio of the median normalized fluorescence) and the area under curve (AUC) of the response operating characteristic (ROC) curve were calculated. Three sets of miRs were excluded from the statistical analysis: (a) miRs that were previously found as highly expressed in blood samples (due to high percentages of blood in FNA samples), (b) miRs whose level of expression did not correlate with decreasing amounts of RNA, i.e: these miRs did not show linear decrease in signal in association with decreasing measured RNA amounts, and (c) miRs whose level of expression correlated with miRs in set (b).

For Examples 14 and 15 (final classifier and the validation set), 95% confidence intervals were calculated using the Clopper-Pearson method. Sensitivity and specificity estimates for the training cohort were calculated as the mean of ten (10) 10-fold cross-validation runs. Only non-medullary samples which had expression levels of assay miRNA above defined thresholds were included in the training performance estimates. For 2×2 contingency tables, either the $\chi^2$ test or Fisher's exact test (in case that the conditions for performing a $\chi^2$ test were not met) was used.

Example 1

Detection of MicroRNA in Pre-Operative Samples

A pilot study of microRNA profiling was conducted in a few Papanicolaou, Giemsa and Diff-Quick stained smears from ex-vivo FNA biopsy samples in order to ensure feasibility of the methodology. Since FNA smears often have very few cells, providing a minuscule amount of RNA for analysis, e.g. 1-1000 ng, it was first necessary to evaluate whether microRNA would be detectable under such low RNA amounts. Thus, microRNA expression levels of about 2200 individual microRNAs was measured in Giemsa-stained papillary carcinoma and non-papillary carcinoma smears. Five microRNAs (hsa-miR-146b-5p, hsa-miR-31-5p, hsa-miR-222-3p, hsa-miR-221-3p, and hsa-miR-21-5p), previously shown to correlate with papillary carcinoma were found over-represented (upregulated) in the papillary-carcinoma smears. A comparison of microRNA expression between Giemsa-stained papillary carcinoma and non-papillary carcinoma samples, revealed the highly up-regulated microRNA markers in the papillary carcinoma were detected. These results strongly suggested that microRNA profiles can be successfully determined in FNA smears stained with any dye.

Example 2

Differential MicroRNA Expression Between Malignant and Benign Thyroid Lesions

The cohort of samples used in the experimental analysis is shown in Table 7 as cohort II. The histological diagnosis assessed ultimately the malignancy or benignity of the thyroid lesions. The cytological classification was based on "The Bethesda System for Reporting Thyroid Cytopathology" (Syed, Z. Ali and Edmund S. Cibas, eds.; DOI 10.1007/978-0-387-87666-5_1; Springer Science+Business Media, LLC 2010). The study protocol was approved by the Institutional Review Board (IRB, equivalent to Ethical Review Board) of the contributing institution. Tumor classification was based on the World Health Organization (WHO) guidelines. An additional cohort consisted of 13 thyroid ex-vivo FNA smears, prepared after thyroidectomy, and obtained from the University Milano-Bicocca (Milan, Italy).

Total RNA (at least 10 ng) was extracted from these samples, and microRNA expression was profiled using custom microarrays containing about 2200 miRs. The results exhibited a significant difference in the expression pattern between benign and malignant lesions of several miRs listed in Table 3 (upregulated or downregulated in malignant versus benign).

TABLE 3 miRNAs up- or downregulated in malignant versus benign thyroid tumor

| miR name | p-value | fold-change | AUC | median malignant | benign |
|---|---|---|---|---|---|
| hsa-miR-146b-5p | 3.80E−05 | 2.57 (+) | 0.77 | 5.70E+02 | 2.20E+02 |
| hsa-miR-222-3p | 1.80E−03 | 2.20 (+) | 0.71 | 4.70E+03 | 2.10E+03 |
| hsa-miR-221-3p | 1.80E−03 | 2.09 (+) | 0.71 | 4.10E+03 | 2.00E+03 |
| hsa-miR-181b-5p | 2.50E−02 | 1.38 (+) | 0.65 | 5.00E+02 | 3.60E+02 |
| hsa-miR-29b-3p | 9.50E−03 | 1.32 (+) | 0.64 | 2.10E+03 | 1.60E+03 |
| hsa-miR-200b-3p | 2.60E−02 | 1.27 (+) | 0.65 | 3.10E+02 | 2.40E+02 |
| hsa-miR-200a-3p | 3.90E−02 | 1.27 (+) | 0.64 | 3.00E+02 | 2.40E+02 |
| hsa-miR-29c-3p | 8.80E−03 | 1.22 (+) | 0.64 | 1.40E+03 | 1.10E+03 |
| hsa-miR-130a-3p | 3.30E−02 | 1.20 (+) | 0.64 | 1.00E+03 | 8.70E+02 |
| hsa-miR-148b-3p | 3.60E−02 | 1.13 (+) | 0.64 | 5.00E+02 | 4.50E+02 |
| MID-23794 | 2.60E−05 | 2.34 (−) | 0.78 | 6.00E+02 | 1.40E+03 |
| hsa-miR-197-5p | 2.20E−03 | 1.90 (−) | 0.74 | 3.40E+02 | 6.60E+02 |
| hsa-miR-486-5p | 3.60E−05 | 1.73 (−) | 0.79 | 2.00E+02 | 3.50E+02 |
| hsa-miR-574-3p | 1.40E−02 | 1.44 (−) | 0.68 | 2.30E+02 | 3.30E+02 |
| hsa-miR-532-3p | 4.80E−03 | 1.30 (−) | 0.71 | 4.50E+02 | 5.80E+02 |
| hsa-miR-199a-5p | 2.50E−03 | 1.25 (−) | 0.73 | 3.90E+02 | 4.80E+02 |
| hsa-miR-22-3p | 3.90E−02 | 1.11 (−) | 0.62 | 3.40E+03 | 3.70E+03 | p-values were calculated using a two-sided (unpaired) Student's t-test.
The fold-change represents the ratio between the median values of each group.
AUC: Area under the curve when using the miRNAs to classify the two groups.
Median: median of expression values (rounded).

A classification algorithm for differentiating between malignant and benign thyroid tumor was developed based on miRNA expression in 35 benign and 38 malignant FNA samples. A logistic regression classifier was trained to distinguish between malignant and benign thyroid lesions, based on eight miRs (hsa-miR-125b-5p, hsa-miR-21-5p, hsa-miR-222-3p, hsa-miR-221-3p, hsa-miR-146b-5p, hsa-miR-181a-5p, hsa-miR-138-5p, and MID-23794) that were found to be differentially expressed in these conditions, either between benign or malignant or between specific thyroid tumor subtypes (data not shown). The classifier reached 89% accuracy with sensitivity of 87% and specificity of 91% for identifying malignant samples. hsa-miR-125b-5p, hsa-miR-21-5p, hsa-miR-222-3p, hsa-miR-221-3p, hsa-miR-146b-5p and hsa-miR-181a-5p exhibited higher expression in malignant lesions, while hsa-miR-138-5p and MID-23794 exhibited higher expression in benign lesions (data not shown).

Example 3

Distinguishing Different Sub-Types of Malignant and Benign Thyroid Lesions

Expression levels of miRs were compared in 18 follicular adenoma samples and 10 follicular carcinoma samples. microRNAs that were upregulated or downregulated in follicular adenoma relative to follicular carcinoma are presented in Table 4.

TABLE 4 miRNAs up- or downregulated in follicular adenoma versus follicular carcinoma

| miR name | p-value | fold-change | AUC | Median Follicular adenoma | Median Follicular carcinoma |
|---|---|---|---|---|---|
| hsa-miR-486-3p | 2.80E−02 | 2.04 (+) | 0.77 | 4.80E+02 | 2.40E+02 |
| MID-01141 | 5.50E−02 | 1.91 (+) | 0.73 | 3.50E+02 | 1.80E+02 |
| hsa-miR-193a-3p | 2.70E−02 | 1.45 (+) | 0.76 | 3.10E+02 | 2.20E+02 |
| hsa-miR-148b-3p | 3.90E−02 | 1.25 (−) | 0.71 | 4.50E+02 | 5.60E+02 | p-values were calculated using a two-sided (unpaired) Student's t-test.
The fold-change represents the ratio between the median values of each group.
AUC: Area under the curve when using the miRNAs to classify the two groups.
Median: median of expression values (rounded).

Expression levels of miRs were compared in 18 follicular adenoma samples versus 9 papillary carcinoma (non-follicular variant) samples, and a classifier was generated for distinguishing between follicular adenoma and papillary carcinoma samples using the expression levels of hsa-miR-146b-5p and hsa-miR-21-5p, with 100% accuracy (data not shown).

Expression levels of miRs were compared in 18 follicular adenoma samples versus 19 follicular variant of papillary carcinoma samples. microRNAs that were upregulated or downregulated in follicular variant of papillary carcinoma relative to follicular adenoma are presented in Table 5.

TABLE 5 miRNAs up- or downregulated in follicular variant papillary carcinoma (FVPC) versus follicular adenoma (FA)

| miR name | p-value | fold-change | AUC | median FVPC | median FA |
|---|---|---|---|---|---|
| hsa-miR-146b-5p | 4.00E−02 | 2.36 (+) | 0.71 | 5.40E+02 | 2.30E+02 |
| hsa-miR-29c-3p | 2.00E−03 | 1.66 (+) | 0.76 | 1.40E+03 | 8.30E+02 |
| hsa-miR-200a-3p | 2.50E−02 | 1.65 (+) | 0.73 | 3.00E+02 | 1.80E+02 |
| hsa-miR-200b-3p | 1.70E−02 | 1.56 (+) | 0.73 | 3.10E+02 | 2.00E+02 |
| hsa-miR-125a-5p | 3.30E−02 | 1.42 (+) | 0.69 | 1.70E+03 | 1.20E+03 |
| hsa-miR-148b-3p | 2.10E−02 | 1.20 (+) | 0.70 | 5.40E+02 | 4.50E+02 |
| hsa-miR-199a-3p | 4.10E−02 | 1.09 (+) | 0.70 | 3.30E+02 | 3.10E+02 |
| hsa-miR-197-5p | 5.60E−05 | 3.73 (−) | 0.89 | 2.70E+02 | 1.00E+03 |
| MID-23794 | 6.50E−03 | 2.39 (−) | 0.84 | 7.70E+02 | 1.80E+03 |
| hsa-miR-486-3p | 2.00E−05 | 2.34 (−) | 0.89 | 2.10E+02 | 4.80E+02 |
| hsa-miR-532-3p | 8.50E−04 | 1.70 (−) | 0.82 | 4.40E+02 | 7.60E+02 |
| hsa-miR-22-3p | 8.10E−03 | 1.33 (−) | 0.75 | 3.40E+03 | 4.50E+03 |
| hsa-miR-199a-5p | 5.80E−03 | 1.30 (−) | 0.76 | 3.70E+02 | 4.80E+02 |
| hsa-miR-23a-3p | 4.50E−02 | 1.26 (−) | 0.68 | 2.60E+03 | 3.30E+03 |
| hsa-miR-34a-5p | 4.10E−02 | 1.09 (−) | 0.63 | 6.00E+02 | 6.60E+02 | p-values were calculated using a two-sided (unpaired) Student's t-test.
The fold-change represents the ratio between the median values of each group.
AUC: Area under the curve when using the miRNAs to classify the two groups.
Median: median of expression values (rounded).

Expression levels of miRs were compared in 6 non-encapsulated follicular variant of papillary carcinoma samples versus 35 benign samples, and a classifier was generated using the expression levels of hsa-miR-221-3p and hsa-miR-200b-3p, with 98% accuracy, 83% sensitivity and 100% specificity (data not shown).

Expression levels of miRs were compared in 8 Hashimoto thyroiditis samples and 9 (non-follicular) papillary carcinoma samples. microRNAs that were upregulated or downregulated in papillary carcinoma relative to Hashimoto thyroiditis are presented in Table 6. The miRs that are the best candidates for the profile signature for comparing these two thyroid lesions are hsa-miR-146b-5p, hsa-miR-200a-3p and MID-23794.

TABLE 6 miRNAs upregulated or downregulated in papillary carcinoma (PC) versus Hashimoto thyroiditis (Ht)

| miR name | p-value | fold-change | AUC | median PC | median Ht |
|---|---|---|---|---|---|
| hsa-miR-146b-5p | 2.20E−02 | 2.46 (+) | 0.75 | 7.90E+02 | 3.20E+02 |
| hsa-miR-200a-3p | 2.30E−02 | 2.46 (+) | 0.75 | 4.50E+02 | 1.80E+02 |
| hsa-miR-200b-3p | 3.40E−02 | 2.13 (+) | 0.76 | 4.30E+02 | 2.00E+02 |
| MID-23794 | 4.10E−05 | 4.85 (−) | 0.88 | 4.80E+02 | 2.30E+03 |
| MID-00387 | 8.70E−07 | 4.18 (−) | 0.92 | 7.70E+01 | 3.20E+02 |
| hsa-miR-486-3p | 5.30E−04 | 2.03 (−) | 0.80 | 1.80E+02 | 3.70E+02 | p-values were calculated using a two-sided (unpaired) Student's t-test.
The fold-change represents the ratio between the median values of each group.
AUC: Area under the curve when using the miRNAs to classify the two groups.
Median: median of expression values (rounded).

Example 4

Identification of Novel MicroRNAs Biomarkers by Deep-Sequencing

Eleven (11) FFPE (Formalin Fixed Paraffin Embedded) thyroid resection samples (obtained from surgical biopsies and fixed in formalin and preserved in paraffin) from follicular lesions were obtained from the Department of Pathology at Rabin Medical Center. The specimens included 6 follicular adenomas and 5 follicular carcinomas. Tumor cellular content was higher than 50% in all the samples.

Figure 1A:
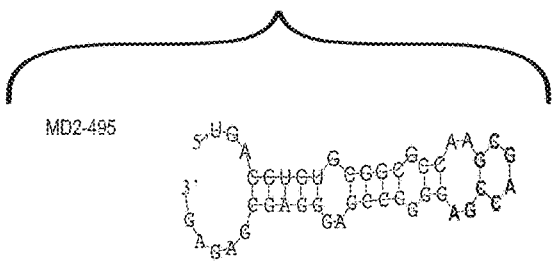
FIGS. 1A-1B: Novel microRNAs detected by next generation sequencing.
Figure 1A:
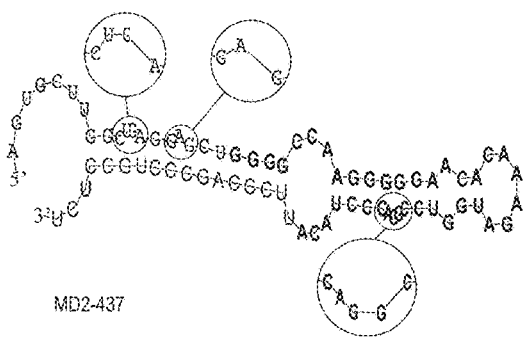
Figure 1B:
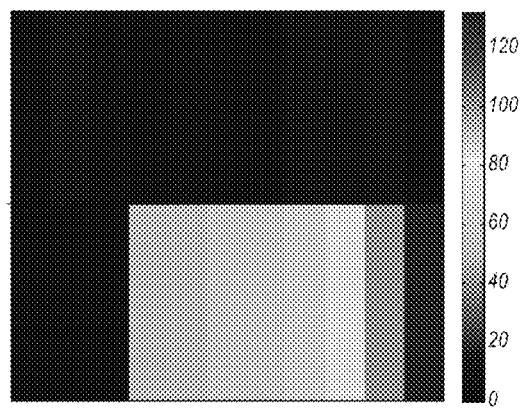

A total of 386 novel candidate microRNAs were found with sequence analysis software, and 27 of those were selected for validation, performed by qPCR. Two novel microRNAs are disclosed herein, MD2-495 and MD2-437, and their sequences are presented in Table 1, and their respective hairpins are shown in Table 2. FIG. 1A shows the secondary structures of the two novel microRNAs, predicted by sequence analysis software. FIG. 1B shows the expression of the two novel microRNAs (normalized number of reads) in each of the 11 samples. The color-coded bar on the right represents a scale for expression.

Example 5

Specific MicroRNAs are Differentially Expressed Between Benign and Malignant Thyroid Lesions Stained thyroid FNA smears were obtained from a medical center in Israel (Cohort I); and thyroid FNA cell blocks were obtained from a medical center in the USA (Cohort II). For both cohorts, thyroid lesions were ultimately classified as malignant or benign based on histological diagnosis of the resected tumor. A summary of the breakdown of the samples from the two cohorts is shown in Table 7.

TABLE 7

FNA Samples - Cohorts I and II

| FNA Sample Description | Cohort I | Cohort II |
|---|---|---|
| Number of lesions (#patients)[1] | 81 (65) | 73 (73) |
| Nodular hyperplasia (nodular Goiter) | 13 | 9 |
| Follicular adenoma | 27 | 18 |
| Graves' disease | 3 | 0 |
| Hashimoto thyroiditis | 3 | 8 |
| Total Benign Nodules | 46 | 35 |
| Papillary carcinoma | 10 | 9 |
| Follicular variant of papillary carcinoma | 13 | 19 |
| Follicular carcinoma | 4 | 10 |

TABLE 7-continued

FNA Samples - Cohorts I and II

| FNA Sample Description | Cohort I | Cohort II |
|---|---|---|
| Medullary carcinoma | 6 | 0 |
| Thyroid carcinoma (Mix histology) | 2 | 0 |
| Total Malignant Nodules | 35 | 38 |
| Bethesda[2] class II, VI | 33 | 0 |
| Bethesda[2] class III, IV, V | 48 | 73 |

[1]Some patients had more than one lesion.
[2]The Bethesda System for Reporting Thyroid Cytopathology (BSRTC) resulted from a conference held at the National Institutes of Health in 2007 (Cibas E S, Ali S Z. The Bethesda System for Reporting Thyroid Cytopathology. Am J Clin Pathol 2009; 132: 658-65). The system led to standardization of FNA reports based on six diagnostic categories: DC I = non-diagnostic, DC II = benign, DC III = atypia/follicular lesion of undetermined significance (AUS/FLUS), DC IV = follicular neoplasm/suspicion for a follicular neoplasm (FN/SFN), DC V = suspicious for malignancy, and DC VI = malignant.

Highly purified RNA, including the microRNA fraction, was extracted from samples using in-house developed protocols as described above. FFPE and cytological (FNA) samples were profiled by custom printed microarrays measuring over 2000 microRNAs to identify differentially expressed microRNAs and to develop a classifier.

Over 150 thyroid FNA samples (Table 7) were profiled by custom-printed microarrays measuring over 2000 microRNAs and on 96 microRNAs by qPCR. FIGS. 3A (cohort I) and 3B (cohort II) show the median microRNA expression levels on microarrays in patients with malignant nodules (y-axis) and in patients with benign nodules (x-axis). For each microRNA, the values in the two groups were compared by Mann-Whitney test with FDR=0.1.

Differential expression of microRNAs was found between benign and malignant neoplasms. Classification of malignant vs. benign smears based on two microRNAs: hsa-miR-146b-5p and hsa-miR-375 results in over 85% accuracy (based on the median of ten 10-fold cross-validation runs, data not shown).

Example 6

Hsa-miR-375 is a Significant Marker for Medullary Thyroid Carcinoma in FNA Samples Expression level of hsa-miR-375 (SEQ ID NO: 8) in FNA cohort I was compared between medullary thyroid cancer samples (n=6) and samples from other thyroid nodules (n=75), and it was significantly higher in medullary lesions compared to malignant non-medullary and benign samples combined, with a fold-change of 201.4 (data not shown). Thus, hsa-miR-375 is a significant marker for medullary thyroid carcinoma.

Example 7

Stained Thyroid Smears can be Used for MicroRNA Profiling

MicroRNA expression level in samples stained with different dyes was compared in order to evaluate microRNA stability and reproducibility of the microRNA level detection upon staining (data not shown). A total of 143 smears from FNA cohort I were stained as follows: 60 with May-Grünwald Giemsa (MGG), 64 with DiffQuik and 19 with Papanicolaou. MicroRNA expression levels in duplicates of the same sample stained with different dyes showed significant correlation (more than expected). The normalized expression level of hsa-miR-146b-5p (SEQ ID NO: 10 or 11) is similar when the same sample is stained with different dyes. Therefore, different cytological dyes used in the clinical setting (Papanicolaou; May-Grünwald Giemsa; and DiffQuik) do not affect the detection and quantification of microRNA expression.

Example 8

Thyroid Classification—Assay Development

A total of twenty-four (24) microRNAs overall were chosen for establishing the status of thyroid samples as malignant versus benign. MicroRNA expression was measured by RT-PCR as described above. The list of miRs and their respective forward primers are provided in Table 8. First-strand generation was done using polyT adaptor presented below. Forward primers were sequence-specific while the reverse primer was universal. Detection of the RT-PCR products was done with the universal MGB probe for miRs hsa-miR-31-5p, hsa-miR-5701, hsa-miR-424-3p (SEQ ID NO: 16), MID-50971, MID-20094, MID-50976, hsa-miR-3074-5p, hsa-miR-222-3p, MID-50969, hsa-miR-146b-5p, hsa-miR-346, MID-16582, or with probes specific for the miRs as provided in Table 9.

The sequences of the reverse primer, the polyT adaptor and the MGB probe are provided below:

```
Reverse primer
                                      (SEQ ID NO: 309)
GCGAGCACAGAATTAATACGAC;

PolyT adaptor
                                      (SEQ ID NO: 310)
GCGAGCACAGAATTAATACGACTCACTATCGGTTTTTTTTTTTTVN,
where "V" may be any one of A, G or C; and "N"
may be any one of G, C, A or U/T;

Universal MGB probe
                                      (SEQ ID NO: 311)
AAAACCGATAGTGAGTCG.
```

TABLE 8

Assay Development - MicroRNAs and forward primers

| microRNA | SEQ ID NO. | Forward primer | SEQ ID NO. |
|---|---|---|---|
| hsa-miR-222-3p | 1,2 | GCAGCTACATCTGGC TACTGGGT | 312 |
| hsa-miR-551b-3p | 3,4 | CAGTCATTTGGCGCG ACCCATACTTGGT | 313 |
| hsa-miR-31-5p | 5,6,7 | AGGCAAGATGCTGGC ATAGCT | 314 |
| hsa-miR-375 | 8 | CAGTCATTTGGGTTT GTTCGTTCGGCTC | 315 |
| hsa-miR-125b-5p | 9 | CAGTCATTTGGGTCC CTGAGACCCTAAC | 316 |
| hsa-miR-146b-5p | 10,11 | TGGCTGAGAACTGAA TTCCATAGGCT | 317 |
| hsa-miR-152-3p | 12,13 | CAGTCATTTGGCTCA AGTGCATGACAGA | 318 |
| hsa-miR-346 | 14 | TGTCTGCCCGCATGC CTGCCTCT | 319 |

TABLE 8-continued

Assay Development-
MicroRNAs and forward primers

| microRNA | SEQ ID NO. | Forward primer | SEQ ID NO. |
|---|---|---|---|
| hsa-miR-181c-5p | 15 | CAGTCATTTGGCAAC ATTCAACCTGTCG | 320 |
| hsa-miR-424-3p | 16 | CAAAACGTGAGGCGC TGCTAT | 321 |
| hsa-miR-342-3p | 17,18 | CAGTCATTTGGGTCT CACACAGAAATCG | 322 |
| hsa-miR-138-5p | 19,20,21 | CAGTCATTTGGCAGC TGGTGTTGTGAAT | 323 |
| hsa-miR-486-5p | 22 | CAGTCATTTGGCTCC TGTACTGAGCTGC | 324 |
| hsa-miR-200c-3p | 23,24 | CAGTCATTTGGGTAA TACTGCCGGGTAA | 325 |
| MID-16582 | 25 | TTGGCAGTGAAGCAT TGGACTGTA | 326 |
| hsa-miR-23a-3p | 26 | CAGTCATTTGGCATC ACATTGCCAGGGA | 327 |
| MID-20094 | 27,28 | CATTTGGCTAAGCCA GTTTCTGTCTGATA | 328 |
| MID-50969 | 29 | TGGCATGACAGATTG ACATGGACAATT | 329 |
| hsa-miR-345-5p | 30,31 | CAGTCATTTGGCGCT GACTCCTAGTCCA | 330 |
| hsa-miR-3074-5p | 32 | CGTTCCTGCTGAACT GAGCCAG | 331 |
| MID-50976 | 33 | CCTGTCTGAGCGCCG CTC | 332 |
| MID-50971 | 34 | CAGTCATTTGGCATA CTCTGGTTTCTTTTC | 333 |
| hsa-miR-5701 | 35 | AGTCATTTGGCTTAT TGTCACGTTCTGATT | 334 |
| hsa-miR-574-3p | 36,37 | CAGTCATTTGGCCAC GCTCATGCACACA | 335 |

TABLE 9

Assay Development-
MicroRNA Specific probes

| microRNA | Specific probe sequence | SEQ ID NO. |
|---|---|---|
| hsa-miR-342-3p | CCGTTTTTTTTTTTACGGGTGC | 336 |
| hsa-miR-181c-5p | CCGTTTTTTTTTTTTACTCACCG | 337 |
| hsa-miR-125b-5p | CCGTTTTTTTTTTTCACAAGTT | 338 |
| hsa-miR-375 | CCGTTTTTTTTTTTCACGCGAG | 339 |
| hsa-miR-486-5p | CCGTTTTTTTTTTTCTCGGGGC | 340 |
| hsa-miR-551b-3p | CCGTTTTTTTTTTTCTGAAACC | 341 |
| hsa-miR-23a-3p | CCGTTTTTTTTTTTGGAAATCC | 342 |
| hsa-miR-574-3p | CCGTTTTTTTTTTTGTGGGTGT | 343 |

TABLE 9-continued

Assay Development-
MicroRNA Specific probes

| microRNA | Specific probe sequence | SEQ ID NO. |
|---|---|---|
| hsa-miR-152-3p | CGTTTTTTTTTTTTCCAAGTTC | 344 |
| hsa-miR-200c-3p | CGTTTTTTTTTTTTCCATCATT | 345 |
| hsa-miR-138-5p | CGTTTTTTTTTTTTCGGCCTGA | 346 |
| hsa-miR-345-5p | CGTTTTTTTTTTTTGAGCCCTG | 347 |

Marker microRNAs were selected based on their patterns of expression in several preliminary studies performed by the inventors (data not shown), and provided the reasoning for classifying the same as "malignant", "cell type" or alternatively, to be used as normalizers.

"Malignant markers" hsa-miR-222-3p, hsa-miR-551b-3p, hsa-miR-31-5p, hsa-miR-375, hsa-miR-125b-5p, hsa-miR-152-3p, hsa-miR-346, hsa-miR-181c-5p, hsa-miR-424-3p and hsa-miR-146b-5p were established according to the level of expression of these microRNAs in malignant samples when compared with their expression in benign samples.

"Cell type" markers hsa-miR-486-5p, hsa-miR-342-3p, hsa-miR-138-5p, hsa-miR-200c-3p, and MID-16582 were chosen by the inventors according to their pattern or expression as exemplified below.

hsa-miR-486-5p (SEQ ID NO: 22) was found enriched in whole blood relative to thyroid epithelial cells. Along with other microRNAs (data not shown), it was found to be associated with the amount of blood in thyroid FNA samples. Thus, hsa-miR-486-5p is one example of whole blood marker. Several microRNAs were detected in high correlation (>0.85) with miR-486-5p, and may also be considered blood markers, including hsa-miR-320a, hsa-miR-106a-5p, hsa-miR-93-5p, hsa-miR-1'7-3p, hsa-let-7d-5p, hsa-miR-107, hsa-miR-103a-3p, hsa-miR-1'7-5p, hsa-miR-191-5p, hsa-miR-25-3p, hsa-miR-106b-5p, hsa-miR-20a-5p, hsa-miR-18a-5p, hsa-miR-144-3p, hsa-miR-140-3p, hsa-miR-15b-5p, hsa-miR-16-5p, hsa-miR-92a-3p, hsa-miR-484, hsa-miR-151a-5p, hsa-let-7f-5p, hsa-let-7a-5p, hsa-let-7c-5p, hsa-let-7b-5p, hsa-let-7g-5p, hsa-let-7i-5p, hsa-miR-185-5p, hsa-miR-30d-5p, hsa-miR-30b-5p, hsa-miR-30c-5p, hsa-miR-19b-3p, hsa-miR-26a-5p, hsa-miR-26b-5p, hsa-miR-425-5p, MID-19433, and hsa-miR-4306.

The inventors observed, upon measuring the microRNA profile of the blood compartments, that a number of microRNAs were found elevated in different blood cell types (data not shown). Thus, hsa-miR-342-3p (SEQ ID NO: 17 or 18) was one of the microRNAs, amongst others, which was enriched in white blood cells, and may therefore be considered an example of white blood cell marker. Interestingly, hsa-miR-342-3p showed to be expressed in correlation with hsa-miR-150-5p, suggesting that also hsa-miR-150-5p is a white blood cell marker. In addition, hsa-miR-146a-5p was also shown to be expressed in white blood cells (data not shown).

hsa-miR-200c-3p (SEQ ID NO: 23 or 24) and hsa-miR-138-5p (SEQ ID NO: 19, 20, or 21) were found enriched in epithelial cells. In a preliminary experiment, smears were generated with blood in the absence of thyroid tissue material, and compared with smears from thyroid tissue. Both hsa-miR-200c-3p and hsa-miR-138-5p were found to be expressed at much higher levels in the thyroid smears (both benign and malignant) compared to blood smears (data not shown). Other microRNAs were also found enriched in epithelial cells (data not shown). Thus, hsa-miR-200c-3p and hsa-miR-138-5p are examples of epithelial cell markers. Interestingly, the inventors found that the expression of hsa-miR-138-5p correlated with the presence of epithelial cells, and in certain subsets of the data hsa-miR-138-5p was found to be upregulated in benign samples (data not shown).

Figure 2A:
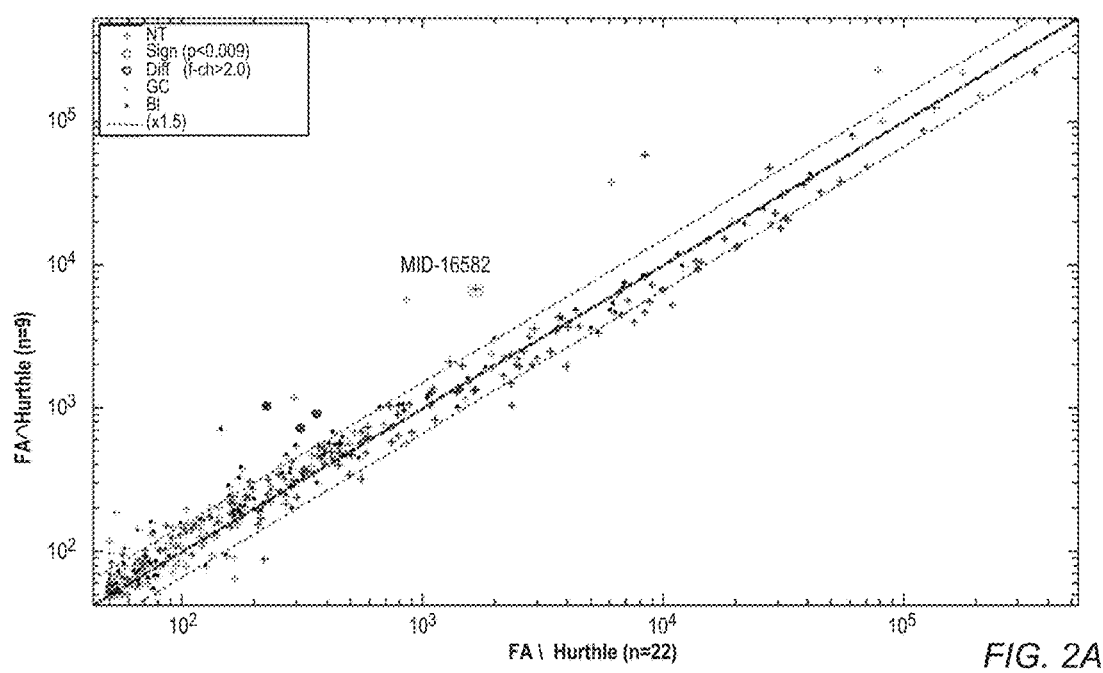
FIGS. 2A-2B: Hurthle cell marker. The plots shows higher expression of MID-16582 in follicular adenoma presenting Hurthle cells versus follicular adenomas with no indication of Hurthle cells. Sign.=significant; Diff.=differential; f-ch=fold change; BL=blood; NT, not tested.
Figure 2B:
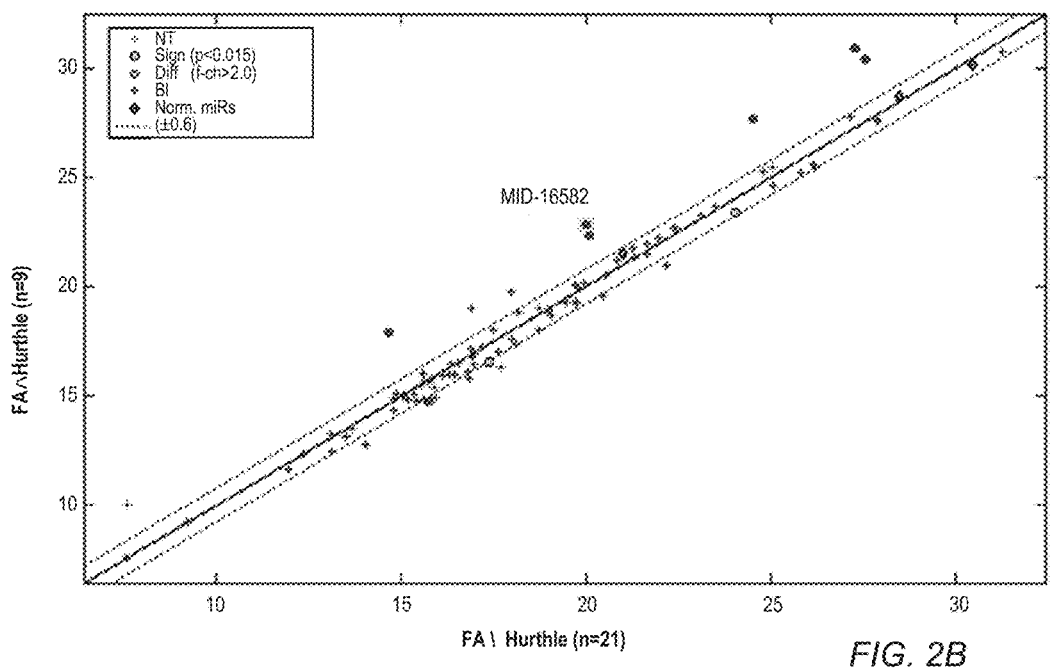

MID-16582 (SEQ ID NO: 25) was found at higher expression levels in Hurthle cells. In preliminary studies, the inventors have surprisingly found that this microRNA is upregulated in follicular adenoma presenting Hurthle cells versus follicular adenomas not indicated to have Hurthle cells (FIGS. 2A-2B). This result may be attributed to the mitochondrial enrichment found in Hurthle cells. The present inventors have found that the sequence of MID-16582, as well as other nucleic acid sequences found in Hurthle cells, can be mapped to mitochondrial DNA (data not shown). Thus, MID-16582 is an example of Hurthle cell marker.

The assay development set included about 360 distinct samples. Most of the samples were stained FNA smears (Papanicolaou, May-Grünwald Giemsa or Diff-Quik). Forty-five (45) FNA samples were in cell blocks. The samples were collected from medical centers in Israel, Europe and USA. Thirty-three of the samples came from thyroid nodules that were less than 1 cm in size. The smallest nodule size was 0.1 cm. Samples of medullary carcinoma were excluded from most of the analyses, unless where indicated. Table 10 provides the distribution of the samples per category.

TABLE 10

Assay Development Cohort Composition and Bethesda distribution

| | No. |
|---|---|
| Histological type | |
| Papillary carcinoma | 84 |
| Papillary carcinoma, follicular variant | 77 |
| Follicular carcinoma | 16 |
| Unspecified carcinoma | 6 |
| Medullary | 14 |
| Nodular hyperplasia | 65 |
| Follicular adenoma | 81 |
| Hashimoto | 6 |
| Graves | 3 |
| Total Malignant | 197 |
| Total Benign | 155 |
| inconclusive | 4 |
| Bethesda | |
| I | 0 |
| II ("determinate") | 38 |
| III ("indeterminate") | 71 |
| IV ("indeterminate") | 113 |
| V ("indeterminate") | 74 |
| VI ("determinate") | 60 |
| unknown | 98 |
| Determinate total | 258 |
| Indeterminate total | 84 |

Samples from FNA smears routinely prepared as well as cell blocks were used for total RNA extraction and RT-PCR amplification. All the samples were tested with a panel of 24 microRNAs.

Figure 3:
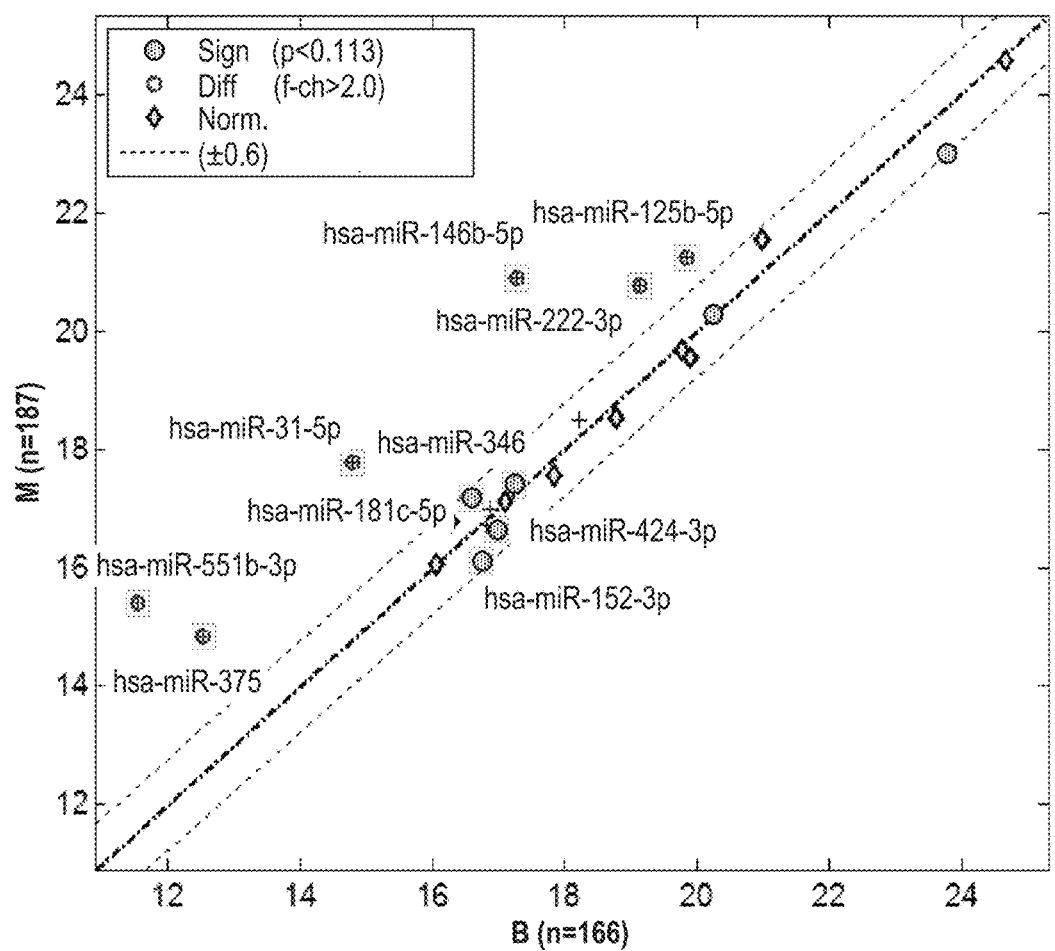
FIG. 3: Profiling of malignant and benign samples with Thyroid assay set of microRNAs. The x and y axis show the expression levels of the miRs in benign (B) (n=166) versus malignant (M) (n=187) samples, respectively. The microRNA median expression levels for hsa-miR-222-3p, hsa-miR-551b-3p, hsa-miR-31-5p, hsa-miR-125b-5p, hsa-miR-146b-5p, hsa-miR-152-3p, hsa-miR-346, hsa-miR-181c-5p, hsa-miR-424-3p, and hsa-miR-375 are highlighted. The numbers refer to (50−normalized Ct value). Diamonds (♦) represent any one of the microRNAs of SEQ ID NOs. 26-37. Sign.=significant; Diff.=differential; f-ch=fold change. The dashed factor line=±0.6.
Figure 4C:
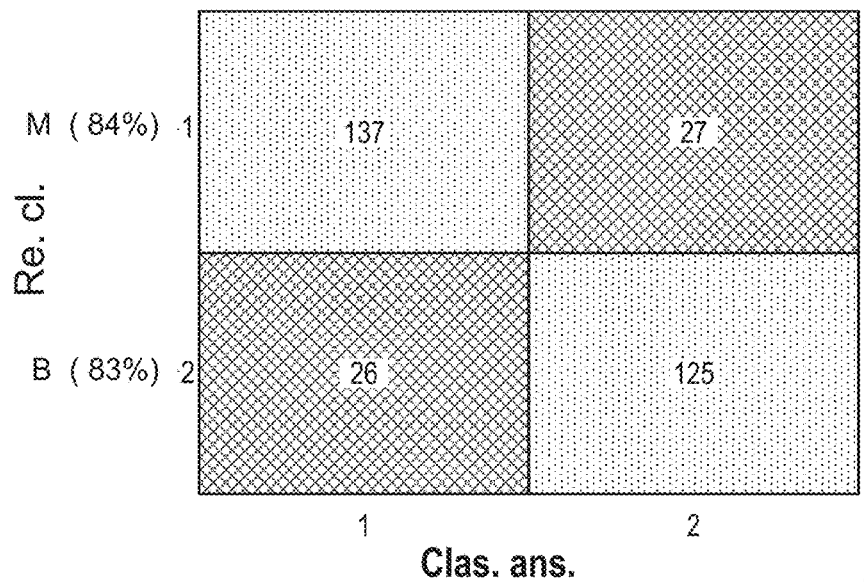
Figure 5A:
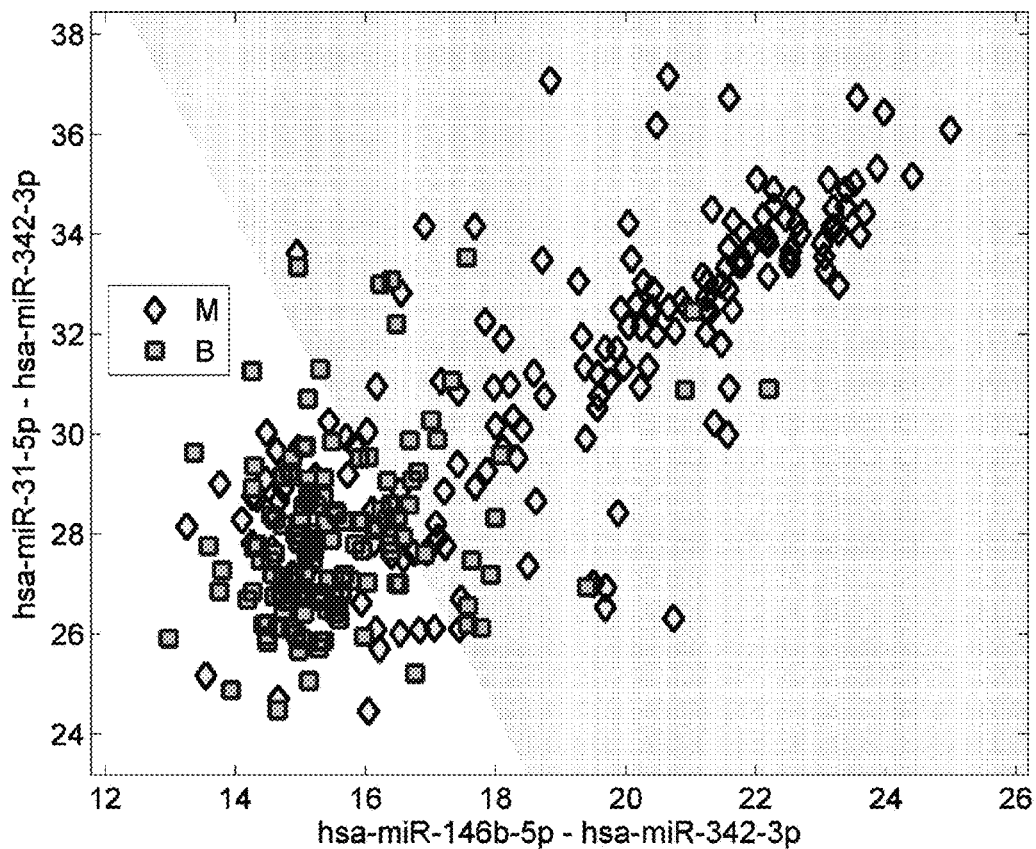
FIGS. 5A-5C: A Discriminant Analysis classifier was used to classify samples from the malignant+benign cohort as malignant (diamonds, M) or benign (squares, B).
Figure 5B:
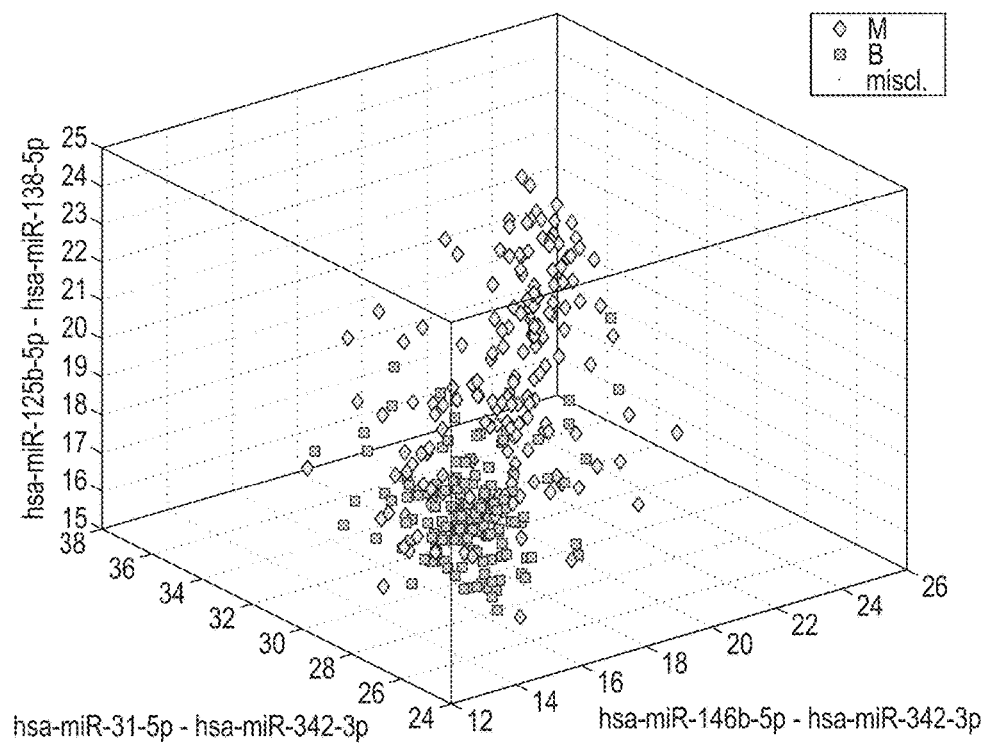
Figure 5C:
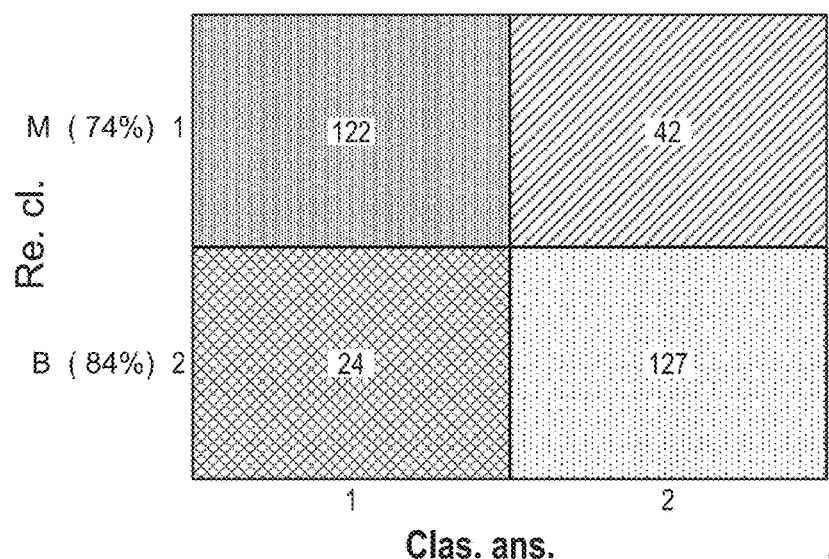
Figure 6C:
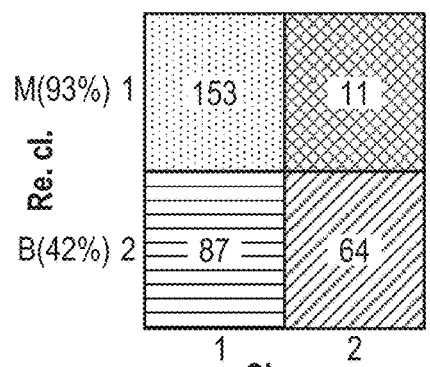
Figure 7A:
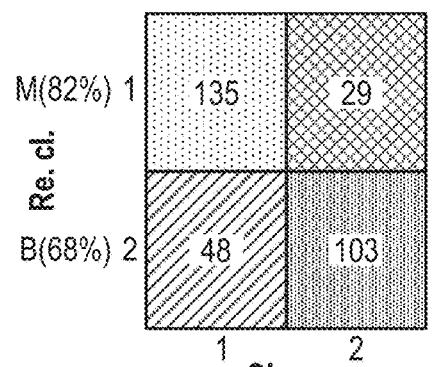
FIG. 7A-7C: A K-nearest neighbor (KNN) classifier was used to classify samples from the malignant+benign cohort as malignant (M) from benign (B).
Figure 7B:
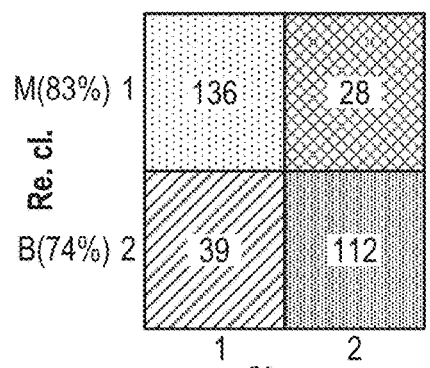
Figure 7C:
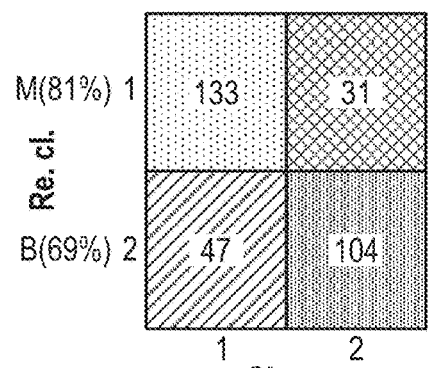
Figure 8A:
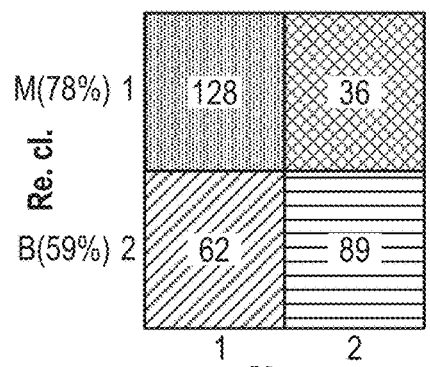
FIG. 8A-8B: A KNN classifier was used to classify samples from the malignant+benign cohort as malignant (M) or benign (B).
Figure 8B:
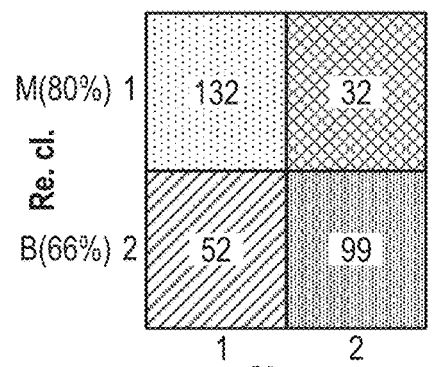
Figure 9A:
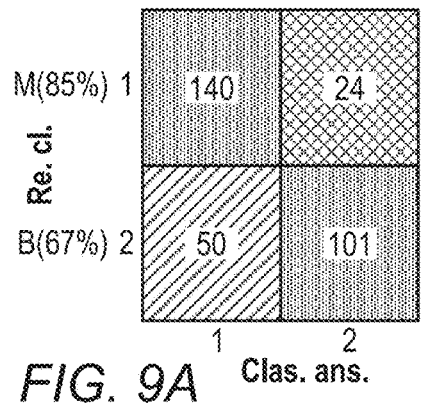
FIG. 9A-9C: A KNN classifier was used to classify samples from the malignant+benign cohort as malignant (M) or benign (B).
Figure 9B:
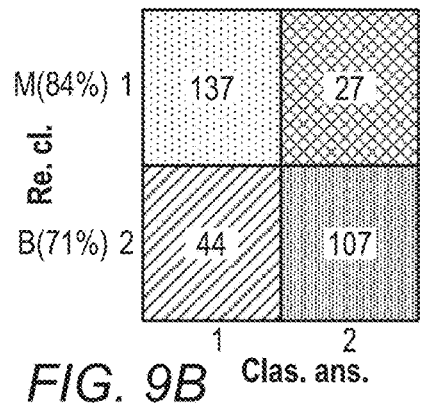
Figure 9C:
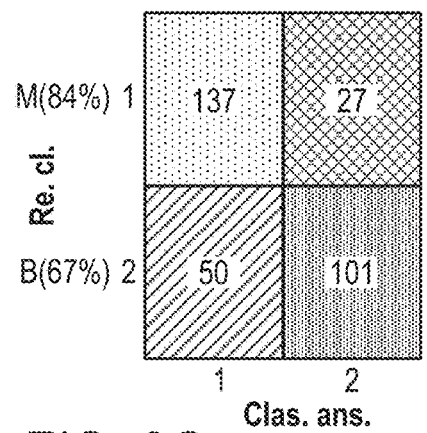
Figure 10C:
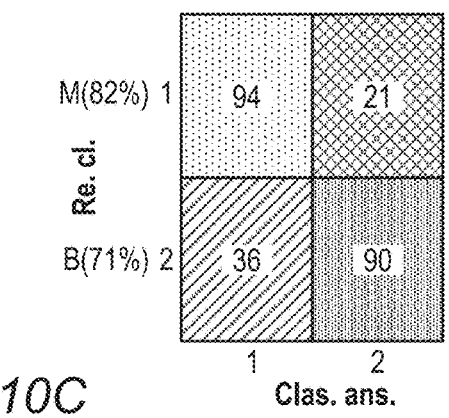
Figure 11A:
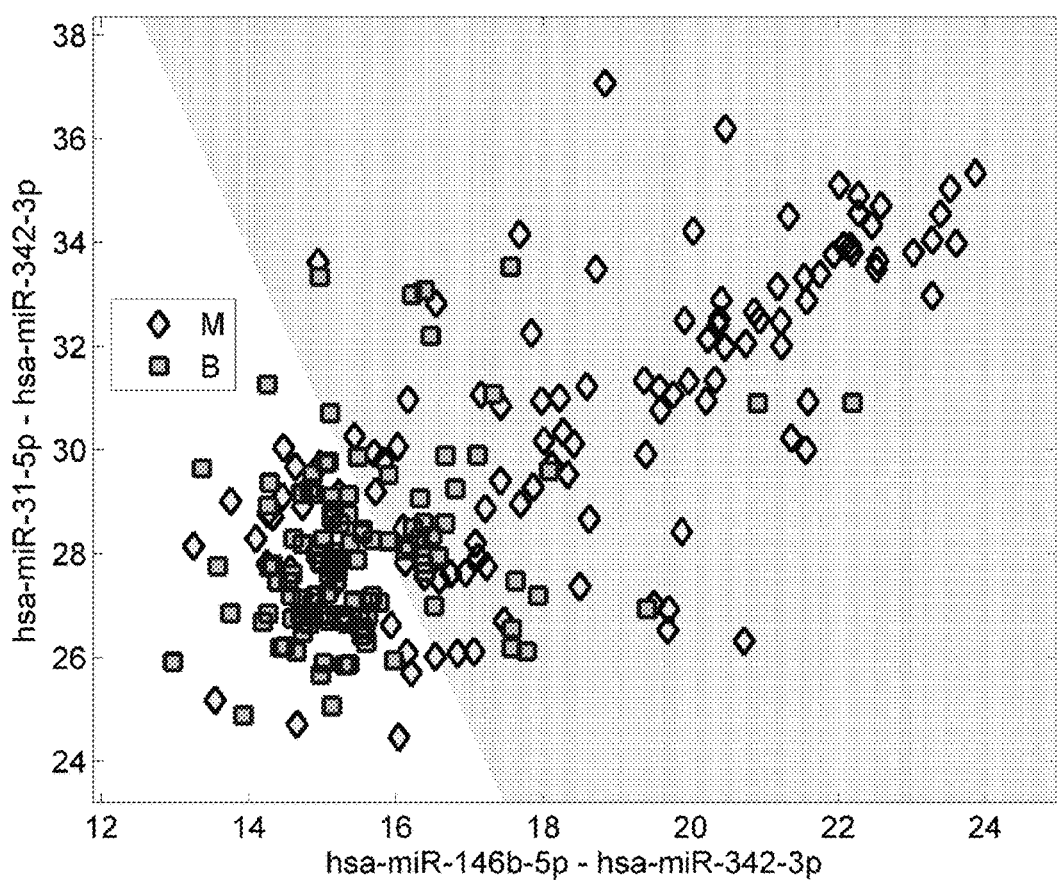
FIG. 11A-11C: A Discriminant Analysis classifier was used to classify samples from the Indeterminate sub-cohort as malignant (diamonds, M) or benign (squares, B)
Figure 11B:
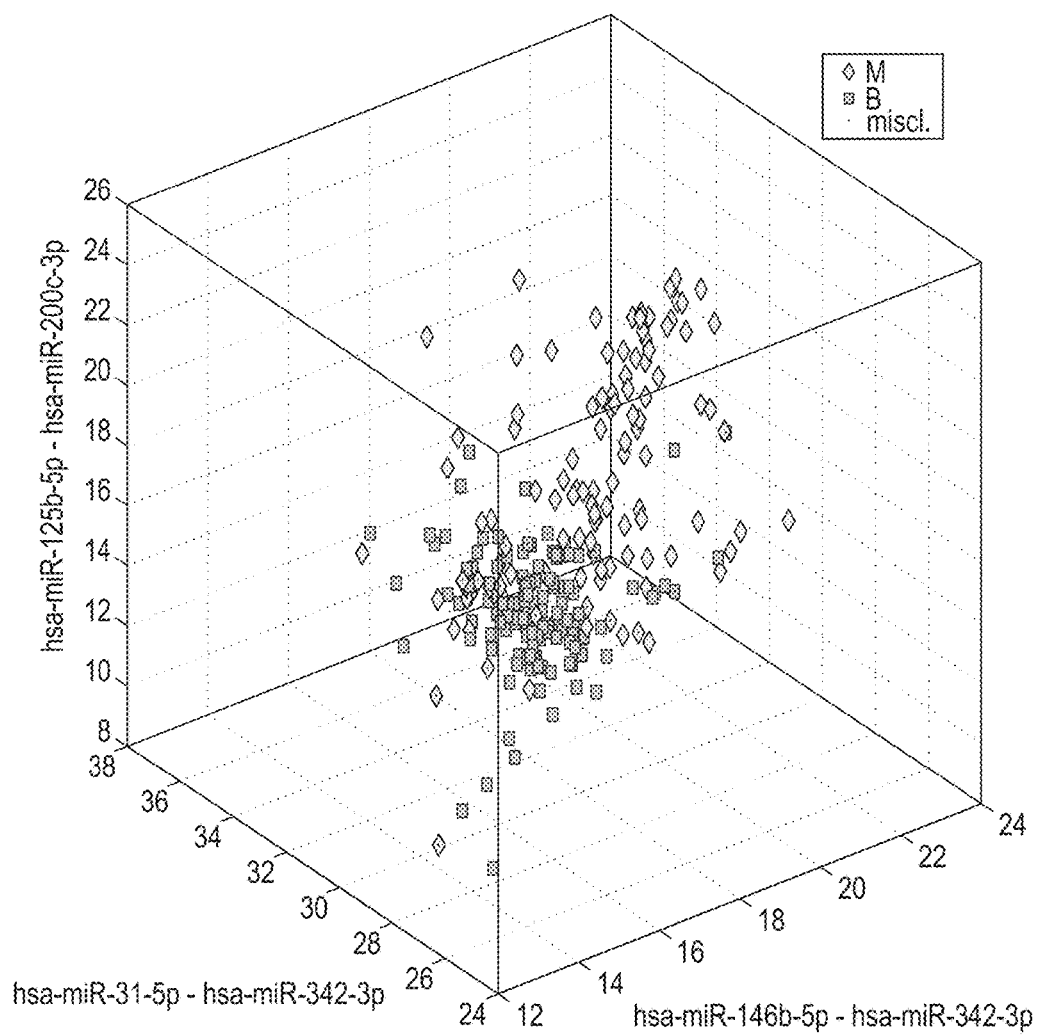
Figure 11C:
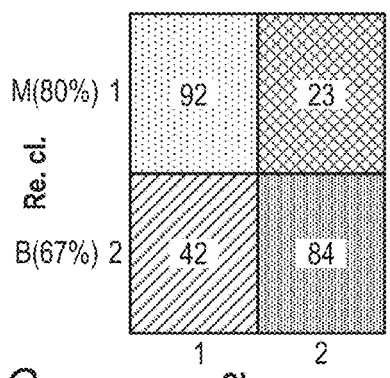
Figure 12A:
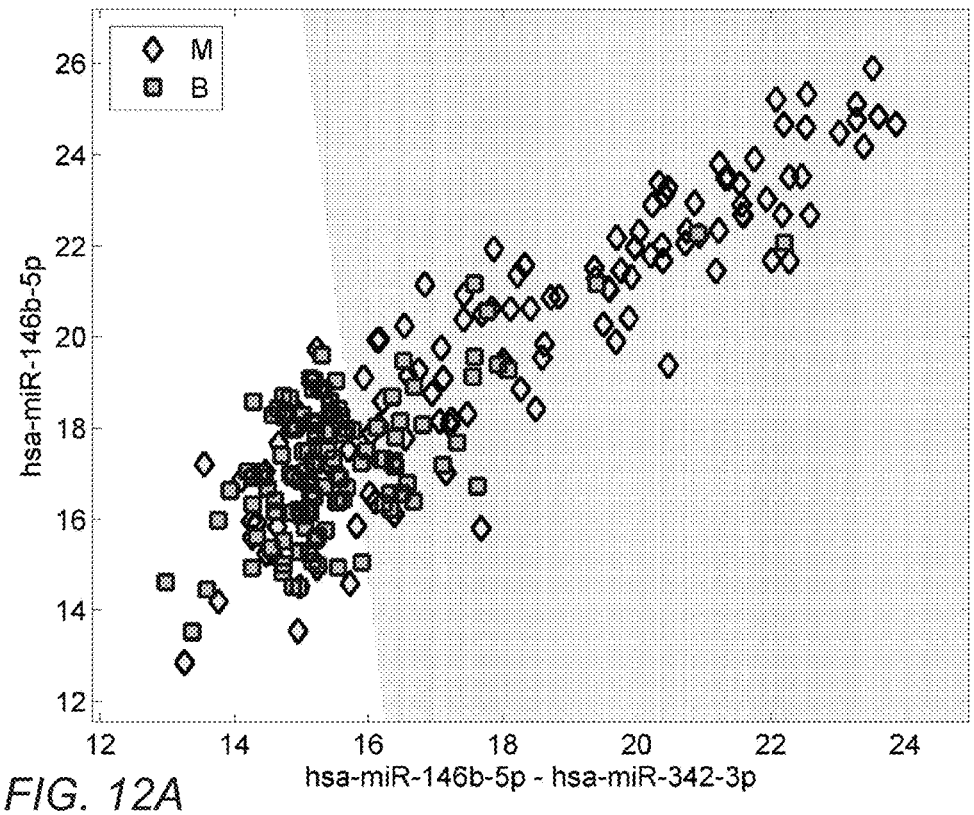
FIG. 12A-12C: A Discriminant Analysis classifier was used to classify samples from the Indeterminate sub-cohort as malignant (diamonds, M) or benign (squares, B), using a combination of microRNAs and microRNA ratios.
Figure 12B:
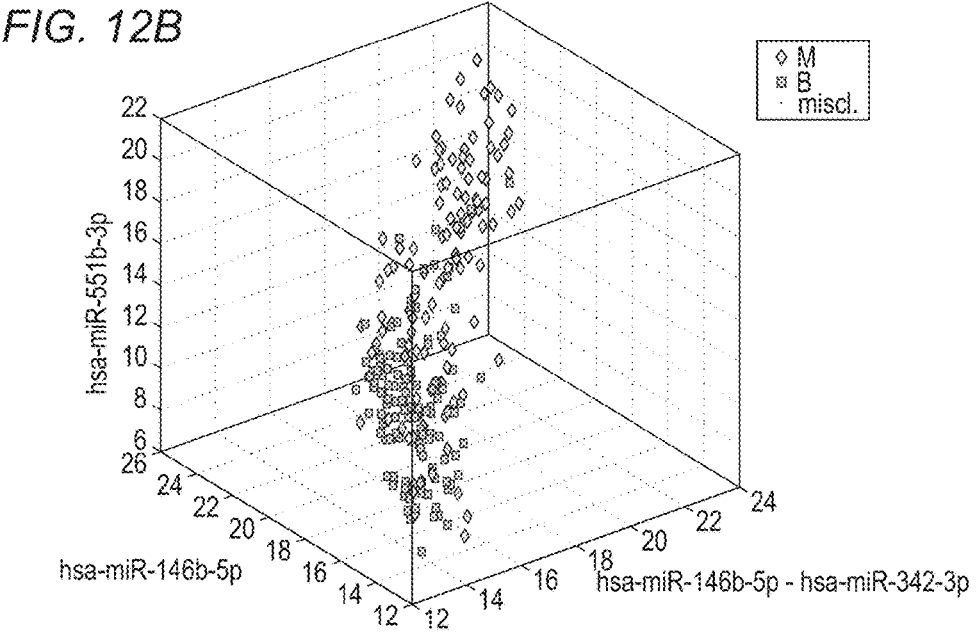
Figure 12C:
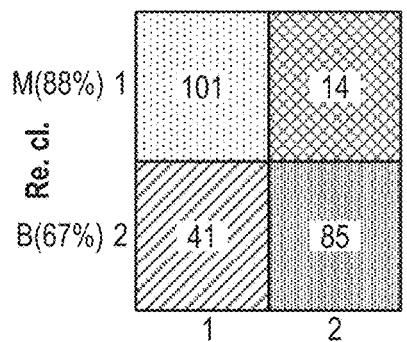
Figure 13A:
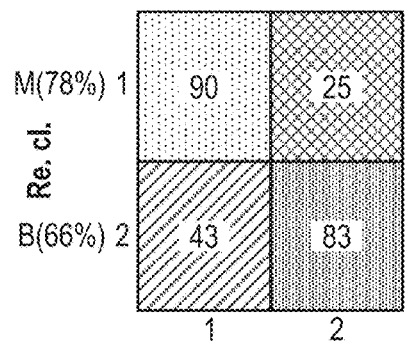
FIG. 13A-13C: A KNN classifier was used to classify samples from the Indeterminate sub-cohort as malignant (M) or benign (B)
Figure 13B:
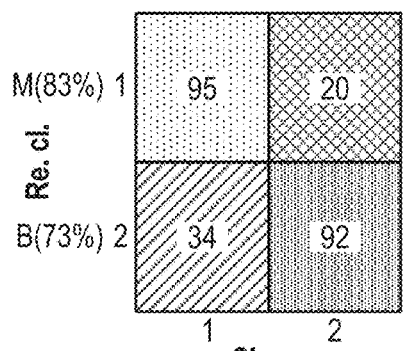
Figure 13C:
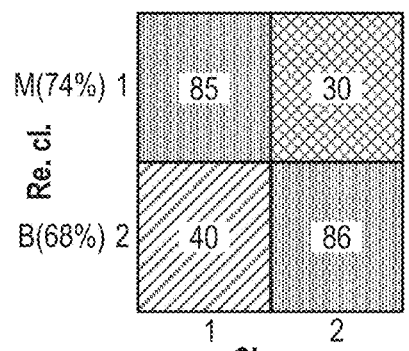
Figure 14A:
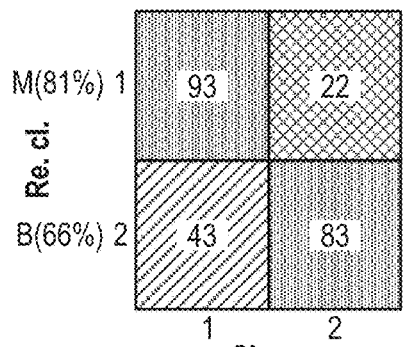
FIG. 14A-14B: A KNN classifier was used to classify samples from the Indeterminate sub-cohort as malignant (M) or benign (B), using microRNA ratios.
Figure 14B:
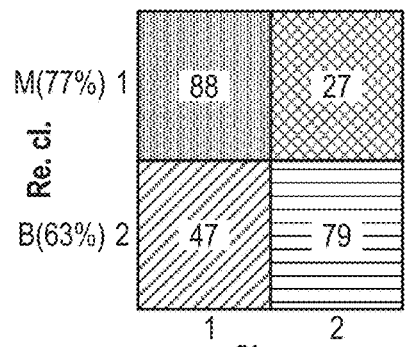
Figure 15A:
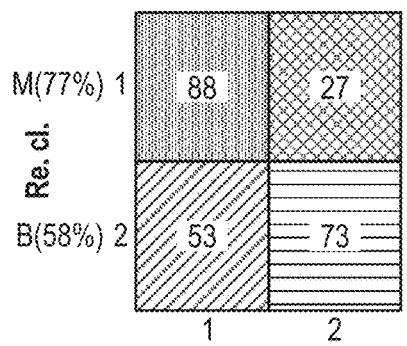
FIG. 15A-15C: A KNN classifier was used to classify samples from the Indeterminate sub-cohort as malignant (M) or benign (B) using microRNAs and microRNA ratios.
Figure 15B:
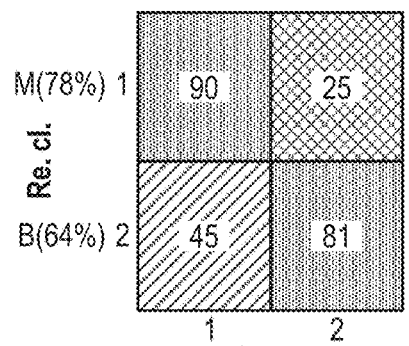
Figure 15C:
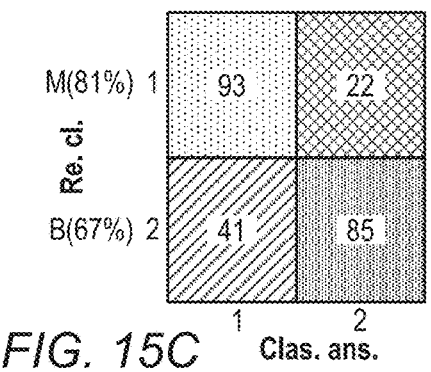
Figure 16B:
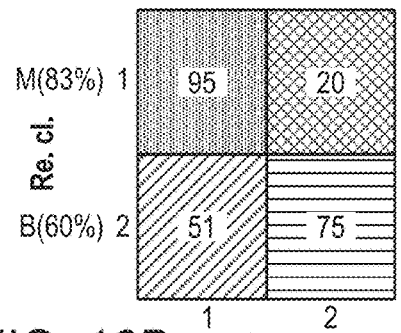
FIG. 16A-16C: A SVM classifier was used to classify samples from the Indeterminate sub-cohort as malignant (diamonds, M) or benign (squares, B)
Figure 16A:
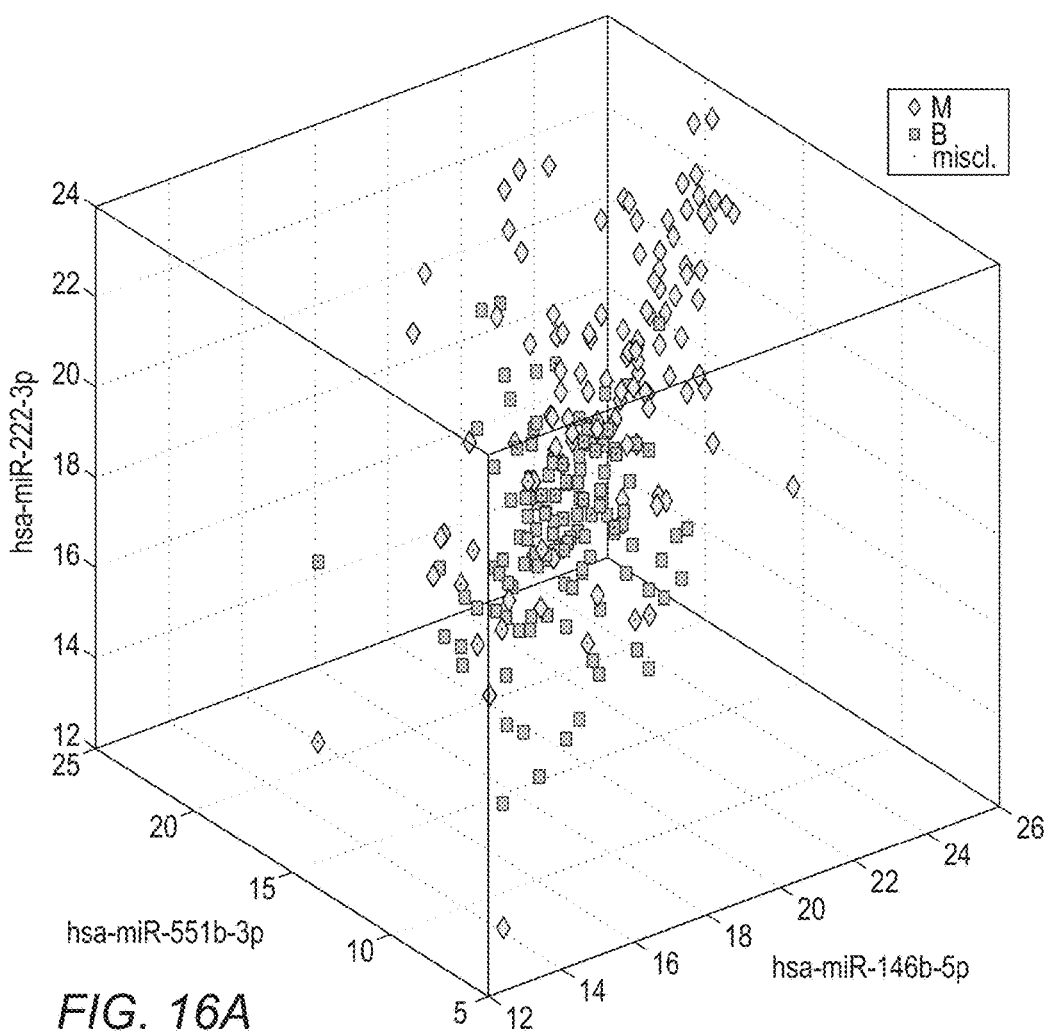
Figure 16C:
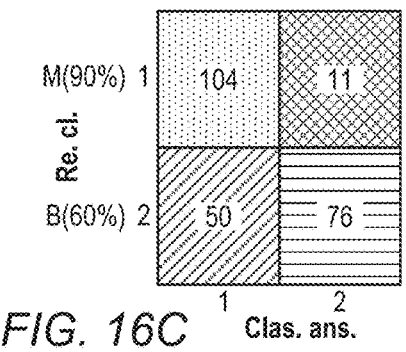
Figure 17B:
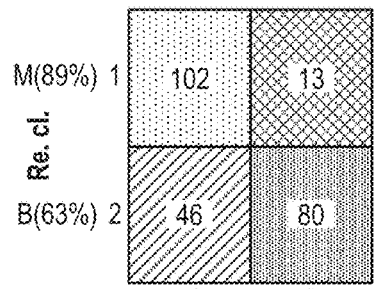
FIG. 17A-17C: A SVM classifier was used to classify samples from the Indeterminate sub-cohort as malignant (diamonds, M) or benign (squares, B) using microRNA ratios.
Figure 17A:
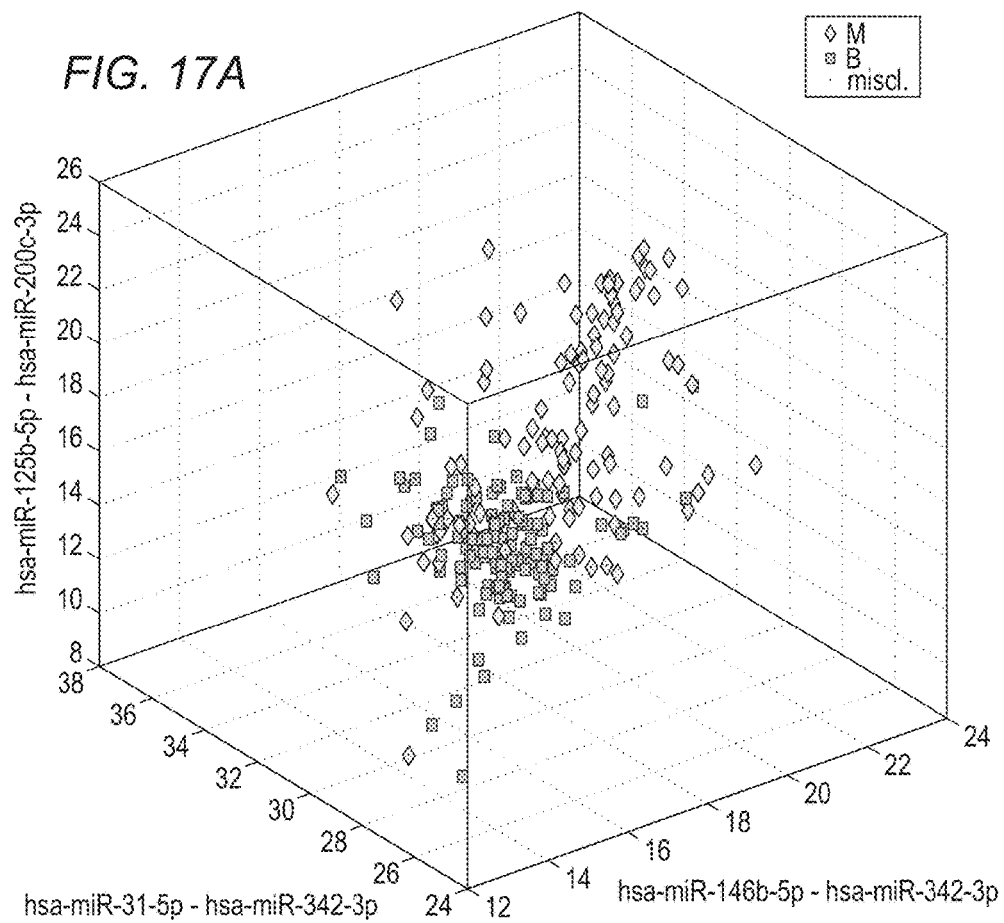
Figure 17C:
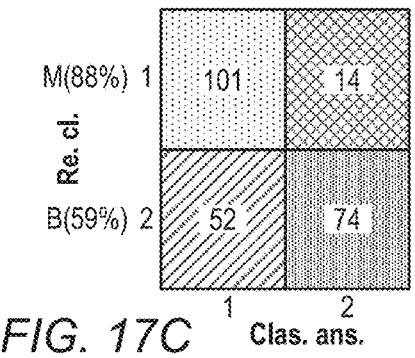
Figure 18B:
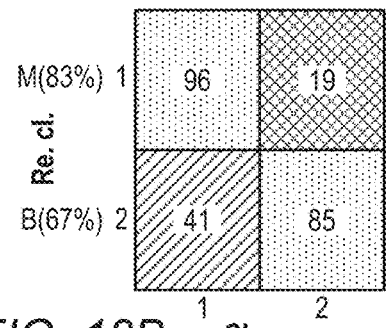
FIG. 18A-18C: A SVM classifier was used to classify samples from the Indeterminate sub-cohort as malignant (diamonds, M) or benign (squares, B) samples using the combination of microRNAs and microRNA ratios.
Figure 18A:
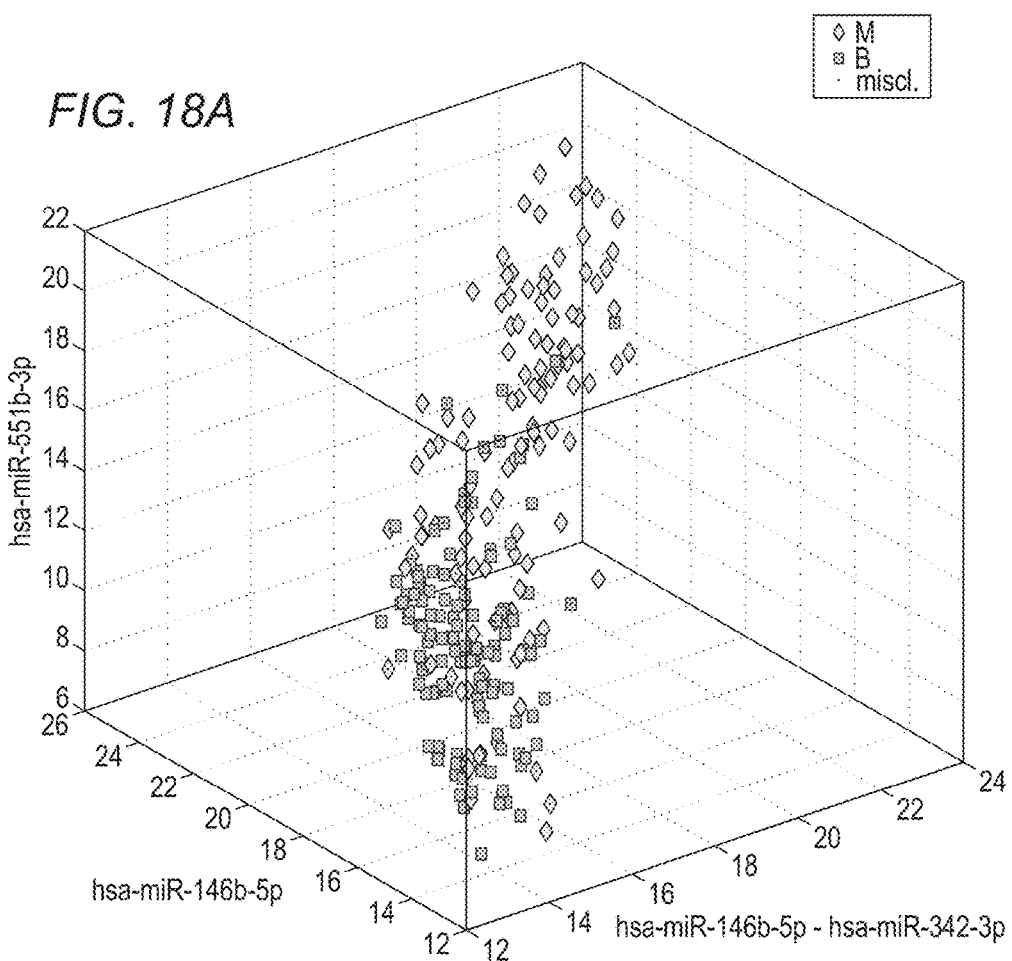
Figure 18C:
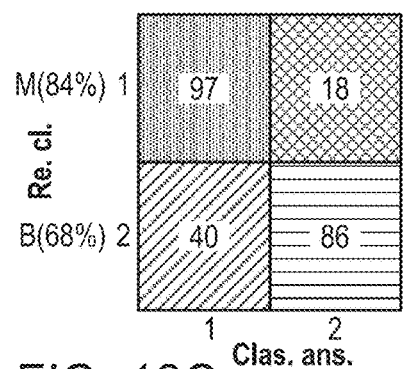
Figure 19A:
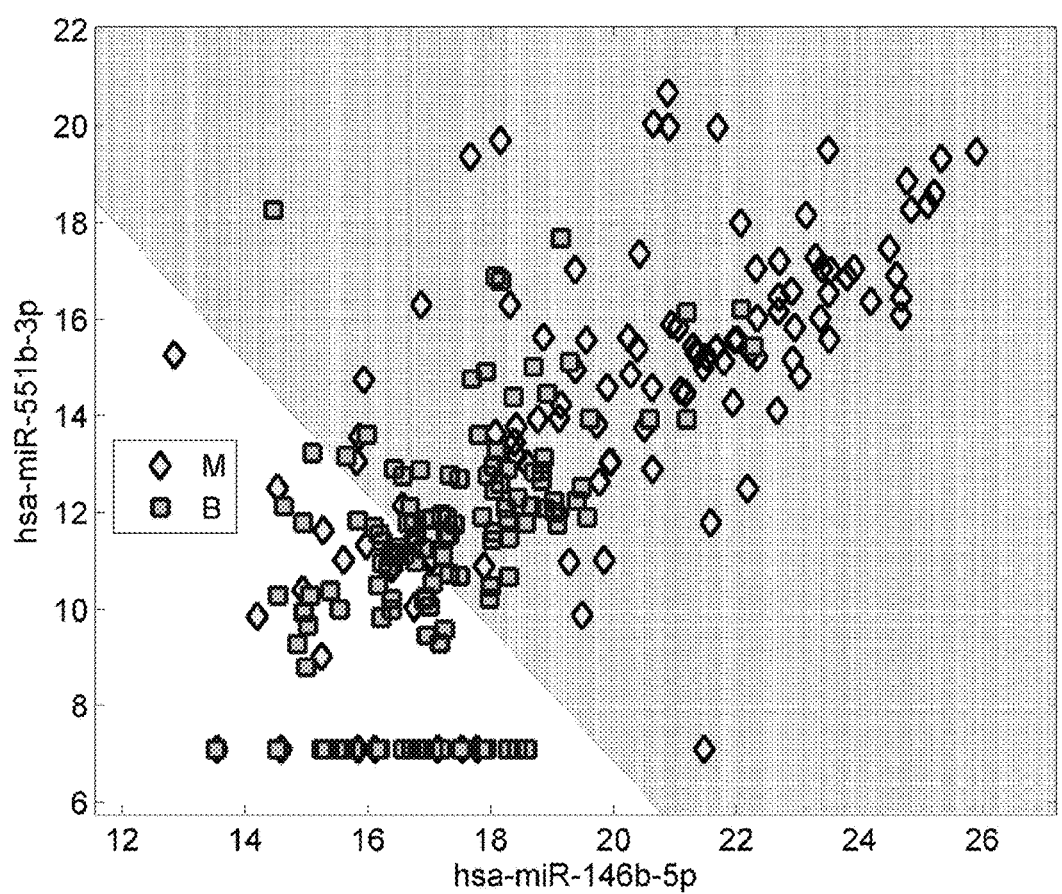
FIG. 19A-19C: A Discriminant analysis ensemble classifier was used to classify samples from the Indeterminate sub-cohort as malignant (diamonds, M) or benign (squares, B).
Figure 19B:
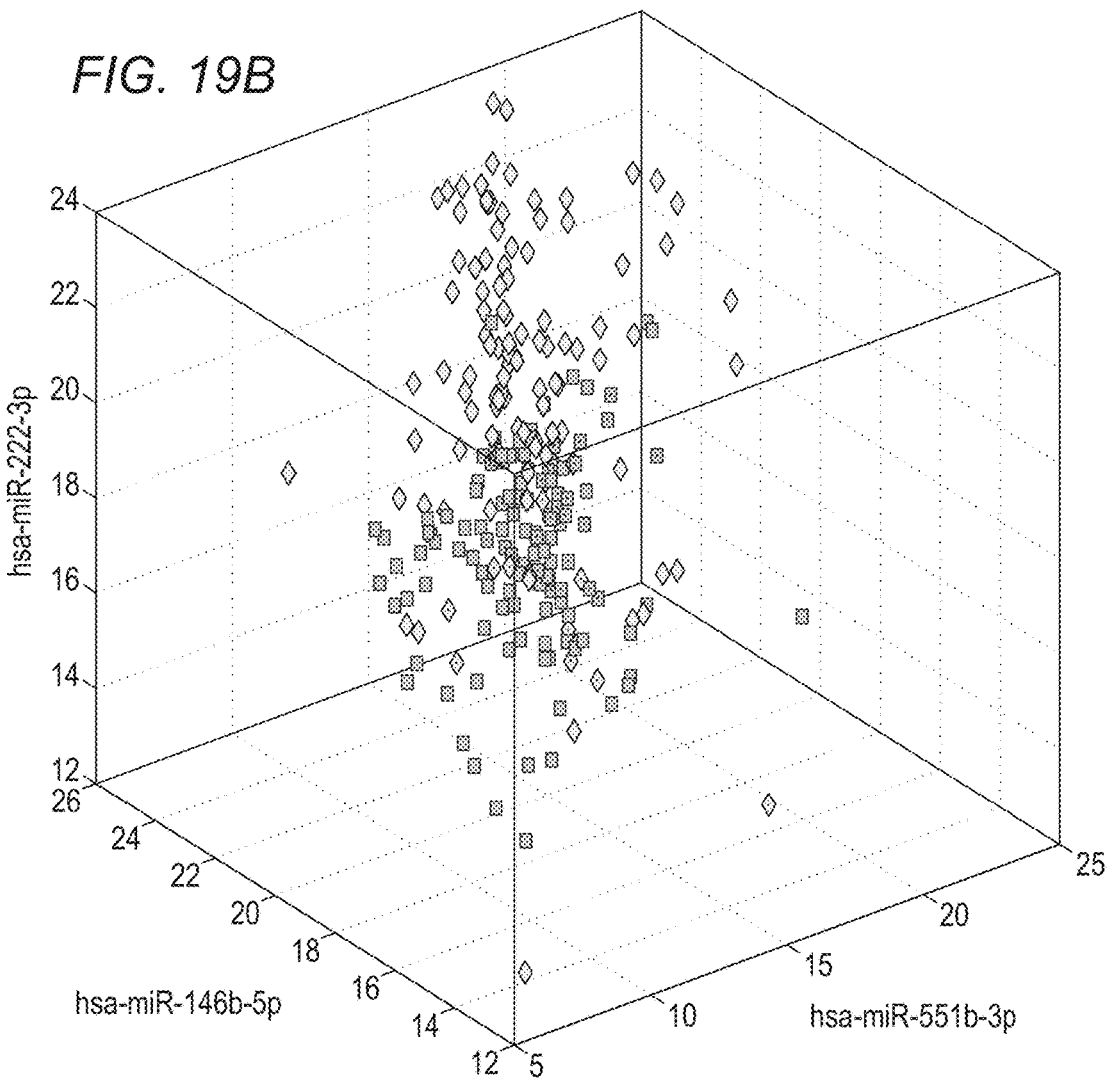
Figure 19C:
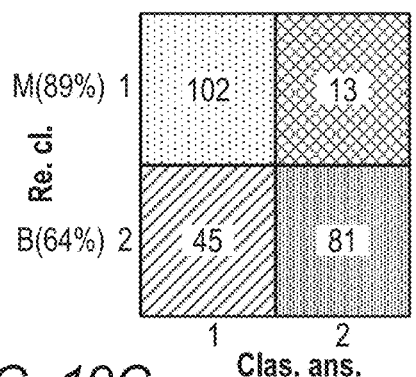
Figure 20C:
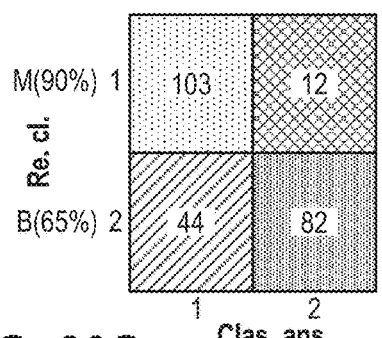
Figure 21A:
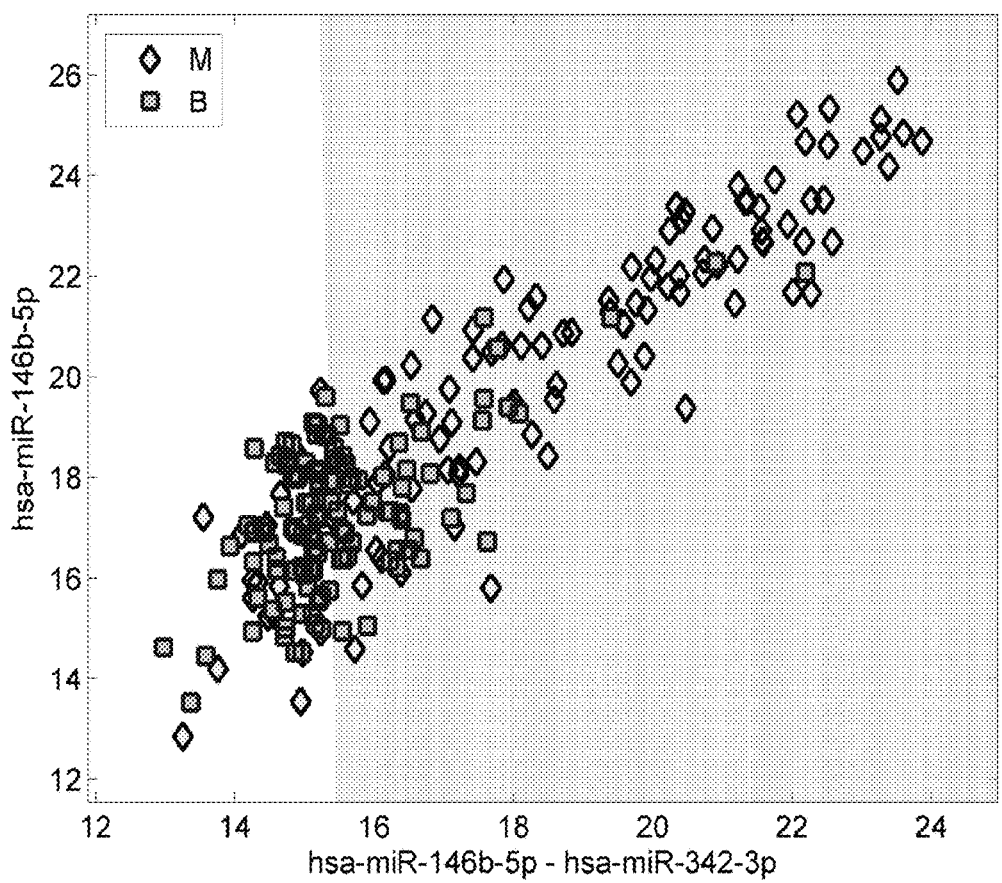
FIG. 21A-21C: A Discriminant analysis ensemble classifier was used to classify samples from the Indeterminate sub-cohort as malignant (diamonds, M) or benign (squares, B) using a combination of microRNAs and microRNA ratios.
Figure 21B:
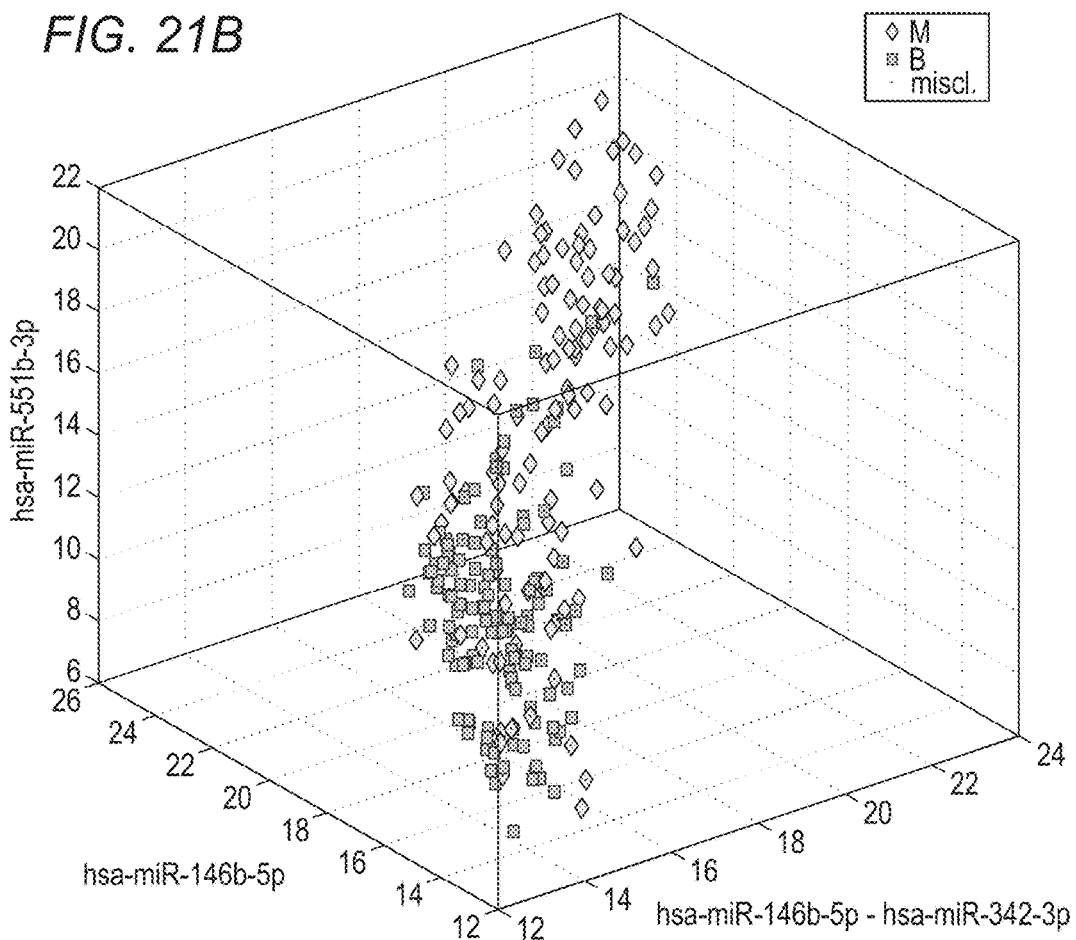
Figure 21C:
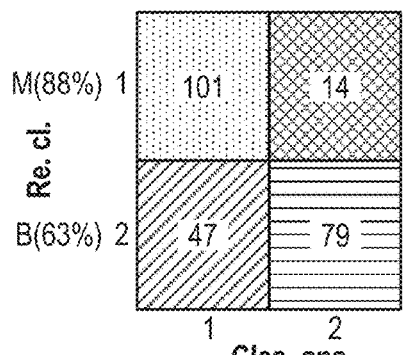
Figure 22C:
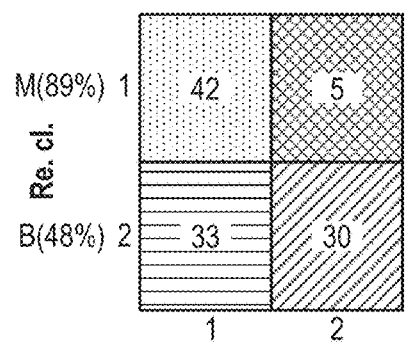
Figure 23A:
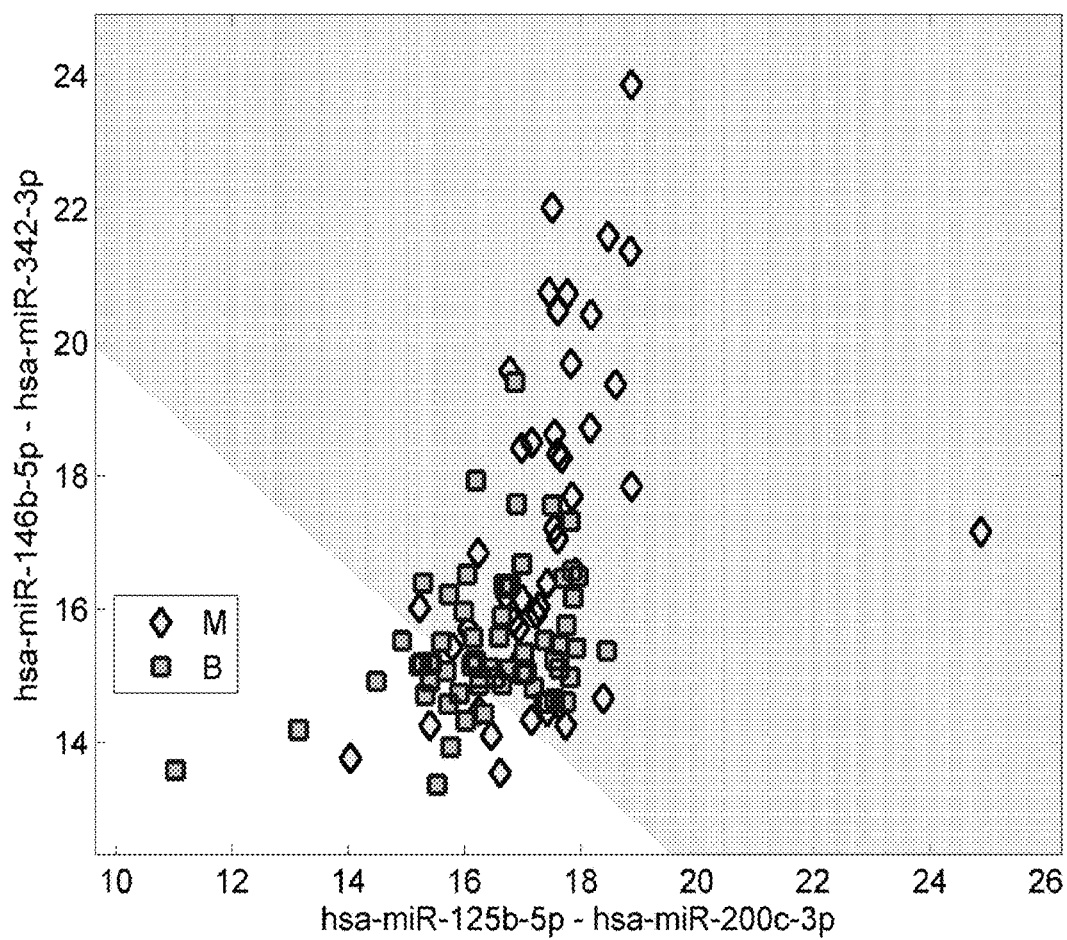
FIG. 23A-23C: A Discriminant analysis classifier was used to classify the samples from the Bethesda IV sub-cohort as malignant (diamonds, M) or benign (squares, B).
Figure 23B:
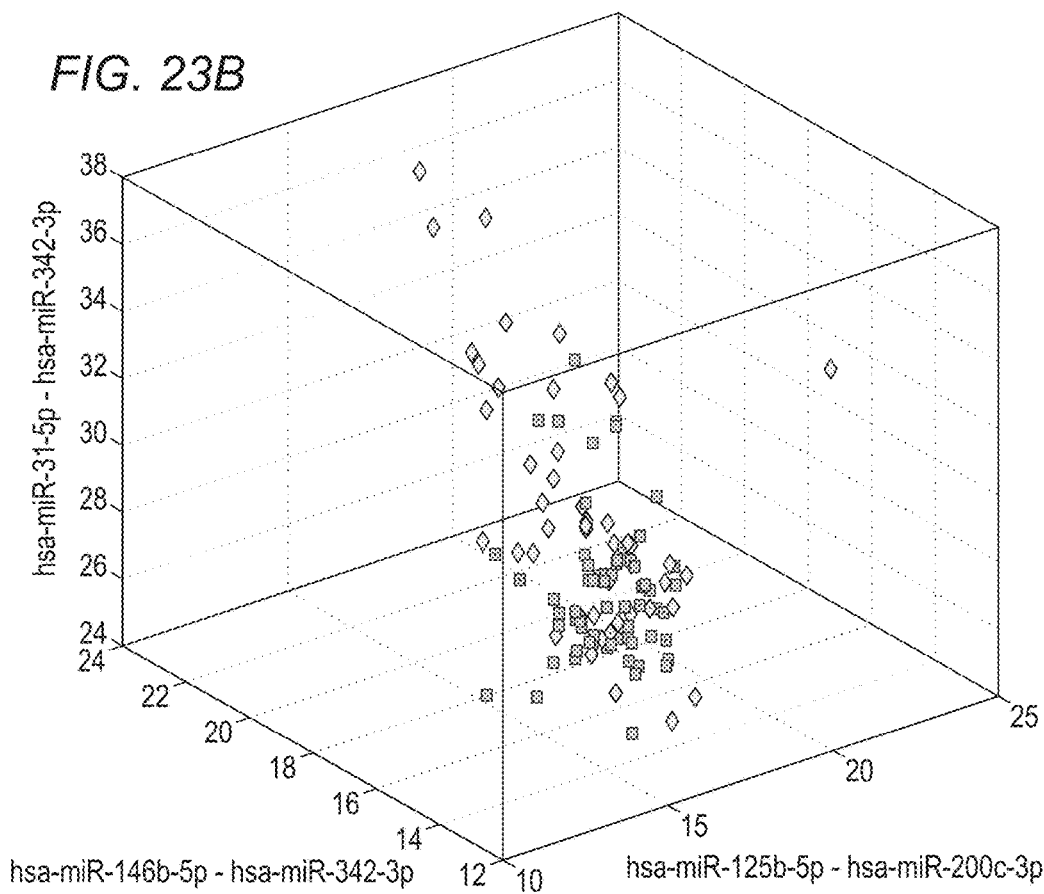
Figure 23C:
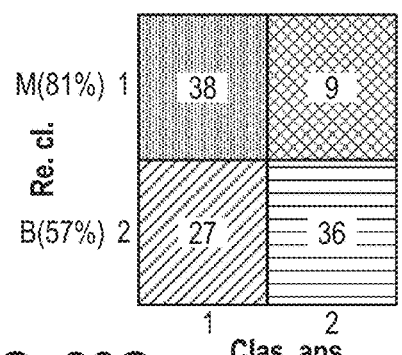
Figure 24C:
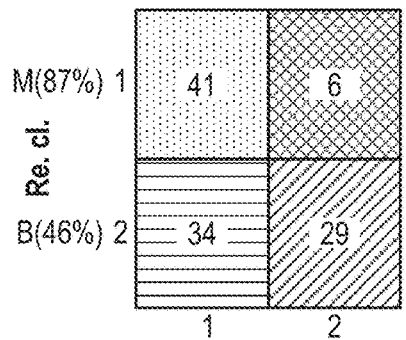
Figure 25A:
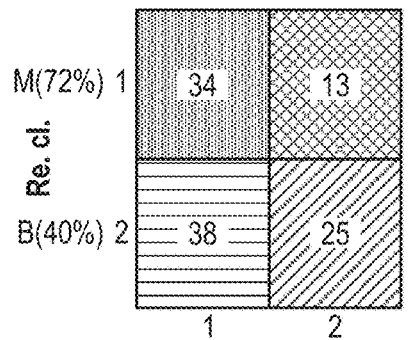
FIG. 25A-25C: A KNN classifier was used to classify samples from the Bethesda IV sub-cohort as malignant or benign. The figures show a confusion matrix where the x-axis shows the classifier answer (Clas. Ans.), while the y-axis shows the true diagnosis (Real class=re.cl.).
Figure 25B:
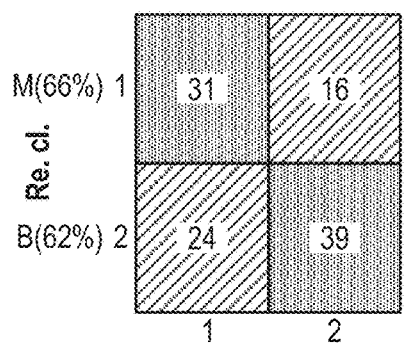
Figure 25C:
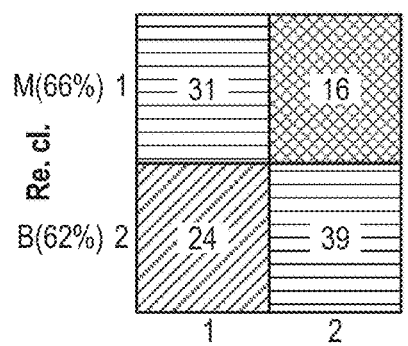
Figure 26A:
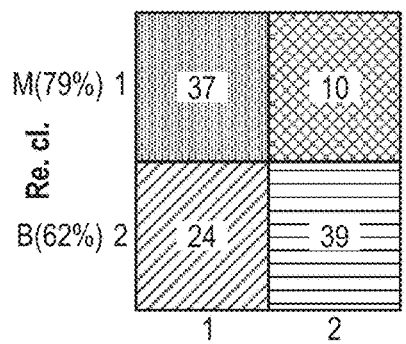
FIG. 26A-26B: A KNN classifier was used to classify samples from the Bethesda IV sub-cohort as malignant or benign. The figures show a confusion matrix where the x-axis shows the classifier answer (Clas. Ans.), while the y-axis shows the true diagnosis (Real class=re.cl.).
Figure 26B:
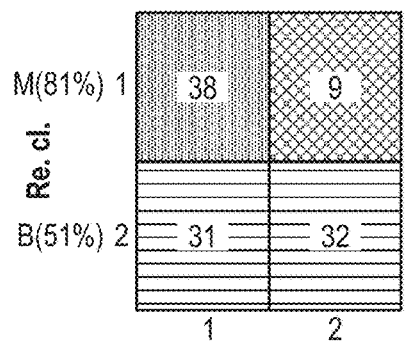
Figure 27A:
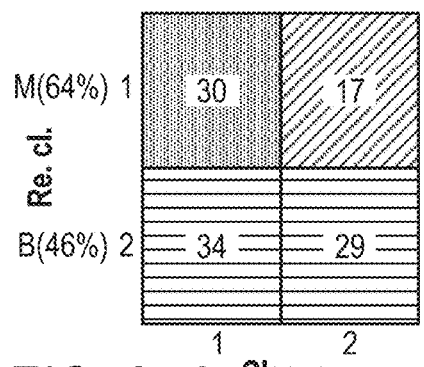
FIG. 27A-27C: A KNN classifier was used to classify samples from the Bethesda IV sub-cohort as malignant or benign using expression of microRNAs and microRNA ratios. The figures show a confusion matrix where the x-axis shows the classifier answer (Clas. Ans.), while the y-axis shows the true diagnosis (Real class=re.cl.).
Figure 27B:
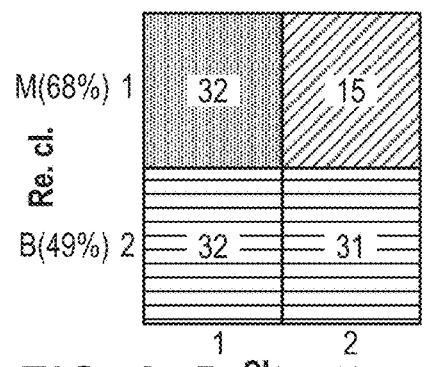
Figure 27C:
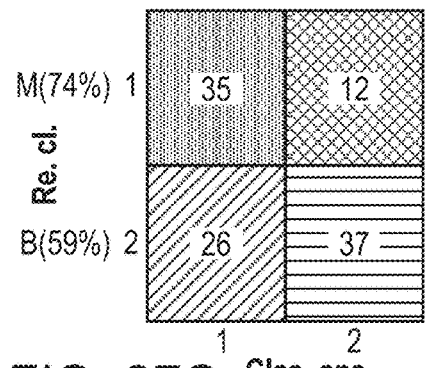

Results of the assay development in a sub-set of samples (n=353) are shown in FIG. 3. Expression of microRNAs hsa-miR-222-3p (SEQ ID NO: 1 or 2), hsa-miR-551b-3p (SEQ ID NO: 3 or 4), hsa-miR-31-5p (SEQ ID NO: 5, 6, or 7), hsa-miR-125b-5p (SEQ ID NO: 9), hsa-miR-146b-5p (SEQ ID NO: 10 or 11), hsa-miR-346 (SEQ ID NO: 14), hsa-miR-181c-5p (SEQ ID NO: 15), and hsa-miR-375 (SEQ ID NO: 8) above the threshold are found in correlation with malignant samples. The expression levels shown in FIG. 3 were obtained by the following formula: [50−normalized Ct of each marker]. The normalization was done by subtracting the mean signal of the normalizers. The value of the mean signal of the normalizers over all the samples used, was added to all the expression values detected, in order to bring the values to a range more manageable for calculation. Interestingly, expression levels of hsa-miR-125a-5p correlate with that of hsa-miR-125b-5p.

Example 9

Establishment of Classifiers for the Thyroid Assay

Four algorithms were used in order to establish the best classifier to be implemented in the thyroid assay, Discriminant Analysis, K-nearest neighbor (KNN), support vector machine (SVM) and Ensemble of discriminant analysis classifiers (Discriminant Analysis Ensemble).

The following parameters were established a priori:

Priors: For all the algorithms used, priors were set to 70% for the malignant and 30% for the benign samples.

Sample Set: In this example, three sample sets were analyzed. One sample set included malignant (n=183) plus benign (n=155) samples, which excludes the malignant medullary samples; referred to below and in the Figures as "malignant+benign". Another sample set included all "indeterminate" samples, which includes all samples classified as Bethesda III, IV and V, referred to below and in the Figures as "indeterminate". A third sample set included samples classified as Bethesda IV only, referred to below and in the Figures as "Bethesda". Samples from thyroid lesions classified as Bethesda IV are usually difficult to classify by cytological parameters. Therefore, it is important to establish a classifier that is based on this sub-group of samples. In addition, specific samples that presented technical problems due to a variety of reasons (e.g. malignant samples with Bethesda II; sample taken from lymph nodes) were excluded.

Medullary samples were excluded from the classification. Therefore, in this Example, when referring to malignant samples it means non-medullary malignant.

MicroRNA Ratios: Ratios were obtained from pairs of microRNAs in an attempt to subtract certain factors from the classifier. Thus e.g. a ratio of hsa-miR-31-5p: hsa-miR-342-3p enables to reduce the contribution of white blood cells (through the expression of hsa-miR-342-3p, the denominator) in the expression of hsa-miR-31-5p (the numerator). Since $C_T$s are in log-scale, ratios were created by subtracting one miR expression from the other. Each ratio was further normalized by adding a constant, in order for the ratios to be within the same range as the microRNA normalized values.

In this Example, microRNA normalized values were obtained by dividing microRNA expression levels by the expression levels of hsa-miR-23a-3p, MID-20094, MID-50969, hsa-miR-345-5p, hsa-miR-3074-5p, MID-50976, MID-50971, hsa-miR-5701 or hsa-miR-574-3p; and were further subtracted from 50, in order for lower $C_T$s to be associated with higher expression values.

Example 9.1

Discriminant Analysis Classifier

When discriminant analysis was used as the algorithm, a linear discriminant type of discriminant analysis (LDA) was applied, in three sets of samples as mentioned above, using as features either different combinations of microRNA expression levels (FIG. 4A-4C, FIG. 10A-10C and FIG. 22A-22C), microRNA ratios (FIG. 5A-5C, FIG. 11A-11C and FIG. 23A-23C), or a combination of microRNA expression levels and microRNA ratios (FIG. 6A-6C, FIG. 12A-12C and FIG. 24A-24C).

Analysis of the malignant+benign samples using (i) different combinations of microRNA expression levels, e.g. two (e.g. hsa-miR-551b-3p and hsa-miR-146b-5p), three (e.g. hsa-miR-551b-3p, hsa-miR-146b-5p, and hsa-miR-31-5p), or eight microRNAs (e.g. hsa-miR-551b-3p; hsa-miR-146b-5p; hsa-miR-31-5p; hsa-miR-222-3p; hsa-miR-375; hsa-miR-125b-5p; hsa-miR-152-3p; hsa-miR-181c-5p), resulted in a sensitivity of between 82-85%, and a specificity of between 68-81.5%; or (ii) microRNA ratios [e.g. hsa-miR-146b-5p:hsa-miR-342-3p and hsa-miR-31-5p:hsa-miR-342-3p], [e.g. hsa-miR-146b-5p:hsa-miR-342-3p; hsa-miR-31-5p:hsa-miR-342-3p; hsa-miR-125b-5p:hsa-miR-138-5p], or [e.g. hsa-miR-146b-5p:hsa-miR-342-3p; hsa-miR-31-5p:hsa-miR-342-3p; hsa-miR-125b-5p:hsa-miR-138-5p; hsa-miR-125b-5p:hsa-miR-200c-3p; hsa-miR-222-3p:hsa-miR-486-5p; hsa-miR-200c-3p:hsa-miR-486-5p; MID-16582:hsa-miR-200c-3p; MID-16582:hsa-miR-138-5p] resulted in a sensitivity of between 74-81.1% and a specificity of between 79.5-84.1%. In an alternative type of analysis a combination of microRNAs and microRNA ratios was used, resulting in a sensitivity of between 83-93.3% and a specificity of between 42.4-82.2% (FIG. 4A-4C, FIG. 5A-5C, FIG. 6A-6C).

Analysis of the indeterminate samples using (i) different combinations of microRNA expression levels, e.g. two, three (hsa-miR-146b-5; hsa-miR-551b-3p; hsa-miR-222-3p), or eight microRNAs resulted in a sensitivity of between 80-82.3%, and a specificity of between 56-71.4%; or (ii) microRNA ratios [e.g. hsa-miR-146b-5p:hsa-miR-342-3p; hsa-miR-31-5p:hsa-miR-342-3p; hsa-miR-125b-5p:hsa-miR-200c-3p] resulted in a sensitivity of around 80% and a specificity of between 66-72.2%. In an alternative type of analysis a combination of microRNAs and microRNA ratios was used, resulting in a sensitivity of between 79-88% and a specificity of between 67.5-73.8% (FIG. 10A-10C, FIG. 11A-11C, FIG. 12A-12C).

Analysis of the Bethesda IV samples using (i) different combinations of microRNA expression levels, e.g. two (hsa-miR-125b-5p; hsa-miR-551b-3p), three (hsa-miR-125b-5p; hsa-miR-551b-3p; hsa-miR-222-3p), or eight (hsa-miR-125b-5p; hsa-miR-551b-3p; hsa-miR-222-3p; hsa-miR-146b-5p; hsa-miR-375; hsa-miR-181c-5p; hsa-miR-31-5p; hsa-miR-138-5p), resulted in a sensitivity of between 89-91.5%, and a specificity of between 39-47%; or (ii) microRNA ratios [e.g.] resulted in a sensitivity of between 80-91.5% and a specificity of up to 57%. In an alternative type of analysis a combination of microRNAs and microRNA ratios was used, resulting in a sensitivity of between 87-93.6% and a specificity of up to 46% (FIG. 22A-22C, FIG. 23A-23C, FIG. 24A-24C).

Example 9.2

KNN Classifier

One analysis was performed using KNN (k-nearest neighbors) as the algorithm, in which k=5 was used with a distance metric of Pearson correlation. The analysis with the KNN algorithm was applied to three sets of samples as mentioned above (malignant+benign, indeterminate and Bethesda IV) using as features either different combinations of microRNA expression levels (FIG. 7A-7C, FIG. 13A-13C and FIG. 25A-25C), microRNA ratios (FIG. 8A-8B, FIG. 14A-14B and FIG. 26A-26B), or a combination of microRNA expression levels and microRNA ratios (FIG. 9A-9C, FIG. 15A-15C and FIG. 27A-27C).

For malignant+benign samples, analysis of six, eight or twelve microRNA expression levels achieved sensitivity of between 81.1-82.9% and specificity of up to 74.2%. Analysis of six or eight microRNA ratios, achieved sensitivity of between 78-80.5% and specificity of up to 65.6%. Analysis of a combination of microRNA expression levels and microRNA ratios achieved sensitivity of between 83.5-85.4% and specificity of up to 70.9% (FIG. 7A-7C, FIG. 8A-8B, FIG. 9A-9C).

For indeterminate samples, analysis of six, eight or twelve microRNA expression levels achieved sensitivity of between 73.9-82.6% and specificity of up to 73%. Analysis of six or eight microRNA ratios, achieved sensitivity of between 76.5-80.9% and specificity of up to 65.9%. Analysis of a combination of microRNA expression levels and microRNA ratios achieved sensitivity of between 76.5-80.9% and specificity of up to 67.5% (FIG. 13A-13C, FIG. 14A-14B, FIG. 15A-15C).

For Bethesda IV samples, analysis of six, eight or twelve microRNA expression levels achieved sensitivity of between 66-72.3% and specificity of up to 61.9%. Analysis of six or eight microRNA ratios, achieved sensitivity of between 78.7-80.9% and specificity of up to 61.9%. Analysis of a combination of microRNA expression levels and microRNA ratios achieved sensitivity of between 63.8-74.5% and specificity of up to 58.7% (FIG. 25A-25C, FIG. 26A-26B, FIG. 27A-27C).

Example 9.3

SVM Classifier

A third analysis was performed applying SVM (Support vector machine) as the algorithm, in which linear kernel was used. The analysis with the SVM algorithm was applied to the three sets of samples as mentioned above (malignant+benign, indeterminate and Bethesda IV), using as features either different combinations of microRNA expression levels, microRNA ratios, or a combination of microRNA expression levels and microRNA ratios, respectively. The results are described below.

For malignant+benign samples, analysis of three, six or eight microRNA expression levels achieved sensitivity of between 82.3-86% and specificity of up to 75.5%. Analysis of three, six or eight microRNA ratios, achieved sensitivity of about 83% and specificity of up to 80.8%. Analysis of a combination of microRNA expression levels and microRNA ratios achieved sensitivity of between 82.9-86.6% and specificity of up to 83.4% (data not shown).

For indeterminate samples, analysis of six, eight or twelve microRNA expression levels achieved sensitivity of between 82.6-90.4% and specificity of up to 60.3%. Analysis of three, six or eight microRNA ratios, achieved sensitivity of between 81.7-88.7% and specificity of up to 67.5%. Analysis of a combination of microRNA expression levels and microRNA ratios achieved sensitivity of between 80-89.9% and specificity of up to 71.4% (FIG. 16A-16C, FIG. 17A-17C, FIG. 18A-18C).

For Bethesda IV samples, analysis of three, six or eight microRNA expression levels achieved sensitivity of between 89.4-97.9% and specificity of up to 55.6%. Analysis of three, six or eight microRNA ratios, achieved sensitivity of between 93.6-100%. Analysis of a combination of microRNA expression levels and microRNA ratios achieved sensitivity of between 91.5-95.7% (data not shown).

Example 9.4

Ensemble Methods Classifier

A fourth analysis was performed applying Ensemble methods as the algorithm. An ensemble of up to 100 discriminant analysis classifiers was created using AdaBoost and applied to the data. The analysis with the Ensemble algorithm was applied to three sets of samples as mentioned above (malignant+benign, indeterminate and Bethesda IV), using as features either different combinations of microRNA expression levels, microRNA ratios, or a combination of microRNA expression levels and microRNA ratios. The results are described below.

For malignant+benign samples, analysis of two, three or eight microRNA expression levels achieved sensitivity of about 85% and specificity of up to 74.8%. Analysis of three, six or eight microRNA ratios, achieved sensitivity of about 83.5-86% and specificity of up to 79.5%. Analysis of a combination of microRNA expression levels and microRNA ratios achieved sensitivity of about 86% and specificity of up to 82.8% (data not shown).

For indeterminate samples, analysis of two, three or eight microRNA expression levels achieved sensitivity of between 84.3-88.7% and specificity of up to 64.3%. Analysis of two, three or eight microRNA ratios, achieved sensitivity of between 86.1-89.7% and specificity of up to 65.1%. Analysis of a combination of microRNA expression levels and microRNA ratios achieved sensitivity of between 83.5-87.8% and specificity of up to 65.9% (FIG. 19A-19C, FIG. 20A-20C, FIG. 21A-21C).

For Bethesda IV samples, analysis of two, three or eight microRNA expression levels achieved sensitivity of between 89.4-93.6% and specificity of up to 46%. Analysis of two, three or eight microRNA ratios, achieved sensitivity of between 89.4-93.6% and specificity of up to 44.4%. Analysis of a combination of microRNA expression levels and microRNA ratios achieved sensitivity of around 91.5% (data not shown).

Example 10

A Classifier for Malignant Samples Including Medullary

The same sample set used in Example 9, but including medullary malignant samples was used for establishing a classifier. All classifiers (LDA, KNN, SVM and Discriminant Analysis Ensemble) were applied, and a representative set of results from the discriminant analysis algorithm showed that when normalized values of two microRNA ratios (e.g. hsa-miR-125b-5p:hsa-miR-138-5p; and hsa-miR-146b-5p:hsa-miR-342-3p) were used as the features for the classification, the sensitivity of the classifier was 84.7% and the specificity, 80.8% (FIG. 30-31). When the normalized values of two microRNAs (e.g. hsa-miR-222-3p and hsa-miR-551b-3p) were used as the features for the classification, the sensitivity was 85.2% and the specificity, 53.6% (FIG. 30-31).

Example 11

Elimination of Samples Through the Expression of Cell Specific Markers

One important consideration throughout this study was the accuracy of the result that is to be provided to a patient who has had an FNA sample collected. Laboratories tend to err in order not to provide false-negative results. On the other hand, in the analysis of FNA specimens, a suspicious diagnostic will send the patient to surgery, which in more than 25% of the cases turns out to be unnecessary. For example, at least one report in the literature described that thyroid tumor samples with large amounts of blood, or even pure blood, are misdiagnosed as suspicious in 7 out of 9 cases (Walsh et al. (2012) J Clin Endocrin Metab. doi: 10.1210/jc.2012-1923).

With this goal in mind, the present inventors searched for microRNAs that could be used as cell type markers and aid in the screening of the quality of the specimen examined. Thus, the expression of hsa-miR-486-5p (SEQ ID NO: 22) and hsa-miR-200c-3p (SEQ ID NO: 23 or 24) was evaluated in the development assay cohort, including cell blocks, having samples from benign and malignant (non-medullary) thyroid lesions, as well as four samples of blood only (slides of blood smears were generated for this purpose, and RNA extracted as described herein). The results showed that the blood microRNA marker, hsa-miR-486-5p is very high and the epithelial marker, hsa-miR-200c-3p, is very low, compared to the threshold established in the development assay set (FIG. 32). The blood smear samples were therefore filtered out using these markers. This expression pattern indicates that these samples do not have enough epithelial cells (for lack of the epithelial cell marker) to continue the test. In a test situation, these four samples of blood smears would be disqualified and discarded. Expression of hsa-miR-138-5p (SEQ ID NO: 19, 20, or 21) has also been shown to be low, compared to the threshold, in blood smears (data not shown). Samples with this profile are eligible to be disqualified and/or discarded from the protocol for classification of thyroid lesion samples.

The inventors had previously established that expression of hsa-miR-342-3p (SEQ ID NO: 17 or 18) correlates with white blood cells (data not shown). Hence, high expression of hsa-miR-342-3p compared to the threshold indicated lack of sufficient thyroid cells, and samples with this profile are eligible to be disqualified and/or discarded from the protocol for classification of thyroid lesion samples.

In parallel, high expression of hsa-miR-200c-3p is an indicator of the presence of epithelial cells in general, and specifically thyroid cells (data not shown and FIG. 32). Hence, the expression of hsa-miR-200c-3p above a threshold may be used as an indicator of sufficiency of thyroid cells in the sample.

Example 12

Classification of Thyroid Tumor Sub-Types

Classification of benign thyroid tumor sub-types was done using samples from Hashimoto (n=6) and follicular adenoma (FA; n=81), from the development assay cohort. Expression of hsa-miR-342-3p and hsa-miR-31-5p in Hashimoto samples was high compared to the threshold established in the assay set (FIG. 33). Thus, high expression of hsa-miR-342-3p alone or in combination with hsa-miR-31-5p may be used for the classification of samples as benign, and further sub-typing as Hashimoto.

Further, the inventors also tested microRNA ratios for sub-typing benign thyroid tumors. In this context, the miR ratio of hsa-miR-125b-5p:hsa-miR-200c-3p was significant for classifying follicular adenoma (FA) versus Hashimoto samples (data not shown).

Classification of malignant thyroid tumor sub-types was done using a subset of samples (n=177) of the assay cohort. In one example of an analysis, 146b-5p, 222-3p, 31-5p, 125b-5p, 551-3p and 375 were found to be highly expressed in papillary carcinoma, while MID-16582 was found to be highly expressed in follicular carcinoma (FIG. 34).

The ratios of the following miR pairs were significant for classifying Papillary Carcinoma (PC) versus Follicular Carcinoma samples: hsa-miR-146b-5p:hsa-miR-342-3p, hsa-miR-125b-5p:hsa-miR-200c-3p, hsa-miR-222-3p:hsa-miR-486-5p, hsa-miR-31-5p:hsa-miR-342-3p, MID-16582:hsa-miR-200c-3p, MID-16582:hsa-miR-138-5p (data not shown).

Therefore, the inventors have demonstrated that malignant thyroid tumor sub-typing may be performed using miR ratios, particularly miR ratios where the denominator is a cell marker microRNA, such as hsa-miR-486-5p, hsa-miR-200c-3p, hsa-miR-138-5p, and hsa-miR-342-3p.

Example 13

Protocol for the Classification of Thyroid Nodules as Malignant or Benign

A flowchart with a protocol for thyroid nodule sample analysis, from collection of FNA samples to laboratory analysis and diagnostic (FIG. 35). FNA samples are collected from patients having thyroid nodules, and are routinely processed. Smears are prepared from the FNA samples. As a first step, a specialist in cytopathology examines the FNA sample and provides an analysis. In cases where the analysis is inconclusive, particularly in samples classified as Bethesda III, IV, or V, i.e. so-called "indeterminate", the sample is sent to Rosetta Genomics' laboratories to undergo microRNA profiling and conclusive diagnostic. Total RNA is extracted from the sample, which undergoes microRNA profiling. MicroRNA profiling may be performed by amplification (RT-PCR or NGS) or hybridization (microarray), as shown in the Examples above.

The protocol may include any one of the following:
One or more algorithms may be used during classification, and will be applied on data comprising single microRNAs expression, microRNA ratios, or a combination thereof.
Samples wherein the hsa-miR-375 expression level is above a specific threshold may be determined as malignant, e.g. a threshold of at least 10, or a threshold of at least 18 (data not shown), when the expression was analyzed by array or PCR, respectively. The threshold is dependent on the normalization of the samples, as well as on the methodology used for measuring the microRNAs. The threshold may also be a function of the target sensitivity and specificity.
Samples wherein the hsa-miR-146b-5p expression level is above a specific threshold will be determined as malignant (e.g. a threshold of at least 16; FIG. 28 and data not shown). The threshold is dependent on the normalization of the samples, as well as on the methodology used for measuring the microRNAs. The threshold may also be a function of the target sensitivity and specificity.
Samples wherein the ratio hsa-miR-146b-5p:hsa-miR-342-3p, further to normalization, is above a specific threshold will be determined as malignant, e.g. a threshold of at least 16 (FIG. 29 and data not shown). The threshold is dependent on the normalization of the samples, as well as on the methodology used for measuring the microRNAs.

The level of expression of the normalizers may be used as an indicator for discarding samples, due to insufficient tumor-derived material. Thus, samples presenting low levels of any of the normalizers, or the minimal, median or maximal value of expression for the normalizers may be discarded. For example, low levels of hsa-miR-23a-3p (compared to the overall levels of hsa-miR-23a-3p expression in the cohort) are likely to be misclassified. In counterpart, high levels of hsa-miR-23a-3p improve the classification by improving sensitivity and specificity (data not shown).

Analysis of the microRNA profiling data leads to diagnostic of the thyroid nodule as benign or malignant. Results permitting, which include the expression of microRNAs that may be associated with thyroid tumor sub-types, as shown in FIGS. 33 and 34, for example, the sample is further classified according to its thyroid tumor subtype.

Example 14

A Classifier for Diagnosing Indeterminate Thyroid Nodules as Benign or Malignant A training set of 375 FNA smears (Table 11) was used to develop a classifier for diagnosing indeterminate thyroid nodules as benign or malignant according to microRNA profiling, using the set of 24 miRNAs established and described in Example 8 above. From the total 375 FNA smear samples, 252 samples were profiled in the RG-IL (Rosetta Genomics, Rehovot, Israel) laboratory and 123 samples were profiled in the RGL-US (Rosetta Genomics, Philadelphia, US) laboratory.

The classifier developed combines several linear discriminant analysis (LDA) steps and a KNN-based classifier. The LDA step which classifies medullary samples is based on the expression of hsa-miR-375 (an indicator of medullary carcinoma) (FIG. 36). Samples classified in this step receive a final classification of malignant, and are marked as being positive for expression of the medullary marker. The KNN classifier (K=9) uses a Pearson correlation distance metric over the $C_T$ values of six of the measured miRNAs, and uses a training set of 314 samples. Samples with at least four benign neighbors are classified as benign by the KNN classifier. Only a subset of the training samples were used to determine the classifier. For example, samples with low microRNA expression in the KNN step were not included in the KNN classifier.

The performance of the training set is summarized in Table 12 and Table 13.

Table 12 shows the result of the classification according to the classifier (malignant or benign), as well as sensitivity and specificity in each sub-group of samples, Indeterminate (all sub-types), Indeterminate (subtypes III and IV) and Determinates. Sensitivity of the classifier on indeterminate samples (Bethesda III-V) was estimated to be 86%, based on the training set, and the specificity was estimated to be 75%. The performance of the classifier on determinate samples (Bethesda II and VI) was estimated to be higher, with a sensitivity of 96% and a specificity of 82% for these samples.

Table 13 shows the performance of the assay per histological type, and indicates the number of samples and the percentage of agreement between the classification obtained with the classifier and the cytopathologist classification.

TABLE 11

Tumor samples used for the final classifier and for the validation

|  |  | Training[a] | Validation |
|---|---|---|---|
| Cohort | #Samples | 375 | 201 |
|  | #Patients | 357 | 201 |
|  | % Malignant | 49 | 30 |
|  | Age (median) | 54 | 53 |
|  | % Females | 73 | 80 |
| Cytology | #Giemsa | 212 | 90 |
|  | #Diff-Quik | 95 | 21 |
|  | #Papanicolaou | 62 | 90 |
|  | #BethesdaII | 27 | 0 |
|  | #BethesdaIII | 80 | 29 |
|  | #BethesdaIV | 142 | 131 |
|  | #BethesdaV | 77 | 41 |
|  | #BethesdaVI | 49 | 0 |

[a]For 64 training samples, the age information was missing and for 10 training samples, the gender was unknown. Three training samples were created by mixing more than one slide (with different stains), two were unstained, and for one the stain was unknown.

TABLE 12

Assay performance for the final classifier training set and validation

|  |  | Indeterminate (all sub-types)[c] | Indeterminate (III, IV)[c] | Bethesda II and VI[c] |
|---|---|---|---|---|
| Training[a] | Malignant | 115 | 59 | 40 |
|  | Benign | 147 | 137 | 26 |
|  | Sensitivity | 86 [78-92] | 78 [65-88] | 96 [85-100] |
|  | Specificity | 75 [67-81] | 76 [68-83] | 82 [62-94] |
| Validation[b], entire set | Malignant | 61 | 31 | 0 |
|  | Benign | 128 | 119 | 0 |
|  | Sensitivity | 85 [74-93] | 74 [55-88] | NA |
|  | Specificity | 72 [63-79] | 74 [65-82] | NA |
|  | NPV | 91 [84-96] | 92 [84-96] | NA |
|  | PPV | 59 [48-69] | 43 [29-57] | NA |
| Validation[b], Agreement set | Malignant | 40 | 14 | 0 |
|  | Benign | 110 | 102 | 0 |
|  | Sensitivity | 98 [87-100] | 100 [77-100] | NA |
|  | Specificity | 78 [69-85] | 80 [71-88] | NA |
|  | NPV | 99 [94-100] | 100 [96-100] | NA |
|  | PPV | 62 [49-74] | 41 [25-59] | NA |

[a]In the training set, estimates are based on the mean of ten 10-fold cross-validation runs. Samples with very low expression in any of the classification steps, as well as medullary samples are not included.
[b]Samples that failed QC are not included.
[c]95% Confidence Intervals are in square brackets [ ].
NA = Non-Applicable.

TABLE 13

Performance of assay per histological type

| Histological type | Training[a] | | Validation | | Validation Full-agreement Set | |
|---|---|---|---|---|---|---|
|  | Samples[b] | % Correct[c] | Samples[b] | % Correct[c] | Samples[bd] | % Correct[c] |
| Medullary | 5 | 100 [48-100] | 3 | 100 [29-100] | 1 (33.3%) | 100 [3-100] |
| PTC Classic | 48 | 94 [83-100] | 17 | 88 [64-99] | 15 (88.2%) | 100 [78-100] |
| FVPTC | 40 | 81 [65-92] | 37 | 84 [68-94] | 23 (62.2%) | 96 [78-100] |
| FC | 16 | 56 [30-80] | 3 | 67 [9-99] | 1 (33.3%) | 100 [3-100] |
| FA | 90 | 76 [66-84] | 95 | 76 [66-84] | 82 (86.3%) | 82 [72-89] |
| Nodular Hyperplasia | 48 | 75 [60-86] | 28 | 64 [44-81] | 23 (82.1%) | 74 [52-90] |
| Hashimoto | 9 | 82 [44-99] | 5 | 40 [5-85] | 5 (100.0%) | 40 [5-85] |
| PDC[e] | 5 | 100 [48-100] | 1 | 100 [3-100] | 0 (0%) | NA |
| Papillary, Other | 6 | 88 [54-100] | 0 | NA | 0 | NA |
| Total | 267 | — | 189 | — | 150 | — |

[a]Only indeterminate training samples are listed in the Table. Estimates are based on the mean of ten 10-fold cross-validation runs. Samples with very low expression in any of the classification steps, as well as medullary samples, are not included.
[b]Number of samples includes only those that passed QC.
[c]95% Confidence Intervals are in square brackets
[d]Numbers in parentheses signify the percentage of validation samples in the agreement set
[e]PDC = Poorly Differentiated Carcinoma
[f]Other Malignant = Non-classic Papillary and non-FVPTC samples.
NA = Not Applicable.

As an additional proof-of-concept of its performance, the classifier was also assessed on a set of 48 FNA cell blocks (used also in Examples 2 and 5), which were run in the final assay format. The performance of the classifier on the indeterminate samples (72% sensitivity and 79% specificity) was similar to the performance of the FNA smears, as can be seen in Table 14, with a slightly lower sensitivity and a slightly higher specificity. The sensitivity of the malignant Bethesda VI smears was 89% and the specificity of the benign Bethesda II samples was 63%.

TABLE 14

Performance of the assay on cell blocks

|  | Malignant | Benign | Sensitivity (%) | Specificity (%) |
|---|---|---|---|---|
| All | 23 | 25 | 78 [56-93] | 80 [59-93] |
| Indeterminate (Bethesda III, IV and V) | 18 | 24 | 72 [47-90] | 79 [58-93] |
| Determinate (Bethesda II and VI) | 5 | 1 | 100 [48-100] | 100 [3-100] |

95% Confidence Intervals are in square brackets

Example 15

Clinical Validation of a Classifier for the Diagnosis of Indeterminate Thyroid Nodules as Benign or Malignant Validation of the classifier described in Example 14 was done on a blinded retrospective cohort of 199 FNA smears. The retrospective validation cohort is an independent set of 201 consecutive, indeterminate FNA samples (Table 11) from five centers, which was tested blindly in the clinical validation assay. This set of 201 samples included only samples for which at least two of the three pathologists (the original pathologist and at least one of the additional pathologists) agreed on the final diagnosis of the excised H&E stained nodule. In addition, samples whose diagnosis was determined to be medullary carcinoma, according to the original pathologist, were included (regardless of the diagnosis of the additional two pathologists). Only twelve of the 201 samples (6%) failed during processing or QC steps, with the most common reason being low miRNA expression. The performance of the validation cohort was found to be very similar to the performance estimates of the training cohort, as can be seen in Tables 12 and 13.

The NPV of the entire set was 91%, the sensitivity was 85%, the specificity was 72% and the PPV was 59% (FIG. 37). When excluding 23 samples with tumor size <1 cm, i.e, when the samples are with tumor size equal or larger than 1 cm, the sensitivity was 84% and the specificity was 72%. Seventy of the validation samples from the US passed QC steps, which demonstrated a sensitivity of 82%, and a specificity of 71%. The nine misclassified malignant samples (Table 15) included samples from all three indeterminate Bethesda classes, both Giemsa and Papanicolaou stains, and were from three medical centers. The misclassified FC sample was described as having minimal capsular invasion, according to the original pathologist, as were the other two, correctly classified FC samples. The Hashimoto samples showed a lower correct classification rate, relative to both the training performance and to the other benign samples. However, this difference may be due to the small number of Hashimoto samples in the validation set.

TABLE 15

The misclassified malignant validation samples

| Bethesda | Stain | Extracted Amount (ng) | Gender | Histological Type | Histological Subtype | In Agreement Set? |
|---|---|---|---|---|---|---|
| V | MGG | 294 | Female | Papillary carcinoma | FVNE | Yes |
| IV | MGG | 4716 | Female | Papillary carcinoma | Classic variant | No |
| IV | PP | 138 | Male | Papillary carcinoma | FVE | No |
| III | PP | 115 | Female | Papillary carcinoma | FVE | No |
| IV | PP | 103 | Female | Papillary carcinoma | FVE | No |
| IV | MGG | 51 | Female | Papillary carcinoma | FVE | No |
| IV | PP | 1242 | Female | Papillary carcinoma | FVE | No |
| IV | MGG | 249 | Female | Follicular carcinoma | MCI | No |
| IV | MGG | 451 | Male | Papillary carcinoma | Classic variant | No |

MGG = May-Grünwald Giemsa;
PP = Papanicolaou;
FVNE = Follicular Variant, Non-encapsulated;
CV = Classic variant;
MCI = Minimal capsular invasion;
FVE = Follicular Variant Encapsulated In order to test the assay on a set of samples for which the final diagnosis has a high degree of certainty, a subset of the validation set ("Agreement set") was compiled. This set comprised 160 samples (80% of the validation set) for which all three pathologists agreed on the final diagnosis. This set demonstrated very high performance (Table 16). The NPV of the Agreement set was 99% (only one malignant sample was misclassified as benign), with a sensitivity of 98%, a specificity of 78%, and a PPV of 62%. If the NPV and PPV are calculated based on the sensitivity, specificity and prevalence, the NPV would remain over 95%, even if the rate of malignancy was above 60%. The samples in the Agreement set (Table 16) had a much higher correct classification rate when compared with samples not in the Agreement set: of the samples that passed QC steps, 150 were in the Agreement set and 25 (17%) of these were misclassified, whereas 39 samples were not in the Agreement set and 20 (51%) of these were misclassified (p<6.14e-06, x2 test). The same conclusion is reached when focusing on the malignant samples, with malignant samples in the Agreement set having a higher correct classification rate: 40 malignant samples were in the Agreement set and one (2.5%) was misclassified, whereas 21 malignant samples were not in the Agreement set and eight (38%) were misclassified (p<5e-4, Fisher's exact test).

The performance of the assay is influenced by the accuracy of the diagnosis. Therefore, the level of agreement between the pathologists for the different histological types (Table 16) was examined.

TABLE 16

The malignant histological types in the Agreement set

| | Agreement set | | Not in Agreement set | |
|---|---|---|---|---|
| | Total | #Misclassified[b] | Total | #Misclassified[b] |
| Medullary | 1 | 0 | 2 | 0 |
| Papillary classic | 15 | 0 | 2 | 2 |
| FVPTC, encapsulated | 12 | 0 | 14 | 5 |
| FVPTC, non-encapsulated | 10 | 1 | 0 | 0 |
| FC | 1 | 0 | 2 | 1 |
| PDC | 0 | 0 | 1 | 0 |
| Total[a] | 39 | 1 | 21 | 8 |

FVPTC = Follicular Variant of Papillary Thyroid Carcinoma

[a] One FVPTC sample (in the full-agreement set and correctly classified) is not included in the Table, since there was no information available regarding the encapsulation status.
[b] Misclassified as benign.

Of the 17 classic/conventional papillary thyroid carcinoma (PTC) samples in the entire validation set, only two were not included in the agreement set; these two samples were the only PTC samples misclassified by the assay as benign. There was a large number of encapsulated Follicular Variant of Papillary Carcinoma (FVPTC) in the entire validation set that were not included in the agreement set. This higher proportion of encapsulated FVPTC in the subset of samples for which there was no agreement, was statistically significant when compared with the proportion of non-encapsulated FVPTC (p<0.0029, Fisher's exact test). Furthermore, of the 26 encapsulated FVPTC samples in the entire validation set, five were misclassified as benign; none of these five cases were in the agreement set. It can also be noted that of the three FC samples, only one was included in the agreement set and this one was correctly classified as malignant. These details highlight the importance of working with a high-quality reference diagnosis set and demonstrate the high performance of the assay on samples for which the reference diagnosis is more reliable.

The foregoing description of the specific embodiments so fully reveals the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims.

It should be understood that the detailed description and specific examples, while indicating preferred embodiments of the invention, are given by way of illustration only, since various changes and modifications within the scope of the invention will become apparent to those skilled in the art from this detailed description.

The invention claimed is:

1. A method of classifying a thyroid lesion sample as malignant or benign, comprising:
   a. providing RNA extracted from a thyroid lesion sample obtained from a human subject using fine needle aspiration (FNA);
   b. obtaining by real time polymerase chain reaction (PCR) performed on the RNA an expression profile comprising expression levels of miRNAs comprising hsa-miR-31-5p (SEQ ID NO: 5, 6, or 7), hsa-miR-222-3p (SEQ ID NO: 1 or 2), hsa-miR-146b-5p (SEQ ID NO: 10 or 11), MID-16582 (SEQ ID NO: 25), hsa-miR-342-3p (SEQ ID NO: 17 or 18), hsa-miR-125b-5p (SEQ ID NO: 9), hsa-miR-375 (SEQ ID NO: 8), hsa-miR-486-5p (SEQ ID NO: 22), hsa-miR-551b-3p (SEQ ID NO: 3 or 4), hsa-miR-152-3p (SEQ ID NO: 12 or 13), hsa-miR-138-5p (SEQ ID NO: 19, 20, or 21), hsa-miR-23a-3p (SEQ ID NO: 26), and hsa-miR-574-3p (SEQ ID NO: 36 or 37); wherein the PCR comprises contacting the RNA with forward and reverse primers for each of the miRNAs, wherein each forward primer is specific for one of the miRNAs; and wherein the forward primers comprise SEQ ID NO: 317;
   c. applying a classifier algorithm to the expression profile; wherein the classifier algorithm compares the expression profile to a reference value; and
   d. classifying the thyroid lesion as benign or malignant based on the result from the classifier algorithm.

2. The method of claim 1, wherein the thyroid lesion has been classified as Bethesda III, IV or V according to the Bethesda system.

3. The method of claim 1, wherein said classifier algorithm is a machine-learning algorithm.

4. The method of claim 1, wherein said classifier algorithm is a multi-step classifier.

5. The method of claim 4, wherein the classifier algorithm comprises at least one linear discriminant analysis (LDA) classifier.

6. The method of claim 5, wherein the classifier algorithm comprises at least one LDA classifier combined with a KNN classifier.

7. The method of claim 1, wherein following step (b), the method further comprises a step of obtaining a ratio between the expression levels of at least one pair of microRNAs; and wherein in step (c) said classifier algorithm is applied to any one of the microRNA expression profile, said ratio of at least one pair of microRNAs, or to a combination thereof.

8. The method of claim 1, wherein said algorithm further combines at least one of clinical or genetic data from said sample.

9. The method of claim 1, further comprising the step of administering a differential treatment to said subject if said thyroid lesion is classified as benign or malignant.

10. The method of claim 9, wherein said lesion is classified as malignant and said treatment is any one of surgery, chemotherapy, radiotherapy, hormone therapy, or any other recommended treatment.

11. The method of claim 1, wherein said classifying further includes a step of eliminating a sample classified as medullary malignant carcinoma.

12. The method of claim 1, wherein said classification has a negative predictive value of between 84 and 96%.

* * * * *